(12) United States Patent
DeForest et al.

(10) Patent No.: US 11,779,646 B2
(45) Date of Patent: Oct. 10, 2023

(54) DYNAMIC USER-PROGRAMMABLE MATERIALS INCLUDING STIMULI-RESPONSIVE PROTEINS

(71) Applicant: UNIVERSITY OF WASHINGTON, Seattle, WA (US)

(72) Inventors: Cole Alexander DeForest, Seattle, WA (US); Jared Shadish, Seattle, WA (US); Luman Liu, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 16/399,882

(22) Filed: Apr. 30, 2019

(65) Prior Publication Data

US 2019/0328890 A1 Oct. 31, 2019

Related U.S. Application Data

(60) Provisional application No. 62/664,859, filed on Apr. 30, 2018.

(51) Int. Cl.

| | |
|---|---|
| *A61K 47/58* | (2017.01) |
| *C07K 17/08* | (2006.01) |
| *C07K 1/113* | (2006.01) |
| *A61K 47/59* | (2017.01) |
| *A61L 31/14* | (2006.01) |
| *A61K 31/74* | (2006.01) |
| *A61K 41/00* | (2020.01) |
| *A61K 47/69* | (2017.01) |

(52) U.S. Cl.
CPC .............. *A61K 47/58* (2017.08); *A61K 31/74* (2013.01); *A61K 41/0042* (2013.01); *A61K 47/593* (2017.08); *A61K 47/6903* (2017.08); *A61L 31/145* (2013.01); *C07K 1/1136* (2013.01); *C07K 17/08* (2013.01)

(58) Field of Classification Search
CPC ...... A61K 47/60; A61K 47/56; A61K 47/593; C07K 17/08
See application file for complete search history.

(56) References Cited

U.S. PATENT DOCUMENTS

| | | | | |
|---|---|---|---|---|
| 8,367,639 B2* | 2/2013 | Kilck | ................... | A61K 9/1647 514/56 |
| 8,535,644 B2 | 9/2013 | Haghgooie et al. | | |
| 2011/0097302 A1* | 4/2011 | Yuan | .................... | C09J 101/286 424/85.2 |
| 2012/0165204 A1* | 6/2012 | Hahn | ....................... | C12N 9/16 506/2 |
| 2012/0228520 A1 | 9/2012 | Tan et al. | | |
| 2014/0219922 A1 | 8/2014 | Shuba | | |
| 2016/0158410 A1 | 6/2016 | Shastri et al. | | |
| 2016/0256604 A1 | 9/2016 | Hanna et al. | | |
| 2017/0182209 A1 | 6/2017 | Branco da Cunha et al. | | |
| 2018/0071409 A1 | 3/2018 | Xu et al. | | |

FOREIGN PATENT DOCUMENTS

| | | |
|---|---|---|
| CN | 202757885 U | 2/2013 |
| WO | 2011/070402 A1 | 6/2011 |
| WO | 2014/116187 A1 | 7/2014 |

OTHER PUBLICATIONS

Tang et al, Therapeutic microparticles functionalized with biomimetic cardiac stem cell membranes and secretome, Nature Communications, 2017, pp. 1-9.*
Liu "Cyclic Stiffness Photomodulation of Cell-Laden Protein-Polymer Hydrogels" A thesis submitted in partial fulfillment of the requirements for the degree of Master of Science in Chemical Engineering University of Washington Jun. 2017 (Year: 2017).*
Veronese et al. "Branched and Linear Poly(Ethylene Glycol): Influence of the Polymer Structure on Enzymological, Pharmacokinetic , and Immunological Properties of Protein Conjugates",Journal of Bioactive and Compatible Polymers, vol. 12 issue: 3, pp. 196-207 (Year: 1997).*
Zhang et al. "Rational design of a photo-responsive UVR8-derived protein and a self-assembling peptide-protein conjugate for responsive hydrogel formation", Nanoscale, Oct. 28, 2015;7(40):16666-70 (Year: 2015).*
Arakawa, C.K. & DeForest, C.A. Designing Smart Biomaterials to Mimic & Control the Stem Cell Niche: "Polymer Design and Development," Biology and Engineering of Stem Cell Niches, Elsevier. Oxford, UK. 295-314 (2017).
Patterson, J. & Hubbell, J. A. "Enhanced proteolytic degradation of molecularly engineered PEG hydrogels in response to MMP-1 and MMP-2," Biomaterials 31, 7836-7845 (Jul. 2010).
Pattison, D. I. & Davies, M. J., "Actions of ultraviolet light on cellular structures," 131-157 (Birkhäuser Basel, 2006). doi:10.1007/3-7643-7378-4_6.
Peng, L., M. You, Q. Yuan, C. Wu, D. Han, Y. Chen, Z. Zhong, J. Xue, W. Tan, "Macroscopic Volume Change of Dynamic Hydrogels induced by Reversible DNA Hybridization," J. Am. Chem. Soc. Jul. 2012, 134, 12302.
Phizicky, E. M. & Fields, S. "Protein-protein interactions: methods for detection and analysis," Microbiol. Rev. 59, 94-123 (Mar. 1995).
Rabuka, D. "Chemoenzymatic methods for site-specific protein modification," Curr. Opin. Chem. Biol. 14, 790-796 (Oct. 2010).

(Continued)

*Primary Examiner* — James W Rogers
(74) *Attorney, Agent, or Firm* — Christensen O'Connor Johnson Kindness PLLC

(57) ABSTRACT

The present disclosure features a protein-polymer conjugate, including a multivalent polymer building block, a stimuli-responsive protein covalently conjugated to the multivalent polymer building block to provide a protein-polymer conjugate, wherein the protein undergoes a modification upon exposure to a predetermined stimulus, and the protein modification triggers a physical and/or chemical response in the protein-polymer conjugate.

9 Claims, 44 Drawing Sheets
Specification includes a Sequence Listing.

(56) References Cited

OTHER PUBLICATIONS

Rabuka, D., Rush, J. S., deHart, G. W., Wu, P. & Bertozzi, C. R. "Site-specific chemical protein conjugation using genetically encoded aldehyde tags," Nat. Protoc. 7, 1052-1067 (May 2012).
Raeber, G. P., Lutolf, M. P. & Hubbell, J. A. "Molecularly engineered PEG hydrogels: A novel model system for proteolytically mediated cell migration," Biophys. J. 89, 1374-1388 (Aug. 2005).
Renicke, C., Schuster, D., Usherenko, S., Essen, L.-O. & Taxis, C. "A LOV2 Domain-Based Optogenetic Tool to Control Protein Degradation and Cellular Function," Chem. Biol. 20, 619-626 (Apr. 2013).
Resh, M. D. "Fatty acylation of proteins: new insights into membrane targeting of myristoylated and palmitoylated proteins," Biochim. Biophys. Acta—Mol. Cell Res. 1451, 1-16 (Jun. 1999).
Riggsbee, C.W. and Deiters, A., "Recent advances in the photochemical control of protein function," Trends in biotechnology, 28(9), pp. 468-475 (2010).
Rombouts, W.H., D. W. De Kort, T. T. H. Pham, C. P. M. van Mierlo, M. W. T. Werten, F. A. De Wolf, J. van der Gucht, "Reversible Temperature-Switching of Hydrogel Stiffness of Coassembled, Silk-Collagen-Like Hydrogels," Biomacromolecules, Jul. 2015, 16, 2506-2513.
Rosales, A. M. & Anseth, K. S. "The design of reversible hydrogels to capture extracellular matrix dynamics," Nat. Rev. Mater. 1, 15012 (2016).
Rosales, A.M., C. B. Rodell, M. H. Chen, M. G. Morrow, K. S. Anseth, J. A. Burdick, "Reversible Control of Network Properties in Azobenzene-Containing Hyaluronic Acid-Based Hydrogels," Bioconjugate Chem. 2018, 29, 905.
Rosales, A.M., K. M. Mabry, E. M. Nehls, K. S. Anseth, "Photoresponsive Elastic Properties of Azobenzene-Containing Poly-(ethylene-glycol)-Based Hydrogels," Biomacromolecules, Jan. 2015, 16, 798-806.
Ruskowitz, E.R., C. A. DeForest, "Photoresponsive biomaterials for targeted drug delivery and 4D cell culture," Nat. Rev. Mater. Jan. 2018, 3, 17087, pp. 1-17.
Salomon, M., J. M. Christie, E. Knieb, U. Lempert, W. R. Briggs, "Photochemical and Mutational Analysis of the FMN-Binding Domains of the Plant Blue Light Receptor, Phototropin," Biochemistry, May 2000, 39, 9401-9410.
Seliktar, D. "Designing Cell-Compatible Hydrogels for Biomedical Applications," Science 336, 1124-1128 (Jun. 2012).
Shadish, J., "Next Generation Biomaterials Generated via Chemoenzymatic Modification of Proteins" General Exam Presentation to Committee at the University of Washington on Nov. 28, 2017, Seattle, Washington.
Sletten, E. M. & Bertozzi, C. R. "Bioorthogonal chemistry: fishing for selectivity in a sea of functionality," Angew. Chemie Int. Ed. 48, 6974-6998 (2009).
Stempien-Otero, A., D. H. Kim, J. Davis, "Molecular networkds underlying myofibroblast fate and fibrosis," J. Mol. Cell. Cardiol., May 2016, 97, 153-161.
Tallini, Y.N., M. Ohkura, B.-R. Choi, G. Ji, K. Imoto, R. Doran, J. Lee, P. Plan, J. Wilson, H.-B. Xin, A. Sanbe, J. Gulick, J. Mathai, J. Robbins, G. Salama, J. Nakai, M. I. Kotlikoff, "Imaging cellular signals in the heart in vivo: Cardiac expression of the high-signal Ca2+ indicator GCaMP2," Proc. Natl. Acad. Sci. USA, Mar. 2006, 103, 4753-4758.
Tam, R. Y., Smith, L. J. & Shoichet, M. S. "Engineering Cellular Microenvironments with Photo- and Enzymatically Responsive Hydrogels: Toward Biomimetic 3D Cell Culture Models," Acc. Chem. Res. 50, 703-713 (Mar. 2017).
Tamesue, S., Y. Takashima, H. Yamaguchi, S. Shinkai, A. Harada, "Photoswitchabe Supramolecular Hydrogels Formed by Cyclodextrins and Azobenzene Polymers," Angew. Chem., Int. Ed. 2010, 49, 7461-7464.
Tibbitt, M. W. & Anseth, K. S. "Dynamic Microenvironments: The Fourth Dimension," Sci. Transl. Med. 4, (Nov. 2012).

Tibbitt, M. W. & Anseth, K. S. "Hydrogels as Extracellular Matrix Mimics for 3D Cell Culture," Biotechnol. Bioeng. 103, 655-663 (Apr. 2009).
Tischer, D. & Weiner, O. D. "Illuminating cell signalling with optogenetic tools," Nat. Rev. Mol. Cell Biol. 15, 551-558 (Aug. 2014).
Tomatsu, Itsuro, Ke Peng, and Alexander Kros "Photoresponsive hydrogels for biomedical applications" Advanced drug delivery reviews, Jul. 2011 vol. 63, Issue 14 pp. 1257-1266.
Towler, D. a, Gordon, J. I., Adams, S. P. & Glaser, L. "The biology and enzymology of eukaryotic protein acylation," Annu. Rev. Biochem. 57, 69-99 (1988).
Towler, D. A., Eubanks, S. R., Towery, D. S., Adams, S. P. & Glaser, L. "Amino-terminal processing of proteins by N-myristoylation," Substrate specificity of N-myristoyl transferase. J. Biol. Chem. 262, 1030-1036 (Jan. 1987).
Uto, K., Tsui, J. H., DeForest, C. A. & Kim, D.-H. "Dynamically tunable cell culture platforms for tissue engineering and mechanobiology," Prog. Polym. Sci. (Feb. 2017). doi:10.1016/j.progpolymsci. 2016.09.004.
Utsumi, T. et al. "Amino Acid Residue Penultimate to the Amino-terminal Gly Residue Strongly Affects Two Cotranslational Protein Modifications, N-Myristoylation and N-Acetylation," J. Biol. Chem. 276, 10505-10513 (Dec. 2000).
Van Valkenburgh, H. & Kahn, R. "Coexpression of Proteins with Methionine Aminopeptidase and/or N-Myristoyltransferase in *Escherichia coli* to Increase Acylation Homogeneity of Protein Preparations," Methods in enzymology 344, (2002) pp. 186-193.
Wagner, K., M. J. Kwakkenbos, Y. B. Claassen, K. Maijoor, M. Böhne, K. F. van der Sluijs, M. D. Witte, D. J. van Zoelen, L. A. Cornelissen, T. Beaumont, A. Q. Bakker, H. L. Ploegh, H. Spits, "Bispecific antibody generated with sortase and click chemistry has broad antiinfluenza virus activity," Proc. Natl. Acad. Sci. USA, Nov. 2014, 111, pp. 16820-16825.
Wang, H. et al. "LOVTRAP: an optogenetic system for photo-induced protein dissociation," Nat. Methods 13, 755-758 (Sep. 2016).
Wang, Shao-Chun, and C. Ted Lee. "Protein secondary structure controlled with light and photoresponsive surfactants" The Journal of Physical Chemistry, Jul. 2006, vol. 110, Issue 32 pp. 16117-16123.
Warden-Rothman, R., I. Caturegli, V. Popik, A. Tsourkas, "Sortase-Tag Expressed Protein Ligation: Combining Protein Purification and Site-Specific Bioconjugation into a Single Step," Anal. Chem., Oct. 2013, 85, pp. 11090-11097.
Wells, R.G., "The Role of Matrix Stiffness in Regulating Cell Behavior," Hepatology, Apr. 2008, 47, pp. 1394-1400.
Wong, D. Y., Ranganath, T. & Kasko, A. M. "Low-Dose, Long-Wave UV Light Does Not Affect Gene Expression of Human Mesenchymal Stem Cells," PLoS One 10, e0139307 (Sep. 2015).
Wu, X., W. Huang, W. H. Wu, B. Xue, D. Xiang, Y. Li, M. Qin, F. Sun, W. Wang, W. Bin Zhang, Y. Cao, "Reversible hydrogels with tunable mechanical properties for optically controlling cell migration," Nano Res. 2018, 11, http://doi.org/10.1007/s12274-017-1890-y, pp. 5556-5565.
Wylie, R. G., Ahsan, S., Aizawa, Y., Maxwell, K. L., Morshead, C. M. & Shoichet, M. S. "Spatially controlled simultaneous patterning of multiple growth factors in three-dimensional hydrogels," Nat. Mater. 10, 799-806 (Aug. 2011).
Yang, C., Tibbitt, M. W., Basta, L. & Anseth, K. S. "Mechanical memory and dosing influence stem cell fate," Nat. Mater. 13, 645-652 (Mar. 2014).
Young, J. L. & Engler, A. J. "Hydrogels with time-dependent material properties enhance cardiomyocyte differentiation in vitro," Biomaterials 32, 1002-1009 (Nov. 2011).
Yuan, W., J. Yang, P. Kopečková, J. Kopeček, "Smart Hydrogels Containing Adenylate Kinase: Translating Substrate Recognition into Macroscopic Motion," J. Am. Chem. Soc., Nov. 2008, 130, pp. 15760-15761.
Zha, J., Weiler, S., Oh, K. J., Wei, M. C. & Korsmeyer, S. J. "Posttranslational N-myristoylation of BID as a molecular switch for targeting mitochondria and apoptosis," Science 290, 1761-1765 (Dec. 2000).

(56) References Cited

OTHER PUBLICATIONS

Zhang, H., Williams, P. S., Zborowski, M. & Chalmers, J. J. "Binding affinities/avidities of antibody-antigen interactions Quantification and scale-up implications," Biotechnol. Bioeng. 95, 812-829 (Aug. 2006).
Zhang, W. et al. "Optogenetic control with a photocleavable protein, PhoCl," Nat. Methods 14, 391-394 (Apr. 2017).
Zhang, Y. S. & Khademhosseini, A. "Advances in engineering hydrogels," Science 356, (May 2017), 12 pages.
Zhao, Y., S. Araki, J. Wu, T. Teramoto, Y.-F. Chang, M. Nakano, A. S. Abdelfattah, M. Fujiwara, T. Ishihara, T. Nagai, R. E. Campbell, "An Expanded Palette of Genetically Encoded Ca2+ Indicators," Science, Sep. 2011, 333, pp. 1888-1891.
Zhong, M., Wang, R., Kawamoto, K., Olsen, B. D. & Johnson, J. A. "Quantifying the impact of molecular defects on polymer network elasticity," Science. 353, pp. 1264-1268 (Sep. 2016).
Zhou, X., C. Li, Y. Shao, C. Chen, Z. Yang, D. Liu, "Reversibly tuning the mechanical properties of a DNA hydrogel by a DNA nanomotor," Chem. Commun., Jul. 2016, 52, pp. 10668-10671.
Heintz, U. et al. "Blue light-induced LOV domain dimerization enhances the affinity of Aureochrome 1a for its target DNA sequence," Elife 5, e11860 (Jan. 2016).
Heuckeroth, R. O. et al. "Novel fatty acyl subsliates for myristoyl-CoA:protein N-myristoyl-transferase," J. Lipid Res. 31, 1121-1129 (1990).
Hinz, B., S. H. Phan, V. J. Thannickal, A. Galli, M.-L. Bochaton-Piallat, G. Gabbiani, "Biological Perspectives," Am. J. Pathol. Jun. 2007, 170, 1807.
Hoi, H. et al. "A Monomeric Photoconvertible Fluorescent Protein for Imaging of Dynamic Protein Localization," J. Mol. Biol. 401, 776-791 (Jul. 2010).
Humphrey, J.D., E. R. Dufresne, M. A. Schwartz, "Mechotransduction and extracellular matrix homeostasis," Nat. Rev. Mol. Cell Biol. Dec. 2014, 15, 802.
Ingber, D. E. "Cellular mechanotransduction: putting all the pieces together again," Faseb J. 20, 811-827 (2006).
Kanisicak, O., H. Khalil, M. J. Ivey, J. Karch, B. D. Maliken, R. N. Correll, M. J. Brody, S.-C. J Lin, B. J. Aronow, M. D. Tallquist, J. D., "Genetic lineage tracing defines myofibroblast origin and function in the injured heart," Molkentin, Nat. Commun., Jul. 2016, 7, 12260, pp. 1-14.
Katritch, V., Cherezov, V. & Stevens, R. C. "Structure-Function of the G Protein-Coupled Receptor Superfamily," Annu. Rev. Pharmacol. Toxicol. 53, 531-556 (Nov. 2012).
Khetan, S. & Burdick, J. A. "Patterning network structure to spatially control cellular remodeling and stem cell fate within 3-dimensional hydrogels," Biomaterials 31, 8228-8234 (Jul. 2010).
Khetan, S. et al. "Degradation-mediated cellular traction directs stem cell fate in covalently crosslinked three-dimensional hydrogels," Nat Mater 12, 458-465 (Nov. 2013).
Khetan, S., Katz, J. S. & Burdick, J. A. "Sequential crosslinking to control cellular spreading in 3-dimensional hydrogels," Soft Matter 5, 1601-1606 (Feb. 2009).
Kim, J., R. C. Hayward, "Mimicking dynamic in vivo environments with stimuli-responsive materials for cell culture," Trends Biotechnol. Aug. 2012, 30, 426.
Kishore, N. S. et al. "The substrate specificity of *Saccharomyces cerevisiae* myristoyl-CoA: protein N-myristoyltransferase," J. Biol. Chem. 266, 8835-55 (May 1991).
Kloxin, A. M., Kasko, A. M., Salinas, C. N. & Anseth, K. S. "Photodegradable Hydrogels for Dynamic Tuning of Physical and Chemical Properties," Science (80-.). 324, 59-63 (Apr. 2009).
Kloxin, A. M., Tibbitt, M. W. & Anseth, K. S. "Synthesis of photodegradable hydrogels as dynamically tunable cell culture platforms," Nat. Protoc. 5, 1867 (Nov. 2010).
Komatsu, N., Aoki, K., Yamada, M., Yukinaga, H., Fujita, Y., Kamioka, Y. & Matsuda, M. "Development of an optimized backbone of FRET biosensors for kinases and GTPases," Mol. Biol. Cell 22, 4647-56 (Dec. 2011).

Kong, N., Q. Peng, H. Li, Adv. "Rationally Designed Dynamic Protein Hydrogels with Reversibly Tunable Mechanical Properties," Advanced Functional Materials, 2014, 24, 7310-7317.
Krauss, Ulrich, Thomas Drepper, and Karl-Erich Jaeger. "Enlightened enzymes: strategies to create novel photoresponsive proteins" Chemistry Feb. 25, 2011;17(9): 2552-2560.
Kredel, S. et al. "mRuby, a Bright Monomeric Red Fluorescent Protein for Labeling of Subcellular Structures," PLoS One 4, e4391 (Feb. 2009).
Kuhl, P. R. & Griffith-Cima, L. G. "Tethered epidermal growth factor as a paradigm for growth factor-induced stimulation from the solid phase," Nat. Med. 2, 1022-1027 (Sep. 1996).
Kulkarni, C., Kinzer-Ursem, T. L. & Tirrell, D. A. "Selective Functionalization of the Protein N Terminus with N-Myristoyl Transferase for Bioconjugation in Cell Lysate," ChemBioChem 14, 1958-1962 (2013).
Kulkarni, C., Lo, M., Fraseur, J. G., Tirrell, D. A. & Kinzer-Ursem, T. L. "Bioorthogonal Chemoenzymatic Functionalization of Calmodulin for Bioconjugation Applications," Bioconjug. Chem. 26, 2153-60 (Oct. 2015).
Langer, R. & Tirrell, D. A. "Designing materials for biology and medicine," Nature 428, 487-492 (Apr. 2004).
Langer, R. & Vacanti, J. P. "Tissue Engineering," Science 260, 920-926 (May 1993).
Lee, K. Y. & Mooney, D. J. "Hydrogels for tissue engineering," Chem. Rev. 101, 1869-1879 (Jul. 2001).
Levskaya, A., Weiner, O. D., Lim, W. A. & Voigt, C. A. "Spatiotemporal Control of Cell Signalling Using a Light-Switchable Protein Interaction," Nature 461, 997-1001 (Oct. 2009).
Lin, D.C., B. Yurke, N. A. Langrana, "Inducing reversible stiffness changes in DNA-crosslinked gels," J. Mater. Res. Jun. 2005, 20, 1456.
Lippincott-Schwartz, J., Snapp, E. & Kenworthy, A. "Studying protein dynamics in living cells," Nat. Rev. Mol. Cell Biol. 2, 444 (Jun. 2001).
Liu, C. C. & Schultz, P. G. "Adding new chemistries to the genetic code," Annu. Rev. Biochem. 79, 413-444 (Mar. 2010).
Liu, D. R. & Schultz, P. G. "Progress toward the evolution of an organism with an expanded genetic code," Proc. Natl. Acad. Sci. U. S. A. 96, 4780-4785 (Mar. 1999).
Liu, L., Shadish, J.A., Arakawa, C.K., Shi, K., Davis, J. & DeForest, C.A. "Cyclic Stiffness Modulation of Cell-Laden Protein-Polymer Hydrogels in Response to User-Specified Stimuli including Light," Advanced Biosystems, 2, 1800240 (Dec. 2018).
Luo, Y. & Shoichet, M. S. "A photolabile hydrogel for guided three-dimensional cell growth and migration," Nat. Mater. 3, 249-253 (Mar. 2004).
Lutolf, M. P. & Hubbell, J. A. "Synthetic biomaterials as instructive extracellular microenvironments for morphogenesis in tissue engineering," Nat. Biotechnol. 23, 47-55 (Jan. 2005).
Lutolf, M. P., Gilbert, P. M. & Blau, H. M. "Designing materials to direct stem-cell fate," Nature 462, 433-441 (Nov. 2009).
Mao, H., Hart, S. A., Schink, A. & Pollok, B. A. "Sortase-mediated protein ligation: a new method for protein engineering," J. Am. Chem. Soc. 126, 2670-1 (Feb. 2004).
Martens, P., Holland, T. & Anseth, K. S. "Synthesis and characterization of degradable hydrogels formed from acrylate modified poly(vinyl alcohol) macromers," Polymer. 43, 6093-6100 (Aug. 2002).
Matz, M. V et al. "Fluorescent proteins from nonbioluminescent *Anthozoa* species," Nat. Biotechnol. 17, 969 (Oct. 1999).
Maurer-Stroh, S. & Eisenhaber, F. "Myristoylation of viral and bacterial proteins," Trends in Microbiology 12, 178-185 (Apr. 2004).
Mazmanian, S. K., Liu, G., Hung, T. T. & Schneewind, O. "*Staphylococcus aureus* sortase, an enzyme that anchors surface proteins to the cell wall," Science 285, 760-763 (Jul. 1999).
McEvoy, A. L. et al. "mMaple: A Photoconvertible Fluorescent Protein for Use in Multiple Imaging Modalities," PLoS One 7, e51314 (Dec. 2012).
Miyawaki, A., J. Llopis, R. Heim, J. M. McCaffery, J. A. Adams, M. Ikura, R. Y. Tsien, "Fluorescent indicators for Ca2+ based on green fluorescent proteins and calmodulin," Nature Aug. 1997, 388, 882.

(56) References Cited

OTHER PUBLICATIONS

Möglich, A. & Moffat, K. "Engineered photoreceptors as novel optogenetic tools," Photochem. Photobiol. Sci. 9, 1286 (Jun. 2010).
Molkentin, J.D., D. Bugg, N. Ghearing, L. E. Dorn, P. Kim, M. A. Sargent, J. Gunaje, K. Otsu, J. Davis, "Fibroblast-Specific Genetic Manipulation of p38 Mitogen-Activated Protein Kinase In Vivo Reveals Its Central Regulatory Role in Fibrosis," Circulation, Aug. 2017, 136, 549.
Mosiewicz, K. A., Kolb, L., Van Der Vlies, A. J. & Lutolf, M. P. "Microscale patterning of hydrogel stiffness through light-triggered uncaging of thiols," Biomater Sci 2, 1640-1651 (Jul. 2014).
Mosiewicz, K. A., Kolb, L., van der Vlies, A. J., Martino, M. M., Lienemann, P. S., Hubbell, J. A., Ehrbar, M., Lutolf, M. P. "In situ cell manipulation through enzymatic hydrogel photopatterning," Nat. Mater. 12, 1072-1078 (Nov. 2013).
Motta-Mena, L. B. et al. "An optogenetic gene expression system with rapid activation and deactivation kinetics," Nat. Chem. Biol. 10, 196-202 (Mar. 2014).
Murphy, W. L., Dillmore, W. S., Modica, J. & Mrksich, M. "Dynamic hydrogels: Translating a protein conformational change into macroscopic motion," Angew. Chemie—Int. Ed. 46, 3066-3069 (2007).
Nakai, J., M. Ohkura, K. Imoto, "A high signal-to-noise Ca2+ probe composed of a single green fluorescent protein," Nat. Biotechnol. Feb. 2001, 19, 137.
Odian, G. "Principles of Polymerization," Fourth Edition (Wiley-Interscience, 2004).
Pastrana, E. "Optogenetics: controlling cell function with light," Nat. Methods 8, 24-25 (Jan. 2011).
Ai, H., Henderson, J. N., Remington, S. J. & Campbell, R. E. "Directed evolution of a monomeric, bright and photostable version of Clavularia cyan fluorescent protein: structural characterization and applications in fluorescence imaging," Biochem. J. 400, 531-540 (2006).
Alexandre, M.T.A., et al., "Conformational Heterogeneity and Propagation of Structural Changes in the LOV2/Jα Domain from Avena sativa Phototropin 1 as Recorded by Temperature-Dependent FTIR Spectroscopy," Biophys. J. 97, 238-247 (Jul. 2009).
Badeau, B.A., M. P. Comerford, C. K. Arakawa, J. A. Shadish, C. A. DeForest, "Engineered modular biomaterial logic gates for environmentally triggered therapeutic delivery," Nat. Chem. Mar. 2018, 10, pp. 251-258.
Baker, B. M. & Chen, C. S. "Deconstructing the third dimension—how 3D culture microenvironments alter cellular cues," J. Cell Sci. 125, (2012), pp. 3015-3024.
Baslé, E., Joubert, N. & Pucheault, M. "Protein Chemical Modification on Endogenous Amino Acids," Chem. Biol. 17, 213-227 (Mar. 2010).
Berman, H. M. et al. "The Protein Data Bank," Oxford University Press, Nucleic Acids Res. 28, 235-242 (2000).
Bieniarz, C., Young, D. F. & Cornwell, M. J. "Chromogenic redox assay for beta-lactamases yielding water-insoluble products, I. Kinetic behavior and redox chemistry," Anal. Biochem. 207, 321-328 (May 1992).
Boutin, J. A. "Myristoylation," Cell Signal 9, 15-35 (1997).
Boutureira, O., G. J. L. Bernardes, "Advances in Chemical Protein Modification," Chem. Rev. 2015, 115, 2174-2195.
Bryant, S. J., Nuttelman, C. R. & Anseth, K. S. "Cytocompatibility of UV and visible light photoinitiating systems on cultured NIH/3T3 fibroblasts in vitro," J. Biomater. Sci. Polym. Ed. 11, 439-457 (2000).
Burdick, J. A. & Murphy, W. L. "Moving from static to dynamic complexity in hydrogel design," Nat. Commun. 3, 1269 (Dec. 2012).
Cai, C., L. Ren, H. Zhao, C. Xu, L. Zhang, Y. Yu, H. Wang, Y. Lan, M. F. Roberts, J. Chuang, M. J. Naughton, Z. Ren, T. C. Chiles, "A molecular imprint nanosensor for ultrasensitive detection of proteins," Nat. Nanotechnol. Aug. 2010, 5, pp. 597-601.
Caliari, S. R. & Burdick, J. A. "A practical guide to hydrogels for cell culture," Nat. Methods 13, 405-414 (May 2016).

Carrico, I. S., Carlson, B. L. & Bertozzi, C. R. "Introducing genetically encoded aldehydes into proteins," Nat. Chem. Biol. 3, 321-322 (Jun. 2007).
Chen, C. S., Mrksich, M., Huang, S., Whitesides, G. M. & Ingber, D. E. "Geometric control of cell life and death," Science. 276, 1425-1428 (May 1997).
Chen, I., Howarth, M., Lin, W. & Ting, A. Y. "Site-specific labeling of cell surface proteins with biophysical probes using biotin ligase," Nat. Methods 2, 99-104 (Feb. 2005).
Cheong, W. F., Prahl, S. A. & Welch, A. J. "A review of the optical properties of biological tissues," IEEE J. Quantum Electron. 26, 2166-2185 (Dec. 1990).
Christie, J. M. "Phototropin Blue-Light Receptors," Annu. Rev. Plant Biol. 58, 21-45 (Oct. 2006).
Clapham, "Calcuim Signaling" D.E., Cell, Dec. 2007, 131, 1047.
Cushing, M. C. & Anseth, K. S. "Hydrogel cell cultures," Science 316, 1133-1134 (May 2007).
Davis, J., A. R. Burr, G. F. Davis, L. Birnbaumer, J. D. Molkentin, "A TRPC6-Dependent Pathway for Myofibroblast Transdifferentiation and Wound Healing in Vivo," Dev. Cell, Oct. 2012, 23, 705-715.
Davis, J., N. Salomonis, N. Ghearing, S.-C. J. Lin, J. Q. Kwong, A. Mohan, M. S. Swanson, J. D. Molkentin, "MBNL1-mediated regulation of differentiation RNAs promotes myofibroblast transformation and the fibrotic response," Nat. Commun. Dec. 2015, 6, 10084, pp. 1-14.
DeForest, C. A. & Anseth, K. S. "Advances in Bioactive Hydrogels to Probe and Direct Cell Fate," Annu. Rev. Chem. Biomol. Eng. 3, 421-444 (Apr. 2012).
DeForest, C. A. & Anseth, K. S. "Cytocompatible click-based hydrogels with dynamically tunable properties through orthogonal photoconjugation and photocleavage reactions," Nat. Chem. 3, 925-931 (Oct. 2011).
DeForest, C. A. & Anseth, K. S. "Photoreversible patterning of biomolecules within click-based hydrogels," Angew. Chem. Int. Ed. 51, 1816-1819 (2012).
DeForest, C. A. & Tirrell, D. A. "A photoreversible protein-patterning approach for guiding stem cell fate in three-dimensional gels," Nat. Mater. 14, 523-531 (Feb. 2015).
DeForest, C. A., Polizzotti, B. D. & Anseth, K. S. "Sequential click reactions for synthesizing and patterning three-dimensional cell microenvironments," Nat. Mater. 8, 659-664 (Jun. 2009).
DeForest, C. A., Sims, E. A. & Anseth, K. S. "Peptide-functionalized click hydrogels with independently tunable mechanics and chemical functionality for 3D cell culture," Chem. Mater. 22, 4783-4790 (May 2010).
Devadas, B. et al. "Subsliate-Specificity of *Saccharomyces cerevisiae* Myristoyl-Coa:Protein N-Myristoyltransferase—Analysis of Fatty-Acid Analogs Containing Carbonyl Groups, Nitrogen Heteroatoms, and Nitrogen-Heterocycles in an in vitro Enzyme Assay and Subsequent Identification of Inhibitors of Human Immunodeficiency Virus I Replication," J. Biol. Chem. 267, 7224-7239 (Apr. 1992).
Discher, D. E., Mooney, D. J. & Zandstra, P. W. "Growth factors, matrices, and forces combine and control stem cells," Science 324, 1673-1677 (Jun. 2009).
Dolmans, D. E. J. G. J., Fukumura, D. & Jain, R. K. Timeline: "Photodynamic therapy for cancer," Nat. Rev. Cancer 3, 380-387 (May 2003).
Dooling, L. J., Buck, M. E., Zhang, W.-B. & Tirrell, D. A. "Programming Molecular Association and Viscoelastic Behavior in Protein Networks," Adv. Mater. 28, 4651-4657 (2016).
Dufort, C.C., M. J. Paszek, V. M. Weaver, "Balanding forces: architectural control of mechanotransduction," Nat. Rev. Mol. Cell Biol. May 2011, 12, pp. 308-319.
Ehrick, J.D., S. K. Deo, T. W. Browning, L. G. Bachas, M. J. Madou, S. Daunert, "Genetically engineered protein in hydrogels tailors stimuli-responsive characteristics," Nat. Mater. Mar. 2005, 4, 298.
Engler, A. J., Sen, S., Sweeney, H. L. & Discher, D. E. "Matrix elasticity directs stem cell lineage specification," Cell 126, 677-689 (Aug. 2006).
Erlanger, B.F., "Photoregulation of biologically active macromolecules," Annual review of biochemistry, 45(1), pp. 267-284 (1976).

(56) References Cited

OTHER PUBLICATIONS

Fan, V. H., Au, A., Tamama, K., Littrell, R., Richardson, L. B., Wright, J. W., Wells, A. & Griffith, L. G. "Tethered Epidermal Growth Factor Provides a Survival Advantage to Mesenchymal Stem Cells," Stem Cells 25, 1241-1251 (Jan. 2007).

Farahani, P. E., Adelmund, S. M., Shadish, J. A. & DeForest, C. A. "Photomediated Oxime Ligation as a Bioorthogonal Tool for Spatiotemporally-Controlled Hydrogel Formation and Modification," J. Mater. Chem. B 5, 4435-4442 (Mar. 2017).

Farazi, T. A., Waksman, G. & Gordon, J. I. "The biology and enzymology of protein N-myristoylation," J. Biol. Chem. 276, 39501-4 (Oct. 2001).

Fenno, L., Yizhar, O. & Deisseroth, K. "The development and application of optogenetics," Annu. Rev. Neurosci. 34, 389-412 (2011).

Fisher, S. A., Baker, A. E. G. & Shoichet, M. S. "Designing Peptide and Protein Modified Hydrogels: Selecting the Optimal Conjugation Strategy," J. Am. Chem. Soc. 139, 7416-7427 (May 2017).

Flory, P.J., J. Rehner, "Statistical Mechanics of Cross-Linked Polymer Networks II. Swelling," J. Chem. Phys. Oct. 1943, 11, pp. 521-526.

Gilbert, P. M. et al. "Substrate Elasticity Regulates Skeletal Muscle Stem Cell Self-Renewal in Culture," Science. 329, 1078-1081 (Aug. 2010).

Gillette, B.M., J. A. Jensen, M. Wang, J. Tchao, S. K. Sia, "Dynamic Hydrogels: Switching of 3D Microenvironments Using To-Component Naturally Derived Extracellular Matrices," Adv. Mater. 2010, 22, 686-291.

Greenfield, N.J., "Using Circular Dichroism spectra to estimate protein secondary structure," Nat. Protoc. 2006, 1, 2876-2890.

Griffin, D. R., Borrajo, J., Soon, A., Acosta-Vélez, G. F., Oshita, V., Darling, N., Mack, J., Barker, T., Iruela-Arispe, M. L. & Segura, T. "Hybrid Photopatterned Enzymatic Reaction (HyPER) for in Situ Cell Manipulation," Chembiochem 15, 233-242 (Jan. 2014).

Guilak, F. et al. "Control of Stem Cell Fate by Physical Interactions with the Extracellular Matrix," Cell Stem Cell 5, 17-26 (Jul. 2009).

Guimaraes, C. P. et al. "Site-specific C-terminal and internal loop labeling of proteins using sortase-mediated reactions," Nat. Protoc. 8, 1787-1799 (Sep. 2013).

Hahn, M. S., Miller, J. S. & West, J. L. "Three-dimensional biochemical and biomechanical patterning of hydrogels for guiding cell behavior," Adv. Mater. 18, 2679-2684 (2006).

Heal, W. P., Wright, M. H., Thinon, E. & Tate, E. W. "Multifunctional protein labeling via enzymatic N-terminal tagging and elaboration by click chemistry," Nat. Protoc. 7, 105-117 (Dec. 2011).

\* cited by examiner

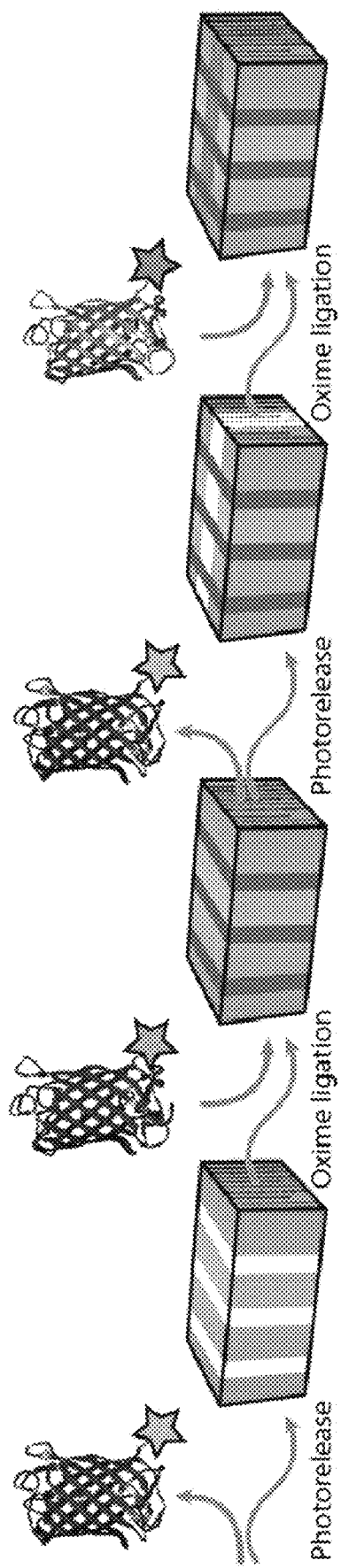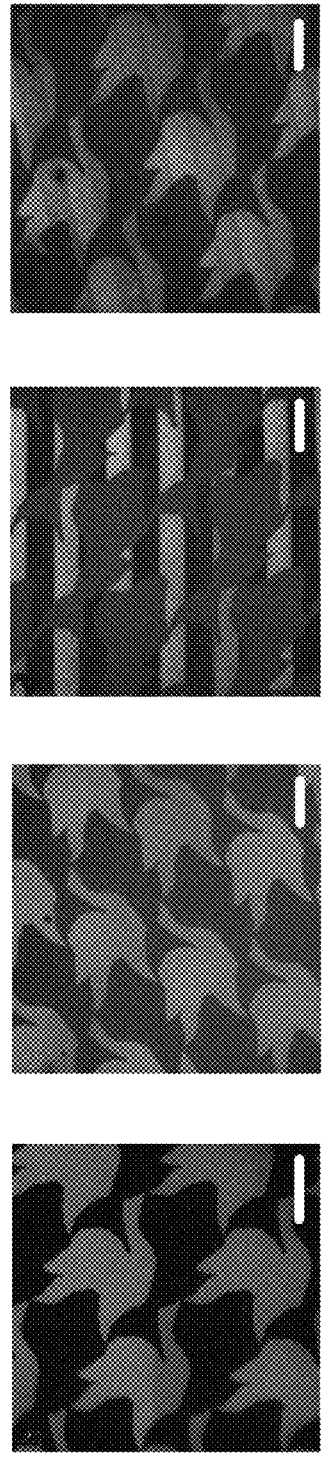
Fig.19A Fig.19B Fig.19C Fig.19D Fig.19E

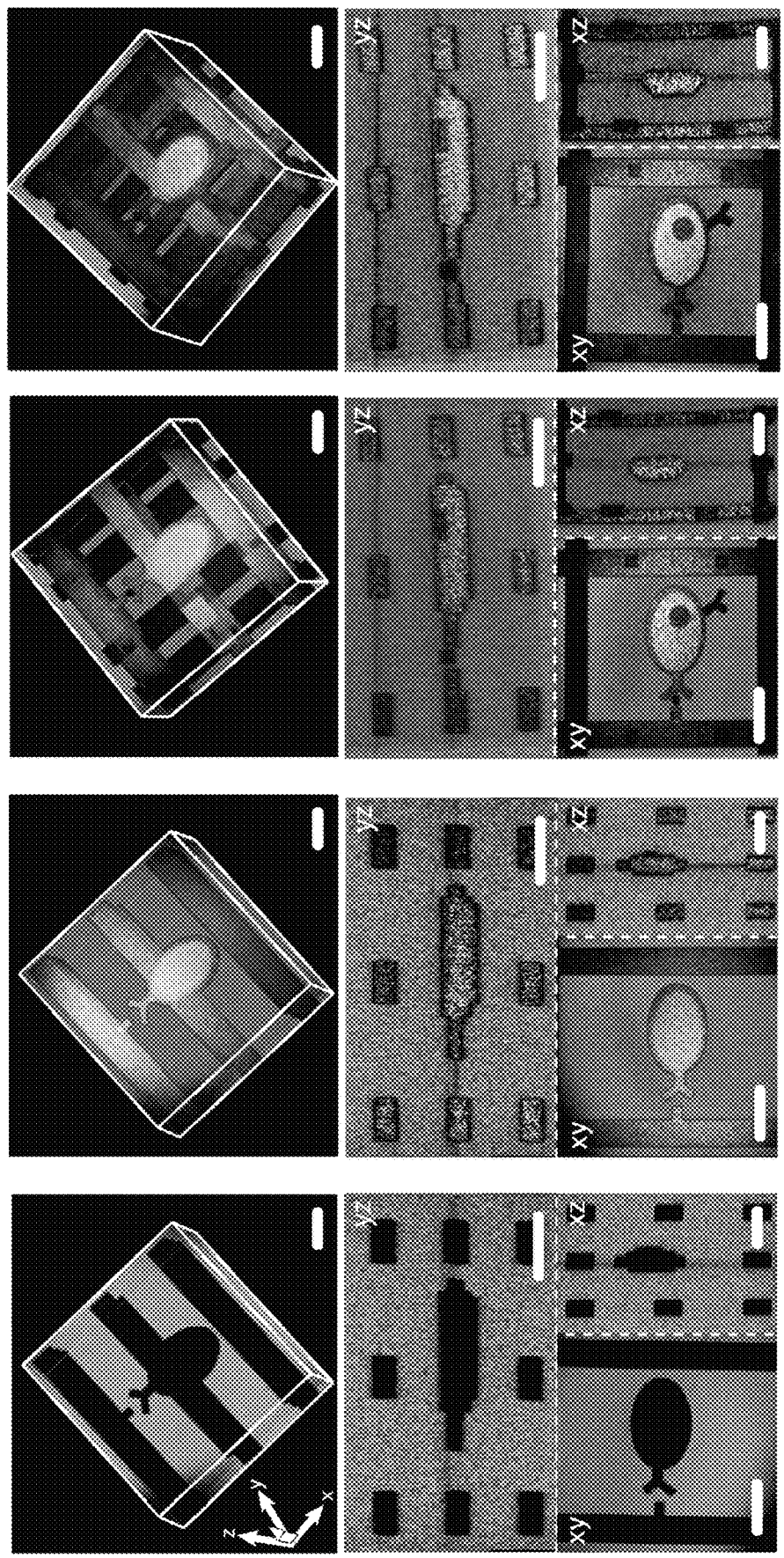

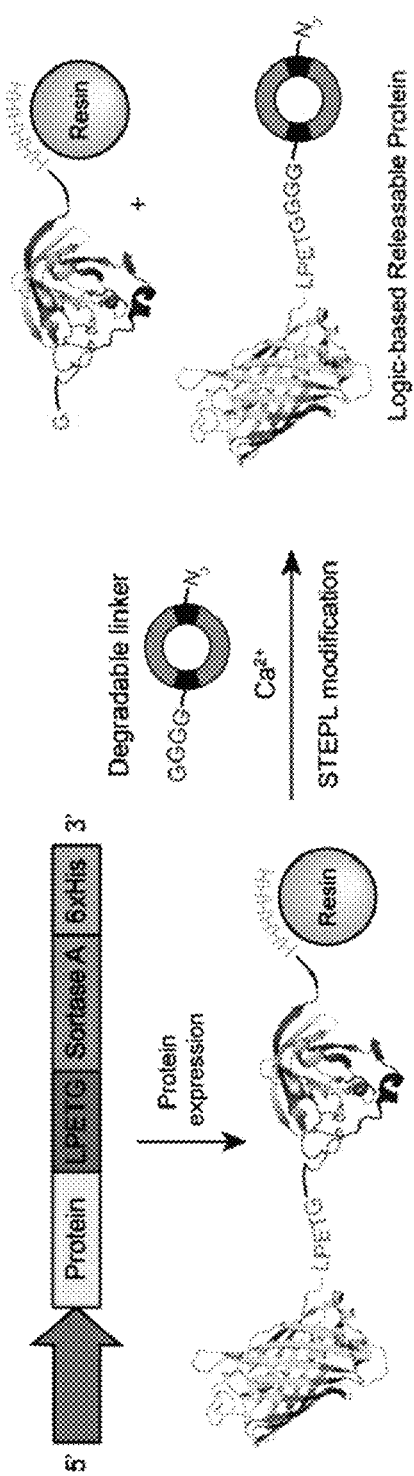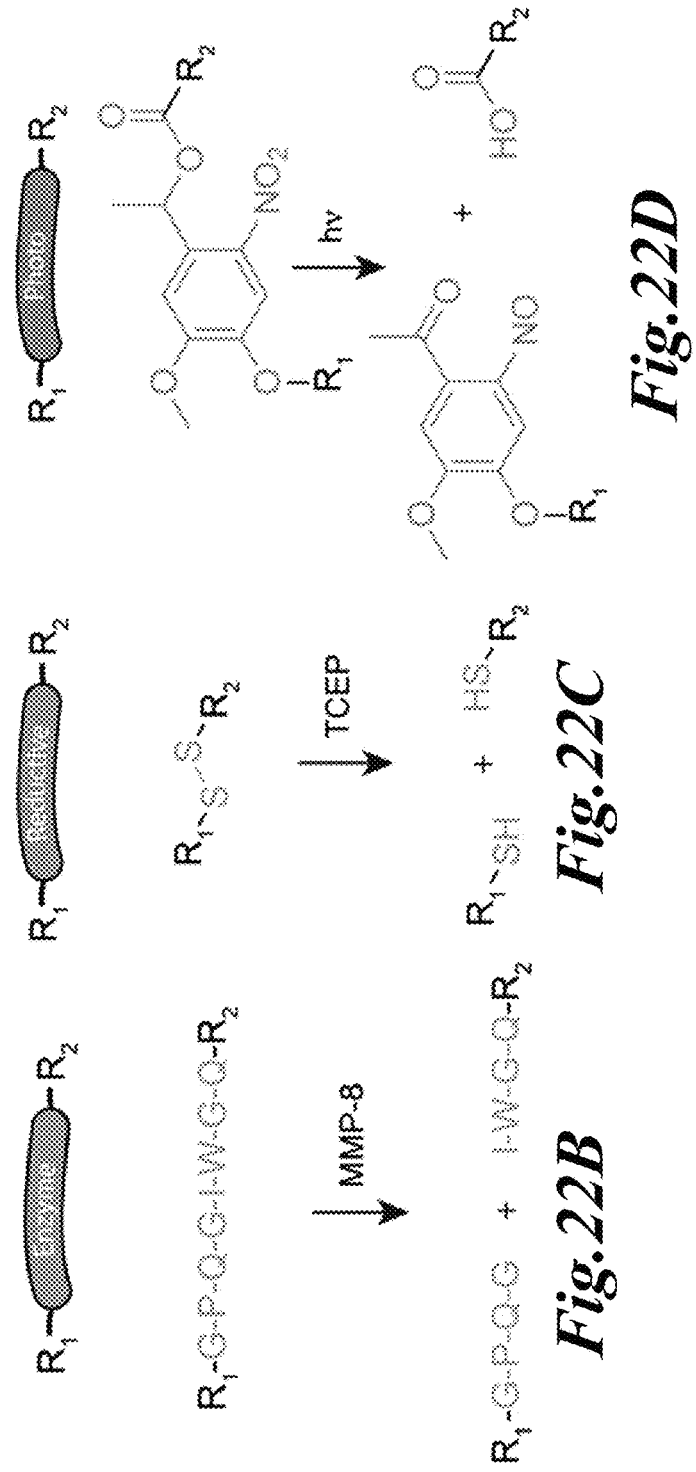
Fig. 22A  Fig. 22B  Fig. 22C  Fig. 22D

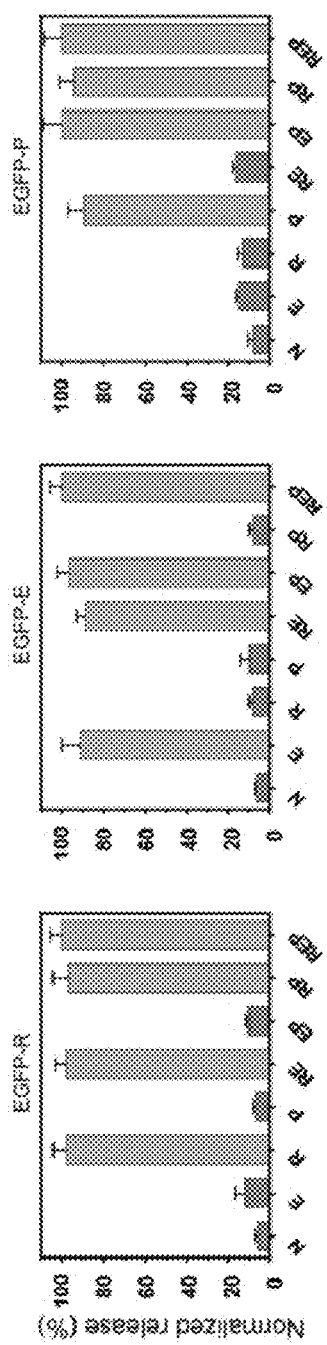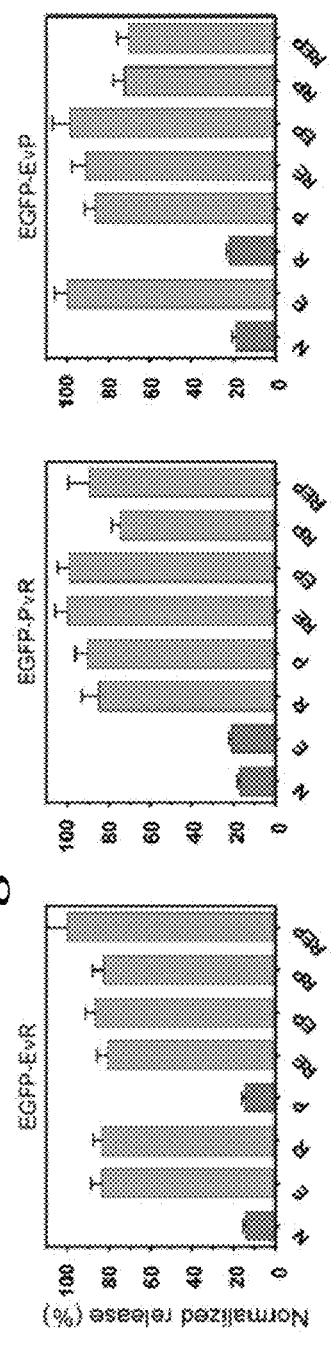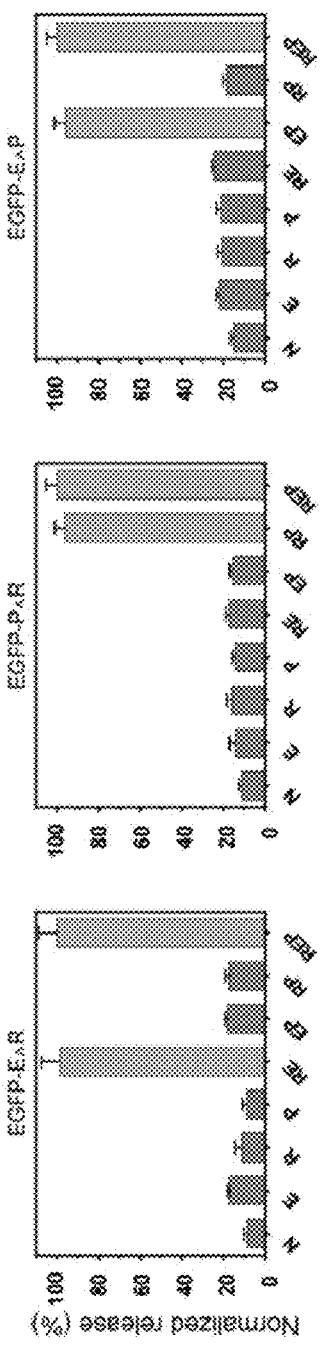
Fig.23A
Fig.23B
Fig.23C

DYNAMIC USER-PROGRAMMABLE MATERIALS INCLUDING STIMULI-RESPONSIVE PROTEINS

CROSS-REFERENCE TO RELATED APPLICATION

This application claims the benefit of U.S. Patent Application No. 62/664,859, filed Apr. 30, 2018, the disclosure of which is incorporated herein by reference in its entirety.

STATEMENT OF GOVERNMENT LICENSE RIGHTS

This invention was made with Government support under DMR 1652141 and DMR 1807398 awarded by the National Science Foundation. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 68596_Seq_Listing_Final_2019-04-30.txt. The text file is 33 KB; was created on Apr. 30, 2019; and is being submitted via EFS-Web with the filing of the specification.

BACKGROUND

In the biomaterials community, there is a growing appreciation for the large role that mechanical signals presented by the local extracellular matrix (ECM) have on cell fate. There is also significant interest in the controlled presentation of proteins from and within materials for many bioengineering applications. Each of these areas of interest is addressed below.

Through direct interaction with physical cues presented in the cellular ECM, external mechanical signals are translated into internal biochemical responses that govern gene expression and cell fate decisions. Findings in the field of cellular mechanotransduction have demonstrated that matrix stiffness alone can drive changes in essential processes including attachment, morphology, migration, proliferation, and differentiation. More recently, it has been observed that stem cells possess mechanical "memory", storing information about past physical culture conditions to influence future functions. These findings represent landmark observations that are rapidly changing standard practices in molecular biology and stem cell culture.

Efforts to elucidate the specific effects that ECM elasticity has on cell physiology have been performed almost exclusively on static biomaterial systems. While these studies have provided valuable insight into the critical roles in which ECM stiffness regulates cellular function and fate, such simple systems fail to recapitulate biophysical dynamics known to accompany tissue/organ development, regeneration, wound healing, and disease progression. Though constructs that undergo spontaneous or cell-mediated transitions have proven beneficial in several applications, those that can be modified on demand are critical for probing biophysical responses at well-defined times. Light-mediated material alteration has proven particularly beneficial in this regard as it uniquely grants near-instantaneous and spatiotemporal control over matrix stiffness in a potentially biocompatible manner. For example, material secondary photocrosslinking can provide one-way stiffening, while photodegradation can provide for irreversible softening, in the presence of live cells.

Beyond unidirectional elasticity changes, cells also experience cyclic loading that periodically and reversibly alter local ECM rigidity; pulsatile flow associated with the circulatory system places cyclic loads on cells virtually everywhere throughout the body (timescale of seconds), just as tissues exhibit sequential stiffening and softening during wound healing (days to weeks). Despite significant interest in understanding these fundamental biological processes, materials capable of recapitulating such dynamic and reversible stiffening remain undeveloped. For example, while several reversibly compliant biomaterials sensitive to a variety of stimuli have been reported, none have proven capable of examining changes in 3D cell response to cyclic moduli alteration, for example, owing to cytotoxic conditions required for material formulation/modification or by unavoidable interference in material modulation chemistries by non-specific interactions with cell culture media components. Moreover, though local heterogeneities guide cell fate anisotropically within tissues, spatial control over reversible stiffening in materials compatible with 3D cell culture has not been demonstrated.

To emulate dynamic ECM biochemical heterogeneity in vitro, significant effort has been dedicated towards the creation of an expansive library of chemical strategies for hydrogel alteration. Preliminary efforts in this regard have largely focused on the exploitation of photochemical techniques to pattern bioactive small molecules and peptides spatially within synthetic hydrogel culture systems. While such approaches have proven successful in directing relatively simple cellular functions (such as adhesion and spreading), the ability to regulate more complex and dynamic decisions of fate using full-length proteins remains of prime interest. Though proteins represent a powerful tool in the quest to govern cell physiology, their fragility necessitates that careful consideration be given to the chemistries employed as well as the precise site of protein modification for material tethering to ensure sustained stability and activity.

Installation of reactive groups onto proteins required for biomaterial decoration has been performed almost exclusively through non-specific reactions with thiols and primary amines on endogenous cysteine and lysine residues. As these amino acids are not uniquely present on native proteins, bioconjugation of this type occurs randomly and stochastically to yield a heterogeneous collection of differently modified species. Such uncontrolled functionalization often leads to protein unfolding, loss of activity, and supraphysiologic doses required to elicit cellular response. Coupled with batch-to-batch variability and ambiguous extents of modification, reproducibility problems dramatically hinder laboratory and clinical translation of these ill-defined samples.

As discussed above, the ECM directs cell function through a complex choreography of biomacromolecular interactions in a tissue-dependent manner. Far from static, this hierarchical milieu of biochemical and biophysical cues presented within the native cellular niche is both spatially complex and constantly changing. As these pericellular reconfigurations are vital for tissue morphogenesis, disease regulation, and healing, in vitro culture platforms that recapitulate such dynamic environmental phenomena would be invaluable for fundamental studies in cell biology, as well as in the engineering of functional human tissue.

As discussed above, controlled presentation of proteins from and within materials also is of significant interest for many bioengineering applications. Though "smart" platforms offer control over protein release in response to a single external cue, no strategy has been developed to trigger delivery in response to user-specified combinations of environmental inputs, nor to independently control the release of multiple species from a homogenous material.

Hydrogels are attractive vehicles for the controlled delivery of proteins due to their readily tunable physical and chemical properties including stiffness, geometry, chemical functionality, degradability, and mesh size. Despite gel-based platforms that swell or degrade in response to biologically relevant signals, which enable the simultaneous release of several proteins, strategies that permit independent triggered release of many species from a single material remain elusive. The ability to regulate release without sacrificing protein stability or bioactivity represents an open challenge within the biomaterials community.

Thus, there is a need for generalizable strategies to create homogeneous protein populations that can be used to modify a wide variety of biomaterial platforms while retaining native levels of bioactivity. There is also a need for strategies that permit independent triggered release of many species from a single material, and a need for the ability to regulate release without sacrificing protein stability or bioactivity in biomaterials. The present disclosure fulfils these needs and provides further advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a protein-polymer conjugate, including a multivalent polymer building block, a stimuli-responsive protein covalently conjugated to the multivalent polymer building block to provide a protein-polymer conjugate, wherein the protein undergoes a modification upon exposure to a predetermined stimulus, and the protein modification triggers a physical or chemical response in the protein-polymer conjugate.

In another aspect, the present disclosure features a method of mimicking a cellular environment, including (a) exposing a protein-polymer conjugate to a predetermined stimulus to provide a physical (e.g., mechanical) response in the protein-polymer conjugate; (b) withdrawing the stimulus to reverse the physical (e.g., mechanical) response in the protein-protein conjugate; and (c) repeating (a) and (b) one or more times to provide a cyclic reversible physical (e.g., mechanical) response in the protein-polymer conjugate, wherein the protein-polymer conjugate includes a multivalent polymer building block, and a stimuli-responsive protein covalently conjugated to the multivalent polymer building block.

In yet another aspect, the present disclosure features a method of delivering a therapeutic agent, including: exposing a protein-polymer conjugate to a predetermined stimulus to release a therapeutic agent from the protein-polymer conjugate; wherein the protein-polymer conjugate comprises a multivalent polymer building block, and a stimuli-responsive protein covalently conjugated to the multivalent polymer building block.

In yet a further aspect, the present disclosure features a method of controlling binding of a protein in a polymeric hydrogel, including, exposing a protein-polymer conjugate to a predetermined stimulus to decrease binding of the protein to the polymer in the protein-polymer conjugate; wherein the protein-polymer conjugate comprises a multivalent polymer building block, and a stimuli-responsive protein covalently conjugated to the multivalent polymer building block. In some embodiments, exposing a protein-polymer conjugate to a predetermined stimulus cleaves one or more covalent bonds of the protein to the polymer in the protein-polymer conjugate. The cleavage can be reversible, or irreversible. In some embodiments, exposing a protein-polymer conjugate to a predetermined stimulus increases binding of the protein to the polymer in the protein-polymer conjugate, and can form one or more covalent bonds between the protein and the polymer in the protein-polymer conjugate.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

FIG. 12A is a drawing a calcium-responsive fusion protein CaM-M13, where calmodulin (CaM) reversibly associates with fusion partner M13 in a calcium-dependent manner.

FIG. 12B shows a whole-protein mass spectrometry trace of end-functionalized $N_3$-CaM-M13-$N_3$, generated with high purity.

FIG. 12C is a far-UV circular dichroism trace showing that $N_3$-CaM-M13-$N_3$ undergoes stimuli-dependent conformational changes in the presence and absence of $Ca^{2+}$. Decreased ellipticity at 222 nm (denoted with an arrow) indicates increased α-helical content of the protein when $Ca^{2+}$ is bound.

FIG. 12D is a photograph of SDS-PAGE gel shift assay of $N_3$-CaM-M13-$N_3$ with a monofunctionalized methoxy-PEG-bicyclononyne, indicating that azides can be selectively and quantitatively introduced at both protein termini, and that installed azides remain active and accessible for SPAAC chemistry.

FIG. 12E is a graph showing the reaction of PEG-tetraBCN (2 mM), $N_3$—PEG-$N_3$ (2 mM), and $N_3$—CaM-M13-$N_3$ (2 mM), as monitored through dynamic time-sweep rheological analysis. The reaction provides robust hydrogels on a timescale that is appropriate for cell encapsulation.

FIG. 12F is a graph showing that a CaM-M13 hydrogels exhibit reversible swelling, as quantified by fractional mass change, in the presence and absence of $Ca^{2+}$. Total responsiveness scales with protein crosslinker content (0, 25, 50, 75 mol % $N_3$-CaM-M13-$N_3$, with the balance comprised of $N_3$-PEG-$N_3$).

FIG. 13A is a drawing of a light, oxygen, and voltage sensing domain 2 (LOV2) that undergoes reversible dissociation with the C-terminal Jα helix in response to blue light (λ=470 nm). This conformational change is reversed under dark conditions.

FIG. 13B is a graph showing that end-functionalized $N_3$-LOV2-Jα-$N_3$ is obtained in high purity, as indicated by whole-protein mass spectrometry.

FIG. 13C is a graph showing the dark recovery photokinetic analysis of $N_3$-LOV2-Jα-$N_3$ immediately following photomediated protein disassociation. Near-complete recovery is observed after 40 seconds, as indicated by curve similarity with "dark" samples never exposed to light.

FIG. 13D is a photograph of SDS-PAGE gel shift assays, showing that azides can be selectively and quantitatively installed to LOV2-Jα termini, as indicated by with a monofunctionalized methoxy-PEG-bicyclononyne. Bioorthogonal handles remain accessible and reactive via SPAAC.

FIG. 13E is a graph showing that LOV2-Jα hydrogel stiffness can be rapidly cycled with negligible material fatigue, shown here for hydrogels comprised of 50 mol % protein crosslinker.

FIG. 14A is a drawing showing that stiffness-patterned hydrogels are readily generated upon masked exposure to blue light (λ=470 nm). In the dark, these materials rapidly reset to a uniformly stiff hydrogel. The patterning process is repeatable and scalable. Photoreversible and spatiotemporal control over LOV2-Jα hydrogel mechanics.

FIG. 14B is a graph showing that LOV2-Jα hydrogels exhibit state-dependent color profiles; stiffer hydrogels appear yellow under ambient light, while softer substrates are visually clearer. Image analysis of hydrogel color following flood light exposure ($\lambda$=470 nm, 1 mW cm$^{-2}$, 30 s) reveals fast dark recovery. Yellow saturation of hydrogels over time is normalized between values preceding and immediately following light exposure (1 and 0, respectively).

FIG. 15A is a drawing depicting the transdifferentiation of fibroblasts into myofibroblasts in response to both chemical and physical stimulation.

FIG. 15B is a graph showing NIH/3T3s fibroblasts cultured within LOV2-Jα hydrogels, each exhibiting a different time-dependent stiffness profile. Dark culture gives stiffer hydrogels; continuous flood exposure ($\lambda$=470 nm, 1 mW cm$^{-2}$) yields comparatively soft hydrogels; and shuttered light exposure (1 min on, 4 min off) provides hydrogels with cycled compliance. In situ rheometric analysis was performed on cell-laden hydrogels with 50% LOV2-Jα crosslinker in culture media.

FIG. 15C is a graph showing results from a LIVE/DEAD staining at 48 h of cells encapsulated within LOV2-Jα hydrogels, where a predominantly viable population was present for all material treatment conditions.

FIG. 15D is a graph showing that fibroblast-to-myofibroblast transformation varies significantly with stiffness dynamics, as indicated by transcriptional activity analysis of NIH/3T3s transfected with an αSMA-luciferase and Postn-luciferase promoter plasmids.

FIG. 16A is a reaction scheme of Sortase-Tag Expressed Protein Ligation (STEPL), which allows for one-step protein biofunctionalization and purification of C-modified proteins for biomaterial decoration. Proteins appended with a genetically encoded sorting signal are expressed as a fusion with the sortase enzyme and a 6xHis tag. Following chromatographic isolation on Ni-NTA resin, intramolecular sortagging is promoted by the addition of calcium and a polyglycine probe, catalyzing peptide ligation to the protein of interest and simultaneous displacement from the 6xHis-functionalized sortase A. Final protein functionality is defined by polyglycine compound identity.

FIG. 16B shows 5 distinct polyglycine probes each with different reactive functional groups that allow for biomaterial decoration using STEPL: triglycine GGG, H-GGGGDDK(N$_3$)—NH$_2$ [SEQ ID No.: 3], H-GGGGDDK(CHO)—NH$_2$ [SEQ ID No.: 4], H-GGGGDDK(oNB—N$_3$)—NH$_2$ [SEQ ID No.: 5], H-GGGG-oNB-DDK(CHO)—NH$_2$ [SEQ ID No.: 6] (denoted respectively with A, B, C, D, and E stars).

FIG. 16C is a graph of whole-protein mass spectrometry of sortagged enhanced green fluorescent protein (EGFP), with the 5 distinct polyglycine probes shown in FIG. 16B, and indicating high sample purity and quantitative functionalization for all polyglycine probes.

FIG. 16D is a graph of whole-protein mass spectrometry of sortagged mCherry, with the 5 distinct polyglycine probes shown in FIG. 16B, and indicating high sample purity and quantitative functionalization for all polyglycine probes. Double peaks indicate incomplete N-terminal methionine excision common to mCherry expression.

FIG. 16E is a graph of whole-protein mass spectrometry of sortagged mCerulean, with the 5 distinct polyglycine probes shown in FIG. 16B, and indicating high sample purity and quantitative functionalization for all polyglycine probes.

FIG. 16F is a graph of whole-protein mass spectrometry of sortagged epidural growth factor (EGF), with the 5 distinct polyglycine probes shown in FIG. 16B, and indicating high sample purity and quantitative functionalization for all polyglycine probes.

FIG. 16G is a graph of whole-protein mass spectrometry of sortagged beta-lactamase (bla), with the 5 distinct polyglycine probes shown in FIG. 16B, and indicating high sample purity and quantitative functionalization for all polyglycine probes.

FIG. 16H is a graph of whole-protein mass spectrometry of sortagged fibroblast growth factor (FGF), with the 5 distinct polyglycine probes shown in FIG. 16B, and indicating high sample purity and quantitative functionalization for all polyglycine probes.

FIG. 17A is a graph comparing bioactivity for proteins azide-tagged by STEPL with H-GGGGDDK(N$_3$)—NH$_2$ [SEQ ID No.: 3] or by conventional NHS labeling with varying molar excesses of N$_3$—OSu (0, 10, 100, 1000×). EGFP fluorescence was used as a surrogate readout of its activity following protein modification.

FIG. 17O is a graph showing relative bioactivity of FGF sortagged with triglycine, H-GGGGDDK($N_3$)—$NH_2$ [SEQ ID No.: 3], H-GGGGDDK(CHO)—$NH_2$ [SEQ ID No.: 4] H-GGGGDDK(oNB—$N_3$)—$NH_2$ [SEQ ID No.: 5] and H-GGGG-oNB-DDK(CHO)—$NH_2$ [SEQ ID No.: 6] (denoted respectively with A, B, C, D, and E stars). * denotes conjugates with a statistically significant reduction in bioactivity ($p<0.05$), as compared to the unmodified species (unpaired two-tailed t-test, $p=1.3\times10^{-4}$ for mCherry-CHO, $p=3.5\times10^{-4}$ for mCherry-oNB—CHO, $p=3.2\times10^{-3}$ for bla-oNB—CHO). Error bars correspond to the standard deviation about the mean for biological replicate experiments ($n=3$ for studies involving fluorescent proteins, β-lactamase, and EGF; $n=4$ for MBP-FGF).

FIG. 18A is an illustration of photopatterned immobilization of sortagged proteins within hydrogels. Proteins modified site-specifically with aromatic aldehydes are immobilized within SPAAC-based hydrogels through photomediated oxime ligation.

FIG. 18B is an illustration of the reaction NPPOC-caged alkoxyamines distributed uniformly throughout hydrogels ($R_1$) undergo, specifically irreversible β-elimination upon mild UV light exposure ($\lambda=365$ nm or 740 nm). The deprotected alkoxyamines react with aldehyde-tagged proteins ($R_2$) to form stable oxime linkages.

FIG. 18C is a photograph a photopatterned hydrogel, where mask-based photolithography ($\lambda=365$ nm) was used to immobilize discrete patterns of EGFP-CHO throughout the hydrogel thickness. Representative individual hydrogels were imaged by fluorescence confocal microscopy.

FIGS. 18D and 18F are graphs showing exponential protein gradients generated in a dose-dependent manner, by exposing hydrogel surfaces to linear gradients of light exposure (created by covering samples with an opaque photomask moving at rates of 0.6, 1.2, 2.4 mm $min^{-1}$, 10 mW $cm^{-2}$, $\lambda=365$ nm). $C_0$ represents the highest possible protein concentration that can be immobilized (determined based on the 100 caged alkoxyamine included during hydrogel formulation). Immobilized protein concentrations are determined through fluorescence correlation. Solid curves are predicted by known NPPOC/oNB photocleavage kinetics. Data was derived from experiments involving single hydrogels for each gradient light condition. Representative individual hydrogels were imaged by fluorescence confocal microscopy.

FIG. 18E is an illustration of full 3D control over protein tethering within hydrogels achieved through multiphoton laser-scanning lithographic patterning ($\lambda=740$ nm). Inset corresponds to a maximum-intensity γ-projection. Representative individual hydrogels were imaged by fluorescence confocal microscopy.

FIG. 18G is an illustration of photopatterned release of sortagged proteins from hydrogels. Site-specifically modified proteins are released from SPAAC-based hydrogels through ortho-nitrobenzyl ester (oNB) photocleavage.

FIG. 18H shows the reaction of oNB moieties linking the sortagged proteins ($R_1$) and the hydrogel ($R_2$) that undergo rapid photoscission upon mild UV light exposure ($\lambda=365$ nm or 740 nm).

FIG. 18I is photograph of photopatterning of hydrogels, where mask-based photolithography ($\lambda=365$ nm) was used to dictate discrete patterns of protein release from hydrogels uniformly functionalized with mCherry-oNB—$N_3$. Representative individual hydrogels were imaged by fluorescence confocal microscopy.

FIGS. 18J and 18L are graphs showing that by exposing hydrogel surfaces to linear gradients of light exposure (created by covering samples with an opaque photomask moving at rates of 0.3, 0.6, 1.2 mm min$^{-1}$, 10 mW cm$^{-2}$, $\lambda=365$ nm), exponential protein gradients were generated in a dose-dependent manner. $C_0$ corresponds to the initial mCherry concentration included during hydrogel formulation (100 μM). Immobilized protein concentrations are determined through fluorescence correlation. Solid curves are predicted by known NPPOC/oNB photocleavage kinetics. Data was derived from experiments involving single hydrogels for each gradient light condition. Representative individual hydrogels were imaged by fluorescence confocal microscopy.

FIG. 18K is an illustration of full 3D control over protein release within hydrogels is achieved through multiphoton laser-scanning lithographic patterning ($\lambda=740$ nm).

FIGS. 19A-19I are related to the 4D photoevolution of hydrogel biomaterials patterned with multiple sortagged proteins.

FIG. 19A is relevant to the 4D photoevolution of hydrogel biomaterials patterned with multiple sortagged proteins. Protein photorelease can be performed in concert with photomediated ligation of an aldehyde-tagged protein to create complex interconnected biochemical patterns. Iteration of this process enables 4D evolution of protein patterns within hydrogels.

FIGS. 19B-19E are photographs of patterned hydrogels, where masked-based photolithographic techniques ($\lambda=365$ nm) were utilized to control sequential protein patterning in defined shapes extending throughout the hydrogel thickness.

FIG. 19B is a photograph showing that following directed exposure of hydrogels uniformly functionalized with mCherry-oNB—$N_3$, mCherry is released while uncaging sites for subsequent mCerulean-CHO immobilization by oxime ligation. Images were generated using fluorescence confocal microscopy on a single hydrogel throughout sequential patterning. Scale bars=100 μm.

FIG. 19C shows protein backfilling of the hydrogel in FIG. 19B with mCerulean-CHO. Images were generated using fluorescence confocal microscopy on a single gel throughout sequential patterning. Scale bars=100 μm.

FIG. 19D is a photograph showing that a second round of directed light exposure released additional mCherry while leaving mCerulean patterns intact. Images were generated using fluorescence confocal microscopy on a single hydrogel throughout sequential patterning. Scale bars=100 μm.

FIG. 19E shows immobilized EGFP-oNB—CHO in the uncaged alkoxyamine sites to create a trifunctional protein pattern. Images were generated using fluorescence confocal microscopy on a single hydrogel throughout sequential patterning. Scale bars=100 μm.

FIGS. 19F-19I are 3D renderings of the photoevolved materials, where gray channels in FIGS. 19B, 19C, and 19F represent minimum intensity projections and the pale gray in FIGS. 19G and 19H are maximum intensity projections, as well as xy, yz, and xz planar slices; showing the evolution of trifunctional protein patterns controlled in 3D space through multiphoton laser-scanning lithography ($\lambda=740$ nm).

FIG. 19F shows the photorelease of mCherry-oNB—$N_3$. Images were generated using fluorescence confocal microscopy on a single hydrogel throughout sequential patterning. Scale bars=100 μm.

FIG. 19G shows protein backfilling of the hydrogel in FIG. 19F with EGFP-oNB—CHO. Images were generated using fluorescence confocal microscopy on a single hydrogel throughout sequential patterning. Scale bars=100 μm.

FIG. 19H shows that further treatment of the hydrogel in FIG. 19G with pulsed laser light released both EGFP-oNB—CHO and mCherry-oNB—$N_3$ within user-specified hydrogel sub-volumes. Images were generated using fluorescence confocal microscopy on a single hydrogel throughout sequential patterning. Scale bars=100 μm.

FIG. 19I shows that anchoring sites for mCerulean-CHO immobilization are created in the hydrogel of FIG. 19H. Images were generated using fluorescence confocal microscopy on a single hydrogel throughout sequential patterning. Scale bars=100 μm.

FIG. 20A is a scheme that shows thioacetate cefalotin is hydrolyzed enzymatically by bla, eliminating proton and thiolate ions that reduce a water-soluble yellow phenazine into a green water-insoluble precipitate.

FIG. 20B is a photograph showing that in-solution treatment of thioacetate cefalotin (5 mM) and phenazine methosulfate (6.5 mM) with bla (30 μM) yields distinct color change and precipitate formation.

FIG. 20C is a photograph of a hydrogel containing photopatterned regions of immobilized bla, visualized by phase contrast microscopy upon treatment with thioacetate cefalotin and phenazine methosulfate. Insoluble precipitation was confined to bla-modified hydrogel subvolumes. Inset corresponds to an EGFP-modified hydrogel with the same tessellated protein pattern.

FIG. 20D is a micrograph of HeLa cells encapsulated in hydrogels and expressing EKAREV FRET reporter for MAPK signaling exhibit basal signaling. Color-coded FRET response normalized to basal MAPK activation is depicted, obtained from confocal z-slices. All experiments were conducted in triplicate (n=3) with similar results. Scale bars=250 μm.

FIG. 20E is a micrograph of HeLa cells encapsulated in hydrogels and showing that average intracellular MAPK activation increases ~2 fold when hydrogels are uniformly functionalized with EGF (12.5 nM). Color-coded FRET response normalized to basal MAPK activation is depicted, obtained from confocal z-slices. All experiments were conducted in triplicate (n=3) with similar results. Scale bars=250 μm.

FIG. 20F is a micrograph of HeLa cells encapsulated in hydrogels and showing that high MAPK activation persisted in EGF-patterned hydrogel regions, whereas no upregulation in MAPK levels is observed in unfunctionalized regions. Color-coded FRET response normalized to basal MAPK activation, obtained from confocal z-slices. All experiments were conducted in triplicate (n=3) with similar results. Scale bars=250 μm.

FIGS. 21A-21F are related to the modulation of cell fate with a photoreleasable sortagged fluorophore-growth factor chimeric protein.

FIG. 21A is a scheme of a patterned population-level control of A431 cell proliferation is achieved through stimulation with hydrogel-immobilized EGFP-EGF-oNB—N$_3$ in 2D culture. Protein photoremoval promotes dynamic cell redistribution. Key analytical timepoints are noted on the experimental timeline with circled numbers.

FIG. 21B are brightfield and fluorescent images highlighting cell response (1$^{st}$ and 3$^{rd}$ column) to patterned EGFP-EGF-oNB—N$_3$ (2$^{nd}$ column) at various experimental endpoints. Relative intensity profiles are given for EGFP (2$^{nd}$ column), nuclei (3$^{rd}$ column), and optical transmission (first column) across hydrogels perpendicular to photopatterned lines, with average values (dark lines) and standard deviations (light error bars) corresponding to data from three biological replicates (n=3). Brightfield insets depict full hydrogel (~0.5 cm in diameter). Images and analysis in condition ③ correspond to the hydrogel half whose protein was photoreleased on Day 3. Scale bar=200 µm FIG. 21C is an illustration of encapsulated cells that bind but cannot internalize hydrogel-tethered EGFP-EGF-oNB—N$_3$. Photoliberation of the soluble protein promotes canonical EGFR activation and associated membrane endocytosis.

FIG. 21D is a micrograph showing that EGFP-EGF protein release is confined to hydrogel subvolumes bisecting a single A431 cell in 3D culture. Endosome formation is visible in <5 minutes and concentrated in the regions of light exposure. Fluorescent images correspond to timepoints immediately preceding protein photorelease within a single hydrogel. Scale bar=10 µm.

FIG. 21E is a micrograph showing that EGFP-EGF protein release is confined to hydrogel subvolumes bisecting a single A431 cell in 3D culture. Endosome formation is visible in <5 minutes and concentrated in the regions of light exposure. Fluorescent images correspond to timepoints 5 minutes after protein photorelease within a single hydrogel. Scale bar=10 µm.

FIG. 21F is a micrograph showing that difference calculations between images pre- and post-release (FIGS. 21D and 21E, respectively) highlight local EGFP-EGF internalization. Scale bar=10 µm.

FIGS. 22A-22E are related to the synthesis and logic-based release of site-specifically modified proteins from hydrogels.

FIG. 22A is a scheme of a one-step purification/functionalization sortase-mediated transpeptidation reaction enables degradable polyglycine probes to be affixed to the C-termini of a protein of interest.

FIG. 22B is a scheme of the interaction of MMP and the proteolytically sensitive peptide sequence GPQGVIWGQ [SEQ ID No.: 7]

FIG. 22C is a scheme of the interaction of a reductant and disulfide bond

FIG. 22D is a scheme of the interaction of near-UV light and the oNB moiety.

FIG. 22E is a scheme showing multiple proteins tethered to a hydrogel through different logical linkers that are independently released when exposed to varying chemical environments. Use of a linker with a cyclic architecture can function as a logical AND gate, requiring two unique stimuli to trigger protein release.

FIGS. 23A-23C are related to logic-based EGFP variants that exhibit programmable protein release in response to environmentally presented inputs combinations. Each region of the Venn diagram corresponds to a unique combination of inputs and indicates whether the material is expected to degrade (colored) or remain intact (white). Protein is C-terminally linked to the hydrogel through linkers containing multiple stimuli-labile bonds. Plot titles correspond to the linker identity, with x-axis labels indicating treatment conditions (N is no treatment, E is MMP enzyme, R is a chemical reductant, P is UV light). Light gray bars signify conditions expected to result in protein release; dark gray bars indicate conditions expected not to yield protein release.

FIG. 23A is a schematic of the logic and response profiles of the YES-gated proteins.

FIG. 23B is a schematic of the logic and response profiles of the OR-gated proteins.

FIG. 23C is a schematic of the logic and response profiles of the AND-gated proteins.

FIG. 25A is a scheme of a hydrogel with homogenously tethered EGFP-R—N$_3$, mCherry-P—N$_3$, and mCerulean-E-N$_3$.

FIG. 25B is a bar graph of the release for each protein under every relevant environment. Colored bars (light gray=EGFP, dark gray=mCherry, black=mCerulean) indicate conditions expected to yield release while unshaded bars indicate conditions not expected to yield release.

DETAILED DESCRIPTION

Figure 1A:
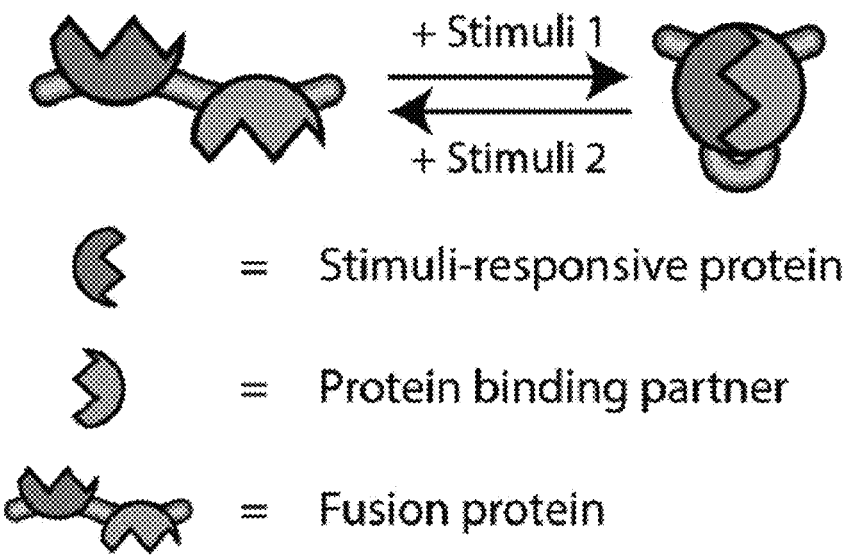
FIG. 1A is a drawing of a genetically-encoded fusion protein having a stimuli-responsive protein with its binding partner. The fusion protein exhibits conformation change and a change in end-to-end length in response to external stimuli.

The present disclosure features a protein-polymer conjugate, including a multivalent polymer building block, a stimuli-responsive protein covalently conjugated to the multivalent polymer building block to provide a protein-polymer conjugate, wherein the protein undergoes a modification upon exposure to a predetermined stimulus, and the protein modification triggers a physical and/or chemical response in the protein-polymer conjugate. The stimulus can be selectively applied in time and space, to provide the physical and/or chemical response in a controlled manner at a defined time, and at a defined location in the protein-polymer conjugate. Depending on the amount of stimulus exposure, the magnitude of the physical and/or chemical response can be modulated. In some embodiments, the physical response is a mechanical response. In some embodiments, the application of the stimulus is the removal of an environmental factor to which the protein-polymer conjugate is subjected to.

The protein-polymer conjugate can be a protein-polymer hydrogel. In some embodiments, the protein can have two or more reactive groups that can crosslink the multivalent polymer building blocks, where the protein crosslinker covalently binds two or more multivalent polymer blocks to one another to form a protein-polymer network. In some embodiments, the protein includes a synthetic peptide. In certain embodiments, the protein is a fusion protein, also known as a chimeric protein, where the protein is made through the joining of two or more genes that originally coded for separate proteins. Translation of this fusion gene results in a polypeptide with functional properties derived from each of the original proteins. The fusion protein can include peptide or protein subunits that bind to one another upon exposure or removal of a stimulus. The multivalent polymer building block has two or more reactive groups configured to react with the reactive groups on the stimuli-responsive protein. In some embodiments, the multivalent polymer building blocks include oligomeric building blocks, and can be linear, branched, a star polymer, and/or a dendritic polymer.

In some embodiments, the modification that the protein undergoes upon exposure to a predetermined stimulus is a conformational change. For example, in the case of a fusion protein, the conformational change can result from binding of a first protein subunit to a linked second protein subunit. In some embodiments, the conformational change can occur in a single protein that is not a fusion protein. The conformational change can be transferred to, amplified by, and/or transformed by the protein-polymer conjugate into a detectable characteristic. For example, the protein conformational change can result in a change, such as a change in the color, transmittance, absorbance, fluorescence, density, water content, crosslinking density, ligand density, ligand accessibility, geometry, or a mechanical change such as elastic modulus in the protein-polymer conjugate, in a spatio-temporally controlled manner depending on where and when the predetermined stimulus is applied to (or withdrawn from).

In some embodiments, the physical or chemical response in the protein-polymer conjugate is detectable using UV-Vis spectroscopy, fluorescence spectroscopy, nuclear magnetic resonance, mass spectrometry, and/or rheological methods. In some embodiments, the chemical response is a complete cleavage of the stimuli-responsive protein from protein-polymer conjugate. In certain embodiments, the chemical response is a scission in the protein that is covalently bound to the polymeric constituent of the protein-polymer conjugate. In some embodiments, the chemical response is a cleavage of a portion of the stimuli-responsive protein from the protein-polymer conjugate. The cleaved protein or portion thereof can diffuse from the protein-polymer conjugate. The chemical response can be independent from a physical response, which can include a mechanical and/or an optical response. In some embodiments, the protein-polymer conjugate undergoes a physical response upon exposure to a predetermined stimulus, but not a chemical response. In some embodiments, the protein-polymer conjugate undergoes both a physical and a concurrent chemical response upon exposure to a predetermined stimulus.

As mentioned above, the response of the protein-polymer conjugate can be modulated depending on the amount, duration, and intensity of the predetermined stimulus exposure. In some embodiments, the response of the protein-polymer conjugate can be modulated by tailoring the composition of the protein-polymer conjugate. For example, the response of the protein-polymer conjugate can be attenuated by including a smaller proportion of the stimuli-responsive protein in comparison to the multivalent polymer building block. As an example, the protein-polymer conjugate can include an amount of one or more crosslinkers that is not stimuli-responsive in addition to the stimuli-responsive protein. In some embodiments, the response of the protein-polymer conjugate can be modulated by varying the distance that accompanies a protein's conformational change, for example, by varying the molecular weight of polymeric building blocks, and/or through addition of spacers between protein binding partners in a fusion protein.

In some embodiments, the protein undergoes cleavage when subjected to the presence or absence of the predetermined stimulus. The cleavage can be reversible and cycled upon the application or withdrawal of the predetermined stimulus. Cleavage of the protein can trigger the spatio-temporally controlled degradation of the protein-polymer conjugate. For example, degradation can occur at a precise portion of the protein-polymer when the stimulus is selectively applied to only the predetermined portion. In some embodiments, the degradation amount and rate can be controlled depending on the amount and intensity of the applied stimulus.

In some embodiments, the protein is covalently bound to or non-covalently associated with one or more therapeutic agents and/or biologically active molecule. Cleavage of the protein can release the therapeutic agent or the biologically active molecule from the protein-polymer conjugate, which can elicit a biological response from cells and/or tissue in contact with (and/or downstream from) the therapeutic agent(s) and/or biologically active molecule.

In some embodiments, the protein-polymer conjugate is a protein-polymer hydrogel and consists essentially of, or consists of, a protein having two or more reactive groups crosslinked to multivalent polymer building blocks. In some embodiments, the protein-polymer conjugate is a protein-polymer hydrogel and consists essentially of, or consists of, a protein having two or more reactive groups crosslinked to multivalent polymer building blocks, and one or more covalently bound or non-covalently associated therapeutic agent, where cleavage of the protein can release the therapeutic agent or the biologically active molecule from the protein-polymer conjugate. In some embodiments, the protein-polymer conjugate is a protein-polymer hydrogel and consists essentially of, or consists of, a protein having two or more reactive groups crosslinked to multivalent polymer building blocks, and one or more non-stimuli-responsive proteins or polymers crosslinked to multivalent polymer building blocks. In some embodiments, the protein-polymer conjugate is a protein-polymer hydrogel and consists essentially of, or consists of, a protein having two or more reactive groups crosslinked to multivalent polymer building blocks, one or more non-stimuli-responsive proteins or polymers crosslinked to multivalent polymer building blocks, one or more covalently bound or non-covalently associated therapeutic agent, where cleavage of the protein can release the therapeutic agent or the biologically active molecule from the protein-polymer conjugate.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the disclosure, which are, for clarity, described in the context of separate embodiments, can also be provided in combination in a single embodiment.

Conversely, various features of the disclosure which are, for brevity, described in the context of a single embodiment, can also be provided separately or in any suitable subcombination.

As used herein, the term "substituted" or "substitution" refers to the replacing of a hydrogen atom with a substituent other than H. For example, an "N-substituted piperidin-4-yl" refers to replacement of the H atom from the NH of the piperidinyl with a non-hydrogen substituent such as, for example, alkyl.

As used herein, the term "alkyl" refers to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 30, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "aryl" refers to monocyclic or polycyclic (e.g., having 2, 3, or 4 fused rings) aromatic hydrocarbons such as, for example, phenyl, naphthyl, anthracenyl, phenanthrenyl, indanyl, and indenyl. In some embodiments, aryl groups have from 6 to about 20 carbon atoms.

As used herein, the term "halo" or "halogen" includes fluoro, chloro, bromo, and iodo.

As used herein, the term "alkylene" refers to a linking alkyl group.

As used herein, "alkenyl" refers to an alkyl group having one or more double carbon-carbon bonds. The alkenyl group can be linear or branched. Example alkenyl groups include ethenyl, propenyl, and the like. An alkenyl group can contain from 2 to about 30, from 2 to about 24, from 2 to about 20, from 2 to about 10, from 2 to about 8, from 2 to about 6, or from 2 to about 4 carbon atoms.

As used herein, "alkenylene" refers to a linking alkenyl group.

As used herein, "alkynyl" refers to an alkyl group having one or more triple carbon-carbon bonds. The alkynyl group can be linear or branched. Example alkynyl groups include ethynyl, propynyl, and the like. An alkynyl group can contain from 2 to about 30, from 2 to about 24, from 2 to about 20, from 2 to about 10, from 2 to about 8, from 2 to about 6, or from 2 to about 4 carbon atoms.

As used herein, "alkynylene" refers to a linking alkynyl group.

As used herein, the term "random copolymer" is a copolymer having an uncontrolled mixture of two or more constitutional units. The distribution of the constitutional units throughout a polymer backbone can be a statistical distribution, or approach a statistical distribution, of the constitutional units. In some embodiments, the distribution of one or more of the constitutional units is favored. For a polymer made via a controlled polymerization (e.g., RAFT, ATRP, ionic polymerization), a gradient can occur in the polymer chain, where the beginning of the polymer chain (in the direction of growth) can be relatively rich in a constitutional unit formed from a more reactive monomer while the later part of the polymer can be relatively rich in a constitutional unit formed from a less reactive monomer, as the more reactive monomer is depleted. To decrease differences in distribution of the constitutional units, comonomers in the same family (e.g., methacrylate-methacrylate, acrylamide-acrylamido) can be used in the polymerization process, such that the monomer reactivity ratios are similar.

As used herein, the term "constitutional unit" of a polymer refers to an atom or group of atoms in a polymer, comprising a part of the chain together with its pendant atoms or groups of atoms, if any. The constitutional unit can refer to a repeat unit. The constitutional unit can also refer to an end group on a polymer chain. For example, the constitutional unit of polyethylene glycol can be —CH$_2$CH$_2$O— corresponding to a repeat unit, or —CH$_2$CH$_2$OH corresponding to an end group.

As used herein, the term "repeat unit" corresponds to the smallest constitutional unit, the repetition of which constitutes a regular macromolecule (or oligomer molecule or block).

As used herein, the term "end group" refers to a constitutional unit with only one attachment to a polymer chain, located at the end of a polymer. For example, the end group can be derived from a monomer unit at the end of the polymer, once the monomer unit has been polymerized. As another example, the end group can be a part of a chain transfer agent or initiating agent that was used to synthesize the polymer.

As used herein, the term "terminus" of a polymer refers to a constitutional unit of the polymer that is positioned at the end of a polymer backbone.

As used herein, the term "biodegradable" refers to a process that degrades a material via hydrolysis and/or a catalytic degradation process, such as enzyme-mediated hydrolysis and/or oxidation. For example, polymer side chains can be cleaved from the polymer backbone via either hydrolysis or a catalytic process (e.g., enzyme-mediated hydrolysis and/or oxidation).

As used herein, "biocompatible" refers to a property of a molecule characterized by it, or its in vivo degradation products, being not, or at least minimally and/or reparably, injurious to living tissue; and/or not, or at least minimally and controllably, causing an immunological reaction in living tissue. As used herein, "physiologically acceptable" is interchangeable with biocompatible.

As used herein, the term "hydrophobic" refers to a moiety that is not attracted to water with significant apolar surface area at physiological pH and/or salt conditions. This phase separation can be observed via a combination of dynamic light scattering and aqueous NMR measurements. Hydrophobic constitutional units tend to be non-polar in aqueous conditions. Examples of hydrophobic moieties include alkyl groups, aryl groups, etc.

As used herein, the term "hydrophilic" refers to a moiety that is attracted to and tends to be dissolved by water. The hydrophilic moiety is miscible with an aqueous phase. Hydrophilic constitutional units can be polar and/or ionizable in aqueous conditions. Hydrophilic constitutional units can be ionizable under aqueous conditions and/or contain polar functional groups such as amides, hydroxyl groups, or ethylene glycol residues. Examples of hydrophilic moieties include carboxylic acid groups, amino groups, hydroxyl groups, etc.

As used herein, the term "cationic" refers to a moiety that is positively charged, or ionizable to a positively charged moiety under physiological conditions. Examples of cationic moieties include, for example, amino, ammonium, pyridinium, imino, sulfonium, quaternary phosphonium groups, etc.

As used herein, the term "anionic" refers to a functional group that is negatively charged, or ionizable to a negatively charged moiety under physiological conditions. Examples of anionic groups include carboxylate, sulfate, sulfonate, phosphate, etc.

As used herein, the term "peptide" refers to natural biological or artificially manufactured short chains of amino acid monomers linked by peptide (amide) bonds. As used herein, a peptide has at least 2 amino acid repeating units.

As used herein, the term "oligomer" refers to a macromolecule having 10 or less repeating units.

As used herein, the term "polymer" refers to a macromolecule having more than 10 repeating units.

As used herein, the term "polysaccharide" refers to a carbohydrate that can be decomposed by hydrolysis into two or more molecules of monosaccharides.

As used herein, the term "hydrogel" refers to a water-swollen, and cross-linked polymeric network produced by the reaction of one or more monomers. The polymeric material exhibits the ability to swell and retain a significant fraction of water within its structure, but does not dissolve in water.

As used herein, the term "protein" refers to any of various naturally occurring substances that consist of amino-acid residues joined by peptide bonds, contain the elements carbon, hydrogen, nitrogen, oxygen, usually sulfur, and occasionally other elements (such as phosphorus or iron), and include many essential biological compounds (such as enzymes, hormones, or antibodies).

As used herein, the term "tissue" refers to an aggregate of similar cells and cell products forming a definite kind of structural material with a specific function, in a multicellular organism.

As used herein, the term "organs" refers to a group of tissues in a living organism that have been adapted to perform a specific function.

As used herein, the term "therapeutic agent" refers to a substance capable of producing a curative effect in a disease state.

As used herein, the term "small molecule" refers to a low molecular weight (<2000 daltons) organic compound that may help regulate a biological process, with a size on the order of 1 nm. Most drugs are small molecules.

As used herein, the term "biomaterial" refers to a natural or synthetic material (such as a metal or polymer) that is suitable for introduction into living tissue, for example, as part of a medical device (such as an artificial joint).

As used herein, the term "ceramic" refers to an inorganic, non-metallic, solid material comprising metal, non-metal or metalloid atoms primarily held in ionic and covalent bonds.

As used herein, the term "composite" refers to a composition material, a material made from two or more constituent materials with significantly different physical or chemical properties that, when combined, produce a material with characteristics different from the individual components. The individual components remain separate and distinct within the finished structure.

As used herein, the term "chelating agent" refers to a ligand that forms two or more separate coordinate bonds to a single central metal ion.

One letter codes for amino acids are used herein. For example, alanine is A, arginine is R, asparagine is N, aspartic acid is D, asparagine or aspartic acid is B, cysteine is C, glutamic acid is E, glutamine is Q, glutamine or glutamic acid is Z, glycine is G, histidine is H, isoleucine is I, leucine is L, lysine is K, methionine is M, phenylalanine is F, proline is P, serine is S, threonine is T, tryptophan is W, tyrosine is Y, valine is V.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of a therapeutic agent (i.e., drug, or therapeutic agent composition) that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

The compounds described herein can be asymmetric (e.g., having one or more stereocenters). All stereoisomers, such as enantiomers and diastereomers, are intended unless otherwise indicated.

Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and can be isolated as a mixture of isomers or as separated isomeric forms.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the disclosure can also include all isotopes of atoms occurring in the intermediates or final compounds. Isotopes include those atoms having the same atomic number but different mass numbers. For example, isotopes of hydrogen include tritium and deuterium.

In some embodiments, the compounds of the disclosure, and salts thereof, are substantially isolated. By "substantially isolated" is meant that the compound is at least partially or substantially separated from the environment in which it was formed or detected. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the FIGURES should not be viewed as limiting. It should be understood that other embodiments may include more or less of each element shown in a given FIGURE. Further, some of the illustrated elements may be combined or omitted. Yet further, an example embodiment may include elements that are not illustrated in the FIGURES. As used herein, with respect to measurements, "about" means+/−5%. As used herein, a recited ranges includes the end points, such that from 0.5 mole percent to 99.5 mole percent includes both 0.5 mole percent and 99.5 mole percent.

Protein-Polymer Conjugate Structures

Without wishing to be bound by theory, it is believed that the protein-polymer conjugates of the present disclosure (e.g., the protein-polymer hydrogels) are highly attractive for in vitro cell culture constructs and can serve as models for dynamic 3D biological studies. The high water content, tissue-like elasticity, and facile transport of nutrients and waste render the protein-polymer conjugates good mimics of the cell's ECM, while their optical clarity can allow imaging of cell function to be performed non-destructively. The protein-polymer conjugates can be produced under mild, cytocompatible conditions that allow for live-cell encapsulation and can be formulated to contain user-defined chemical functionalities, physical properties (e.g., mechanical properties), and degradability. In particular, by using chemoenzymatic strategies in the synthesis of the protein-polymer conjugates, the proteins can be modified in a manner that is site-specific, selective, and quantitative, thereby permitting the introduction of reactive chemical handles at defined locations.

The protein-polymer conjugates of the present disclosure can provide, inter alia, in vitro cell culture platforms that mimic the anisotropic and periodic reversible stiffening that occurs in vivo. Fundamental knowledge resulting from these materials can be useful for therapeutic tissue regeneration and precision medicine. Towards these ends, the present disclosure describes robust synthetic strategies that afford user-programmable release of site-specifically modified proteins from the protein-polymer conjugates. Furthermore, by tethering proteins of interest to the protein-polymer conjugates through degradable linkers of defined molecular architecture, Boolean YES/OR/AND logic-based control over protein release can be achieved, in response to complex sets of inputs. Thus, in some embodiments, the protein-polymer conjugates of the present disclosure can provide biomacromolecular delivery only when user-specified combinations of external cues are present, permitting the sequential and independent triggered release of multiple proteins from hydrogel biomaterials. In some embodiments, the protein and/or therapeutic agent is directly released from the protein-polymer conjugate occurs without an intermediary linker, such as a Boolean YES/OR/AND logic-based linker. Thus, prior to release, the protein and/or therapeutic agent is directly linked to the polymer, or is linked to the polymer without a Boolean YES/OR/AND logic-based linker. Boolean YES/OR/AND logic-based linkers are described, for example, in U.S. application Ser. No. 16/335,664, filed Mar. 21, 2019, incorporated herein by reference in its entirety.

In some embodiments, the multivalent polymer building blocks can include polymers including repeating units derived from ethylene glycol, NIPAM, lactic acid, glycolic acid, styrene, vinyl alcohol repeating units. Examples of polymeric building blocks are described, for example, in Arakawa, C. K. and DeForest, C. A. Designing Smart Biomaterials to Mimic & Control the Stem Cell Niche: Polymer Design and Development. *Biology and Engineering of Stem Cell Niches*, Elsevier. Oxford, UK. 295-314 (2017), incorporated herein in its entirety. For example, the multivalent polymer building blocks can include multivalent polysaccharides such as cellulose, agarose, alginate, hyaluronic acid, chondroitin sulfate, and chitosan; protein-based biomaterials; synthetic materials such as polylactic acid, polyglycolic acid, polycaprolactone, poly(ethylene glycol), poly(vinyl alcohol); elastomers, polyanhydrides, polyacetals, polyphosphazenes; smart polymers such as thermally responsive polymers (polyNIPAM), conductive polymers (polypyrrole, polyaniline, PEDOT), and/or copolymers thereof. The multivalent polymer building blocks are functionalized with one or more reactive groups (e.g., two or more reactive groups) that can react with the stimuli-responsive protein, such as alkyne, maleimide, alkene, and/or alkyne.

In some embodiments, the stimuli-responsive protein is LOV2-Jα, LOV2/-Zdk1, Phy-PIF, CaM-M13, PhoCl, Dronpa, pMag/nMag, and/or Cph1. In some embodiments, the stimuli-responsive protein is non-naturally occurring. Proteins that can undergo stimuli-dependent binding with known partners are described, for example, in Berman, H. M. et al. The Protein Data Bank. *Nucleic Acids Res.* 28, 235-42 (2000). In some embodiments, the stimuli-responsive protein is PhoCl. Without wishing to be bound by theory, it is believed that PhoCl can be advantageous, as light having a wavelength in the visible spectrum can be used to effect a response. For example, UV light can induce damage on biological systems, particularly to DNA. By using visible light, such as a wavelength of 405 nm, toxicity to cells and cellular structures can be reduced. Longer wavelengths of light are also advantageous in that they penetrate deeper into tissue, and can be amenable to light-induced drug delivery applications. For example, photodynamic therapy (PDT) uses a combination of light and a photosensitizer to specifically target certain skin cancers, leading to precise cancer cell death.

In some embodiments, the stimuli-responsive protein can undergo non-covalent protein-protein interactions whose affinities can be altered upon exposure to light. The conformational change need not involve the breaking or formation of covalent bonds, and can be fully reversible. As light exposure can be easily spatially and temporally defined, a protein that changes binding affinity in response to light can be used, for example, for fully reversible photopatterning. For example, *Arabidopsis thaliana* protein Phytochrome B (PhyB) undergoes a conformational change (end-to-end changes estimated to be on the order of tens of Angstroms) upon exposure to red light that promotes its binding with Phytochrome Interaction Factor 3 (PIF3). As another example, Light-Oxygen-Voltage-Sensing-Domain 2 (LOV2) can undergo a conformational change in the Jα domain upon exposure to blue light (~470 nm) that leads to partial unfolding of the Jα helix. A variety of binding partners can be engineered whose binding affinity is dependent upon the conformational state of the Jα helix. Termed "LOVTRAP" a binding partner, termed Zdark (Zdk), can be used to form LOV2-fusion proteins. Without wishing to be bound by theory, it is believed that there is a 150-fold difference in binding affinity of Zdk with the LOV2 Jα helix between the light and dark states. Zdk fusion proteins and an azide-tagged LOV2 can be recombinantly expressed. Furthermore, the LOVTRAP system is that LOV2 is sensitive to 470 nm blue light, well outside of the UV region that could be damaging to cellular DNA. Blue light also has increased penetration into tissues, allowing for applications in drug delivery.

The stimuli responsive protein can be functionalized with one or more reactive groups such as an azide, an amine, a thiol, an alkyne, an alkene, and/or tetrazine. When the stimuli-responsive protein is a crosslinker, the protein is functionalized with two or more reactive groups. The reactive groups on the protein can be complementary to the reactive groups on the multivalent polymer building blocks.

In some embodiments, the stimuli-responsive protein has been modified prior to incorporation into the protein-polymer conjugate. In some embodiments, sortase is used for protein modification and can be used to generate a variety of functional biomacromolecules for reaction with polymers. For example, STEPL expression systems can be used to make proteins spanning a wide variety of classes. As an example, protein functional modification by sortase can be defined by engineered peptide identity, and various polyglycine probes can be synthesized with different reactive handles (azides, aromatic aldehydes, nitrobenzyl moieties). These bioorthogonal handles can allow proteins to be conjugated to polymers using click chemistries (such as azide/alkyne, oxime, and hydrazine conjugation). In some embodiments, the stimuli-responsive protein can include a genetically encoded photocleavable group.

In some embodiments, the stimuli-responsive protein is covalently conjugated to the multivalent polymer building block via a reaction such as azide-alkyne cycloaddition, oxime ligation, hydrazide formation, thiol-maleimide, michael-type addition, thiol-ene, thiol-yne, strain-promoted alkyne-nitrone cycloaddition (SPANC), strain-promoted, azide-alkyne cycloaddition (SPAAC), copper(I)-catalyzed azide-alkyne cycloaddition (CuAAC), staudinger ligation, tetrazine-cyclooctene, diels-alder, inverse electron-demand diels-alder, native chemical ligation, cinnamate/coumarin/anthracine dimerization, amide formation through amine reacting with activated ester (e.g., N-hydroxysuccinimidyl esther, NHS), and enzymatic crosslinking (e.g., sortase ligation). The stimuli-responsive protein and the multivalent polymer building block can have complementary reactive groups, and can react with one another under appropriate reaction conditions, which are readily understood by a person of ordinary skill in the art.

In some embodiments, the protein-polymer conjugates are made by functionalizing a stimuli-responsive protein with an azide moiety; functionalizing a multivalent polymer building block with an alkyne moiety; and reacting the protein with the multivalent polymer building block. The stimuli-responsive protein can be made by protein expression.

The protein-polymer conjugate of the present disclosure can have a stimuli-responsive protein in an amount of 0.01 mole percent or more (e.g., 0.1 mole percent or more, 1 mole percent or more, 5 mole percent or more, 10 mole percent or more, 25 mole percent or more, 50 mole percent or more, 75 mole percent or more, or 90 mole percent or more) and/or 99.99 mole percent or less (e.g., 90 mole percent or less, 75 mole percent or less, 50 mole percent or less, 25 mole percent or less, 10 mole percent or less, 5 mole percent or less, 1 mole percent or less, 0.1 mole percent or less), relative to the total content of the conjugate. The protein-polymer conjugate can have a multivalent polymer building block in an amount of 0.01 mole percent or more (e.g., 0.1 mole percent or more, 1 mole percent or more, 5 mole percent or more, 10 mole percent or more, 25 mole percent or more, 50 mole percent or more, 75 mole percent or more, or 90 mole percent or more) and/or 99.99 mole percent or less (e.g., 90 mole percent or less, 75 mole percent or less, 50 mole percent or less, 25 mole percent or less, 10 mole percent or less, 5 mole percent or less, 1 mole percent or less, 0.1 mole percent or less), relative of the total content of the conjugate. In some embodiments, the protein-polymer conjugate includes therapeutic agents in an amount of 0 mole percent or more (e.g., 1 mole percent or more, 5 mole percent or more, 25 mole percent or more, or 40 mole percent or more) and/or 50 mole percent or less (e.g., 40 mole percent or less, 25 mole percent or less, 5 mole percent or less, or 1 mole percent or less), relative to the total content of the conjugate. In certain embodiments, the protein-polymer conjugate includes non-stimuli-responsive crosslinking agents (e.g., a polymeric crosslinking agent, a non-stimuli-responsive protein crosslinker) in an amount of 0 mole percent or more (e.g., 0.1 mole percent or more, 1 mole percent or more, 5 mole percent or more, 10 mole percent or more, 25 mole percent or more, 50 mole percent or more, 75 mole percent or more, or 90 mole percent or more) and/or 95 mole percent or less (e.g., 90 mole percent or less, 75 mole percent or less, 50 mole percent or less, 25 mole percent or less, 10 mole percent or less, 5 mole percent or less, 1 mole percent or less, 0.1 mole percent or less), relative to the total content of the conjugate.

In some embodiments, the multivalent polymer building block can have a weight average molecular weight ($M_w$) of 1 kDa or more and/or 100 kDa or less. Without wishing to be bound by theory, it is believed that a multivalent polymer building block having a low molecular weight provides a stiffer protein-polymer conjugate, while a higher molecular weight provides a softer protein-polymer conjugate.

In some embodiments, the stimuli-responsive protein and the multivalent polymer building block can be present in the conjugate in a stoichiometric ratio of 0.0001:1 or more (e.g., 0.001:1 or more, 0.01:1 or more, 0.1:1 or more, 1:1 or more, 10:1 or more, 100:1 or more, or 1000:1 or more) and/or 10000:1 or less (e.g., 1000:1 or less, 100:1 or less, 10:1 or less, 1:1 or less, 0.1:1 or less, 0.01:1 or less, or 0.001:1 or less). A higher ratio can provide a stiffer protein-polymer conjugate.

In some embodiments, the predetermined stimulus is light having a predetermined wavelength, a peptide or a protein (e.g., an enzyme), an ion (e.g., $Ca^{2+}$), a small molecule, a nucleic acid, a predetermined temperature, a predetermined pH, ultrasound, a reductant, an oxidant, and a predetermined mechanical force. In certain embodiments, the predetermined stimulus is light having a predetermined wavelength. For example, the light having a predetermined wavelength is visible light, having a wavelength of from 380 nm to 760 nm.

In some embodiments, the protein-polymer conjugate undergoes a reversible physical or chemical response when exposed to the predetermined stimulus. In some embodiments, the stimuli-responsive protein undergoes a reversible conformational change upon exposure to a stimulus. The response of the protein-polymer conjugate and/or the protein's conformational change can be cycled 1 time or more (e.g., 10 times or more, 100 times or more, 1,000 times or more) and/or 10,000 times or less (e.g., 1,000 or less, 100 times or less, or 10 times or less), with little to no loss in responsive intensity. For example, the response intensity decrease can be 30 percent or less (e.g., 20 percent or less, 10 percent or less, 5 percent or less, 1 percent or less, or 0.1 percent or less) and/or 0.05 percent or more (e.g., 0.1 percent or more, 1 percent or more, 5 percent or more, 10 percent or more, or 20 percent or more) over 10 cycles. In certain embodiments, the response of the protein-polymer conjugate and/or the protein conformational change is not reversible.

In some embodiments, the stimuli-responsive protein decreases in length upon exposure to a light of a predetermined wavelength. Thus, the protein-polymer conjugate can contract in turn, upon exposure to the light of the predetermined wavelength. In some embodiments, the stimuli-responsive protein increases in length upon exposure to a light of a predetermined wavelength. In turn, the protein-polymer conjugate can expand, when the conjugate is exposed to the light of the predetermined wavelength. As discussed above, in some embodiments, the stimuli-responsive protein is cleaved from the multivalent polymer upon exposure to a stimulus. The protein-polymer conjugate can degrade when exposed to the predetermined stimulus.

In some embodiments, the protein-polymer conjugate is cytocompatible and can be used as a substrate for cells or tissues, and is amenable to high cell viability, such as where greater than 70 percent (e.g., greater than 80 percent, greater than 90 percent, or greater than 95 percent) of cells survive over a period of 24 hours. Cells can be encapsulated or otherwise impregnated into the protein-polymer conjugate. In certain embodiments, the protein-polymer conjugate can be used in a cell-culturing article, a sensor, drug screening, tissue engineering, disease modeling, and/or a drug delivery device.

Exemplary Protein-Polymer Conjugates

In some embodiments, to couple changes in biomolecular conformation to material crosslinking density, stimuli-responsive proteins are fused with their stimuli-dependent binding partners. For example, when the stimulus is light, in the dark, the stimuli-responsive protein can undergo a conformational change that promotes binding to its fusion partner, which in some embodiments, provides a shortened end-to-end length compared to when the stimuli-responsive protein is not bound to the fusion partner. When light is applied, intramolecular protein-protein interactions can be destroyed, thereby yielding relaxation to a large end-to-end length. When these fusion proteins are covalently incorporated into a polymer framework, molecular shortening can translate to a physical tightening and an increased elastic moduli of the network while the extended conformation can provide a softer material. In some embodiments, the reverse conformational change and associated elastic moduli change can occur upon exposure to a stimulus, where little to no protein-protein interaction is present when the stimulus is present, thus providing a soft material; and lack of stimulus provides protein-protein interactions to result in a harder material. As the stimulus introduction/removal can be repeated indefinitely and with spatiotemporal control, fully reversible modulation over 4D material mechanics can be obtained. In certain embodiments, the conformational change is irreversible when the stimulus is applied or removed.

In some embodiments, to reversibly alter a material's biochemical or physical characteristics, materials can be functionalized uniformly or in part (e.g., in a patterned manner) with a stimulus-responsive protein. The binding partner fusion domain can be genetically fused to a protein of interest, allowing for immobilization of the modified binding partner and stimulus-responsive protein within the materials with reversible spatiotemporal control via directed stimulus (e.g., light) exposure.

In some embodiments, instead of or in addition to providing a conformational change, the stimuli-responsive protein can provide the polymer framework to which it is attached the ability to be degraded on demand, and with spatiotemporal control, depending on when and where the stimulus is applied. In certain embodiments, the protein can be conjugated to a polymeric framework, for example, as a pendant moiety, to provide stimuli-responsive release of the protein with spatiotemporal control, depending on when and where the stimulus is applied.

Stiffness-Tunable Hydrogel Biomaterials

Without wishing to be bound by theory, it is believed that hydrogel elasticity is inversely correlated with its crosslinking density, and materials formulated with relatively small distances between chemical crosslinks yield "stiff" networks, while those with large physical separations between crosslinks give rise to "soft" materials. The distance between crosslinks can be explicitly controlled at the time of hydrogel formation through varied component identity, molecular weight, functionality, stoichiometric ratio, and total amount, to define the initial physical properties (e.g., mechanical properties) of these synthetic networks. However, altering biomaterial stiffness after hydrogel synthesis is significantly more challenging. In particular, materials capable of dynamic reversible stiffening and softening have proven elusive, particularly under physiologically relevant conditions. The protein-polymer conjugates of the present disclosure are capable of providing dynamic reversible physical (e.g., mechanical) responses when subjected to the application and withdrawal of a stimulus. For example, moduli-switchable protein-polymer conjugates can be made by crosslinking a polymer with protein-based crosslinkers that exhibit altered conformations in response to different external stimuli. The conformational change can cause a change in the distance between chemical crosslinks upon introduction and removal of a stimulus.

Referring to FIG. 1A, a protein-polymer conjugate can have stimuli-responsive proteins and their stimuli-dependent binding partners. In the presence of the external stimulus, the responsive protein can undergo a conformational change that promotes binding to its fused partner and a shortened end-to-end length. When this stimulus is removed, the original protein conformation is restored and intramolecular protein-protein interactions are destroyed, thereby providing a return to the original large end-to-end length. When these fusion proteins are used to crosslink a polymer network (FIG. 1B), molecular shortening translates to a physical tightening and an increased elastic moduli of the network while the extended confirmation yields a soft material (FIG. 1C). As stimuli introduction and removal can be repeated, fully reversible control over biomaterial physical (e.g., mechanical) properties can be obtained.

Protein-Based Hydrogel Crosslinker

In some embodiments, the stimuli-responsive proteins are responsive to light, such that i) photo-induced changes to protein binding affinity does not rely on slow molecular diffusion events, enabling on-demand and near-instantaneous changes to network physics (e.g., mechanics); ii) the extent of modification can be controlled by adjusting total light amount shone onto the system, providing access to intermediate states and varied rates of material alteration; and iii) by regulating when and where light is shone onto the material, spatiotemporal control over binding and accompanying stiffness changes can be obtained. The protein can be a fusion protein. In some embodiments, the proteins of the present disclosure include LOV2-Jα, LOV2/−Zdk1, Phy-PIF, CaM-M13, PhoCl, Dronpa, pMag/nMag, and/or Cph1. In some embodiments, the stimuli-responsive protein is the photoswitchable LOV2-Jα binding pair.

Figure 1B:
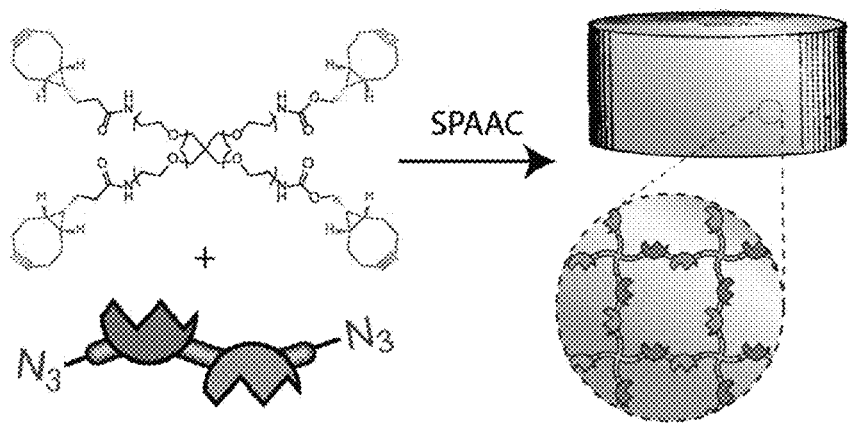
FIG. 1B is a drawing depicting the functionalization of the fusion proteins of FIG. 1A with reactive azides (—$N_3$), which facilitates incorporation of the fusion proteins into hydrogels by strain-promoted azide-alkyne cycloaddition (SPAAC) reactions.
Figure 1C:
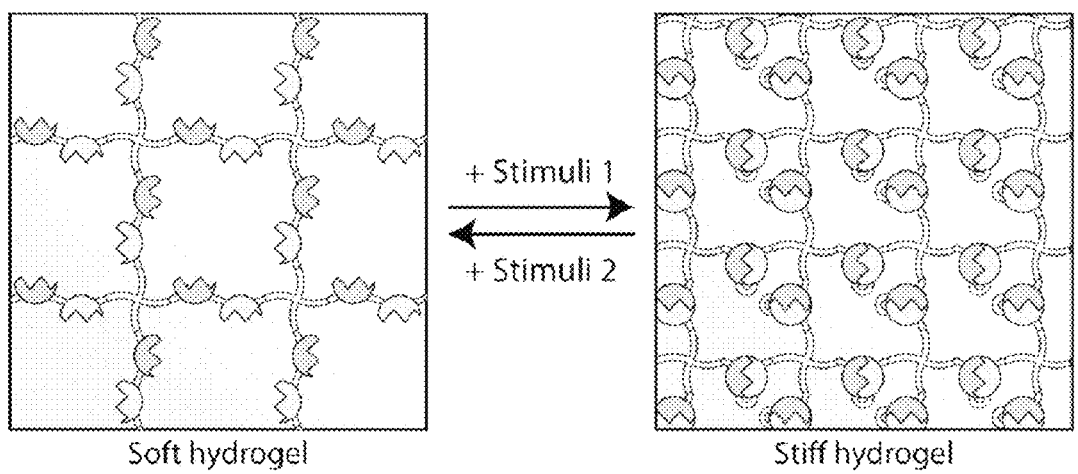
FIG. 1C is a drawing of a hydrogel of FIG. 1B, where, after hydrogel formation, the fusion protein crosslinker can undergo conformational changes that translate to reversible stimuli-dependent material stiffening.
Figure 2:
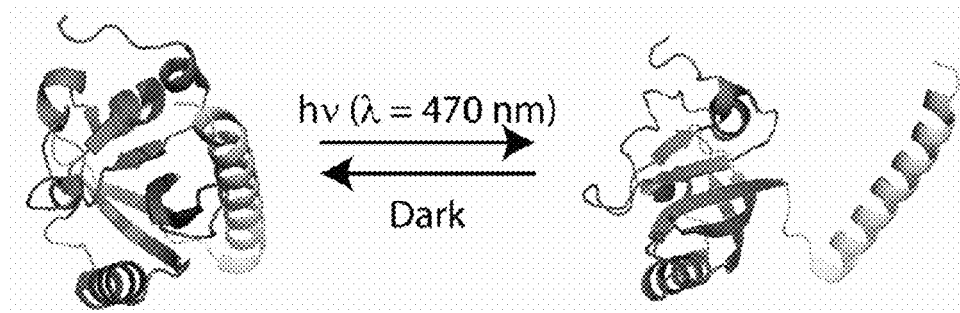
FIG. 2 is a drawing of a light, oxygen, and voltage sensing domain 2 (LOV2) which undergoes reversible dissociation with the C-terminal-linked Jα helix in response to blue light ($\lambda$=470 nm). This conformational change can be reversed under dark conditions.

Referring to FIG. 1B, in some embodiments, the incorporation of LOV2-Jα into a polymeric framework without destroying its light responsiveness can be accomplished via the strain-promoted azide-alkyne cycloaddition (SPAAC) reaction, where LOV2-Jα is flanked with two reactive azides (—$N_3$) that undergo specific and spontaneous reaction with a cyclooctyne-multifunctionalized polymer (FIG. 1B). SPAAC proceeds fully bioorthogonally, enabling cell-laden hydrogels to be formed rapidly and robustly in serum-containing media. The bio-orthogonal SPAAC reaction is specific, compared to protein-functionalization of polymer using non-specific covalent reactions with acidic (e.g., glutamate, aspartate) or nucleophilic amino acids (e.g., lysine, cysteine). Furthermore, the bio-orthogonal SPAAC reaction can confine reactions to specific residues so as to maintain high levels of protein activity. Moreover, LOV2's photoactivation mechanism, which results in a covalent adduct between an essential cysteine residue and the FMN chromophore, precludes usage of thiol-based reactions (e.g., Michael-type reactions, thiol-ene) for hydrogel formation.

Figure 3:
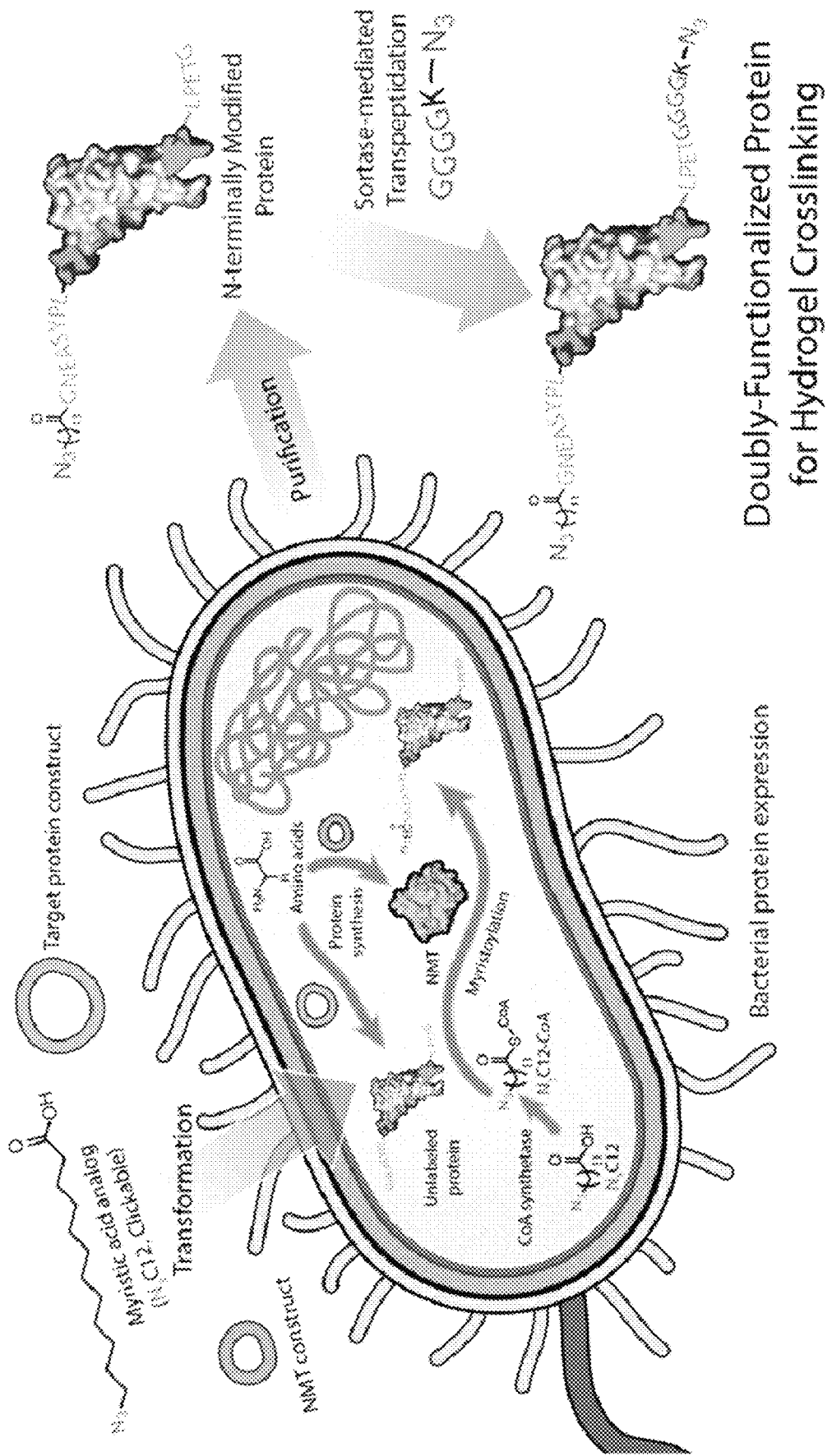
FIG. 3 is a drawing of $E.\ coli$-co-transformed with constructs for the expression of N-myristoyl transferase (NMT) and a target protein of interest, cultured with an azide-functionalized myristic acid analog ($N_3C12$). $N_3C12$ is activated in vivo to form $N_3C12$-CoA, the substrate for myristoylation of the target protein by NMT. The tagged protein can be purified prior to sortase-mediated transpeptidation with an azide-functionalized polyglycine probe. The final protein is doubly-functionalized and can form hydrogels with a multivalent polymeric building block via, for example, bioorthogonal SPAAC chemistry.

In some embodiments, to create a light-responsive protein hybrid that can be used for SPAAC-based material cross-linking, and to maximize the dynamic range in stiffness obtainable through photoregulation, LOV2-Jα is functionalized at both the N and C termini with azide residues. Chemoenzymatic methods can allow the quantitative introduction of chemically-defined, non-natural moieties within proteins via enzymatic transformations. While the general structure and location of these modifications are biologically predetermined, it is believed that other proteins can be labeled so long as it contains the proper enzymatic recognition sequence. For example, referring to FIGS. 3 and 4, reactive azides can be introduced at the N and C termini of a given protein through an orthogonal pair of chemoenzymatic modifications: N-terminal modification by N-myristoyl transferase (NMT) and C-terminal functionalization via a sortase-mediated transpeptidation reaction.

In some embodiments, the azide functionality can be introduced on the N-terminus of a protein (e.g., LOV2-Jα) through a fatty acylation event known as N-myristoylation. This lipid anchor addition process involves the irreversible transfer of a saturated 14-carbon fatty acid (myristic acid) to an N-terminal glycine residue either during or post translation and is catalyzed by the enzyme myristoyl-CoA:protein N-myristoyl transferase (NMT). NMT operates on the "GXXXS/T(K)" signature sequence (where X is any amino acid), which can be readily included in the recombinant production of any protein of interest. As long as this N-terminal recognition sequence is present, NMT can readily label proteins of different sizes, characteristics, and functions in a manner that is site-specific, selective, and quantitative. The NMT enzyme tolerates many synthetic analogs of its natural substrate, which can be engineered to contain desired biofunctionality. Variants that contain oxygen, sulfur, and nitrogen heteroatoms, aromatic residues, and carbonyls can be successfully utilized as NMT substrates for acylation. Additionally, azide- (—$N_3$) and alkyne- (—C≡C) containing analogs can be synthesized as known by a person of ordinary skill in the art, opening up the door for performing the SPAAC click chemistry on the resultant modified proteins.

In some embodiments, to introduce a reactive azide onto the C terminus of proteins, a sortase-mediated transpeptidation reaction can be used. *Staphylococcus aureus* sortase A is a calcium-assisted transpeptidase that recognizes the C-terminal sorting signal "LPXTG" [SEQ ID No.: 8], forming an acyl-enzyme intermediate with the protein while simultaneously displacing the C-terminal portion of the sorting signal's threonine residue. The thioester of the acyl-enzyme intermediate can be nucleophilically displaced with a polyglycine probe, thereby conjugating the probe onto the C-terminus while regenerating the sortase A enzyme. The polyglycine compound can contain non-natural functionality, providing a route to "sortag" bioorthogonal moieties including reactive azides onto the C-terminus of proteins of interest.

Figure 4A:
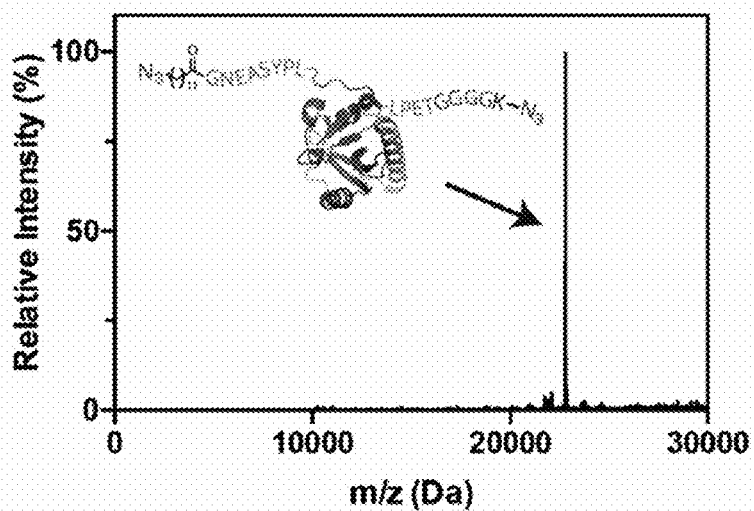
FIG. 4A is liquid chromatograph-mass spectrometry trace, confirming that an embodiment of a protein of the present disclosure, $N_3$-LOV2-Jα-$N_3$, has been successfully expressed and purified.
Figure 4B:
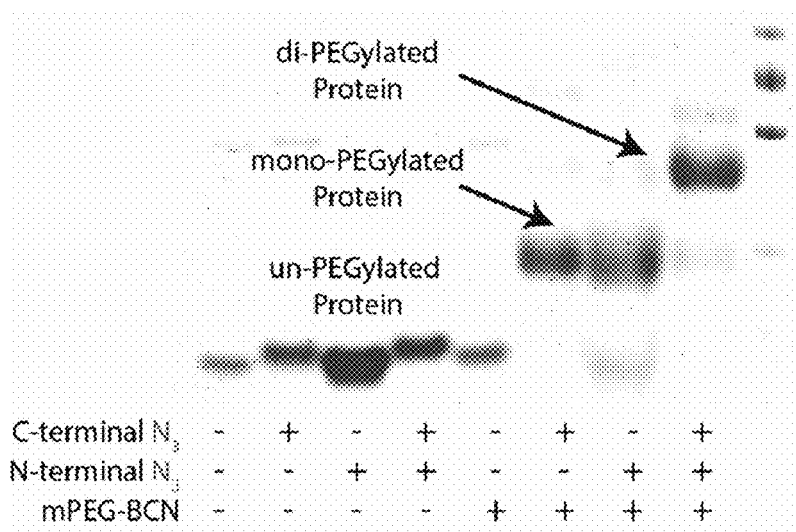
FIG. 4B is a photograph of an SDS-PAGE gel shift assay with a monofunctionalized methoxy-PEG-cyclooctyne, indicating quantitative functionalization at both termini of an embodiment of a protein of the disclosure, and that the introduced azides remain active for SPAAC chemistry.
Figure 5A:
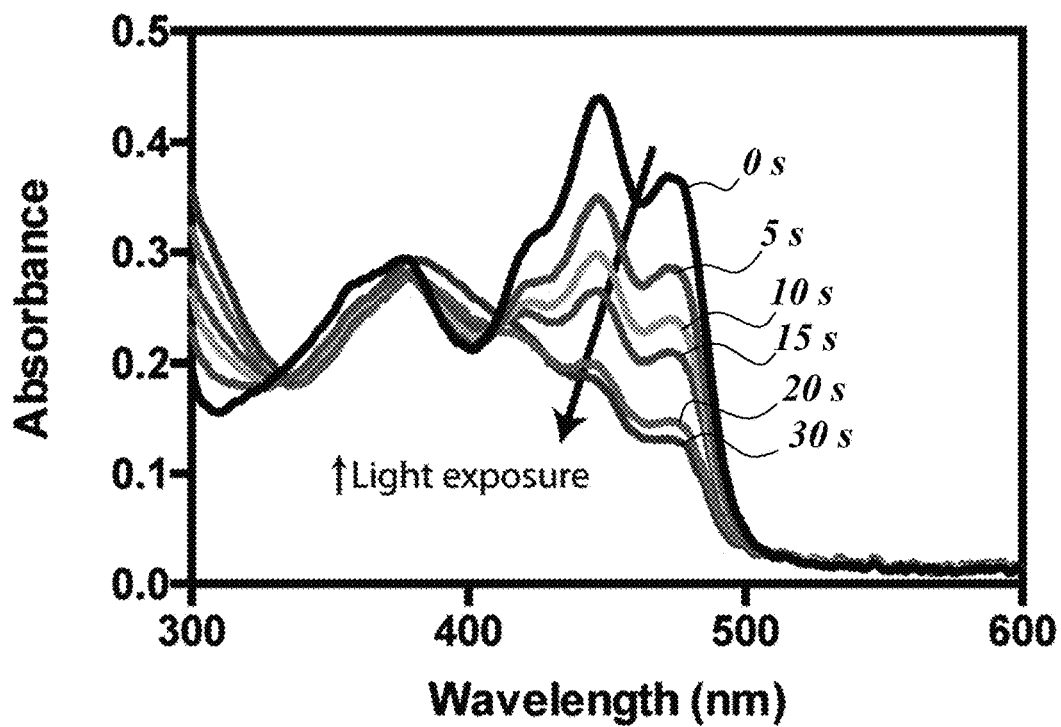
FIG. 5A is a graph showing spectrophotometric changes of $N_3$-LOV2-Jα-$N_3$ in response to various amounts of light exposure ($\lambda$=470 nm, I=10 mW $cm^{-2}$, t=0-30 sec). Studies were performed in aqueous solution.
Figure 5B:
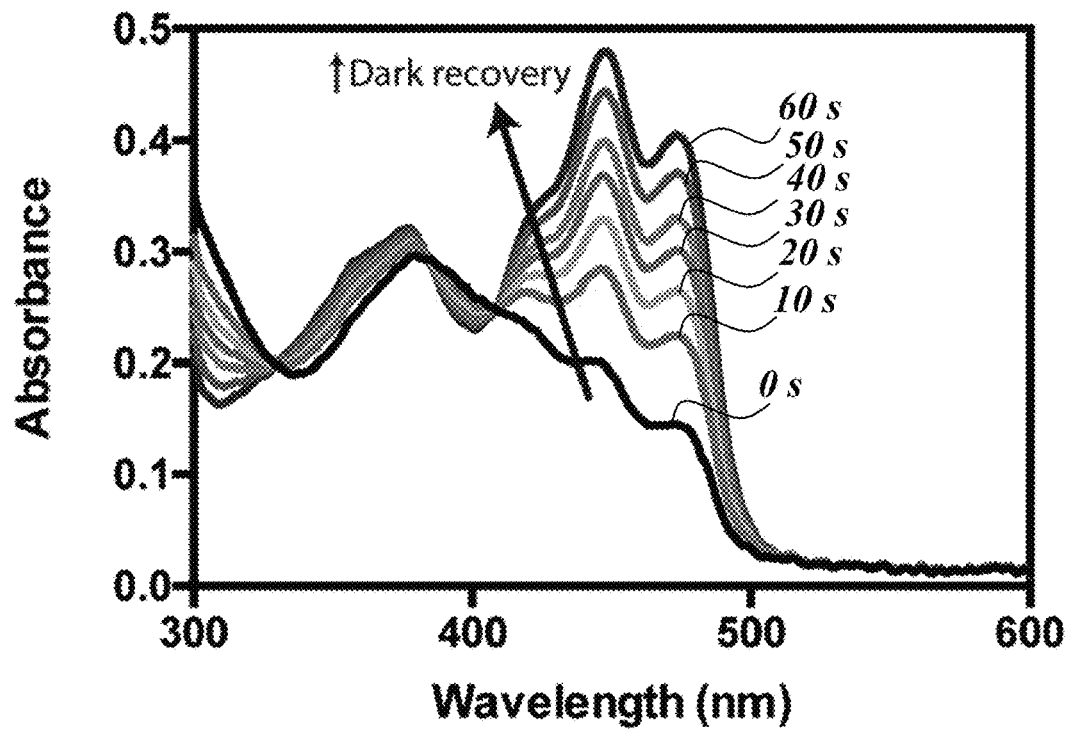
FIG. 5B is a graph showing spectrophotometric changes throughout dark recovery of an embodiment of a protein of the present disclosure ($N_3$-LOV2-Jα-$N_3$ (t=0-60 sec). Studies were performed in aqueous solution.

For example, to synthesize doubly-functionalized protein for conjugation to polymers, standard molecular cloning techniques to introduce recognition sequences for NMT (GNEASYPL [SEQ ID No.: 1]) and sortase (LPETG [SEQ ID No.: 9]) respectively to the N- and C-termini of a protein (e.g., LOV2-Jα) can be undertaken prior to bacterial recombinant protein expression. A C-terminal 6×His tag sequence can be added to aid in purification. As NMT is not endogenous to *E. coli*, cells can be co-transformed with plasmids encoding NMT as well as the protein (e.g., LOV2-Jα). In some embodiments, the expression medium can be supplemented with 12-azidododecanoic acid ($N_3$C12), an azide-containing myristic acid analog. Following expression, $N_3$-protein (e.g., LOV2-Jα)-LPETG-6×His can be purified by Ni-NTA affinity chromatography. This protein can then incubated with a 6×His-tagged sortase and an azide-containing polyglycine probe [H-GGGGK($N_3$)—$NH_2$ [SEQ ID No.: 10]]. Following transpeptidation, the doubly functionalized protein can purified on Ni-NTA, where the column flow-through contains the desired protein: $N_3$-protein (e.g., LOV2-Jα)-$N_3$ (see FIG. 3, 6×His tag displaced during sortagging). Protein purity can be verified with SDS-PAGE and the extent of modification can be assessed by MALDI-TOF, or ESI LC/MS mass spectrometry and gel shift assays (FIG. 4). Quantification of the stimuli-responsiveness of the protein can then be carried out, for example, by monitoring changes in UV-Vis absorbance spectra under irradiation and dark conditions for light-responsive proteins (FIG. 5).

The methods above can be readily adapted to other stimuli proteins (including fusion proteins), using methods known to a person of ordinary skill in the art.

Protein-Polymer Conjugate Synthesis

Figure 6:
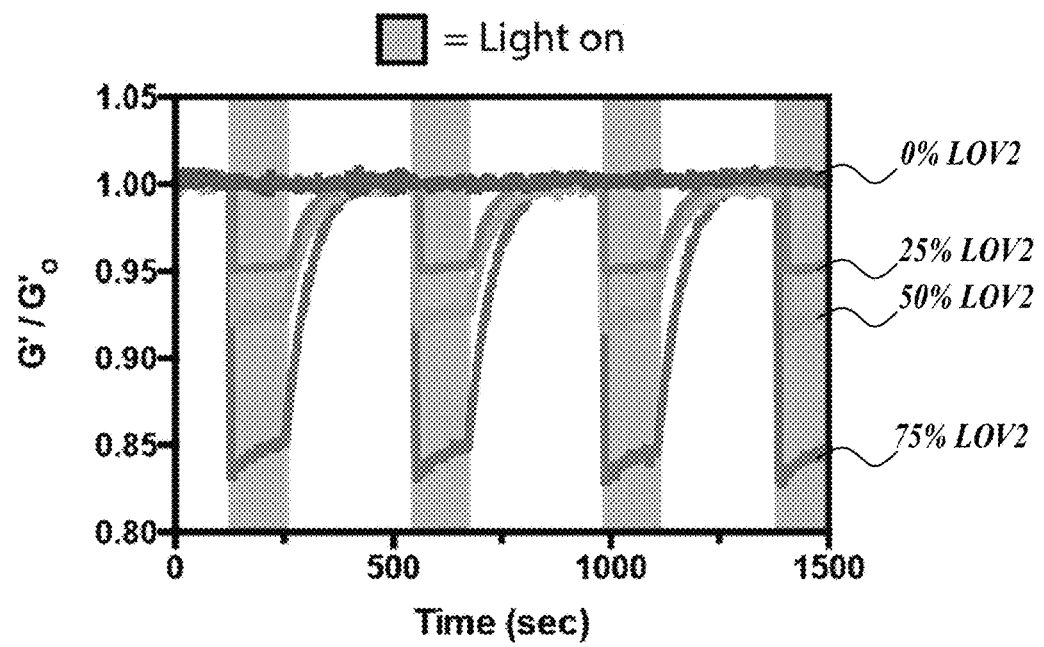
FIG. 6 is a graph showing that LOV2-Jα-based gels exhibit repeated and reversible changes in elastic moduli in response to blue light (λ=470 nm, 10 mW cm$^{-2}$), as determined by in situ photorheometry. Total responsiveness scales with protein crosslinker content (0, 25, 50, 75 mol % $N_3$-LOV2-Jα-$N_3$, with the balance comprised of $N_3$-PEG-$N_3$).

Protein-polymer conjugates can be formed, for example, via SPAAC between a multivalent polymer having one or more reactive functionalities (e.g., four-arm poly(ethylene glycol) tetrabicyclononyne (PEG-tetraBCN, $M_n$~1-20 kDa)) and the modified protein having one or more complementary reactive functionalities (e.g., an azide-functionalized protein such as the $N_3$-LOV2-Jα-$N_3$ protein). The reaction can proceed quickly, and in some embodiments, gelation can occurs within minutes of mixing the multivalent polymer and the protein, and can provide homogeneous networks with protein moieties homogeneously conjugated and dispersed in the polymer network. Materials can be formed with different polymer:protein stoichiometric ratios, total water content, as well as different molecular weight multivalent polymers. For example, to tune the degrees of stiffness changes that accompany light exposure, a portion of photoresponsive protein (e.g., $N_3$-LOV2-Jα-$N_3$ crosslinker) can be replaced with a non-stimuli-responsive polymer (e.g., $N_3$—PEG-$N_3$ ($M_n$~1-10 kDa) (FIG. 6). The methods described herein can be adapted using methods known to a person of ordinary skill in the art.

In some embodiments, to study a photoresponsive behavior of a light responsive protein-polymer conjugate, in situ photorheometry can be carried out (FIG. 6). For example, elastic (G') and inelastic (G") moduli can be monitored in the presence and absence of collimated light (λ=470 nm) of various intensities (0.1, 1, 5, 10, 20 mW cm$^{-2}$). Different light intensities can affect the rate of elastic change that accompanies each of these light exposures, and the timescale for hydrogel stiffening/softening can be precisely controlled.

In some embodiments, specific regions of a protein-polymer conjugate can be exposed to a stimulus. For example, photopatterning can be performed either by masked-based or multiphoton laser-scanning lithography. Masked-based photopatterning can allow 2D patterns to be quickly generated over a relatively large surface area (FIG. 7), while multiphoton laser-scanning lithograph can allow for full 3D manipulation in of light exposure in small areas (including single cells). Both masked-based photopatterning and multiphoton laser-scanning lithography can allow for cycled and reversible change in material properties.

Reversible Biochemical Functionalization of Hydrogel Biomaterials

Figure 8A:
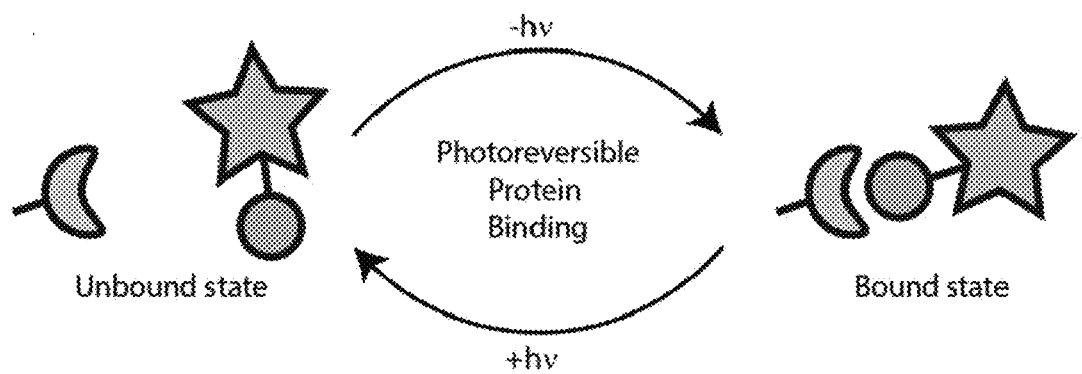
FIG. 8A is a drawing of an embodiment of light-responsive proteins of the present disclosure (e.g., LOV2 and Zdk1 as part of the LOVTRAP system, or Phy-PIF), undergoing reversible dimerization in the presence or absence of light.
Figure 8B:
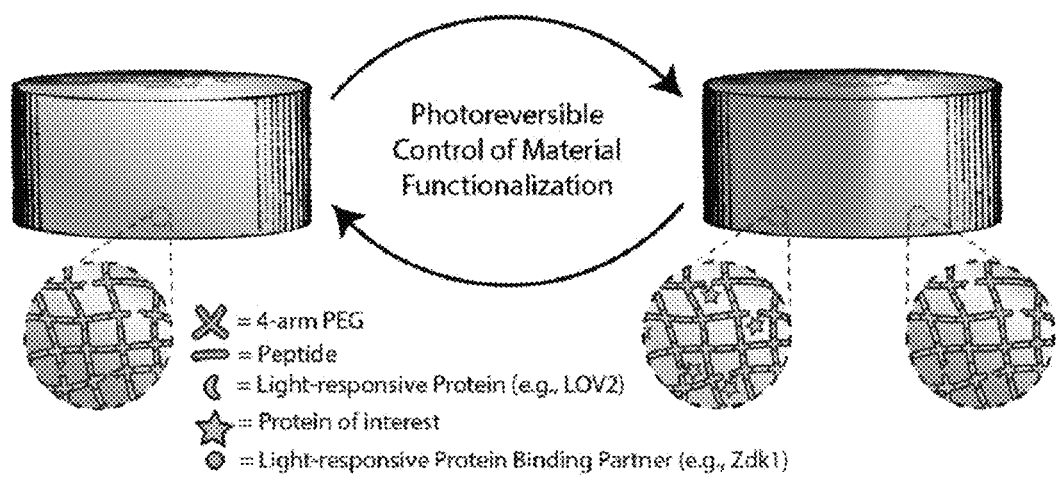
FIG. 8B is a drawing of an embodiment of a protein-polymer conjugate of the present disclosure, showing that polymers uniformly functionalized with a light-responsive protein can be reversibly decorated with protein substrates fused to the protein-binding partner, thereby affording user-programmable biochemical immobilization through directed light exposure.

In some embodiments, stimuli-response proteins (e.g., photoresponsive proteins such as LOV2 and Zdk1 as part of the LOVTRAP system, Phy-PIF) undergo reversible dimerization in the presence or absence of stimulus. Materials (e.g., hydrogels, surfaces, ceramics, polymers, etc.) uniformly functionalized with a stimulus-responsive protein can be modified for immobilization via a number of techniques (e.g., chemoenzymatic modification including NMT and sortase as described above, statistic labeling, site-specific modification, inclusion of reactive non-canonical amino acids (nCAAs), random modification) and included in initial material formulation or in subsequent functionalization. Directed stimulus exposure can be used to control spatiotemporal binding affinities in stimulus-responsive proteins for its binding partner, affording user-programmable biochemical immobilization through directed stimulus exposure (FIG. 8). Such materials can be useful for dynamically and spatially probing and controlling cell function (which is useful for tissue engineering, disease modeling, stem cell differentiation, promoting specific cell functions including protein expression), as well as sensors.

Material Photodegradation Using Photocleavable Proteins

Figure 9A:
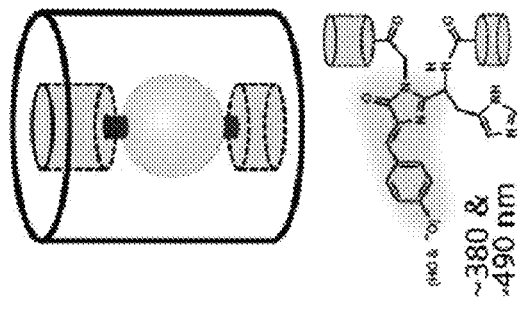
FIG. 9A is a drawing showing the excitation of photocleavable protein chromophore (shown for PhoCl) leads to photoconversion and backbone cleavage.
Figure 9B:
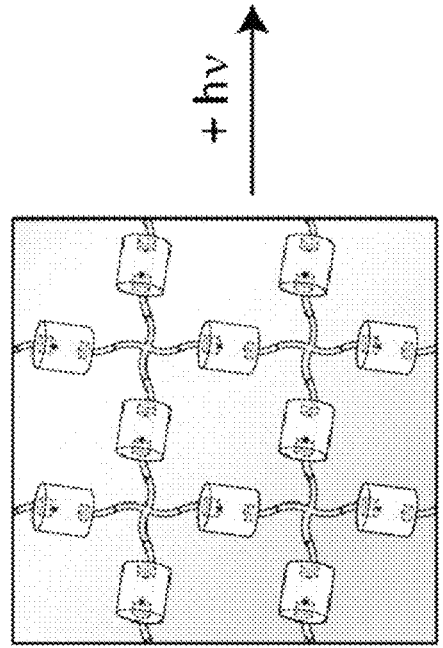
FIG. 9B is a drawing showing incorporation of photocleavable protein in a polymer backbone, which allows for complete or patterned photo-triggered degradation.

In some embodiments, stimuli-responsive proteins can undergo backbone cleavage in response to directed stimulus exposure. When such proteins (such as PhoCl) are conjugated to a polymer, such as to the backbone of hydrogel networks, the resulting materials can undergo user-directed stimulus-induced degradation (FIG. 9). Proteins can be functionalized with NMT and sortase (as well as other aforementioned chemistries) to enable incorporation into polymeric materials. Photodegradable materials can be used useful for 3D cell culture, creating engineered vasculature, sensors, tissue engineering, and cell/drug delivery. The protein-polymer conjugate can minimize concern over immunogenicity if these systems are used in a biological context, can be amenable to scalable synthesis through bacterial fermentation, and can provide expanded access to visible wavelengths of light that are compatible with the optical window of tissue.

Stimulus-Mediated Drug Delivery

Figure 10:
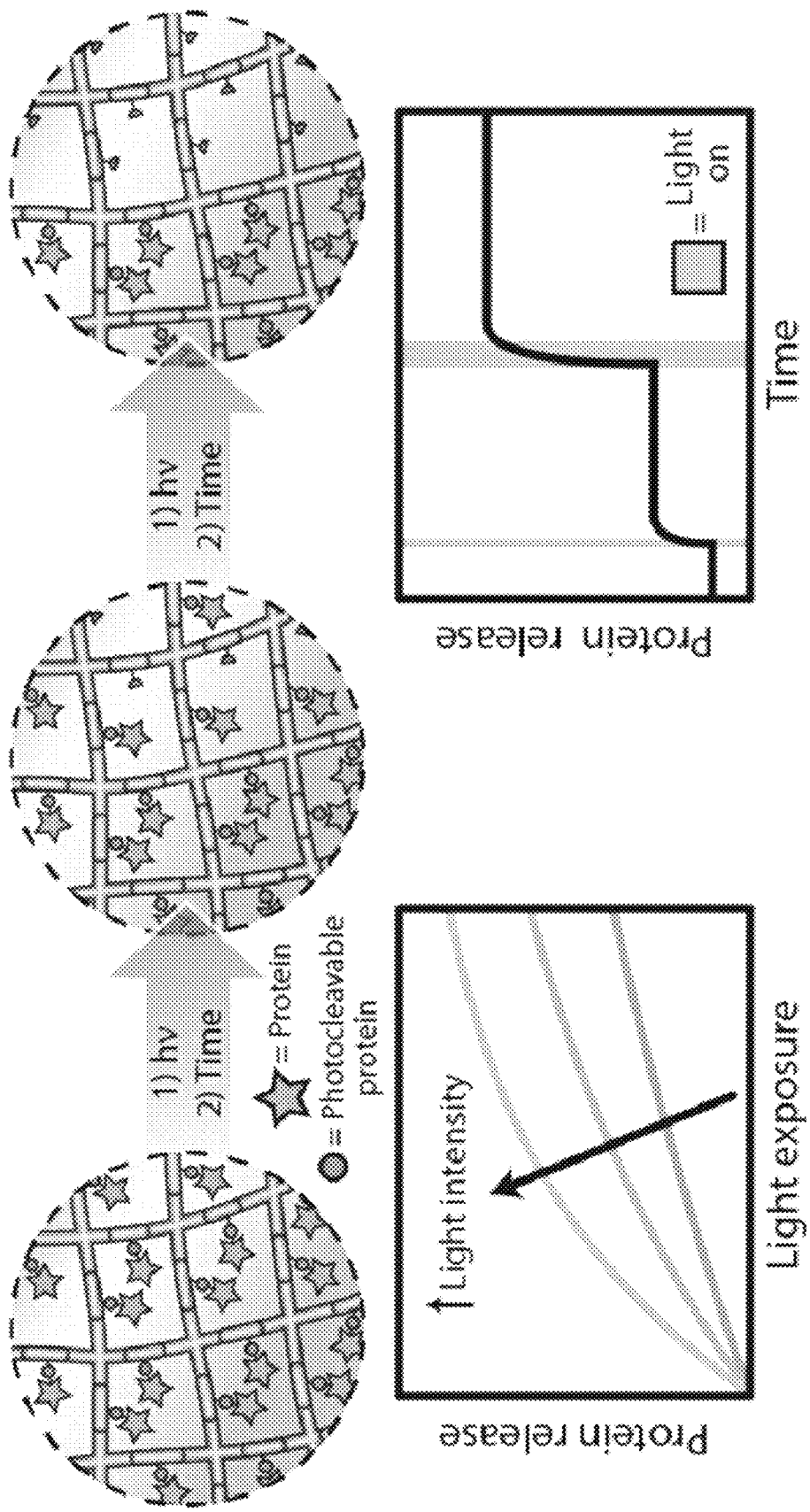
FIG. 10 is a drawing showing spatially-controlled on-demand photomediated protein drug delivery. By covalently attaching biomolecules to a polymeric material though a photodegradable protein-based linker (such as PhoCl), therapeutic protein delivery can be initiated and controlled with light exposure. This approach, which allows for delayed burst release as well as the ability to control the dosage amount and release location, explicitly, provides control over payload delivery.

In some embodiments, biomolecules can be covalently conjugated to a material though a degradable protein-based linker, where the degradation is initiated by exposure to a predetermined stimulus (e.g., PhoCl), and in turn, therapeutic delivery is controlled by stimulus exposure. This strategy can be utilized to release tethered small molecules, peptides, proteins, nucleic acids, cells, and other species. This approach, which enables delayed burst release as well as the ability to dictate the dosage amount and release location explicitly, provides control over payload delivery (FIG. 10). In one embodiment, a therapeutic protein is genetically fused to the C-terminus of PhoCl and modified by NMT for incorporation on/within a material. Upon light exposure, PhoCl can undergo photocleavage, thereby releasing the therapeutic protein. Such an approach can be useful for drug delivery, biosensors, and tissue engineering. The advantages of a protein-based approach is minimized concern over immunogenicity if these systems are used in a biological context, fully scalable synthesis through bacterial fermentation, and expanded access to visible wavelengths of light that may be more compatible with the optical window of tissue.

Logic-Gated Protein-Polymer Conjugates

In some embodiments, the release of site-specifically modified proteins from a polymeric network can follow Boolean logic. For example, a sortase-mediated transpeptidation reaction can be used to generate recombinant proteins C-terminally tethered to hydrogels through environmentally sensitive degradable linkers. By varying the connectivity of multiple stimuli-labile moieties within these customizable linkers, YES/OR/AND control of protein release in response to one and two-input combinations (e.g., using enzyme, reductant, and/or light) can be provided. Tethering of multiple proteins each through a different stimuli-sensitive linker permits their independent and sequential release from a common material. An example of a logic-gated protein-polymer conjugate is described below, in Example 4. Molecular logic gates are described, for example, in U.S. application Ser. No. 16/335,664, filed Mar. 21, 2019, herein incorporated in its entirety.

Methods of Use

During use, the protein-polymer conjugate can mimic a cellular environment. The protein-polymer conjugate can be exposed to a predetermined stimulus to provide a physical (e.g., mechanical) response in the protein-polymer conjugate; the stimulus can be withdrawn to reverse the physical response in the protein-protein conjugate; and the exposure and withdrawal of the stimulus can be repeated one or more times to provide a cyclic reversible physical (e.g., mechanical) response in the protein-polymer conjugate. The protein-polymer conjugate can include a multivalent polymer building block, and a stimuli-responsive protein covalently conjugated to the multivalent polymer building block. The protein-polymer conjugate can contract and stiffen upon exposure to the predetermined stimulus, and expand and soften upon removal of the predetermined stimulus; or the protein-polymer conjugate can expand and soften upon exposure to the predetermined stimulus, and contract and stiffen upon removal of the predetermined stimulus.

In some embodiments, the protein-polymer conjugate can deliver a therapeutic agent. The protein-polymer conjugate can be exposed to a predetermined stimulus to release a therapeutic agent from the protein-polymer conjugate. The protein-polymer conjugate comprises a multivalent polymer building block, and a stimuli-responsive protein covalently conjugated to the multivalent polymer building block. The stimuli-responsive protein can undergo cleavage to release a therapeutic agent upon exposure to the predetermined stimulus.

EXAMPLES

Example 1. Cyclic Stiffness Modulation of Cell-Laden Protein-Polymer Hydrogels in Response to User-Specified Stimuli Including Light Although mechanical signals presented by the extracellular matrix are known to regulate many essential cell functions, the specific effects of these interactions, particularly in response to dynamic and heterogeneous cues, remain largely unknown. Here, a modular semisynthetic approach to create protein-polymer hydrogel biomaterials that undergo reversible stiffening in response to user-specified inputs is presented. Employing a novel dual-chemoenzymatic modification strategy, fusion protein-based hydrogel crosslinkers that exhibit stimuli-dependent intramolecular association is described in this Example. Linkers based on calmodulin provided calcium-sensitive materials, while those containing the photosensitive LOV2 (light, oxygen, and voltage sensing domain 2) protein gave phototunable constructs whose moduli could be cycled on demand with spatiotemporal control about living cells. These unique materials were exploited to demonstrate the significant role that cyclic mechanical loading plays on fibroblast-to-myofibroblast transdifferentiation in three-dimensional (3D) space. The moduli-switchable materials can be useful for studies in mechanobiology, providing avenues to probe and direct matrix-driven changes in 4D cell physiology.

Introduced herein is a generalizable strategy to create hydrogel biomaterials whose moduli could be reversibly switched in response to user-specified inputs, potentially with spatial control, and the use of these unique materials to probe the effects of cyclic mechanical loading on encapsulated cell fate. Wedding changes of biomolecular conformation to those in hydrogel crosslinking density, stimuli-responsive proteins were fused with their stimuli-dependent binding partners (FIG. 1A). In the presence of the external stimulus, the responsive protein underwent a conformational change that promoted binding to its fused partner and a shortened end-to-end length. Following removal of this stimulus (or introduction of another), intramolecular protein-protein interactions were destroyed and the original protein conformation was restored. When these fusion proteins were incorporated into the hydrogel crosslinker itself, molecular shortening translates to an elastic stiffening of the network while the extended conformation yields a softer material (FIG. 1C). As stimuli introduction and removal could be repeated ad infinitum, fully reversible control over biomaterial mechanical properties was readily obtained. Since several hundred proteins have been determined to undergo stimuli-dependent binding with known partners, many smart moduli-switchable materials responsive to distinct classes of stimuli (e.g., ligands, pH, temperature, ions, light) could be readily produced, for example, in a similar manner.

To generate stiffness-cyclable hydrogels, a step-growth polymerization was performed via a strain-promoted azide-alkyne cycloaddition (SPAAC) between a four-arm poly (ethylene glycol) (PEG) tetrabicyclononyne (BCN) ($M_n$~20 kDa), a linear PEG diazide ($N_3$—PEG-$N_3$, $M_n$~3.5 kDa), and a fusion protein uniquely end-functionalized with reactive azides (—$N_3$) at both the N- and C-termini. Precisely installed bioorthogonal handles enable almost any protein species to be used as a crosslinker without the loss-of-activity typical of site-directed mutagenesis or the uncontrollable heterogeneity that accompanies statistical functionalization of endogenous amino acid residues. By varying the ratio of the azide-modified crosslinkers (i.e., $N_3$—PEG-$N_3$ vs. fusion protein) present during gelation, the maximal extent of material response could be precisely controlled.

Figure 11:
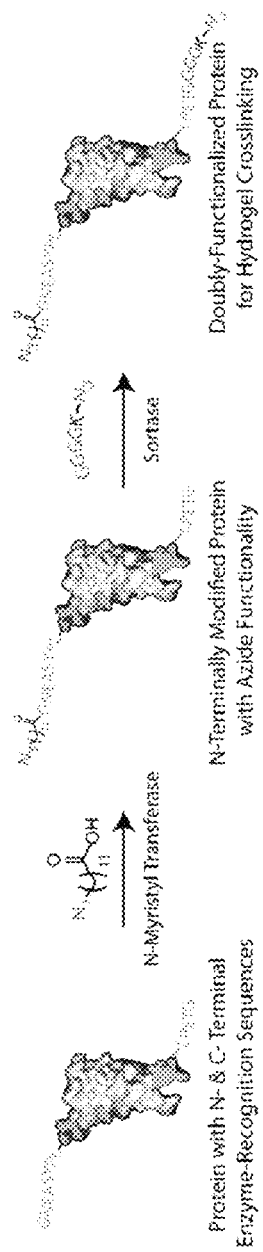
FIG. 11 is a drawing of an embodiment of stimuli-responsive end-functionalized protein crosslinker, in particular a recombinant fusion protein bearing the N-terminal GNEASYPL sequence [SEQ ID No.: 1]. The recombinant fusion protein is readily myristoylated with 12-azidododecanoic acid (12-ADA) by N-myristoyl transferase (NMT). Species containing the C-terminal LPETG sequence can be modified via a sortase-mediated transpeptidation with an azide-functionalized polyglycine probe. The chemoenzymatic reactions can be performed sequentially on proteins that contain both peptide motifs; the final protein is end-functionalized with reactive azides, which can then be used to form hydrogel biomaterials with a multivalent polymer building block via bioorthogonal SPAAC chemistry.

End-modified protein crosslinkers were prepared through a novel orthogonal pair of chemoenzymatic modifications (FIG. 11). N-terminal labeling was achieved by N-myristoyl transferase (NMT), which promoted co-translational fatty acylation on proteins bearing the "GXXXS/T" signature sequence (where X is any amino acid). NMT tolerated many synthetic analogs of its natural myristic acid substrate; enzymatic modification with 12-azidododecanoic acid (12-ADA) yielded site-specific installation of azide functionality at the N-terminus. To append bioorthogonal handles onto the C-terminus of proteins, a versatile sortase-mediated transpeptidation reaction was employed. Specifically, *Staphylococcus aureus* sortase A is a calcium-assisted transpeptidase that catalyzes the cleavage of a C-terminal sorting signal "LPXTG [SEQ ID No.: 8]" with the concomitant amide linkage of a polyglycine probe and the target protein. "Sortagging" with an azide-bearing oligoglycine permits efficient C-terminal installation of azido functionality. Without wishing to be bound by theory, it is believed that although both NMT and sortase have each been used in isolation to introduce a single reactive azide onto either the N- or C-terminus of a protein, their combined usage has not been demonstrated in literature. It is believed that modification of a single protein by multiple chemoenzymatic reactions has not yet been established. Here, it is shown that recombinant proteins bearing both enzymatic recognition sequences could be readily prepared through standard molecular cloning and expression techniques. As chemoenzymatic transformations proceed with exceptionally high labeling efficiencies, it is believed that uniform populations of dually functionalized protein-based material crosslinkers could be created from virtually any monomeric or fused species, and that they could function uniquely as macromolecular precursors for the controlled step-growth polymerization of protein-polymer hydrogels.

Figure 12A:
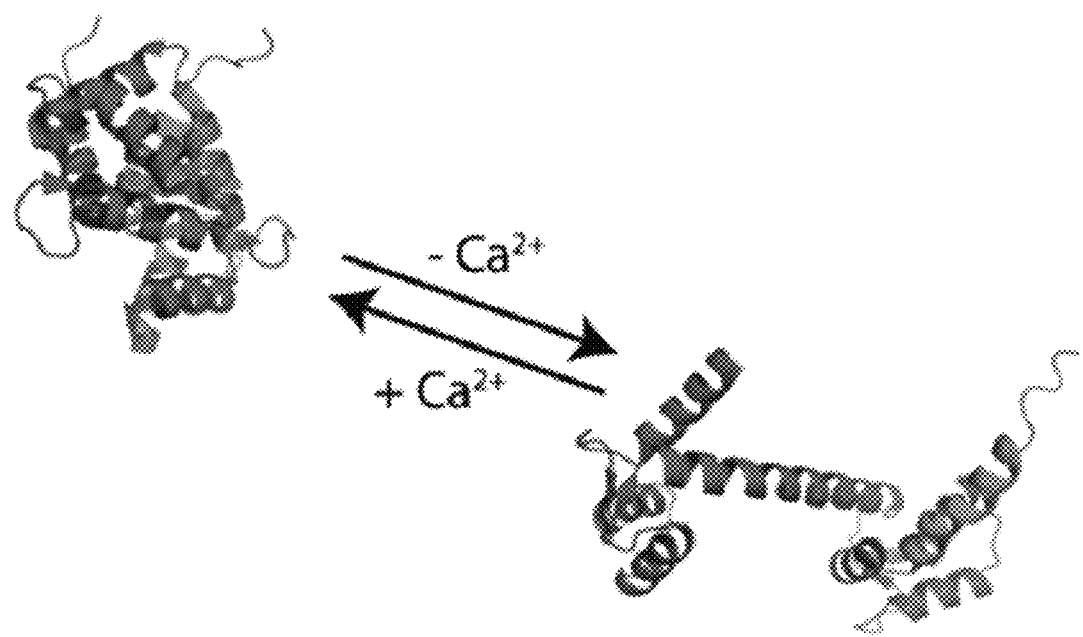
FIGS. 12A-12F are directed to calcium-responsive hydrogels based on CaM-M13 intramolecular binding.
Figure 12B:
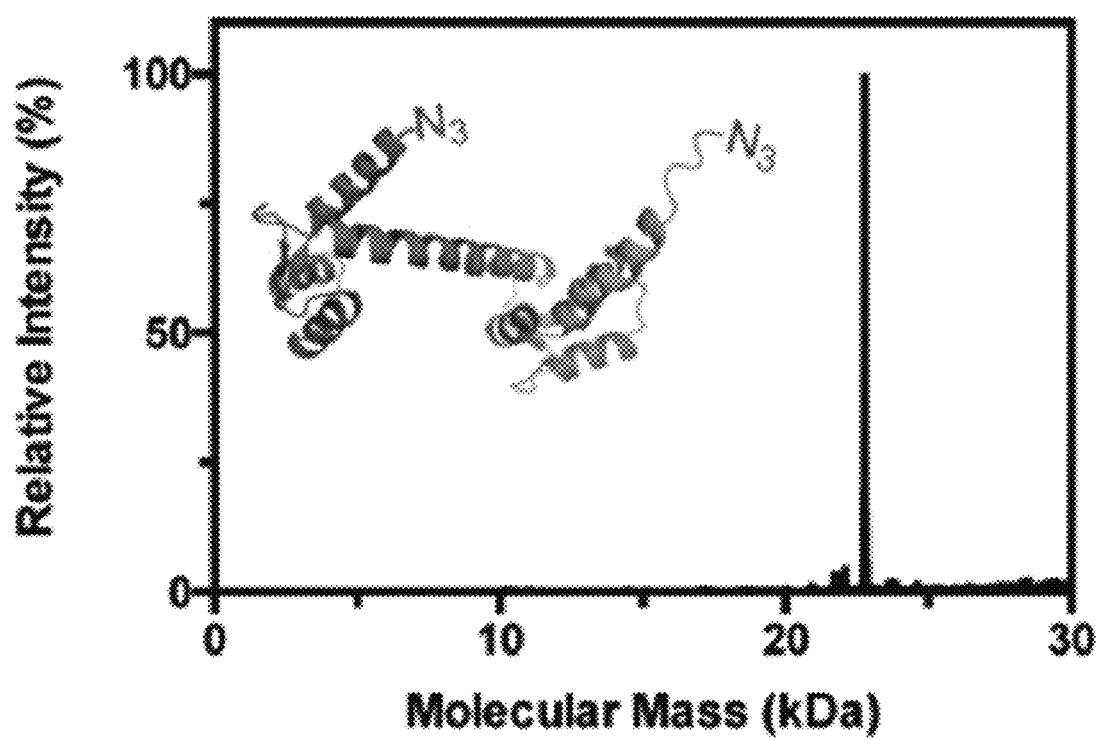
Figure 12C:
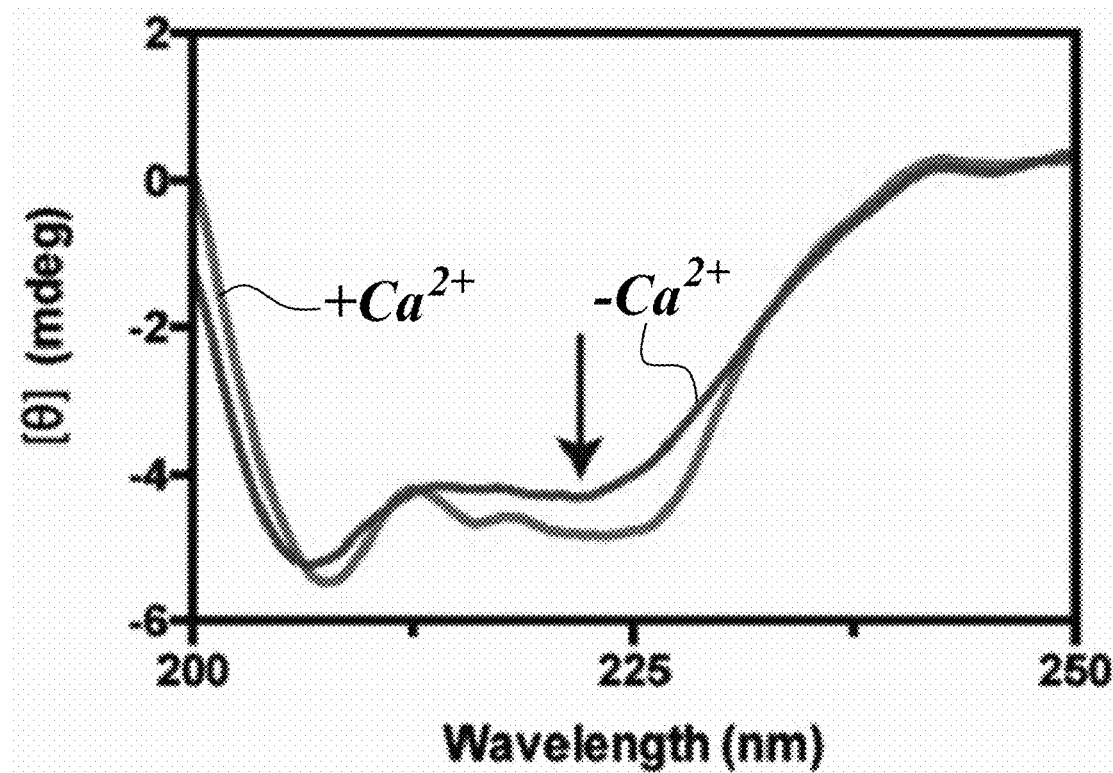
Figure 12D:
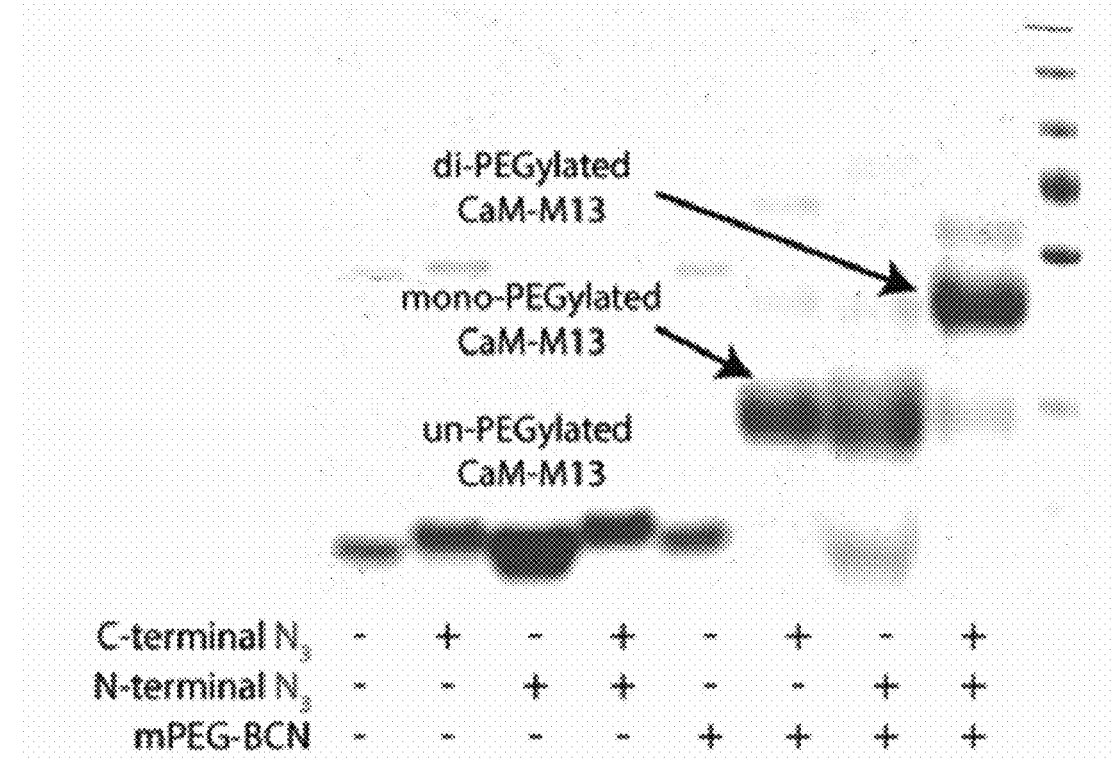

Having identified a strategy to create stiffness-cyclable hydrogels using dually modified responsive proteins, initial efforts were focused on calmodulin (CaM). A fusion of CaM and the M13 peptide fragment of myosin light chain kinase was created that could be dually modified for hydrogel crosslinking. When $Ca^{2+}$ was present, CaM underwent a conformation changes that permitted high-affinity binding with M13; when the $Ca^{2+}$ ion was chelated away, CaM structure and intramolecular association relaxed (FIG. 12A). Following expression and modification by NMT and sortase, the end-modified $N_3$-CaM-M13-$N_3$ complex was obtained in good yield (~5 mg $L^{-1}$ culture, non-optimized expression). Whole-protein mass spectrometry revealed exceptionally high sample purity and quantitative functionalization at both termini (FIG. 12B); the observed mass for $N_3$-CaM-M13-$N_3$ (22,807 Da) correlated well with its expected value (22,805 Da). Far-UV circular dichroism confirmed responsiveness of the complex to calcium (FIG. 12C), consistent with similar analysis performed on purified CaM, where α-helical content increased upon $Ca^{2+}$ binding as indicated by decreasing ellipticity at 222 nm. To verify that the introduced azides were functionally accessible and maintained reactivity by SPAAC, an SDS-PAGE gel shift assay was used involving C-/N-terminal PEGylation by BCN-monofunctionalized methoxy-PEG (mPEG-BCN, $M_n$~10 kDa) (FIG. 12D); the near-complete disappearance of the starting protein band, accompanied by the simultaneous appearance of a new band upshifted by the average molecular weight of the correct number of PEG chains (0, 1, or 2, depending on condition), indicated the ability to install reactive azides site-specifically onto CaM-M13 proteins using NMT and/or sortase. Collectively, these results demonstrated the successful generation of a bioresponsive fusion protein-based crosslinker, as well as the first utilization of two different chemoenzymatic reactions to modify a single recombinant protein.

Figure 12E:
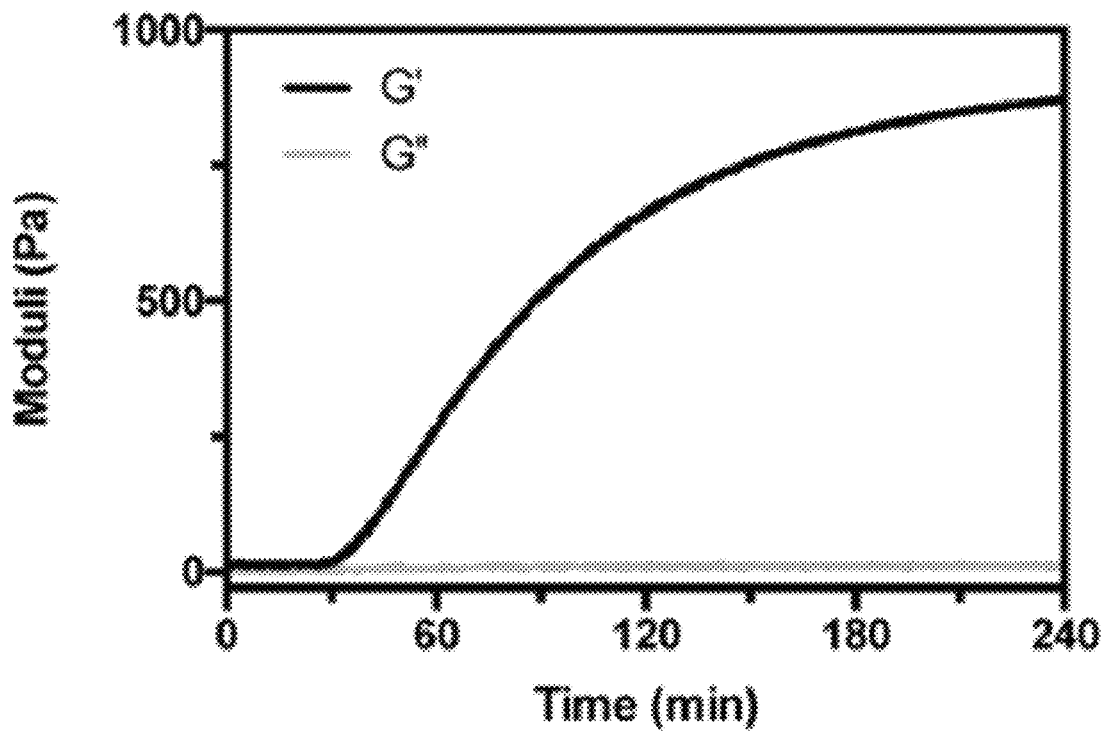
Figure 12F:
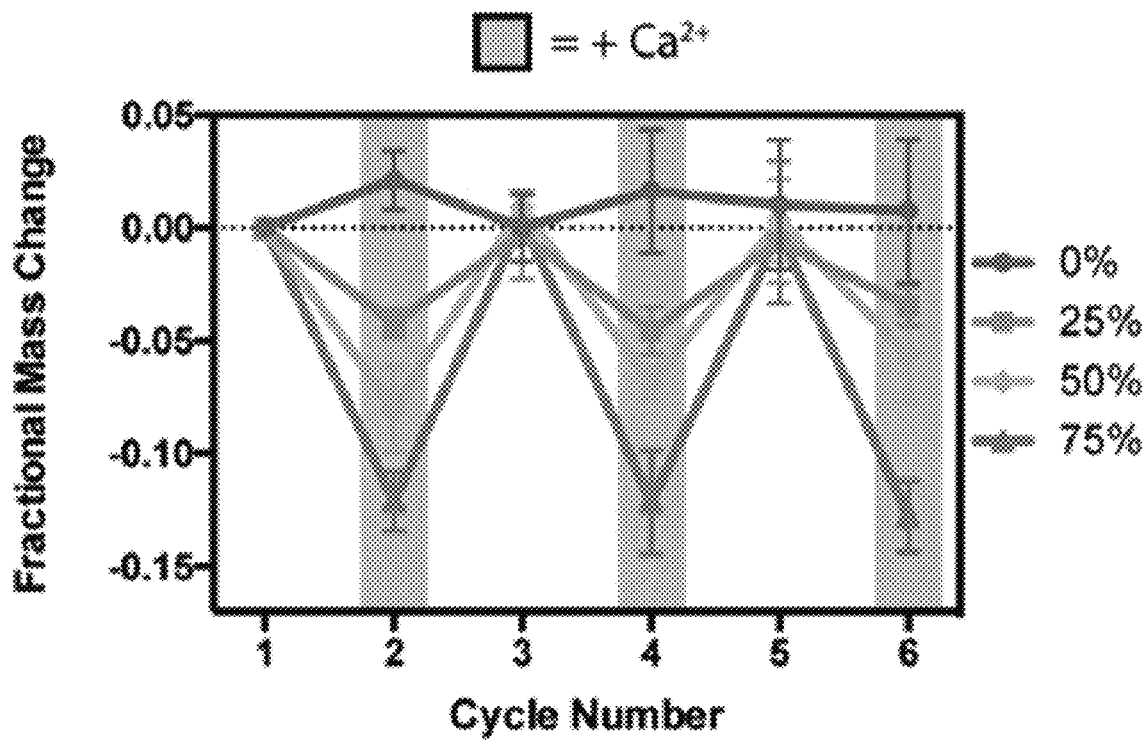

Calcium-responsive hydrogel networks were formed based on the SPAAC reaction of PEG-tetraBCN (2 mM), $N_3$—PEG-$N_3$ (2 mM), and $N_3$—CaM-M13-$N_3$ (2 mM). Dynamic time-sweep rheological experiments indicated gelation ~30 min after mixing, estimated by the crossover point between the elastic (G') and storage moduli (G"), and a final G' of 920±50 Pa and G" of 15±5 Pa at t 5 h (FIG. 12E). To assess changes in network composition in response to free-ion treatment, cycled changes of mass swelling ratios in the presence or absence of calcium were examined. When incubated with $Ca^{2+}$, materials crosslinked with 50 mol % CaM-M13 exhibited a 6.8±1.5% decrease in swollen hydrogel mass, reflecting the overall network constriction and a net loss in equilibrium water retention that accompanied CaM association with M13 (FIG. 12F). Varying the ratio of $N_3$-PEG-$N_3$ to $N_3$-CaM-M13-$N_3$ while keeping their total concentration constant (4 mM) gave materials with scaled responsiveness; hydrogels formed with 0, 25, 50, and 75 mol % CaM-M13 respectively exhibited 1.5±2.3%, 4.1±0.9%, 6.8±1.5%, and 12.4±1.7% $Ca^{2+}$-promoted decrease in mass swelling. Based on Flory-Rehner polymer network theory, which predicts that swelling ratio (Q) of highly swollen materials scales with crosslinking density ($\rho_x$) as $Q \sim \rho_x^{-3/5}$ and shear moduli (G) as $G \sim \rho_x^{6/5}$, $Ca^{2+}$-promoted decrease in swelling observed for the 25, 50, and 75 mol % CaM-M13 respectively resulted in a 8.7±2.0%, 15±3.8%, and 30±4.8% relative hydrogel stiffening. In all cases, initial hydrogel mass was restored following egtazic acid (EGTA)-mediated chelation of free $Ca^{2+}$. Alternate treatments of $Ca^{2+}$ and EGTA gave rise to reproducible material cyclability. It is believed that the extent of hydrogel stiffening could be further tuned by varying the distance change that accompanied the fusion protein's conformational switch, which could be accomplished by varying molecular weight of multi-arm PEG or through addition of spacers between protein binding partners.

Figure 13A:
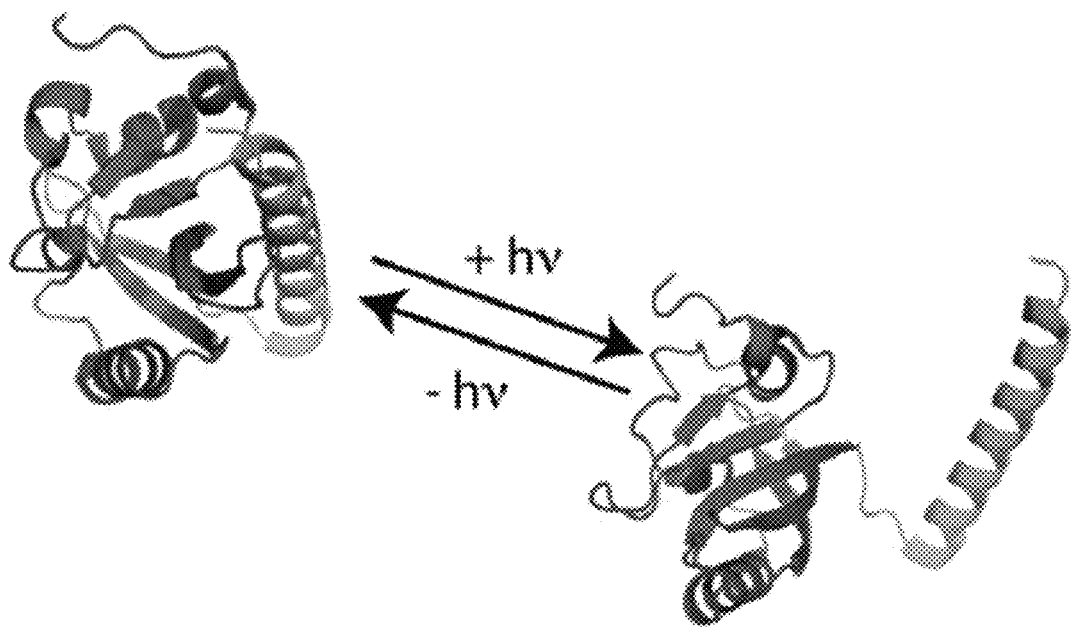
FIGS. 13A-13E are directed to moduli-switchable hydrogels based on LOV2-Jα intramolecular photodisassociation.

The CaM-M13 system proved useful in validating the overall fusion-protein-based approach, its utility in probing cell fate response to cyclic stiffening is influenced by, for example: 1) alterations to network mechanics, which rely on slow molecular diffusion events, decreasing the likelihood of rapid control over material switchability; 2) because calcium signaling is involved in almost all aspects of cellular life, it can be difficult to alter network parameters without also perturbing biological function; and 3) spatial control over network mechanics is not readily possible. To address each of these limitations, the photoswitchable LOV2-Jα binding pair was identified for use as a stimuli-responsive fusion protein. The light, oxygen, and voltage sensing domain 2 (LOV2) is a plant-derived photoreceptor protein with a high binding affinity towards the C-terminal Jα helix. In the presence of blue light (λ=470 nm), LOV2 initiates a photochemical reaction with a flavin mononucleotide chromophore (FMN), forming a covalent linkage between FMN and a critical cysteine residue on LOV2, that results in a displacement of the Jα domain and a large conformational shift (end-to-end changes estimated to be on the order of tens of Angstroms). This change occurs rapidly in response to low levels of blue light, and reverses quickly in the dark (FIG. 13A). As cells were considered fully tolerant to light with wavelengths ≥365 nm, there was no concern over UV-induced DNA damage when visible light sources were employed. That utilization of LOV2-Jα as a hydrogel crosslinker would provide unique photoreversible and spatiotemporal control over hydrogel stiffness in the presence of live cells.

Figure 13B:
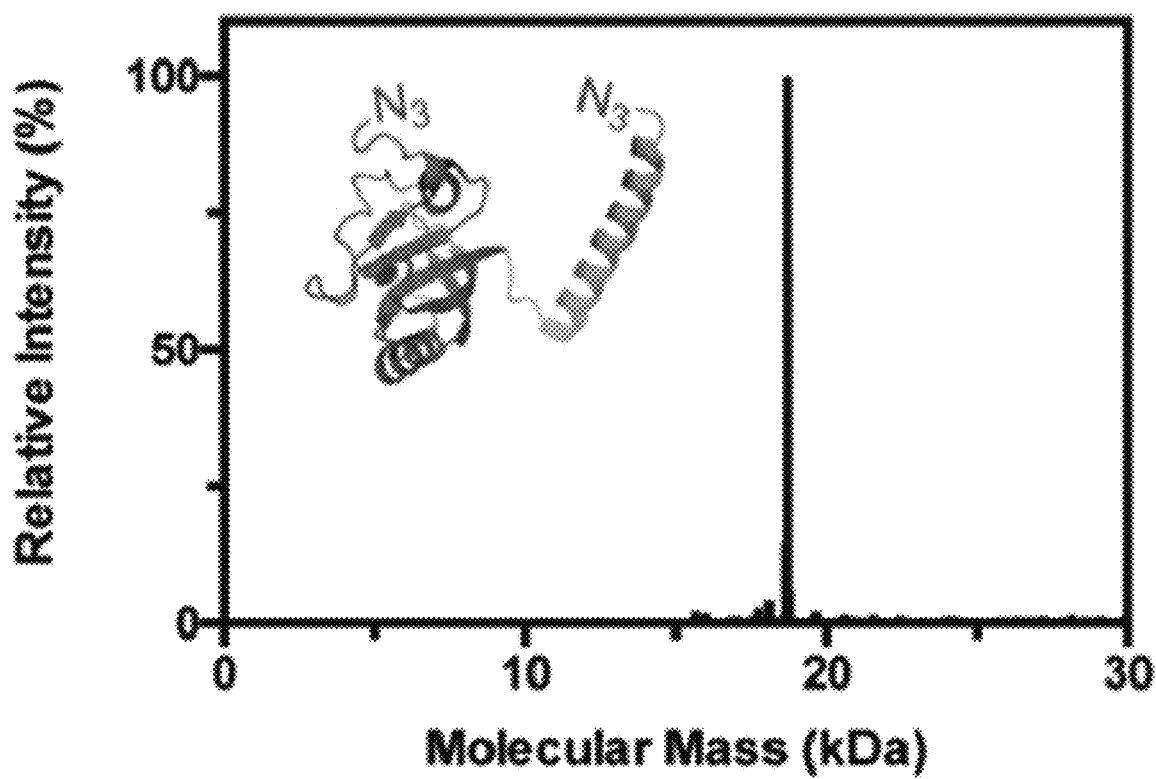
Figure 13C:
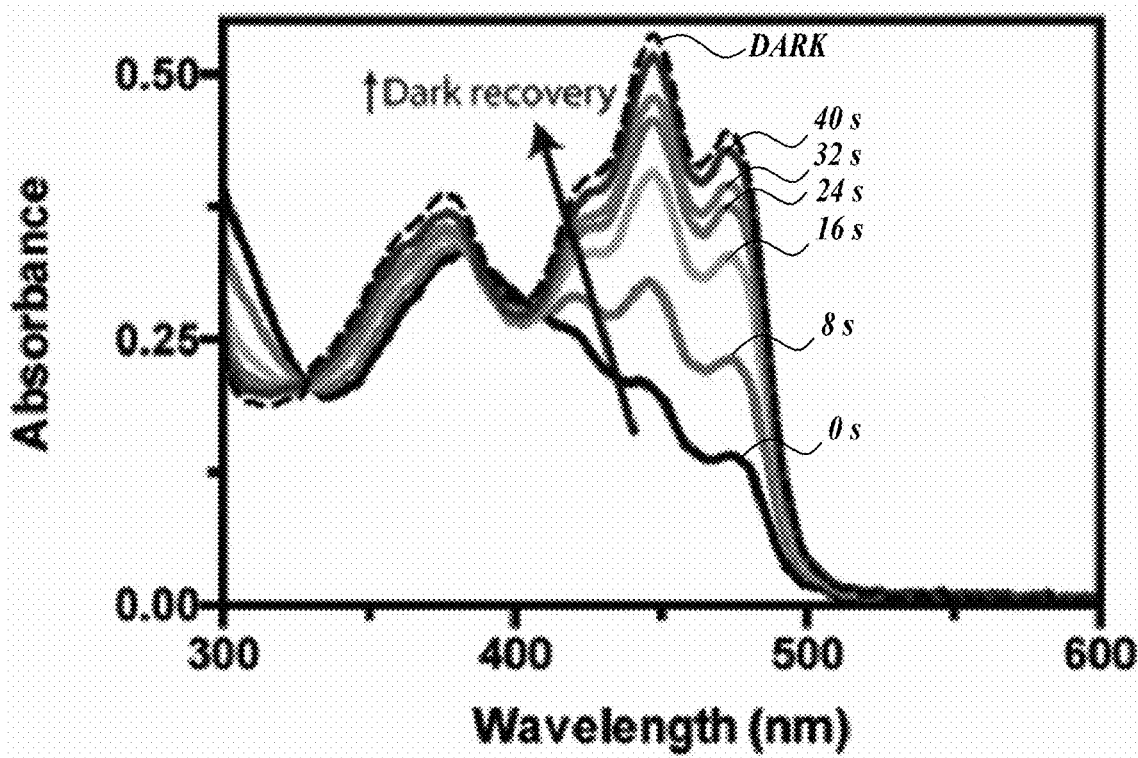
Figure 13D:
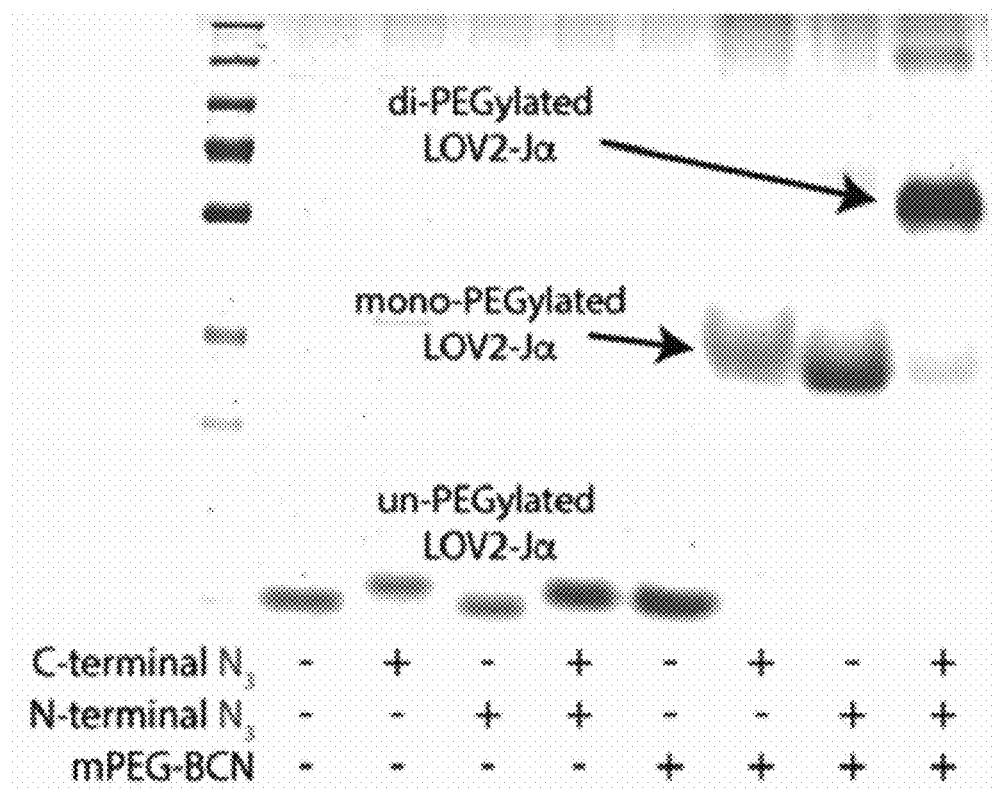

Expression of $N_3$-LOV2-Jα-$N_3$ yielded a pure species with quantitative functionalization, as confirmed by whole-protein mass spectrometry (FIG. 13B); the observed mass for $N_3$-LOV2-Jα-$N_3$ (18,841 Da) correlated well with its expected value (18,848 Da). The diazide protein exhibited the near-instantaneous shift in absorbance in response to blue light (λ=470 nm), followed by a rapid dark recovery ($t_{1/2}$=12±5 s, high standard deviation based on equipment sampling frequency limitations) characteristic to the unmodified LOV2, indicating that the protein was properly folded and that the FMN chromophore survived purification (FIG. 13C). Gel shift assays performed with mPEG-BCN confirmed that azides affixed at both the N- and C-terminus of LOV2-Jα were accessible and maintained reactivity, as well as successful generation of a light-responsive protein-based crosslinker (FIG. 13D).

Figure 13E:
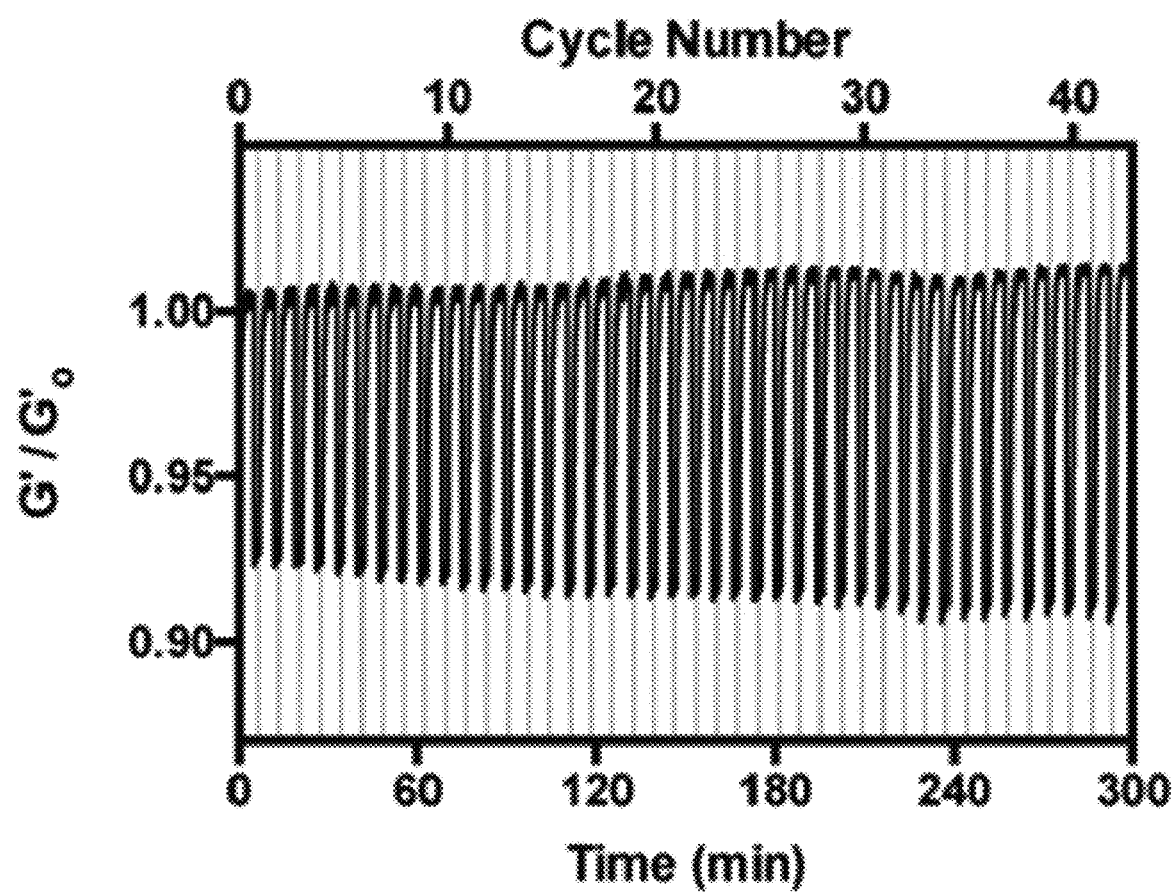

Photoswitchable hydrogels were formed by reaction of PEG-tetraBCN (2 mM), $N_3$—PEG-$N_3$ (2 mM), and $N_3$-LOV2-Jα-$N_3$ (2 mM). In situ rheometry indicated that hydrogels formed on similar timescales and with comparable mechanics as CaM-M13-based materials. Photorheometry studies revealed that fully formed hydrogels exhibited rapid softening ($t_{1/2}$=0.9±0.2 s) in response to mild visible light (λ=470 nm, 10 mW $cm^{-2}$) (FIG. 6). Varying the ratio of $N_3$-PEG-$N_3$ to $N_3$-LOV2-Jα-$N_3$ while keeping their total concentration constant (4 mM) gave materials with scaled responsiveness; hydrogels formed with 0, 25, 50, and 75 mol % LOV2-Jα respectively exhibited 0.0±0.1%, 4±1%, 8±1%, 15±1% photomediated moduli deflation. The softened state was retained until light exposure was ceased, upon which full material recovery was observed ($t_{1/2}$=35±1 s). As expected, the timescale for hydrogel recovery is similar but slightly slower (~3 fold) than that of LOV2's covalent separation from FMN, as presumably some time is required for LOV2-Jα binding partners to re-associate following LOV2's conformational change. Characteristic timescales for material softening and stiffening were statistically indistinguishable for each LOV2-Jα hydrogel composition. LOV2's temporary "bleaching" following exposure at wavelengths used to trigger its conformational change (FIG. 13C) minimized light attenuation and enabled rapid modulation of relatively thick materials. In comparison with reported hydrogels that soften through photoinduced intermolecular dissociation, such as those employing high concentrations of photoactive moieties with large molar absorptivity, LOV2-Jα hydrogels can be uniformly softened throughout the bulk material without inducing surface erosion. By shuttering light exposure to hydrogels, full cyclability was obtained for all materials. Negligible material fatigue was observed for 50 mol % LOV2-Jα hydrogels cycled >40 times over 5 h (FIG. 13E). Such moduli cyclability, made possible by rapid molecular rearrangement events, had not been demonstrated previously with any other biocompatible system.

Figure 7:
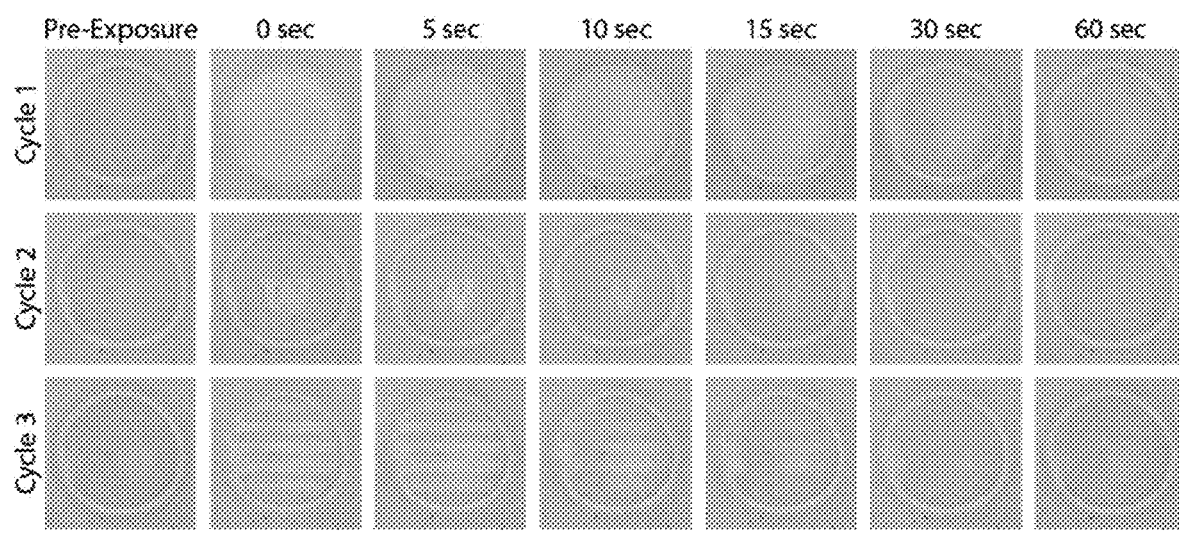
FIG. 7 is a series of photographs showing that a hydrogel of the present disclosure (LOV2-Jα-gels) undergoes reversible stiffness changes based on masked blue light exposure (λ=470 nm, I=20 mW cm$^{-2}$, 30 sec). Photographic images of hydrogels (darker regions=soft, corresponding to light exposed regions; white regions=hard, corresponding to unexposed regions) were taken at different points following cycled light exposure. Full recovery was observed ~1 minute after light exposure was ceased. In particular, mask-based photolithography was used to confine LOV2-Jα gel softening to user-defined physical locations. Following flood light exposure and full recovery (Cycle 1), a single hydrogel was softened in regions corresponding "W." After returning to a uniform stiffness, the hydrogel was softened in interspaced line patterns prior to complete recovery (Cycle 3). Hydrogel diameter ~1 cm, thickness ~200 μm.
Figure 14A:
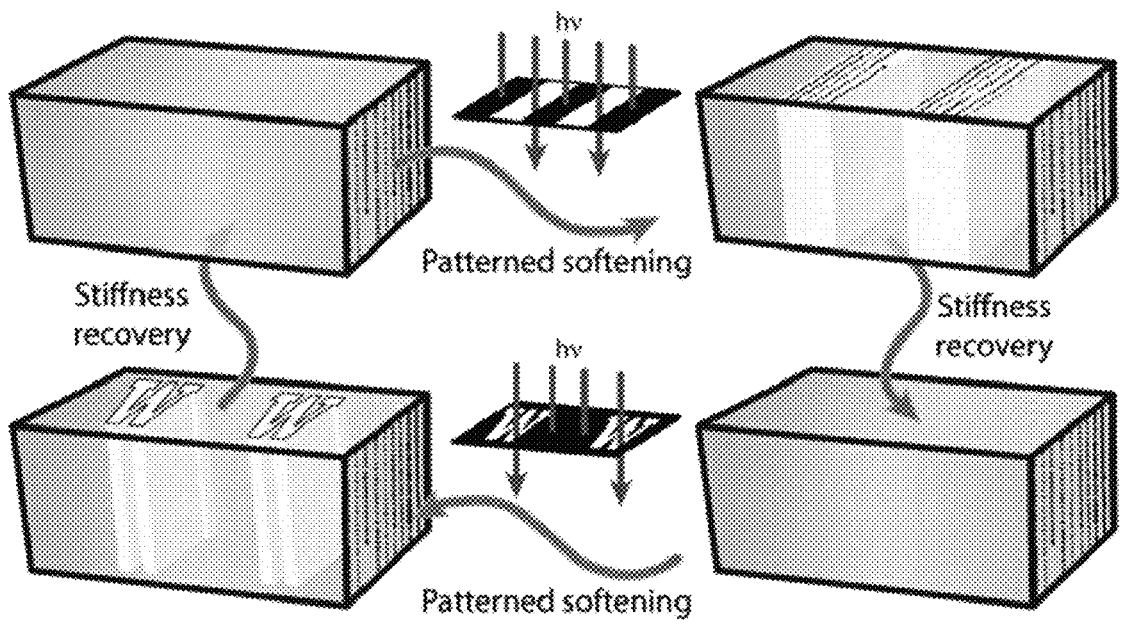
FIGS. 14A-14B illustrate photoreversible and spatiotemporal control over LOV2-Jα hydrogel mechanics.
Figure 14B:
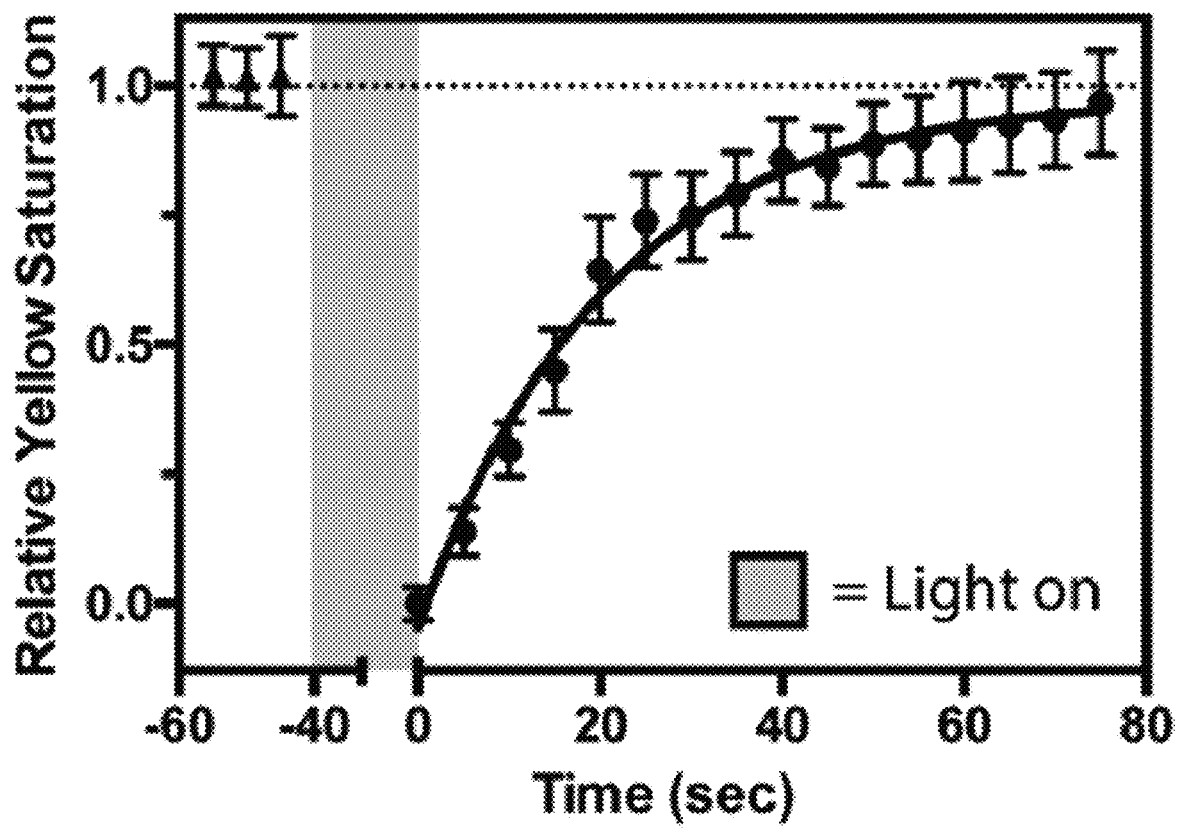

In addition to providing unprecedented temporal and cycled control over matrix properties, directed light exposure could be used to confine LOV2-Jα hydrogel softening to user-defined physical locations (FIG. 14A). As the fast hydrogel transition times and light responsiveness render localized mechanical characterization by many conventional techniques difficult (e.g., atomic force microscopy, nanoindentation, microrheology), the distinct visible color shift that accompanies LOV2 photoactivation was used to monitor local stiffness changes within hydrogels (FIG. 7); stiffer materials where LOV2 was non-covalently bound to FMN but was associated with Jα appear yellow under ambient light, while softer substrates in which LOV2 is covalently bound to FMN and disassociated from Jα were visually clearer. Image analysis of hydrogel color following blue light flood exposure ($\lambda=470$ nm, 1 mW cm$^{-2}$, 30 s) revealed a dark recovery rate ($t_{1/2}=14\pm3$ s, FIG. 14B) consistent with in-solution LOV2-Jα analysis. Patterned regions of hydrogel softening were created by traditional photolithographic techniques, whereby collimated light was shone through a photomask onto the surface of an optically thin sample. Hydrogels were imaged before and after photopatterning; temporary changes in hydrogel color and moduli matched masked-defined shapes (FIG. 7). Upon complete stiffness recovery, sequential patterning was performed using the same hydrogel and a different photomask. Results highlight the platform's unique spatiotemporal control over material compliance as well as its reversibility, where patterning could be repeated many times over to soften different material regions as desired. Furthermore, laser-scanning lithographic techniques enabled hydrogels to be reversibly softened with micron-scale features that approach the size of single cells.

Figure 15A:
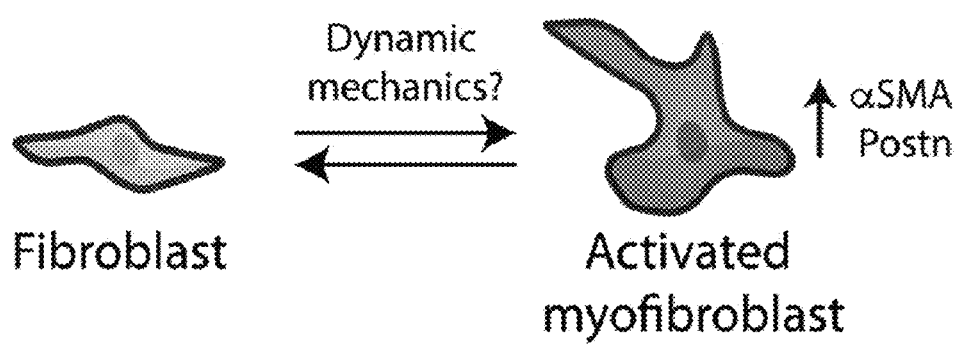
FIGS. 15A-15D illustrate that cyclic mechanical loading drives myofibroblast activation.
Figure 15B:
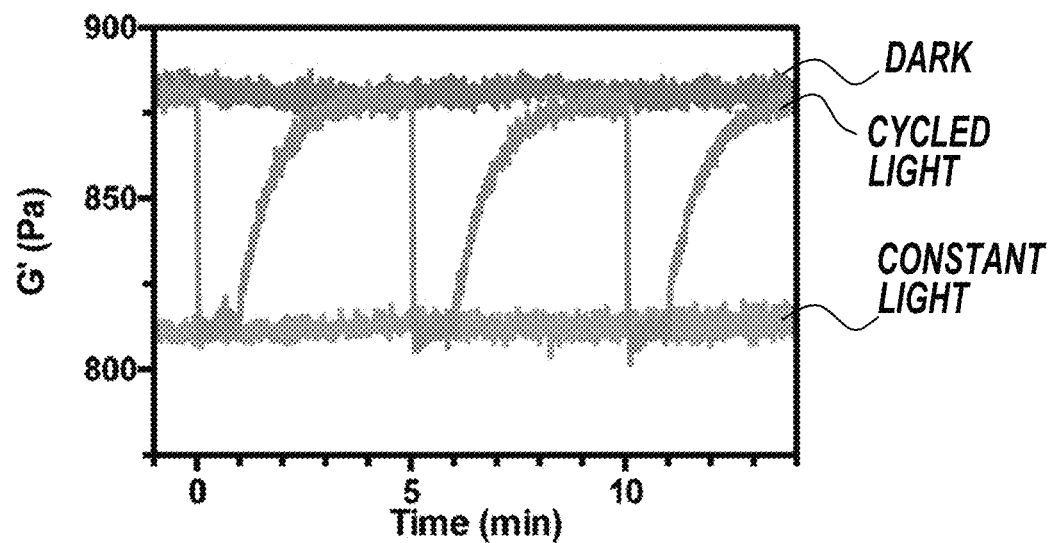
Figure 15C:
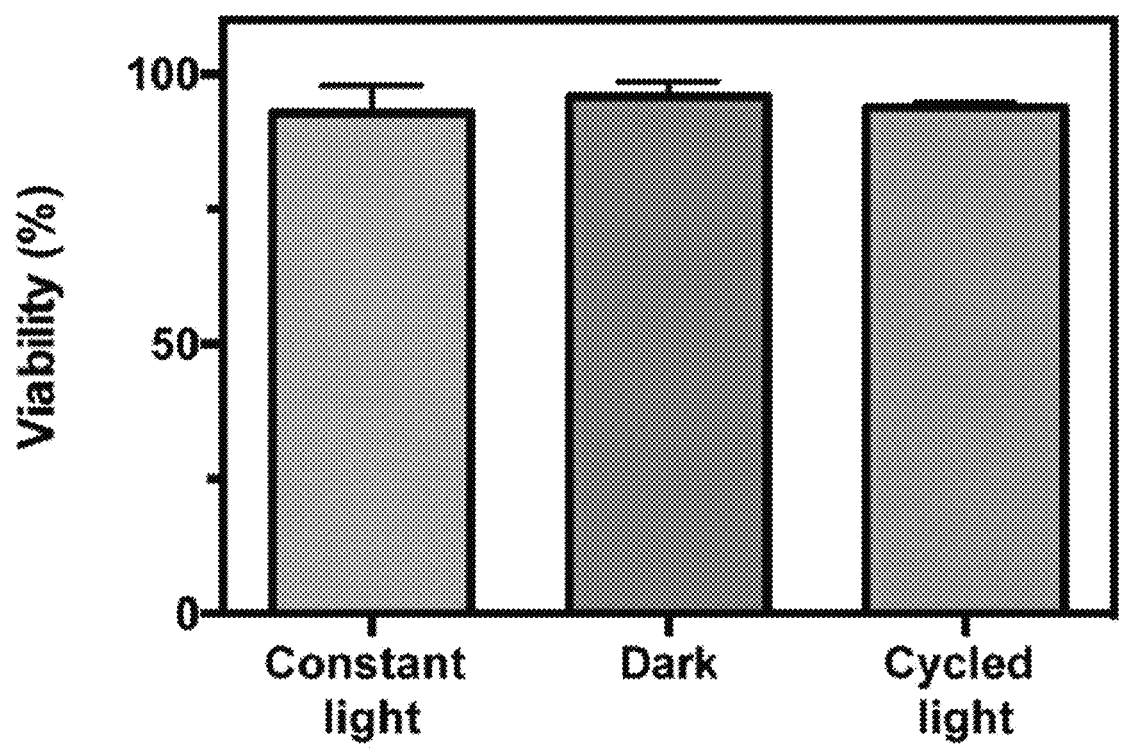
Figure 15D:
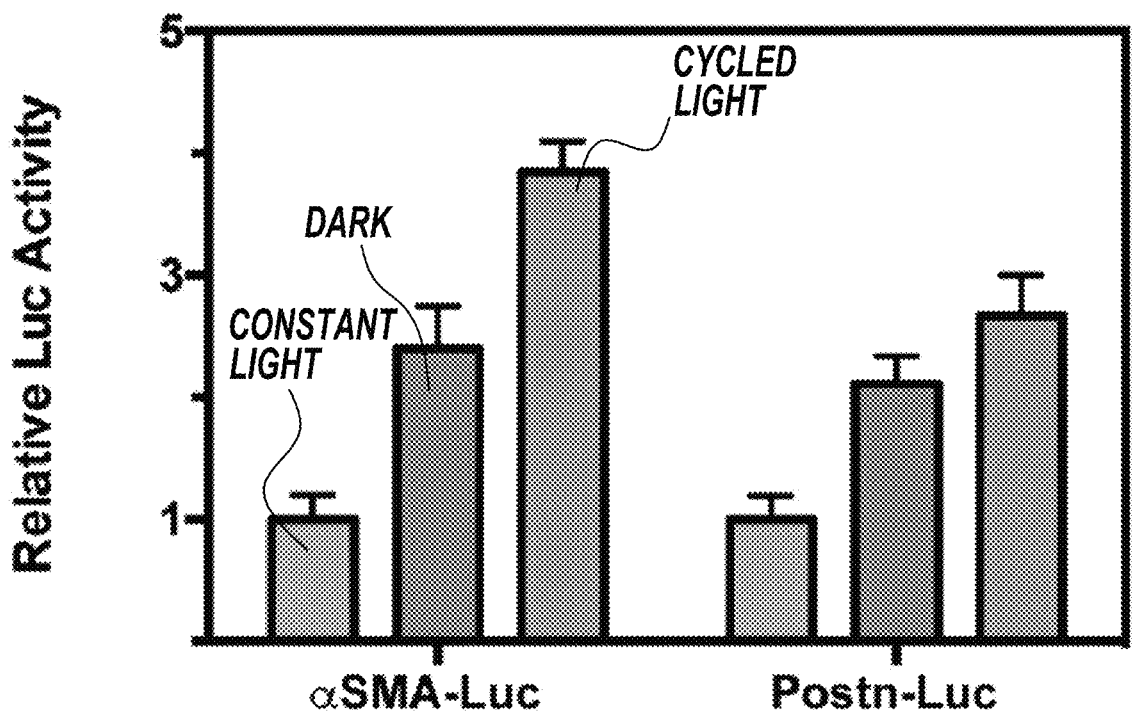

Using the reversibly compliant LOV2-Jα hydrogels of the present example, the role of cyclic mechanical loading on myofibroblast activation in 3D was investigated. Upon injury, fibroblasts transdifferentiate into a myofibroblast phenotype that promotes ECM remodeling. This activation can be regulated chemically through cytokine stimulation as well as through physical interactions with matrix substrates, and is associated with increased smooth muscle α-actin (αSMA) and periostin (Postn) gene expression. Though material stiffness and cyclic stretching of flexible 2D materials can drive changes in enhanced activation, material limitations have prevented investigation of the effects of dynamic mechanical loading on 3D myofibroblast transformation (FIG. 15A). To probe these effects, NIH/3T3 fibroblasts were encapsulated ($5\times10^6$ cells mL$^{-1}$) in 50 mol % LOV2-Jα hydrogels (a composition initially chosen to minimize protein consumption while still yielding materials with robust mechanical tunability) and cultured for 48 h under three different material conditions: 1) continuous flood exposure ($\lambda=470$ nm, 1 mW cm$^{-2}$) giving rise to softer hydrogels; 2) dark culture yielding comparatively stiff materials; and 3) shuttered light exposure (1 min on, 4 min off) providing hydrogels with cycled compliance (FIG. 15B). The extent of softening (~8% of initial moduli) and the dark material recovery rate ($t_{1/2}$~35 s) were similar for hydrogels containing encapsulated cells in culture media (FIG. 15B) or simply swollen in PBS (FIGS. 6 and 13E), indicating that the system functions equally well in the presence or absence of complex biological components. High cell viability (~95%) was observed in all conditions, demonstrating the overall cytocompatibility of hydrogel formation and subsequent photomechanical material alterations (FIG. 15C). To determine the effects of each culture condition on fibroblast-to-myofibroblast differentiation, the associated changes in luciferase activity of fibroblasts transfected with an αSMA-luciferase transcriptional reporter plasmid were quantified (FIG. 15D). Significant changes in αSMA transcriptional activity was observed for cells cultured between "stiff" and "soft" materials. Interestingly, myofibroblast activation was further enhanced within reversibly stiffening hydrogels. This activating effect was reconfirmed by Western blot analysis of untransfected fibroblasts for expression of αSMA relative to housekeeper protein GAPDH. The observed effects were further confirmed using fibroblasts transfected with a Postn-luciferase transcriptional reporter plasmid, which acts as an additional transcriptional surrogate of myofibroblast differentiation. These findings were further substantiated by studies in 2D, where fibroblasts seeded on silicon membranes and subjected to cyclic stretching exhibited enhanced activation. Observed differences in 3D fibroblast transdifferentiation motivate further investigation, whereby differences in anisotropic cyclic mechanical loading are believed to play a large role in regulating powerful, yet largely unexplored, biological phenomena.

The results described here illustrate a generalizable strategy to create biomaterials whose mechanics can be cycled in response to user-defined inputs. Through the first demonstrated dual-chemoenzymatic modification of a recombinant protein, fusion species exhibiting stimuli-dependent intramolecular association were created that can be used as the basis for step-growth polymerization of hydrogels. Implementation of the technique with the photoactive LOV2 protein yielded unprecedented reversible and spatiotemporal control over network dynamics, newly capturing critical aspects of the cellular microenvironment. These unique materials were used to investigate 3D biological response to cyclic loading, an important aspect of native ECM that has not been previously replicated in vitro. This approach can provide a new dimension to the growing field of mechanobiology, and can useful in the creation of a wide variety of protein-based and stimuli-responsive materials for applications such as tissue engineering and drug delivery.

Synthesis and Purification of End-Functionalized Stimuli-Responsive Fusion Proteins Plasmids encoding for CaM-M13 and LOV2-Jα, flanked with an N-terminal NMT- and a C-terminal sortase-recognition peptide sequence (GNEASYPL [SEQ ID No.: 1] and LPETG [SEQ ID No.: 9], respectively), were constructed using standard cloning techniques and each co-transformed with those encoding for NMT/methionine aminopeptidase (Met-AP) into BL21(DE3) *E. coli* (Thermo Fisher). Successful co-transformants were grown at 37° C. in lysogeny broth containing ampicillin (100 μg mL$^{-1}$) and kanamycin (50 μg mL$^{-1}$). After reaching an optical density of 0.6 ($\lambda=600$ nm), isopropyl β-D-1-thiogalactopyranoside was added (final concentration of 0.5 mM) to induce expression. Expression was carried out with or without 12-ADA (final concentration of 140 mg L$^{-1}$) overnight under reduced temperature (18° C.). Cells were harvested via centrifugation and lysed by sonication. Clarified lysate was loaded onto HisPur Ni-NTA resin (ThermoFisher), which was washed (20 mM Tris, 50 mM NaCl, 20 mM imidazole) to remove unbound proteins. Following treatment of the resin with triglycine or an azide-containing polyglycine probe (20×, 4 h, 37° C.), sortagged proteins were eluted and purified by dialysis (molecular weight cut-off, MWCO~10 kDa). Protein identity and purity was confirmed by liquid chromatography-tandem mass spectrometry, sodium dodecyl sulfate polyacrylamide gel electrophoresis, and gel shift analysis. Ultraviolet absorption (λ=280 nm) and bicinchoninic acid assays were used to determine protein concentrations prior to use. Purified proteins remained stable for several weeks, based on their ability to form responsive hydrogels, when kept refrigerated (4° C.) in phosphate buffered saline (PBS, pH=7.4).

Assessing $Ca^{2+}$-Dependent Conformational Changes of CaM-M13:

Far-UV circular dichroism (CD) measurements were performed on a Jasco 720 CD spectrophotometer (1 mm path length, quartz cuvette) purged with nitrogen gas from 200≤λ≤250 nm (scan rate=100 nm $min^{-1}$). Spectra were recorded for $N_3$-CaM-M13-$N_3$ (0.025 mg $mL^{-1}$) in buffer (20 mM Tris, 30 mM KCl) supplemented with either calcium (1 mM $CaCl_2$) or EGTA (1 mM), and were normalized against protein-free controls.

Determining Extent of Protein Chemoenzymatic Modifications:

To assess the ability for sortase and NMT to generate homogenous protein samples with quantitative reactivity, an SDS-PAGE gel shift assay was performed for each purified protein species (CaM-M13, CaM-M13-$N_3$, $N_3$—CaM-M13, $N_3$—CaM-M13-$N_3$, LOV2-Jα, LOV2-Jα-$N_3$, $N_3$-LOV2-Jα, $N_3$-LOV2-Jα-$N_3$). Following reaction (24 h at 37° C.) with mPEG-BCN (100×) in buffer (20 mM Tris, 50 mM NaCl, 20 μL), denatured proteins (1 μg) were separated electrophoretically in polyacrylamide gels and visualized by Coomassie Brilliant Blue (Thermo Fisher) staining.

Step-Growth Polymerization of Protein-Polymer Hydrogels:

Protein-polymer hydrogels were formed by SPAAC between PEG-tetraBCN (2 mM) and diazide crosslinking species in PBS (pH=7.4). The diazide crosslinker mixture (4 mM total) was comprised of modified fusion proteins ($N_3$—CaM-M13-$N_3$ or $N_3$-LOV2-Jα-$N_3$, 0-3 mM) and a balance of $N_3$-PEG-$N_3$ (1-4 mM) to yield hydrogels with 0, 25, 50 or 75 mol % protein crosslinker content. Upon component mixing, gelation was permitted to proceed for 2 hours between Rain-X®-treated glass slides (500 μm spacing) prior to slide separation and subsequent equilibration in PBS. For cell-laden hydrogel formation, PEG-tetraBCN was pre-reacted (1 h) with $N_3$-GRGDS-$NH_2$ [SEQ ID No.: 11] (0.5 mM final in-gel concentration) prior to mixture with crosslinking species and cells in culture media. Protein-polymer hydrogels based on CaM-M13 and LOV2-Jα each remained fully stable after two weeks of storage in cell culture media at 37° C., indicating that the PEGylated protein crosslinkers are not particularly prone to hydrolytic or enzymatic degradation.

Mechanical Testing of Protein-Polymer Hydrogels:

In situ rheological experiments were performed on optically thin (50 μm) protein-polymer hydrogels formed between parallel quartz plates (8-mm diameter). The rheometer (Discovery HR-2, TA Instruments) was outfitted with a collimated blue light source (λ=470 nm, 10 mW $cm^{-2}$, ThorLabs) whose exposure was shuttered with an automated controller (NEARPOW) in experiments investigating the light-responsiveness of LOV2-Jα hydrogels. The storage and loss moduli (G' and G", respectively) were measured by oscillatory rheology at constant strain (1%) and frequency (1 rad $s^{-1}$), conditions determined to fall within the linear viscoelastic region of the hydrogels. A thin coating of mineral oil around hydrogel perimeter was employed to prevent evaporation during measurements.

$Ca^{2+}$-Dependent Changes in CaM-M13 Hydrogel Swelling:

CaM-M13 hydrogels (0-75 mol % protein content) were equilibrated in buffer (20 mM 4-(2-hydroxyethyl)-1-piperazineethanesulfonic acid, 50 mM NaCl), alternating between that supplemented with $CaCl_2$ (1 mM, 4 h) or EGTA (1 mM, 8 h) to cycle hydrogel swelling. Fractional mass changes, defined as the change in swollen hydrogel mass relative to that of the initial swollen hydrogel, were determined for each hydrogel type after full equilibration and immediately preceding buffer exchange.

Spatiotemporal Control of Reversible Hydrogel Softening:

50 mol % LOV2-Jα hydrogels were exposed to collimated blue light (λ=470 nm, 1 mW $cm^{-2}$, 30 s) through a patterned chrome photomask (Photo Sciences, Inc.). Hydrogels were visualized before and immediately after light exposure through time-lapse videography using a digital camera (Nikon). Image analysis of hydrogel color following flood light exposure (λ=470 nm, 1 mW $cm^{-2}$, 30 s) was performed (ImageJ) to determine yellow saturation content (interval=5 s).

3T3 Fibroblast Cell Culture:

Unmodified and transfected NIH 3T3 fibroblast cells were cultured in Dulbecco's Modified Eagle's Medium (DMEM) supplemented with fetal bovine serum (10%, Corning) and penicillin/streptomycin (1%, Corning) in a 5% $CO_2$ atmosphere at 37° C. Culture medium was changed every two to three days, and cells were passaged at ~90% confluency. Following trypsinization, fibroblasts were encapsulated ($5 \times 10^6$ cells $mL^{-1}$) in 50 mol % LOV2-Jα hydrogels modified with $N_3$-GRGDS-$NH_2$ [SEQ ID No.: 11] (0.5 mM).

Cell Responses to Reversible Matrix Stiffness Modulation:

NIH/3T3 fibroblasts were transfected with an αSMA-luciferase and Postn-luciferase promoter plasmids. Transfection conditions (1.66 μg DNA/μL Lipofectamine 3000) were selected so as to maximize transfection efficiency (here, 65%) while retaining cell morphology and health. Transfected NIH/3T3 fibroblasts were encapsulated ($5 \times 10^6$ cells $mL^{-1}$) in 50 mol % LOV2-Jα hydrogels in three polystyrene 24-well cell culture plates (Corning) under three different material conditions: 1) continuous flood exposure (λ=470 nm, 1 mW $cm^{-2}$) giving rise to softer hydrogels; 2) dark culture yielding comparatively stiff materials; and 3) shuttered light exposure (1 min on, 4 min off). After cultured maintenance of these light exposure conditions for 48 h, samples were ground with a mortar and pestle and resuspended in lysis buffer (50 μL, 1% Triton, 100 mM Tris-HCl, 2 nM EDTA, 2 mM DTT) prior to luciferase analysis (Pierce Firefly Luciferase Glow Assay, Thermo Fisher). Luciferase activity was measured in triplicate for each material condition.

Example 2. Bioactive Site-Specifically Modified Proteins for 4D Patterning of Hydrogel Biomaterials Protein-modified biomaterials can be used to modulate cellular function in 3D. However, as dynamic heterogeneous control over complex cell physiology continues to be sought, strategies that permit reversible and user-defined tethering of fragile proteins to materials remain in great need. In this Example, a modular and robust semisynthetic approach to reversibly pattern cell-laden hydrogels with site-specifically modified proteins is presented. Exploiting a versatile sortase-mediated transpeptidation, a diverse library of homogenous, singly functionalized proteins with bioorthogonal reactive handles for biomaterial modification was generated. The photoreversible immobilization of fluorescent proteins, enzymes, and growth factors to hydrogels was demonstrated, with excellent spatiotemporal resolution while retaining native protein bioactivity. Dynamic regulation of proliferation, intracellular mitogen-activated protein kinase signaling, and subcellularly resolved receptor endocytosis was accomplished through localized epidermal growth factor presentation. The method presented herein broadly permits modification and patterning of a wide range of proteins, providing newfound avenues to probe and direct advanced cellular fates in 4D.

Figure 16A:
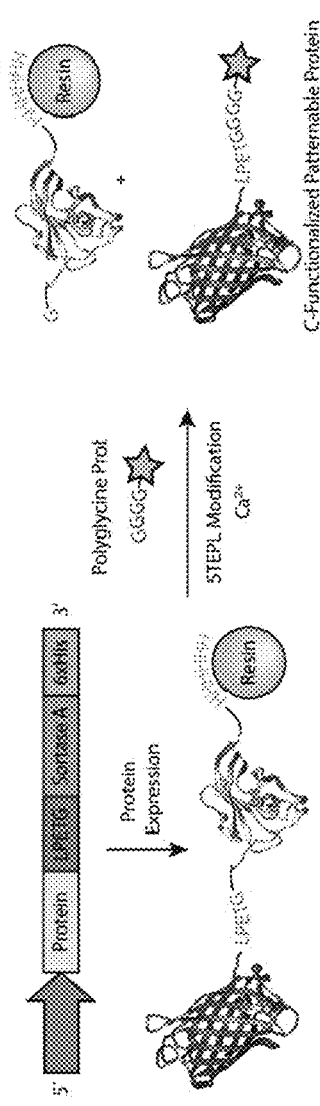
FIGS. 16A-16H are directed to the generation of sortagged protein library for biomaterial modification.

To facilitate one-step protein biofunctionalization and purification, sortagging through the recently developed Sortase-Tag Enhanced Protein Ligation (STEPL) technique was implemented (FIG. 16A). In STEPL, the protein of interest, sorting sequence LPETG [SEQ ID No.: 9], (GGS)$_5$ flexible linker [SEQ ID No.: 12], sortase A, and a 6×His-Tag are fused into a single protein construct which is recombinantly expressed. The flexible (GGS)$_5$ linker [SEQ ID No.: 12] allows intramolecular sortagging through the encoded LPETG motif and the fused sortase domain. The sortase-LPETG intermediate is displaced by the addition of calcium and a customizable probe with an N-terminal polyglycine moiety, ligating the protein of interest to the engineered peptide while simultaneously separating it from the remaining 6×His-functionalized sortase A. This step can be performed during immobilized metal ion affinity chromatography, where sortase A remains bound to the nickel-nitrilotriacetic acid (Ni-NTA) column, allowing for site-specific labeling and purification of proteins in a single step.

Figure 16B:
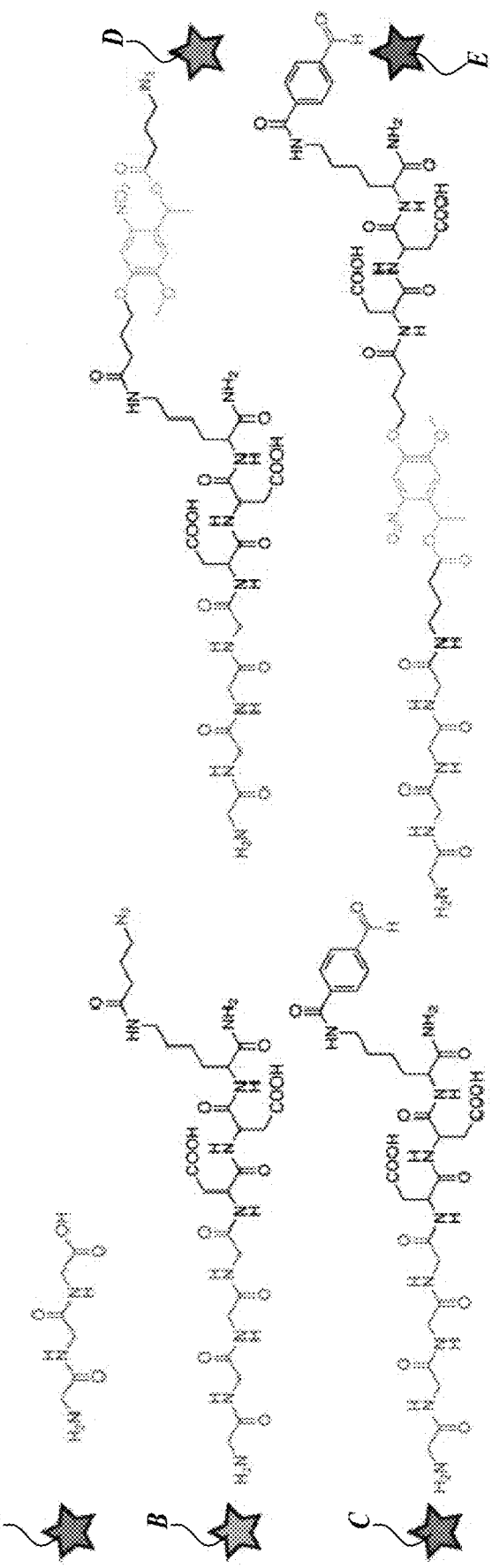
Figure 16C:
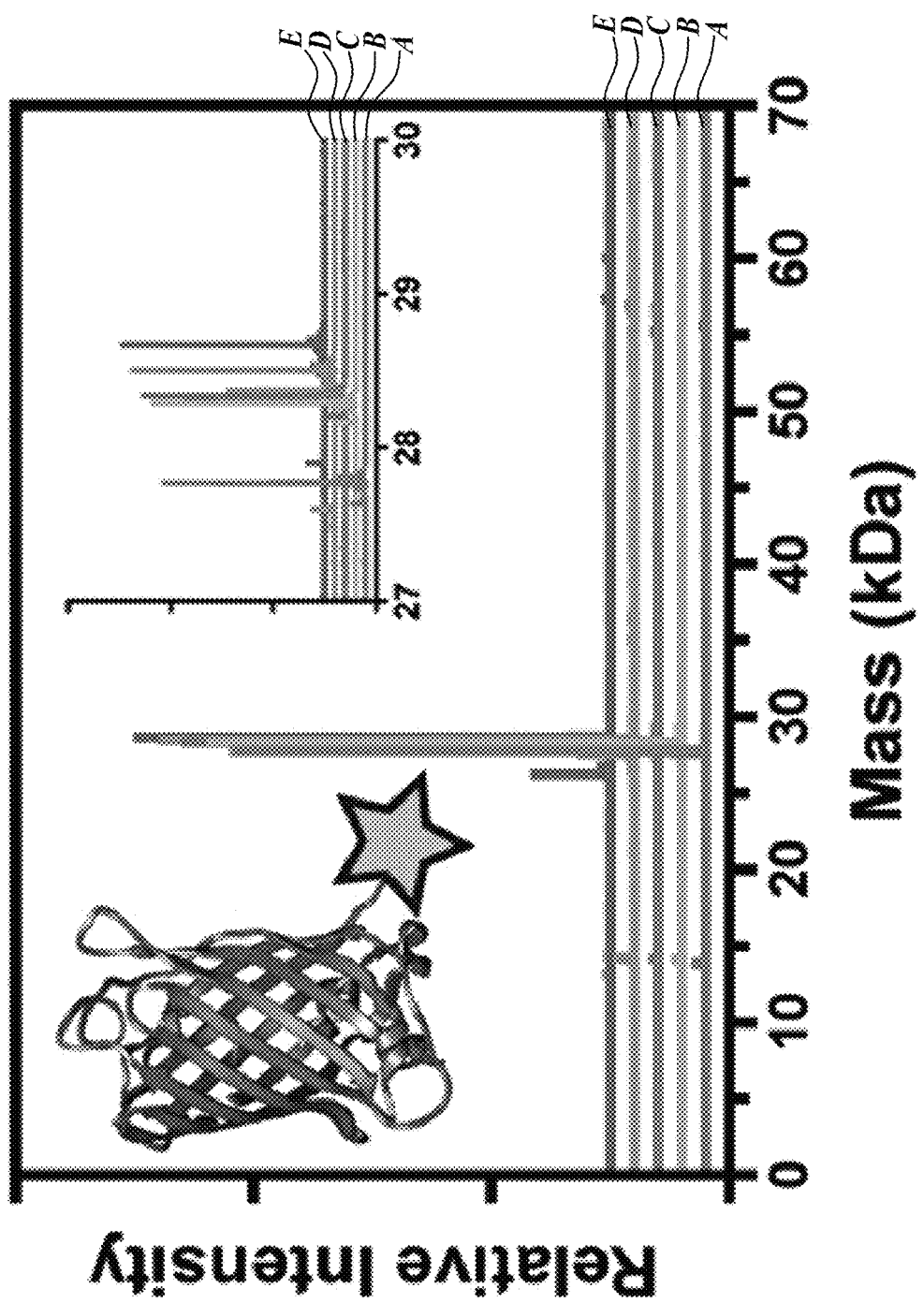
Figure 16D:
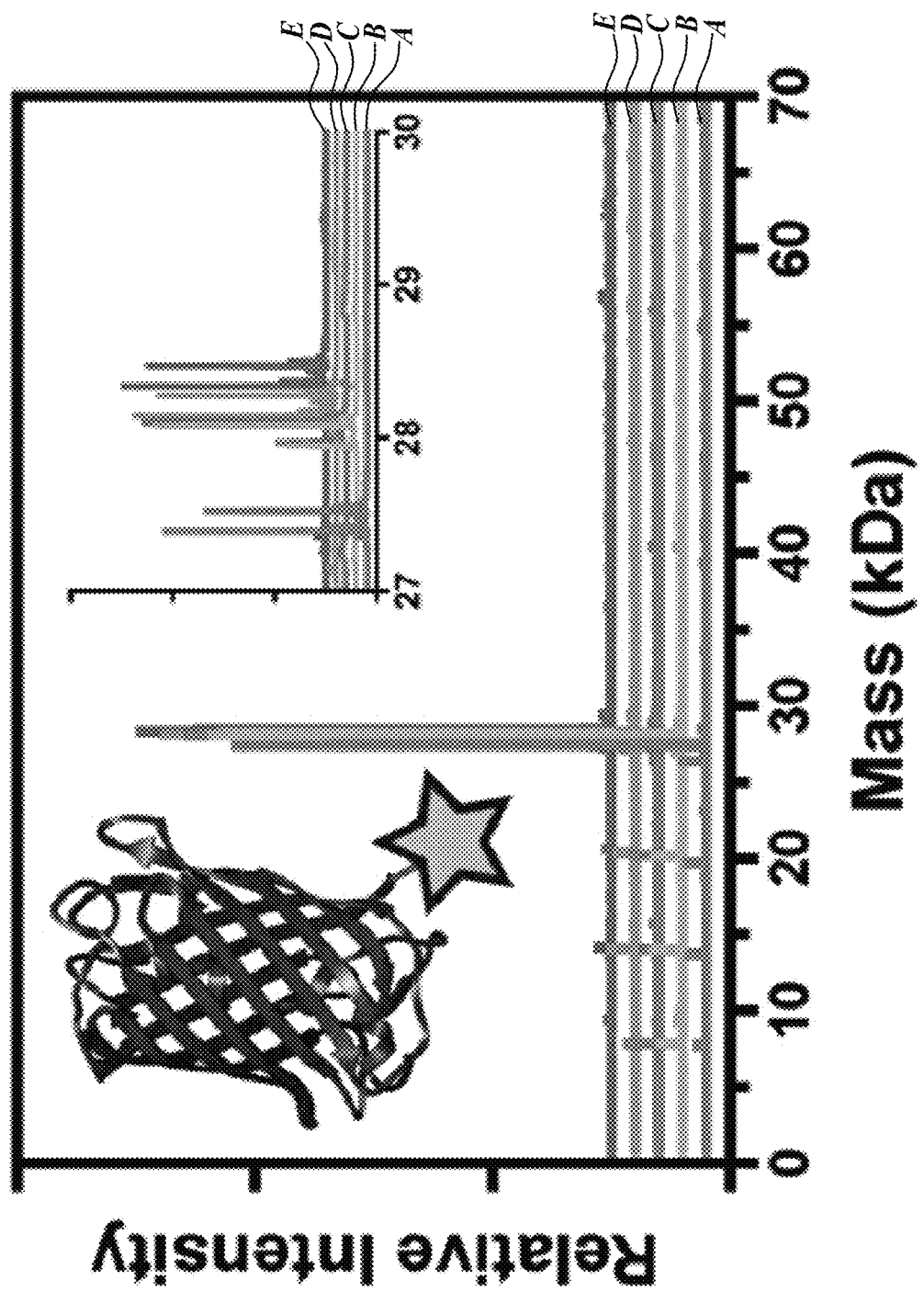
Figure 16E:
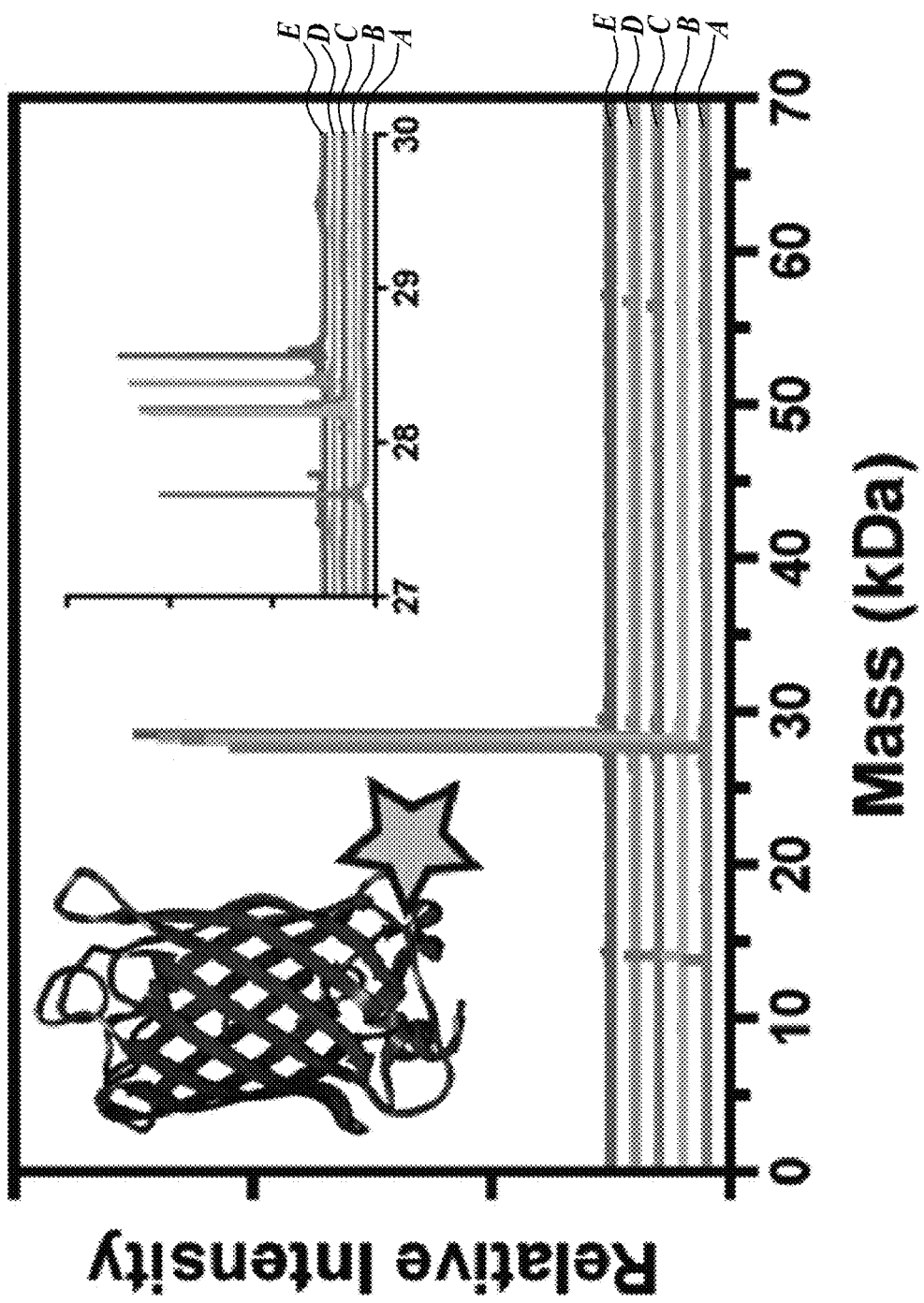
Figure 16F:
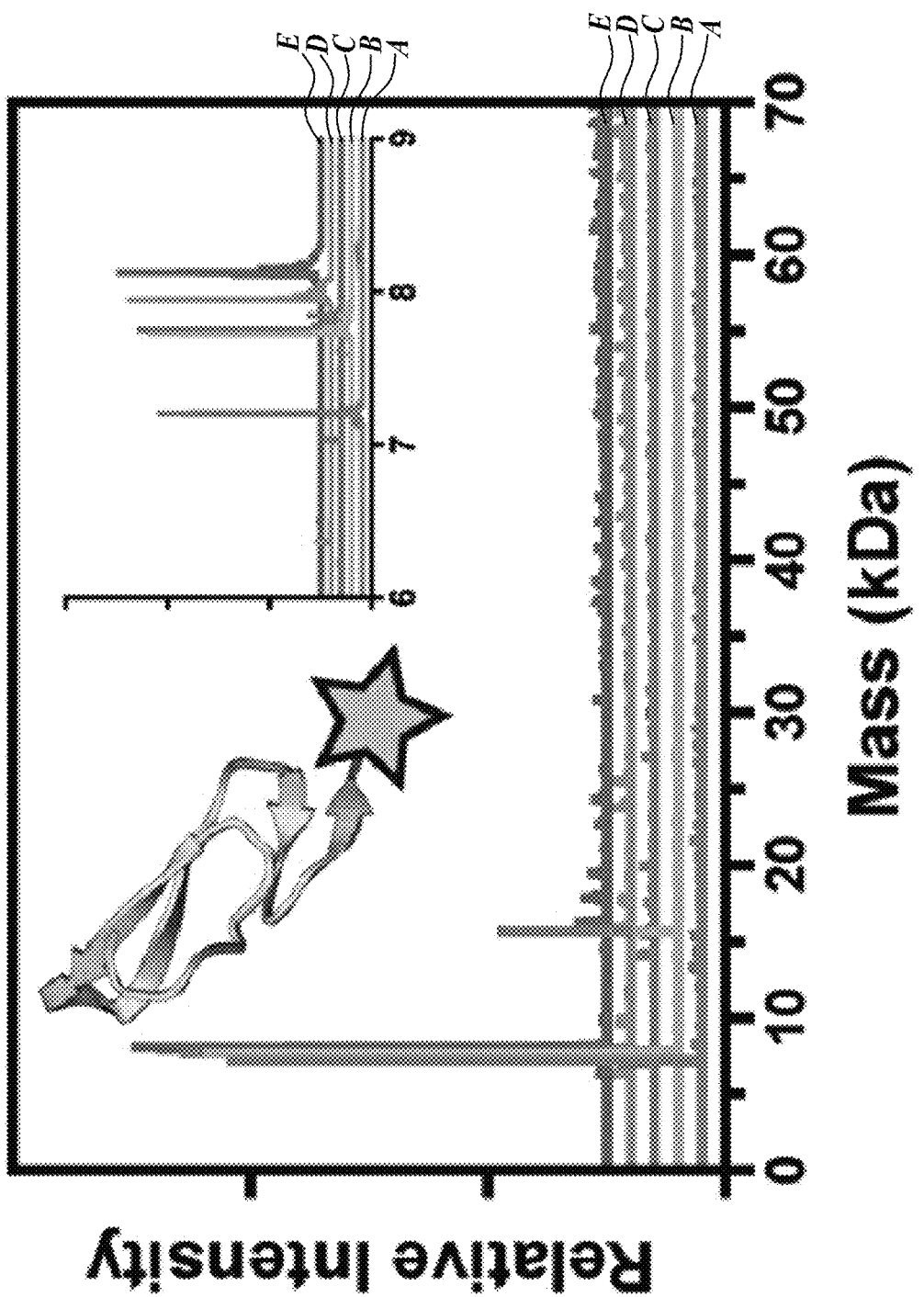
Figure 16G:
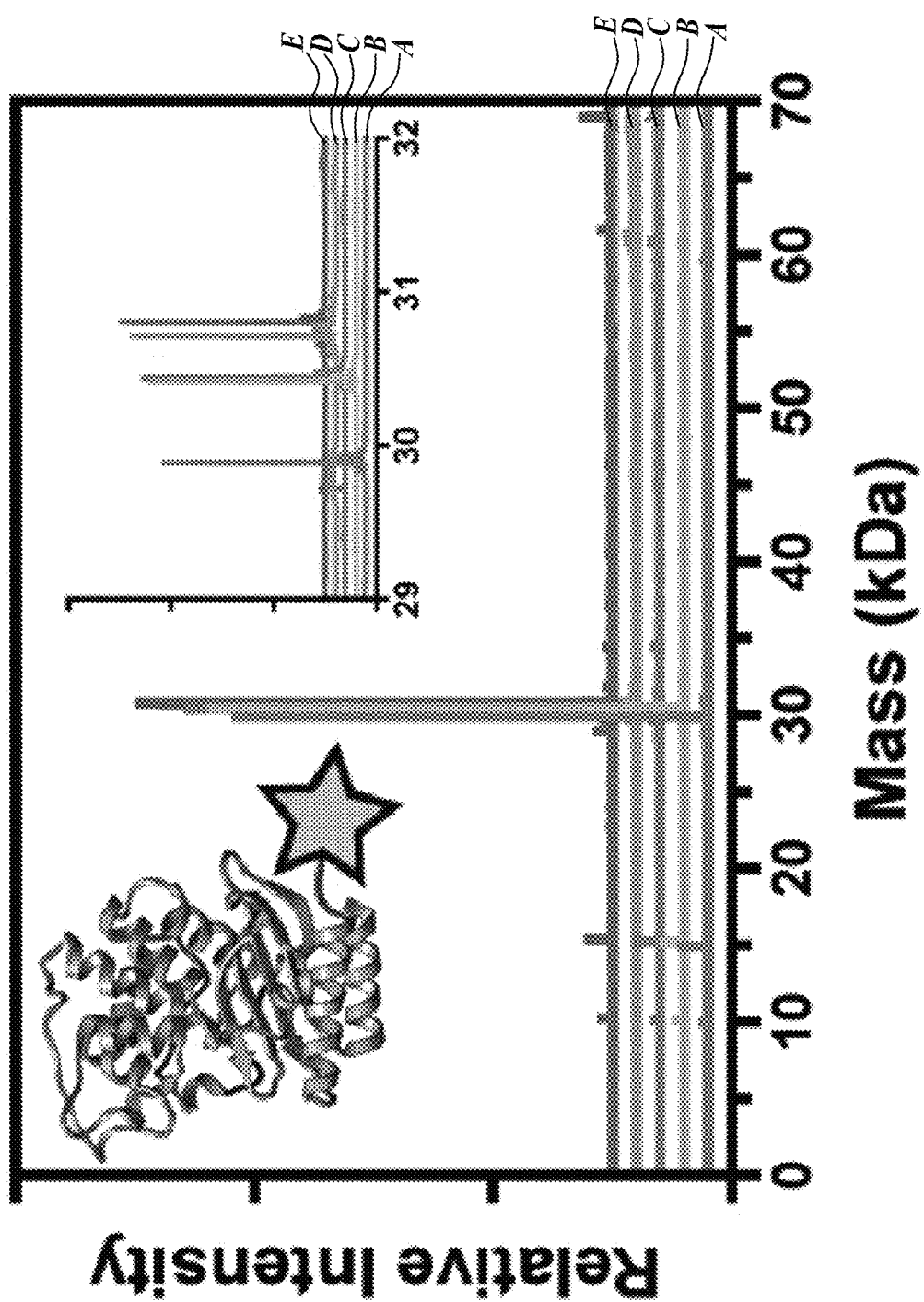
Figure 16H:
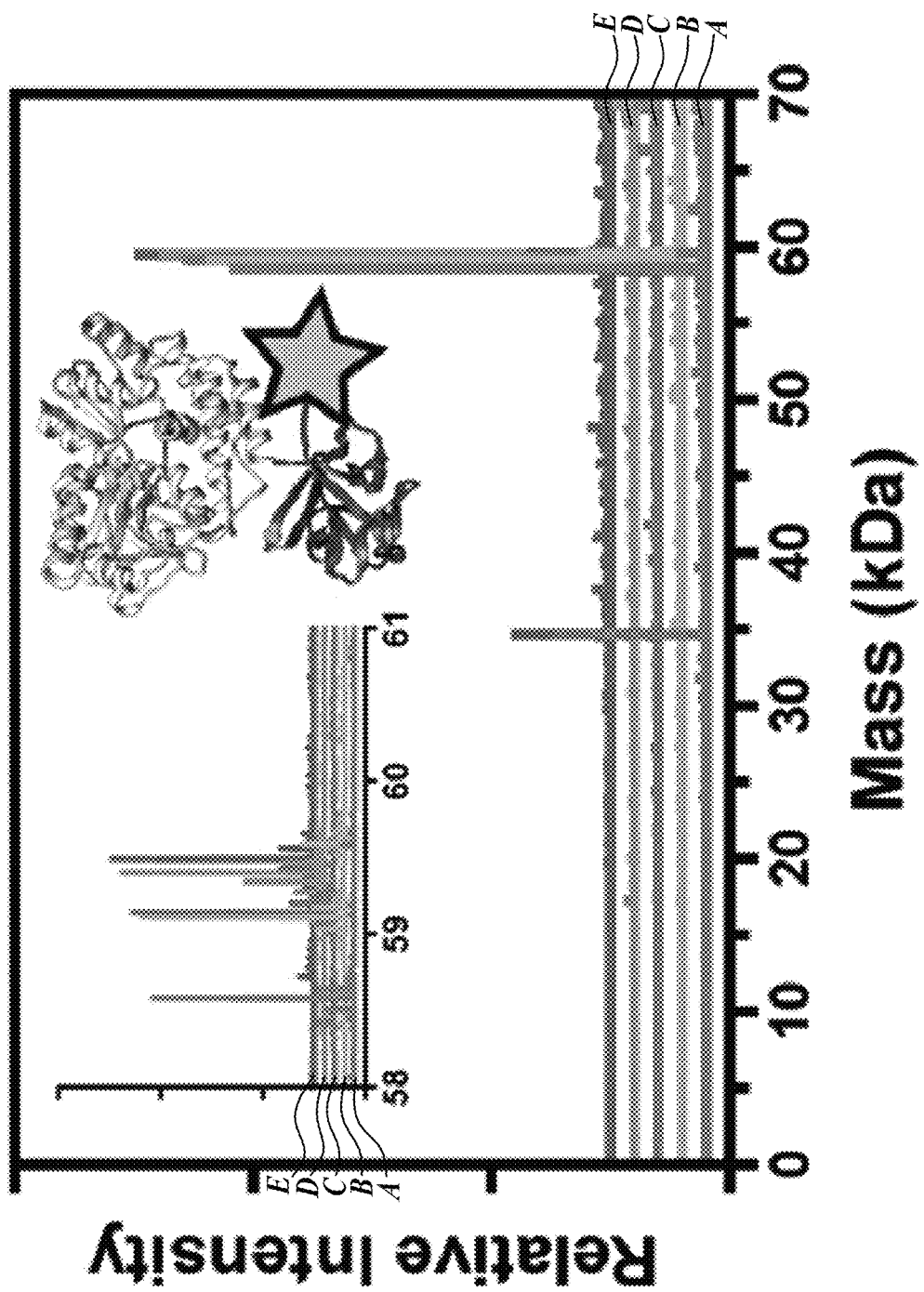
Figure 17A:
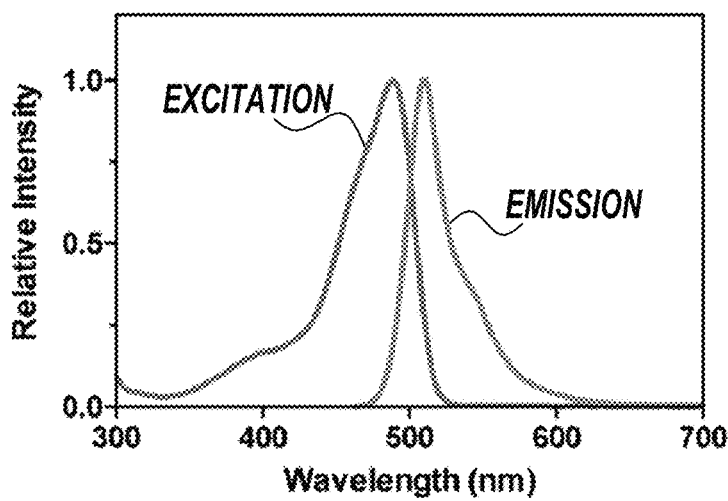
FIGS. 17A-17O compare the activity of differently modified proteins.
Figure 17B:
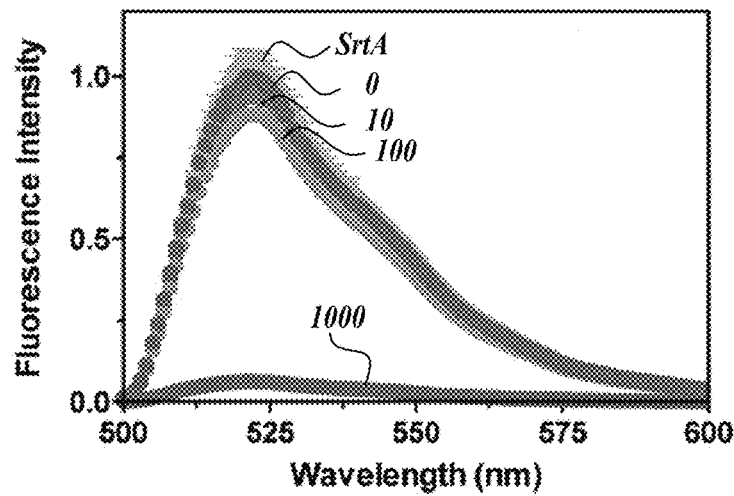
FIG. 17B is a graph comparing bioactivity for proteins azide-tagged by STEPL with H-GGGGDDK(N$_3$)—NH$_2$ [SEQ ID No.: 3] or by conventional NHS labeling with varying molar excesses of N$_3$—OSu (0, 10, 100, 1000×). Fluorescence emission spectra was determined for modified EGFP ($\lambda_{excitation}$=470 nm).
Figure 17C:
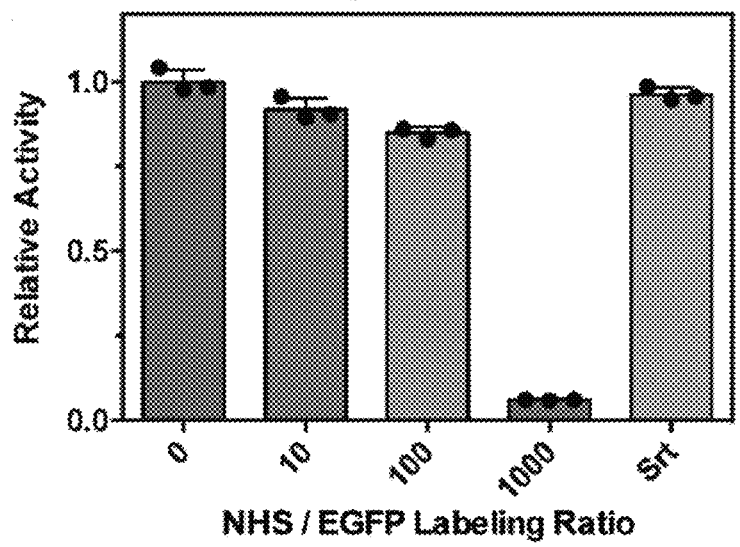
FIG. 17C is a graph comparing bioactivity for proteins azide-tagged by STEPL with H-GGGGDDK(N$_3$)—NH$_2$ [SEQ ID No.: 3] or by conventional NHS labeling with varying molar excesses of N$_3$—OSu (0, 10, 100, 1000×). Increasing NHS modification led to a decrease in EGFP emission ($\lambda_{excitation}$=470 nm, $\lambda_{emission}$=530 nm), while sortagged EGFP retained native-like fluorescence.
Figure 17D:
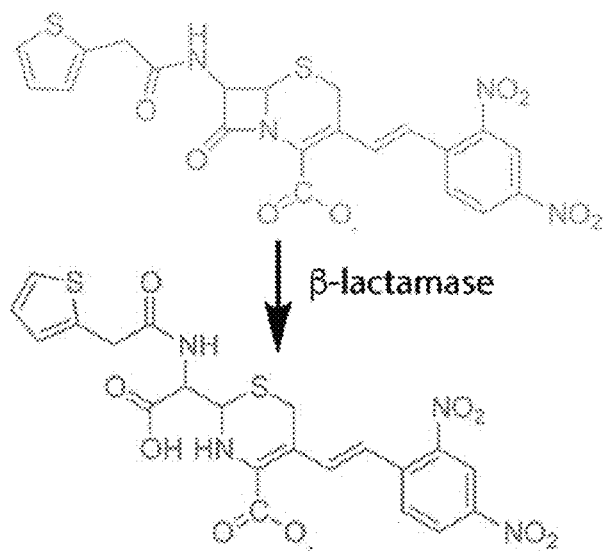
FIG. 17D is a drawing of the chemical structure of bla, where bla activity was determined by its ability to degrade a chromogenic nitrocefin substrate, which changes from yellow to red upon β-lactam cleavage.
Figure 17E:
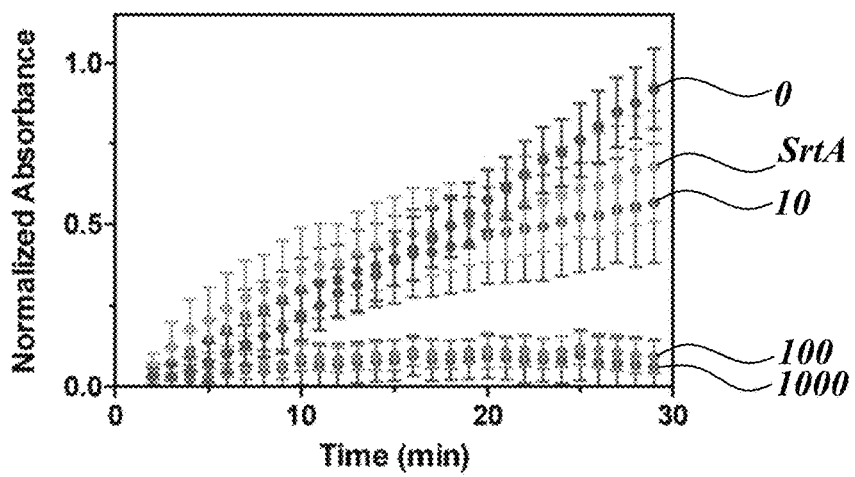
FIG. 17E is a graph comparing bioactivity for proteins azide-tagged by STEPL with H-GGGGDDK(N$_3$)—NH$_2$ [SEQ ID No.: 3] or by conventional NHS labeling with varying molar excesses of N$_3$—OSu (0, 10, 100, 1000×). Time-course spectrophotometric analyses ($\lambda_{abs}$=386 nm) indicate nitrocefin degradation for NHS-modified and sortagged bla.
Figure 17F:
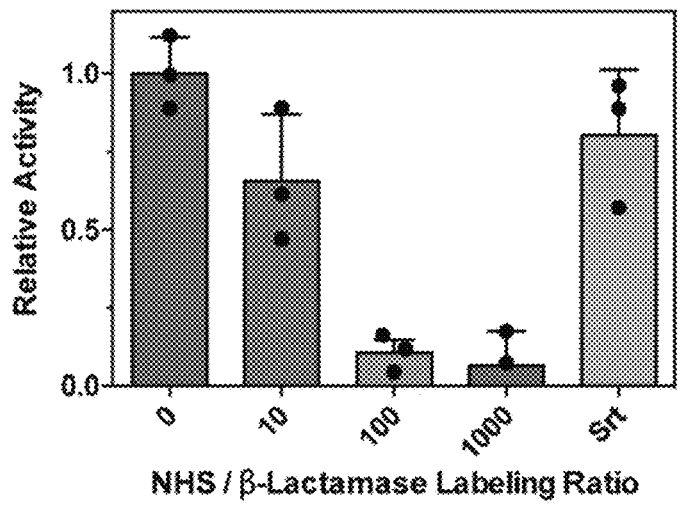
FIG. 17F is a graph comparing bioactivity for proteins azide-tagged by STEPL with H-GGGGDDK(N$_3$)—NH$_2$ [SEQ ID No.: 3] or by conventional NHS labeling with varying molar excesses of N$_3$—OSu (0, 10, 100, 1000×). Sortagged and unmodified bla exhibited statistically indistinguishable levels of bioactivity, as indicated by similar values for $k_{cat}$. Bla displayed high sensitivity to NHS labeling, likely due to the presence of a critical lysine residue in its active pocket.
Figure 17G:
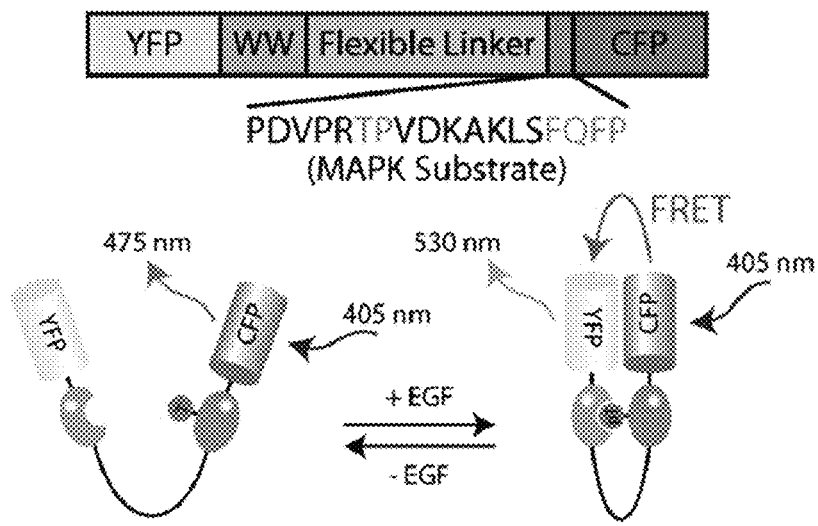
FIG. 17G is a graph comparing bioactivity for proteins azide-tagged by STEPL with H-GGGGDDK(N$_3$)—NH$_2$ [SEQ ID No.: 3] or by conventional NHS labeling with varying molar excesses of N$_3$—OSu (0, 10, 100, 1000×). Activity of EGF was quantitatively determined with a HeLa cell line expressing EKAREV Førster resonance energy transfer (FRET) reporter for MAPK activation. Functional EGF catalyzes phosphorylation of a MAPK substrate, resulting in an intramolecular association that colocalizes a Yellow Fluorescent Protein (YFP) and Cyan Fluorescent Protein (CFP) FRET pair.
Figure 17H:
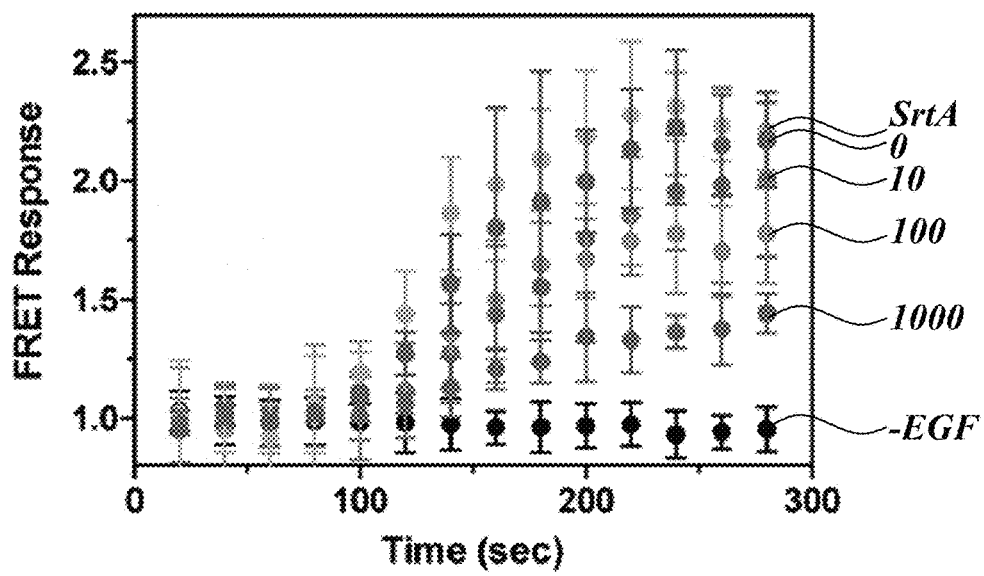
FIG. 17H YFP/CFP FRET ratios following growth factor stimulation were determined for modified EGF.
Figure 17I:
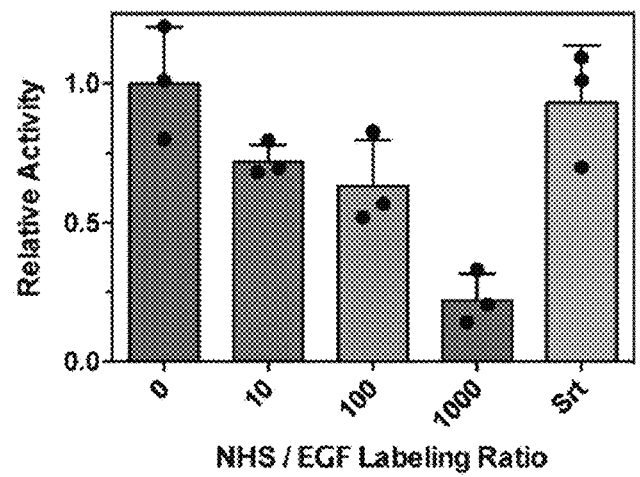
FIG. 17I Increased NHS labeling of EGF yielded decreased bioactivity, as determined by the initial rate of change in FRET response, while the sortagged growth factor exhibited native levels of activity.
Figure 17J:
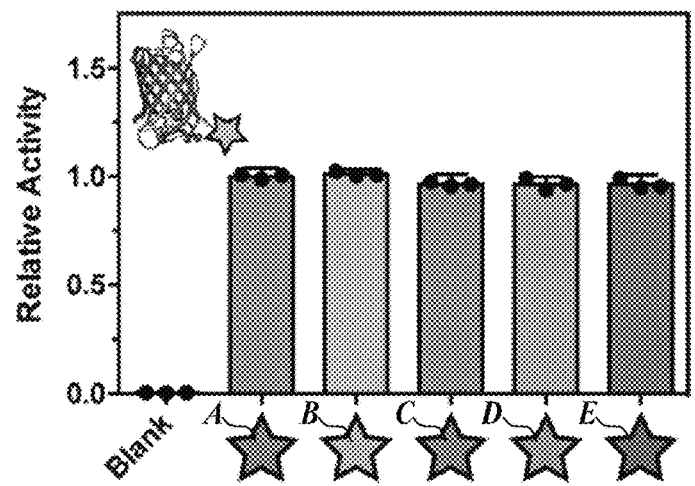
FIG. 17J is a graph showing relative bioactivity of EGFP sortagged with triglycine, H-GGGGDDK($N_3$)—$NH_2$, H-GGGGDDK(CHO)—$NH_2$, H-GGGGDDK(oNB—$N_3$)—$NH_2$, and H-GGGG-oNB-DDK(CHO)—$NH_2$ (denoted respectively with A, B, C, D, and E stars). * denotes conjugates with a statistically significant reduction in bioactivity ($p<0.05$), as compared to the unmodified species (unpaired two-tailed t-test, $p=1.3\times10^{-4}$ for mCherry-CHO, $p=3.5\times10^{-4}$ for mCherry-oNB—CHO, $p=3.2\times10^{-3}$ for bla-oNB—CHO). Error bars correspond to the standard deviation about the mean for biological replicate experiments ($n=3$ for studies involving fluorescent proteins, β-lactamase, and EGF; $n=4$ for MBP-FGF).
Figure 17K:
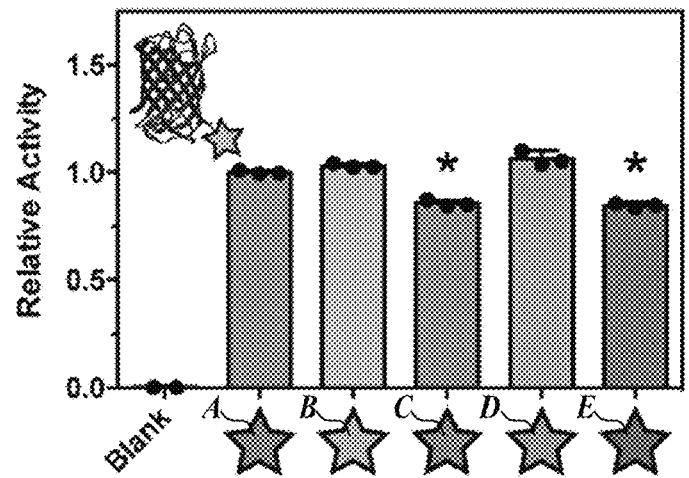
FIG. 17K is a graph showing relative bioactivity of mCherry sortagged with triglycine, H-GGGGDDK($N_3$)—$NH_2$, H-GGGGDDK(CHO)—$NH_2$, H-GGGGDDK(oNB—$N_3$)—$NH_2$, and H-GGGG-oNB-DDK(CHO)—$NH_2$ (denoted respectively with A, B, C, D, and E stars). * denotes conjugates with a statistically significant reduction in bioactivity ($p<0.05$), as compared to the unmodified species (unpaired two-tailed t-test, $p=1.3\times10^{-4}$ for mCherry-CHO, $p=3.5\times10^{-4}$ for mCherry-oNB—CHO, $p=3.2\times10^{-3}$ for bla-oNB—CHO). Error bars correspond to the standard deviation about the mean for biological replicate experiments ($n=3$ for studies involving fluorescent proteins, β-lactamase, and EGF; $n=4$ for MBP-FGF).
Figure 17L:
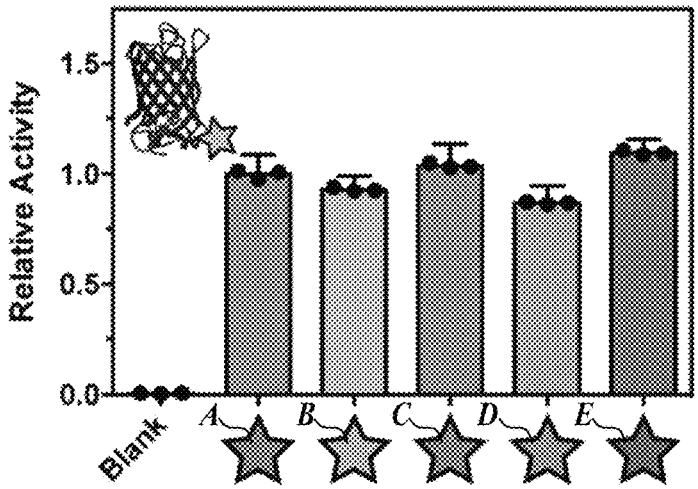
FIG. 17L is a graph showing relative bioactivity of mCerulean sortagged with triglycine, H-GGGGDDK($N_3$)—$NH_2$ [SEQ ID No.: 3] H-GGGGDDK(CHO)—$NH_2$ [SEQ ID No.: 4], H-GGGGDDK(oNB—$N_3$)—$NH_2$ [SEQ ID No.: 5], and H-GGGG-oNB-DDK(CHO)—$NH_2$ [SEQ ID No.: 6] (denoted respectively with A, B, C, D, and E stars). * denotes conjugates with a statistically significant reduction in bioactivity ($p<0.05$), as compared to the unmodified species (unpaired two-tailed t-test, $p=1.3\times10^{-4}$ for mCherry-CHO, $p=3.5\times10^{-4}$ for mCherry-oNB—CHO, $p=3.2\times10^{-3}$ for bla-oNB—CHO). Error bars correspond to the standard deviation about the mean for biological replicate experiments ($n=3$ for studies involving fluorescent proteins, β-lactamase, and EGF; $n=4$ for MBP-FGF).
Figure 17M:
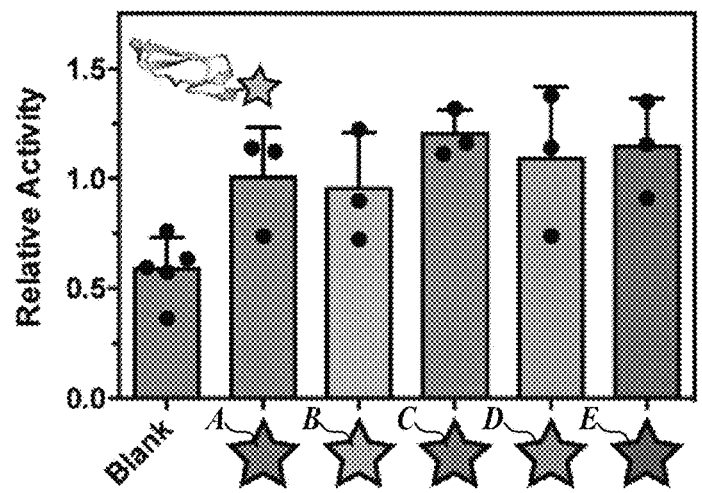
FIG. 17M is a graph showing relative bioactivity of EGF sortagged with triglycine, H-GGGGDDK($N_3$)—$NH_2$ [SEQ ID No.: 3], H-GGGGDDK(CHO)—$NH_2$ [SEQ ID No.: 4], H-GGGGDDK(oNB—$N_3$)—$NH_2$ [SEQ ID No.: 5], and H-GGGG-oNB-DDK(CHO)—$NH_2$ [SEQ ID No.: 6] (denoted respectively with A, B, C, D, and E stars). * denotes conjugates with a statistically significant reduction in bioactivity ($p<0.05$), as compared to the unmodified species (unpaired two-tailed t-test, $p=1.3\times10^{-4}$ for mCherry-CHO, $p=3.5\times10^{-4}$ for mCherry-oNB—CHO, $p=3.2\times10^{-3}$ for bla-oNB—CHO). Error bars correspond to the standard deviation about the mean for biological replicate experiments ($n=3$ for studies involving fluorescent proteins, β-lactamase, and EGF; $n=4$ for MBP-FGF).
Figure 17N:
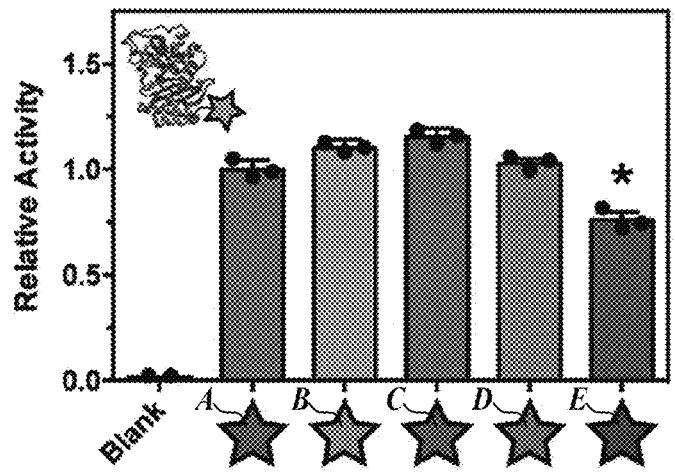
FIG. 17N is a graph showing relative bioactivity of bla sortagged with triglycine, H-GGGGDDK($N_3$)—$NH_2$ [SEQ ID No.: 3], H-GGGGDDK(CHO)—$NH_2$ [SEQ ID No.: 4] H-GGGGDDK(oNB—$N_3$)—$NH_2$ [SEQ ID No.: 5] and H-GGGG-oNB-DDK(CHO)—$NH_2$ [SEQ ID No.: 6] (denoted respectively with A, B, C, D, and E stars). * denotes conjugates with a statistically significant reduction in bioactivity ($p<0.05$), as compared to the unmodified species (unpaired two-tailed t-test, $p=1.3\times10^{-4}$ for mCherry-CHO, $p=3.5\times10^{-4}$ for mCherry-oNB—CHO, $p=3.2\times10^{-3}$ for bla-oNB—CHO). Error bars correspond to the standard deviation about the mean for biological replicate experiments ($n=3$ for studies involving fluorescent proteins, β-lactamase, and EGF; $n=4$ for MBP-FGF).
Figure 17O:
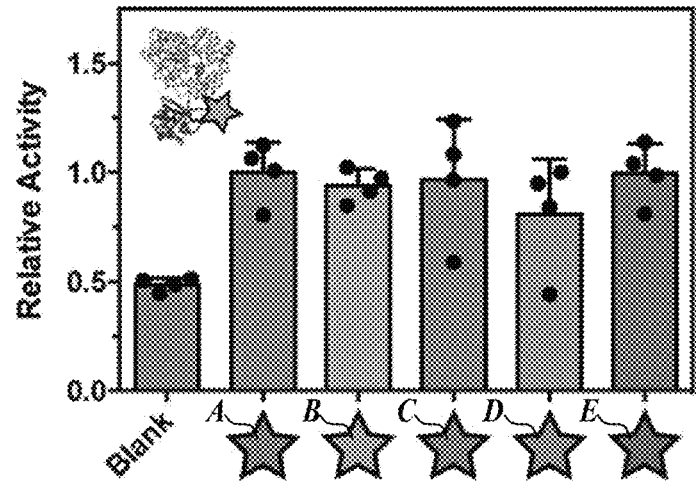

To highlight the versatility of sortase for protein modification and to generate a library of functional biomacromolecules for hydrogel modification, STEPL expression systems for six proteins spanning three distinct classes were constructed: fluorescent [Enhanced Green Fluorescent Protein (EGFP), mCherry, and mCerulean], enzymatic [β-lactamase (bla)], and growth factor [epidermal growth factor (EGF) and fibroblast growth factor (FGF)]. As protein functional modification by sortase is defined by engineered peptide identity, five distinct polyglycine probes were synthesized (FIG. 16B) each with different reactive handles (azides, aromatic aldehydes, nitrobenzyl moieties). These bioorthogonal handles enable proteins to be conjugated to materials formed by a variety of common hydrogel formation click chemistries (such as azide/alkyne, oxime, and hydrazine conjugation), as well as dictate how functionalized proteins interface with materials over time. With these six expression vectors and five sortaggable probes in hand, STEPL was utilized to generate all 30 possible protein-peptide conjugates. Whole-protein mass spectrometry and gel shift assays revealed exceptionally high protein purity and quantitative functionalization in all cases (FIGS. 16C-16H), indicating efficient generation of a diverse collection of singly modified proteins for hydrogel patterning. It is believed that this represents the largest library of sortagged proteins created to date.

Having successfully generated site-specifically modified proteins bearing functionality required for hydrogel decoration, the effects of sortagged modification versus stochastic N-hydroxy succinimide (NHS) ester labeling of solvent-accessible amines, the most commonly employed method to modify proteins, were compared, using a representative protein from each class (FIGS. 17A-17I). EGFP activity was evaluated directly through fluorescence measurements. Activity of bla was determined through a standard colorimetric assay involving hydrolysis of the chromogenic cephalosporin nitrocefin. EGF activity was quantified using HeLa cells expressing EKAREV, a Förster resonance energy transfer (FRET) reporter for mitogen-activated protein kinase (MAPK) signaling. In all cases, azide-modified proteins sortagged with H-GGGGDDK(N$_3$)—NH$_2$ exhibited activity that was statistically indistinguishable from that of the native species. In contrast, protein bioactivity decreased significantly when azide tagging occurred through conventional NHS ester labeling involving 2,5-dioxopyrrolidin-1-yl 4-azidobutanoate (N$_3$—OSu). Large molar excesses of the NHTS-activated compound relative to the protein of interest were required for even modest levels of protein labeling, as NHS ester hydrolysis represents the dominant reaction pathway when this chemistry is performed in aqueous systems. Individual proteins tolerate different amounts of random modification, as higher excesses of the NHS species were required to diminish EGFP fluorescence (a protein that has been engineered for its stable structure) than bla enzyme activity. Taken together, these experiments demonstrate that sortagging allows for the creation of modified protein conjugates with higher purity and bioactivity than their NETS-modified counterparts.

Having observed that sortagging outperformed NHS chemistry when introducing reactive azides onto EGFP, bla, and EGF, the bioactivity of all 30 protein-peptide library members were quantified (FIGS. 17J-17O). Similar to EGFP, mCherry and mCerulean activity was evaluated directly through fluorescence measurements. FGF and EGF activity were determined based on their ability to stimulate cell proliferation, quantified by increased dsDNA synthesis and content. In total, the overwhelming majority (27/30) of modified proteins exhibit bioactivity that is statistically indistinguishable from the unmodified species. Moreover, the least active conjugate (bla-oNB—CHO, based on the kinetically perfect bla enzyme that had previously proven highly sensitive to modification) retained 76±4% of its native bioactivity. It is believed that the ability to singly modify functionally diverse bioactive proteins with several different reactive handles, each of which influences how they form the basis of and interact with materials, would be enabling for a variety of biological applications. Additionally, the relative ease and lack of specialized equipment required for protein expression/purification, coupled with the commercial availability of sortaggable peptides containing functional handles (including azides, alkynes, (meth) acrylates, thiols, aldehydes, maleimides, allyl sulfides), render these strategies practically accessible to non-specialists.

After verifying that sortagged proteins retained native bioactivity, their controlled incorporation within biomaterials was demonstrated. Model hydrogels were formed through strain-promoted azide-alkyne cycloaddition (SPAAC) between a four-arm poly(ethylene glycol) (PEG) tetrabicyclononyne and a linear PEG diazide. Reaction kinetics and bioorthogonality permitted encapsulation of live cells with high viability, while the bioinert PEG provides a non-fouling "blank slate" for subsequent decoration with proteins. The optical clarity of these materials rendered them useful for photochemical modification with biomolecules, as well as for microscopy-based assays of encapsulated cell fate.

Figure 18A:
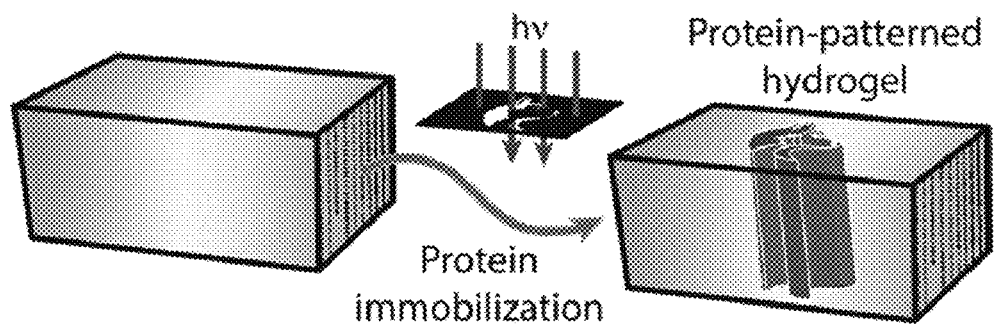
FIGS. 18A-18L are related to the photopatterned alteration of hydrogel biomaterials with sortagged proteins.
Figure 18B:
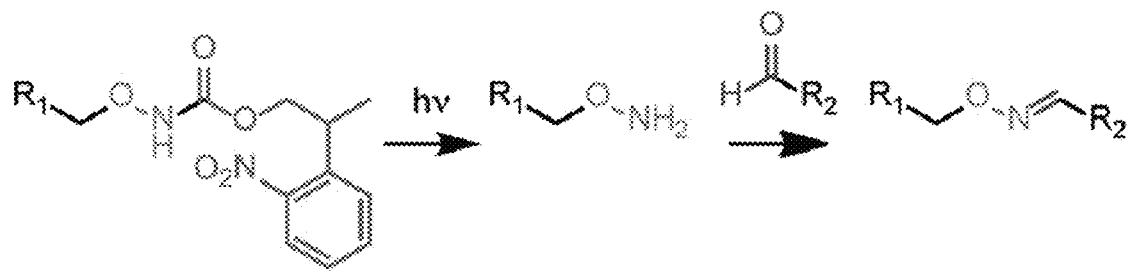
Figure 18C:
Figure 18D:
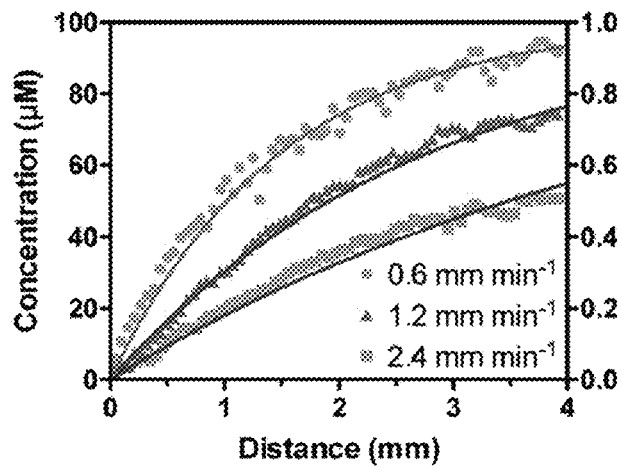
Figure 18E:
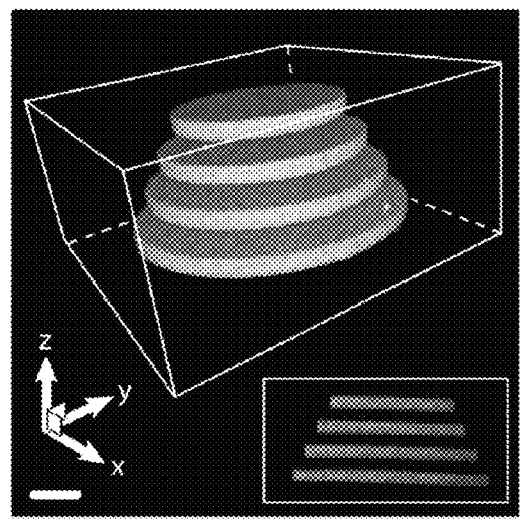
Figure 18F:

A cytocompatible photomediated oxime ligation was exploited to immobilize site-specifically modified proteins within hydrogels containing a 2-(2-nitrophenyl)propyloxycarbonyl (NPPOC)-photocaged alkoxyamine with spatiotemporal control (FIGS. 18A and 18B). Upon mild near-UV irradiation (λ=365 nm), NPPOC is cleaved, liberating the reactive alkoxyamine and permitting localized condensation with hydrogel-swollen aromatic aldehyde-modified proteins to form a stable oxime linkage. Removal of unbound proteins by diffusion yields patterned hydrogel substrates defined by user-selected light exposure locations and parameters. Hydrogel patterning was performed with EGFP sortagged with H-GGGGDDK(CHO)—NH$_2$ [SEQ ID No.: 4] (EGFP-CHO), whereby immobilized protein fluorescence permitted visualization and quantification. Traditional photolithographic techniques were utilized to control patterning of mask-defined shapes throughout hydrogel thickness (FIG. 18C), and to generate continuous gradients that followed a dose-dependent response predicted by NPPOC photocleavage kinetics (FIGS. 18D and 18F). EGFP-CHO was immobilized within hydrogels with excellent 3D control through multiphoton laser-scanning lithography, whereby programmed laser rastering within the hydrogel material dictated protein tethering location and concentration (FIG. 18E). These experiments represent the first demonstration of 3D patterned covalent immobilization of a site-specifically modified protein within a material.

Figure 18G:
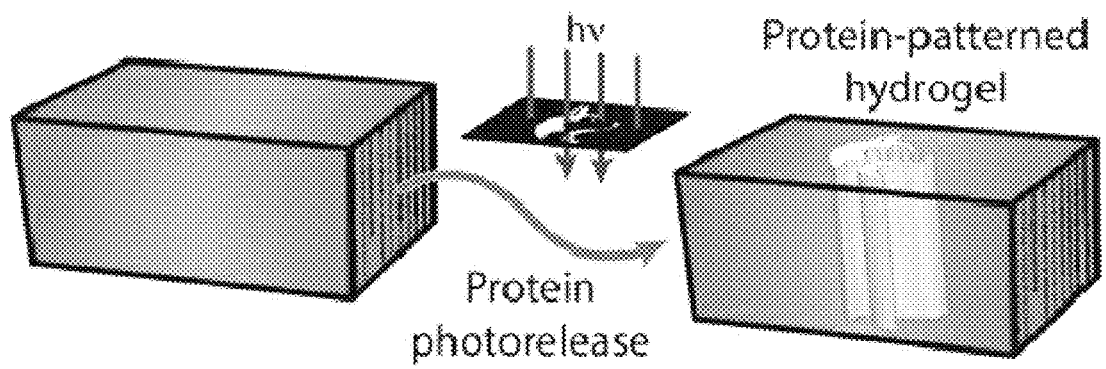
Figure 18H:
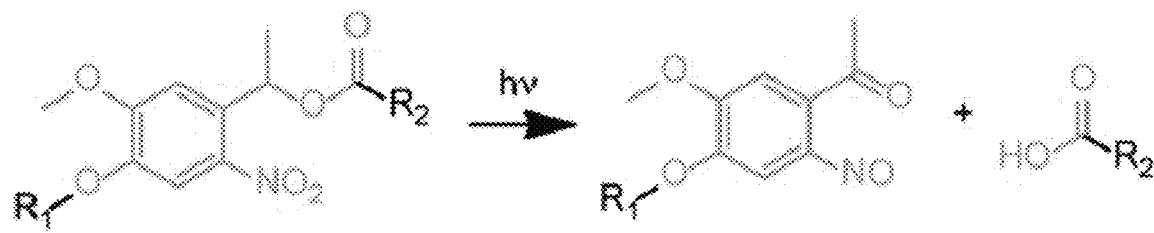
Figure 18I:
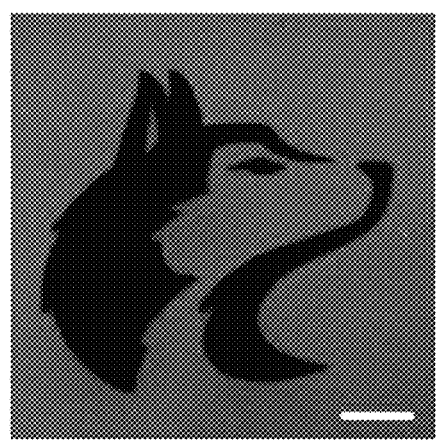
Figure 18J:
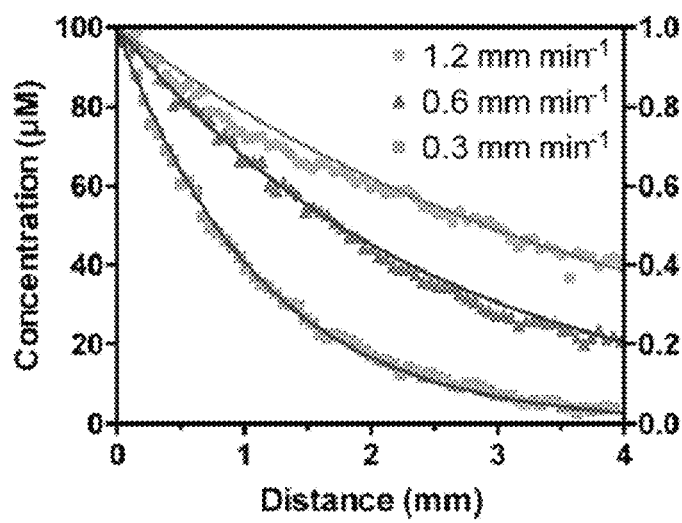
Figure 18K:
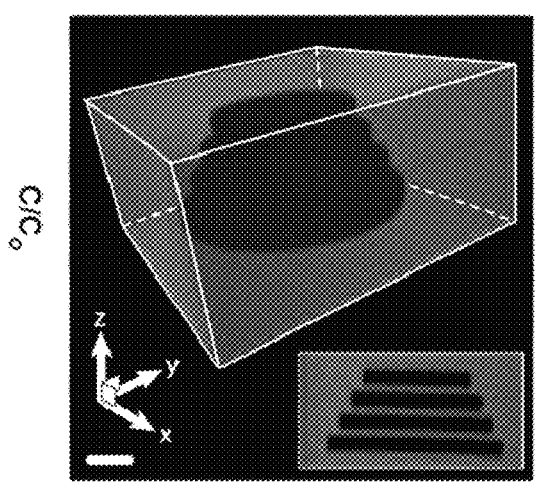
Figure 18L:

After having demonstrated the ability to immobilize sortagged proteins within biomaterials with excellent 3D control, the patterned photorelease of such species from hydrogels was performed (FIG. 18G). For this, an ortho-nitrobenzyl ester (oNB) moiety was used that undergoes rapid photoscission in response to cytocompatible near-UV light ($\lambda$=365 nm) (FIG. 18H). mCherry sortagged with H-GGGGDDK(oNB—N$_3$)—NH$_2$ (mCherry-oNB—N$_3$) was tethered uniformly throughout materials during SPAAC-based gelation. After directed light exposure, released protein was diffused from the hydrogel prior to sample imaging and quantification through fluorescent confocal microscopy. Mask-based photolithographic techniques were again exploited to control mCherry-oNB—N$_3$ removal and concentration throughout full hydrogel thickness in a predictable and dose-dependent manner (FIGS. 18I-18L). Multiphoton lithography afforded excellent 3D patterning at user-specified regions within hydrogels (FIG. 18K). These results represent the first photorelease of a site-specifically modified protein from a 2D or 3D material. In addition to controlling the location of immobilized proteins that persist within a hydrogel, the fully defined and homogenous protein population photoreleased from the material can have significant implications for controlled drug delivery.

Figure 20A:
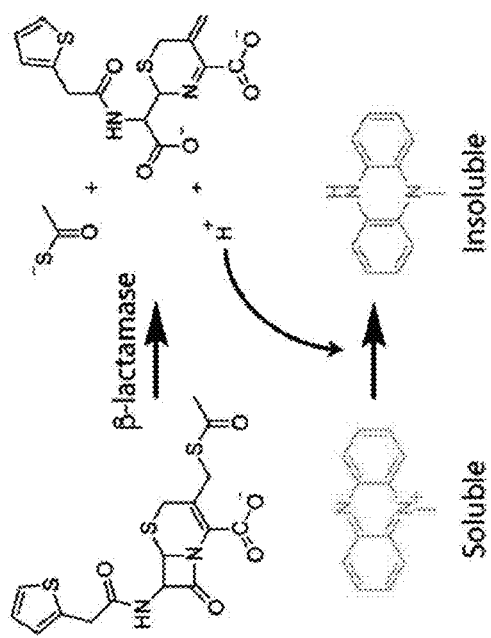
FIGS. 20A-20F are related to spatial patterning of hydrogels with bioactive site-specifically modified enzymes and growth factors.
Figure 20B:
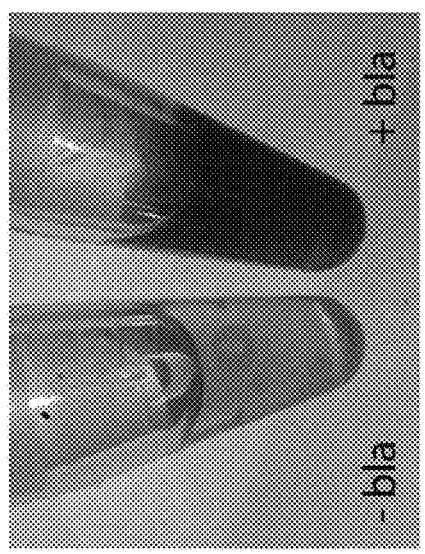
Figure 20C:
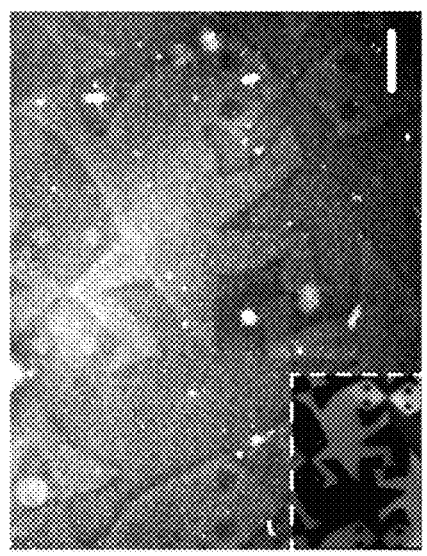
Figure 20D:
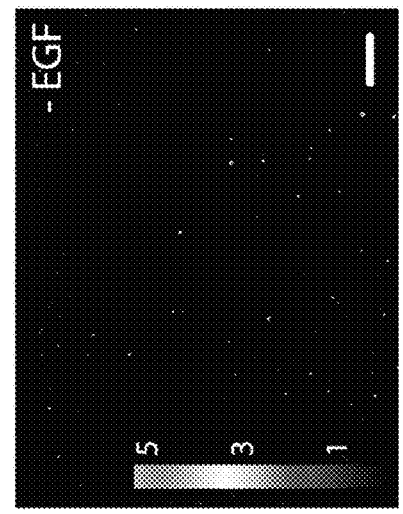
Figure 20E:
Figure 20F:
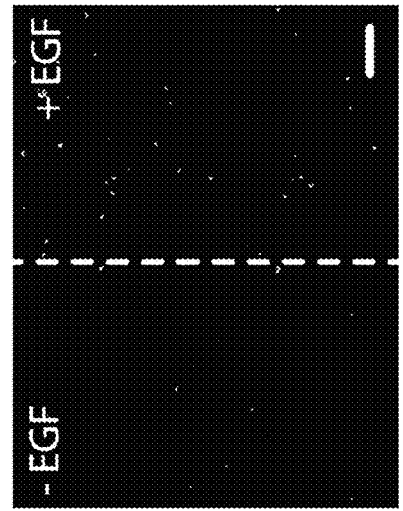

Sortase's versatility in introducing diverse functional handles onto different proteins of interest enables protein-patterned materials of unprecedented complexity to be photoevolved in 4D. To demonstrate dynamic material patterning, three differentially modified and spectrally separated fluorescent proteins were selected from the library of sortagged species. Hydrogels containing the NPPOC-caged alkoxyamine were uniformly functionalized with mCherry-oNB—N$_3$. Upon directed light exposure, mCherry photorelease was performed in concert with photomediated ligation of an aldehyde-tagged protein (either mCerulean-CHO or EGFP-oNB—CHO) to create interconnected biochemical patterns. The photorelease/oxime ligation sequence was repeated, enabling a third protein (either EGFP-oNB—CHO or mCerulean-CHO) to be immobilized (FIG. 19A). This approach was utilized to create an Escher-inspired tessellation of fish/bird shapes through masked lithography (FIGS. 19B-19E), as well as a 3D schematic depiction of a cell binding to an ECM-presented ligand via multiphoton patterning (FIG. 19F-19I). Collectively, this data demonstrates dynamic control over multiple factors in time and space with unmatched precision, as well as the first 4D regulation of site-specifically modified proteins within materials.

mCherry, mCerulean, and EGFP each retained their fluorescence and spatial patterning for several weeks following hydrogel tethering. Thus, whether enzymatic activity could be confined to user-specified hydrogel subvolumes was investigated. Utilizing bla-oNB—N$_3$, hydrogels were functionalized and patterned through mask-based protein photoremoval. Protein-patterned hydrogels were treated with 7-thiophenylacetamido-3-thioacetoxymethyl-3-cephem-4-carboxylate (thioacetate cefalotin), a thiocephalosporin that eliminated a proton and a thiolate ion following β-lactam enzymatic hydrolysis that reduced a water-soluble yellow phenazine into a green water-insoluble precipitate (FIGS. 20A and 20B). Phase contrast microscopy indicated changes in localized refractive index, corresponding to enzyme-induced precipitation confined to bla-modified regions within the hydrogel (FIG. 20C). It is believed that this is the first successful example of confining enzymatic activity to photopatterned locations within a material, a task enabled by site-specific modification and that can be useful in enzymatically regulating critical ECM parameters.

Having demonstrated that sortagged enzymes remain active when photopatterned within hydrogels and that hydrogel formation and modification chemistries were cytocompatible, the ability of these techniques to direct local cell function was tested using immobilized growth factors. HeLa cells transfected with the EKAREV FRET reporter for MAPK activation were encapsulated in materials uniformly functionalized with EGF-oNB—N$_3$. Following complete bulk protein photorelease, cells displayed basal levels of MAPK activation; those where EGF remained immobilized elicited significantly higher (~2 fold) intracellular signaling (FIGS. 21D and 21E). The extent of FRET responses for cells in 3D was consistent with 2D studies involving soluble EGF and was not directly affected by light treatments used for hydrogel photomodulation. Taking advantage of the spatial control afforded by protein photorelease, hydrogels with patterned EGF were created through masked exposure; MAPK activation remained high in hydrogel subvolumes still functionalized with EGF, but returned to basal levels in those where the protein had been photoreleased. Since MAPK signaling plays a key role in regulating cell proliferation, migration, and differentiation, its patterned activation represents a powerful step towards regulating advanced cell fates with spatiotemporal control. It is believed that these results are the first example of photopatterned regulation over a specific biochemical pathway in a 3D material.

Figure 21A:
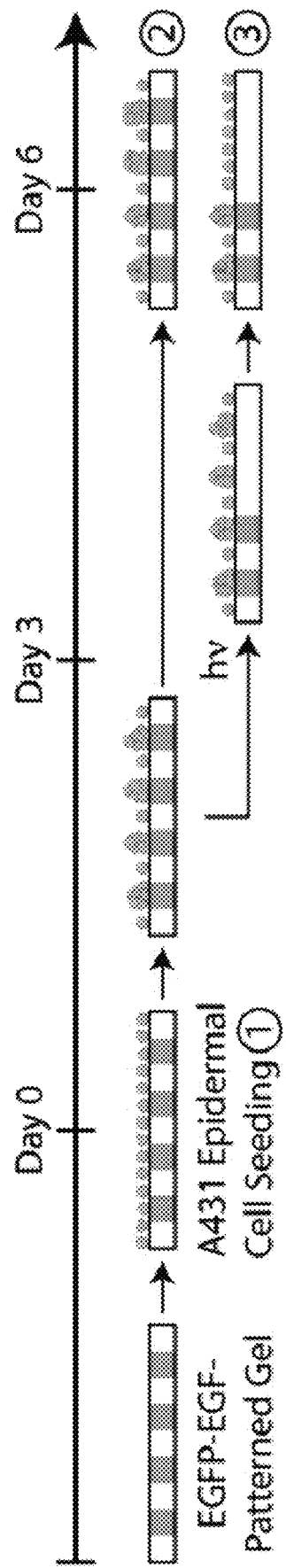
Figure 21B:
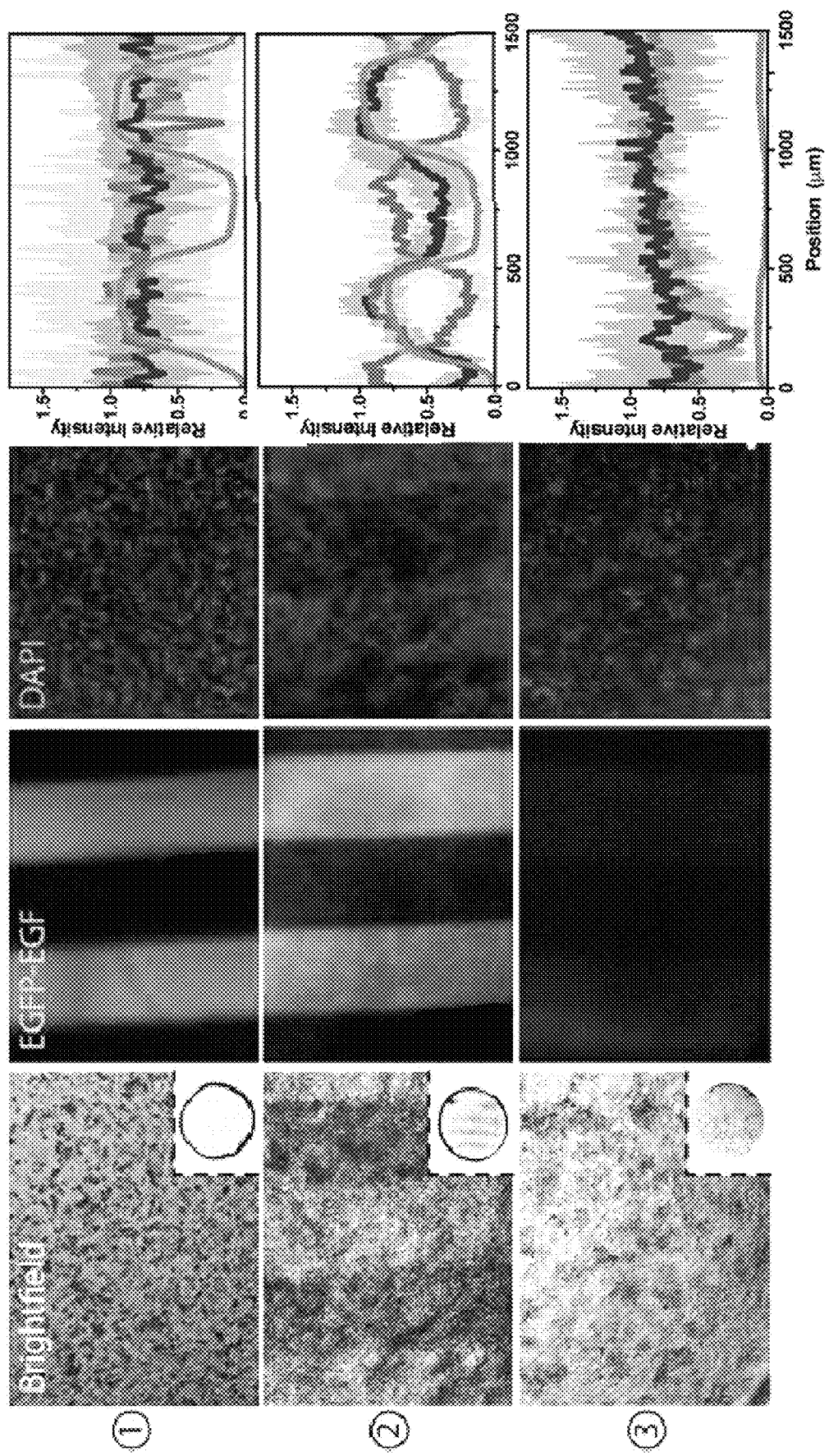

An added benefit of using STEPL to modify proteins for material decoration is its compatibility with many standard protein engineering strategies. Though the photoremovable EGF proved successful in spatially regulating MAPK activation in 3D hydrogels, its location cannot be directly visualized during experimentation. To address this limitation, an expression vector was constructed for an EGFP-EGF fusion and STEPL was performed using H-GGGGDDK(oNB—N$_3$)—NH$_2$ [SEQ ID No.: 5] to generate EGFP-EGF-oNB—N$_3$. Taking advantage of its fluorescence, bioactivity, tetherability, and photoreleasability, this tetrafunctional protein was used to pattern proliferation through dynamic EGF stimulation (FIGS. 21A and 21B). Epidermal A431 cells were seeded on hydrogels containing interspaced lines of EGFP-EGF-oNB—N$_3$. The immobilized EGFP-EGF remained effective in driving proliferation, where cell patterning was visibly evident by Day 3; functionalized regions yielded ~2-fold increased cell densities relative to those lacking EGF by Day 6. Control experiments with patterned EGFP exhibited homogenous surface coverage with no significant difference in cell localization based on the underlying fluorescent protein pattern at any observed time point. To assay the effects of dynamically patterned EGF stimulation on cell function, a parallel experiment was constructed in which the EGFP-EGF was photoreleased from one half of each individual line-patterned hydrogel three days into culture. Though the persistently functionalized hydrogel portions exhibited the expected patterning in cell density, uniform surface coverage was observed across the photoreleased hydrogel portions where presumably cells had redistributed through migration to eliminate any previously patterned heterogeneity. 3D experiments involving encapsulated HeLa cells yielded similar results, where spheroid growth was enhanced with persistently patterned EGFP-EGF. Through reversibly controlled presentation of bioactive growth factors, the newfound ability to modulate local proliferation/migration of cells in 2D and 3D was demonstrated.

Figure 21C:
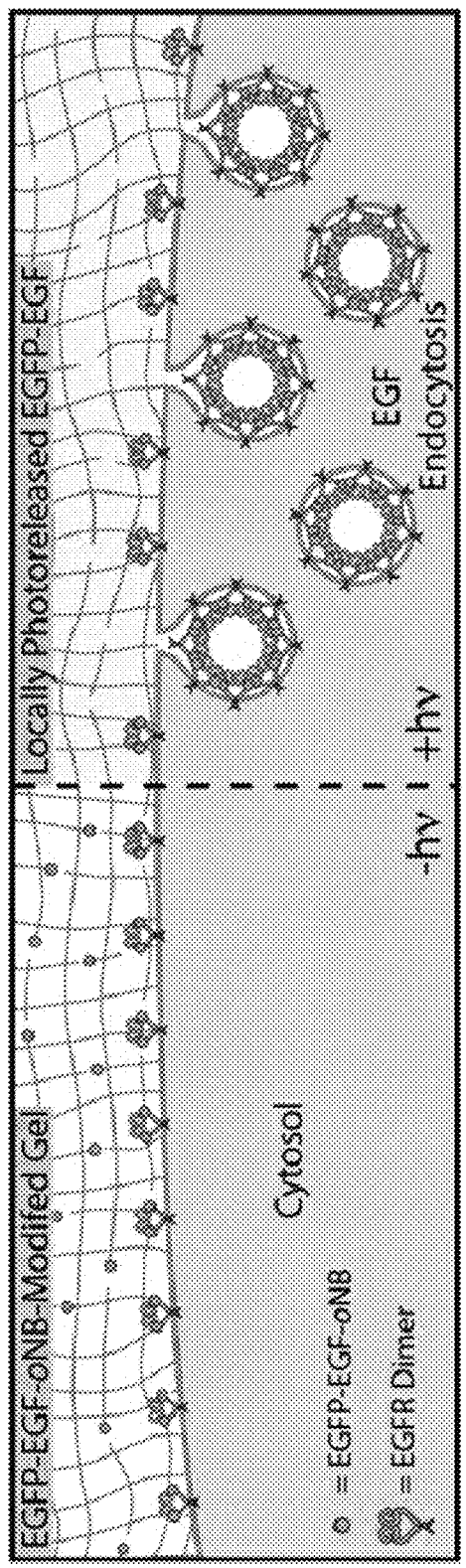
Figure 21C:
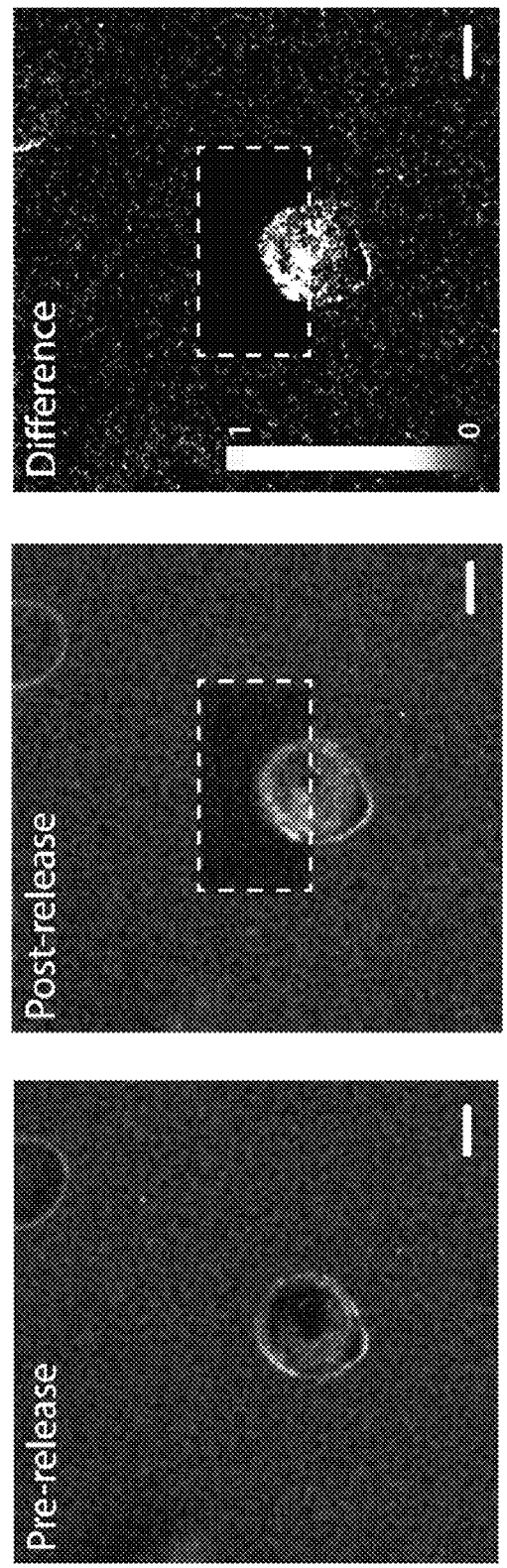

Armed with the EGFP-EGF-oNB—$N_3$ tetrafunctional chimera, the ability of photoreleased proteins to influence dynamic biological fate with resolutions previously inaccessible to biomaterials-based approaches was investigated. EGF binds cell surface protein epidermal growth factor receptor (EGFR), yielding an activated transmembrane protein that undergoes homodimerization. Canonical EGFR activation is coupled with membrane endocytosis, receptor trafficking, and downstream signal transduction. Though matrix-bound EGF binds EGFR, growth factor tethering inhibits ligand-receptor internalization, endocytotic trafficking, and canonical signaling. It was hypothesized that photoliberation of soluble EGFR-EGF could be used to "turn on" canonical EGFR activation locally within culture, and that downstream endosome formation could be visualized with fluorescent microscopy (FIG. 21C). To test this hypothesis, A431 cells were encapsulated in hydrogels modified with EGFP-EGF-oNB—$N_3$. Confocal imaging revealed a fluorescent halo initially outlining each cell, indicating ligand-receptor binding and the presence of concentrated membrane-bound EGFP-EGF (FIG. 21D). Multiphoton laser scanning lithography was used to selectively release the EGFP-EGF protein on one side of an individual encapsulated cell, triggering EGFP-EGF untethering and local endocytic vesicle formation, visible in <5 minutes and concentrated in the regions of light exposure (FIGS. 21E and 21F). Cells within the same imaging window (~50 μm away) were unaffected by the photoreleased EGF, further indicating that activation could be specified with single micron-scale precision. Control studies involving photoreleasable EGFP did not yield endocytosis. It is believed that this is the first demonstration of using dynamic materials to govern 3D fate with single cell and/or subcellular resolution.

The results described here introduce and highlight the sortase-mediated transpeptidation as a uniquely powerful strategy to create a diverse library of homogenous, singly modified proteins with non-natural functionality. Sortagged proteins can be efficiently expressed and purified by STEPL, and exhibit near-native bioactivity while affording the ability to decorate biomaterials in a user-dictated manner. By specifying reactive handle identity, functional proteins can be reversibly immobilized within hydrogels with excellent spatiotemporal resolution through a variety of bioorthogonal photochemical reactions. Such patterned control over niche biochemical properties with homogenous proteins permits unprecedented regulation of complex biological functions and cellular pathways. This approach can be useful in probing the effects of ECM-presented cues on single cell fate and in the design of materials for tissue engineering, potentially opening the door to multi-lineage patterning of 3D stem cell differentiation.

Synthesis of Polyglycine Probes for Sortagging

Polyglycine-containing peptides [H-GGGGDDK($N_3$)—$NH_2$ [SEQ ID No.: 3], H-GGGGDDK(CHO)—$NH_2$ [SEQ ID No.: 4], H-GGGGDDK(oNB—$N_3$)—$NH_2$ [SEQ ID No.: 5], H-GGGG-oNB-DDK(CHO)—$NH_2$ [SEQ ID No.: 6]] were synthesized through standard Fmoc solid-phase methodologies involving a butyloxycarbonyl-protected N-terminal glycine and a 4-methyltrityl (Mtt)-protected C-terminal lysine reside. Following selective deprotection of Mtt (1% trifluoroacetic acid, TFA, in dichloromethane, DCM) on resin, azide ($N_3$), aldehyde (CHO), and photoreleasable azide (oNB—$N_3$) functionality were installed respectively by condensation with 4-azidobutanoic acid, 4-formylbenzoic acid, or 4-(4-(1-(4-azidobutanoyloxy)ethyl)-2-methoxy-5-nitrophenoxy)butanoic acid and the ε-amino group of the C-terminal lysine. Resin was washed (dimethylformamide, DMF, 3×; DCM, 3×) prior to peptide cleavage/deprotection (95:5 TFA:$H_2O$, 20 mL, 2 hr) and precipitation (diethyl ether, 180 mL, 0° C., 2×). The crude peptide was purified via semi-preparative reversed-phase high-performance liquid chromatography using a 55-minute gradient (5-100% of acetonitrile and 0.1% TFA in $H_2O$) and lyophilized to give final product. Peptide purity was confirmed by matrix-assisted laser desorption/ionization time-of-flight mass spectrometry.

Generation of Homogenous Protein-Peptide Conjugates by STEPL.

STEPL plasmids for EGFP, mCherry, mCerulean, bla, EGF, FGF, and EGFP-EGF were constructed from pSTEPL using standard cloning techniques and transformed into BL21(DE3) E. coli (Thermo Fisher). For protein expression, transformants were grown at 37° C. in lysogeny broth containing ampicillin (100 μg $mL^{-1}$) until an optical density of 0.6 (λ=600 nm). Expression was induced with isopropyl β-D-1-thiogalactopyranoside (0.5 mM) and then agitated overnight at 18° C. Cells were harvested via centrifugation and lysed by sonication. Clarified lysate was loaded onto HisPur Ni-NTA resin (ThermoFisher), which was washed (20 mM Tris, 50 mM NaCl, 20 mM imidazole) to remove unbound proteins. Following treatment of the resin with polyglycine probe of interest (20×, 4 h, 37° C.), sortagged proteins were eluted and purified by dialysis (molecular weight cut-off, MWCO~10 kDa). Protein identity and purity was confirmed by liquid chromatography-tandem mass spectrometry, sodium dodecyl sulfate polyacrylamide gel electrophoresis, and gel shift analysis. Protein concentrations were determined by ultraviolet absorption (λ=280 nm) and bicinchoninic acid assay prior to use.

Random Modification of Proteins by NHS Chemistry.

Statistically modified proteins were prepared by reacting $N_3$—OSu (0×, 0 μM; 10×, 300 μM; 100×, 3 mM; 1000×, 30 mM) with protein (30 μM) in phosphate buffered saline (PBS, 900 μL) and DMF (100 μL) overnight at room temperature. Resulting protein solutions were purified with Zeba™ Spin Desalting Columns (MWCO~7 kDa, Thermo Fisher) and buffer-exchanged into fresh PBS. Protein concentrations were determined by ultraviolet absorption (λ=280 nm) and bicinchoninic acid assay prior to use.

Activity Determination of Native and Modified Proteins.

EGFP, mCherry, and mCerulean fluorescence was quantified on a fluorescent plate reader (EGFP: $\lambda_{excitation}$=470 nm, $\lambda_{emission}$=530 nm; mCherry: $\lambda_{excitation}$=575 nm, $\lambda_{emission}$=620 nm; mCerulean: $\lambda_{excitation}$=430 nm, $\lambda_{emission}$=475 nm). Bla enzymatic activity was measured through a chromogenic assay, whereby bla (1 ng) was incubated with nitrocefin (2 mM) in PBS (100 μL). Sample absorbance ($\lambda_{abs}$=386 nm) was measured over time at 37° C.; the initial slope was calculated as a measure of the $k_{cat}$ of the enzyme. To determine EGF activity, HeLa cells expressing EKAREV were plated in a 96-well plate (5,000 cells well$^{-1}$) and allowed to attach overnight in Dulbecco's Modified Eagle Medium (DMEM) (Life Technologies) supplemented with fetal bovine serum (FBS, 10%). 16 hours prior to imaging, cells were transitioned to serum-free DMEM. Time-series images (20 sec interval) were acquired on a fluorescent confocal microscope ($\lambda_{excitation}$=405 nm, 1% argon laser power; $\lambda_{emission,CFP}$=450-484 nm, $\lambda_{emission,YFP}$=520-524 nm) following stimulation with EGF (12.5 nM) in serum-free DMEM. The YFP/CFP FRET response ratio was calculated for each frame (ImageJ) and plotted over time. The relative activity of each EGF species was taken as the initial rate of change of the FRET response after EGF stimulation, normalized to native EGF. Alternatively, EGF activity was determined through a commercially available DNA synthesis assay (Click-iT EdU Alexa Fluor 488, Thermo Fisher). NIH3T3 cells were placed in a 96-well plate (5,000 cells well$^{-1}$) and cultured overnight in DMEM containing FBS (10%). Cells were washed with PBS (2×) and transferred to serum-free DMEM. After one day, cells were transitioned to serum-free DMEM containing 5-Ethynyl-2'-deoxyuridine (10 μM) with or without EGF (100 ng mL$^{-1}$). After two days of culture, cells were fixed in formaldehyde and processed following kit manufacturer recommendations. The relative activity of each EGF species was taken as the percentage of cells actively synthesizing DNA after EGF stimulation, normalized to unmodified EGF. FGF activity was determined through a proliferation assay using a commercially available assay (Quant-iT PicoGreen, Thermo Fisher) for dsDNA content. NIH3T3 cells (5,000 cells well$^{-1}$) were cultured overnight in 96-well plate in DMEM containing FBS (10%) prior to being transferred to serum-free DMEM. After one day, cells were transferred to serum-free DMEM with or without FGF (100 ng mL$^{-1}$), incubated for two days, and assayed following manufacturer protocol. The relative activity of each FGF species corresponds to the total dsDNA content, normalized to unmodified FGF.

Formation of SPAAC-Based Hydrogels.

A solution of PEG-tetraBCN ($M_n$~20,000 Da, 4 mM), $N_3$—PEG-$N_3$ ($M_n$~3,500 Da, 8 mM), and $N_3$-TEG-ONH—NPPOC (0.1 mM) was prepared in PBS. Network formation was allowed to proceed for 1 hour between Rain-X®-treated glass slides with silicone rubber spacers (McMaster-Carr, 0.5 mm thick). The slides were separated, and hydrogels were equilibrated overnight in PBS prior to use.

Photopatterning Conditions for Protein Tethering and Release.

For photolithographic patterning, hydrogels were exposed to collimated UV light (λ=365 nm, 10 mW cm$^{-2}$, 0-1200 s) through a patterned chrome photomask (Photo Sciences) using a Lumen Dynamics OmniCure S1500 Spot UV Curing system equipped with an internal 365 nm band-pass filter and a second in-line 360 nm cut-on longpass filter. Protein gradients were created by moving an opaque plate attached to a programmable linear motion stage over hydrogels during light exposure at various rates (0.3-2.4 mm min$^{-1}$). For 3D patterning experiments within hydrogels, an Olympus FV1000 MPE BX61 Multi-photon Microscope with a 20× objective was used. ROIs were scanned 16 times with pulsed laser light (λ=740 nm, 50% laser power) with a 2.5 μm z-interval to generate 3D patterns. After NPPOC cleavage, hydrogels were incubated for 8 hours with aldehyde-tagged protein (100 μM in PBS) at room temperature and protected from light. To remove unbound protein, hydrogels were gently agitated in PBS (16 h) prior to imaging. Following light exposure, hydrogels containing photoreleasable proteins were incubated in PBS (16 h) prior to analysis. This process was repeated iteratively for patterning of multiple proteins. Experiments involving patterning of fluorescent proteins were visualized by fluorescent confocal or multiphoton microscopy, while those involving immobilized bla were imaged by phase-contrast microscopy. For experiments involving encapsulated mammalian cells, PBS was replaced with culture media during hydrogel formation and patterning.

Spatial Assessment of Bla Enzymatic Activity.

SPAAC-based hydrogels uniformly functionalized with bla-oNB—$N_3$ (30 μM) were subjected to masked light (λ=365 nm, 10 mW cm$^{-2}$, 10 min). Protein-patterned hydrogels were incubated with thioacetate cefalotin (5 mM) and phenazine methosulfate (6.5 mM) in PBS (37° C., 1 h). The hydrogels were then washed with PBS (3×, 15 min) prior to visualization by phase contrast microscopy.

Encapsulation of MAPK FRET Reporter Cells.

HeLa cells stably transfected with the EKAREV FRET sensor were expanded in high-glucose DMEM supplemented with FBS (10%) and penicillin/streptomycin (1%) in a 5% $CO_2$ atmosphere at 37° C. Culture medium was changed every two to three days, and cells were passaged at ~70% confluency. HeLa cells were encapsulated (2×10$^6$ cells mL$^{-1}$) in SPAAC-based hydrogels (10 μL) modified with EGF-oNB—$N_3$ (12.5 nM) and an $N_3$-GRGDS-$NH_2$ peptide (100 μM) for cell attachment. Photopatterning was performed 24 hours after encapsulation. Prior to FRET imaging (16 h), culture media was replaced with serum-free DMEM containing penicillin/streptomycin (1%).

Visualization of Patterned MAPK Signaling.

HeLa EKAREV-laden hydrogels were imaged using a Leica SP8× confocal microscope at a constant distance below hydrogel surface (100 EKAREV was excited using an argon laser (λ=405 nm, 10% laser power); CFP excitation was monitored from $\lambda_{emission,CFP}$=450-484 nm, while YFP fluorescence was measured from $\lambda_{emission,YFP}$=520-524 nm. After image acquisition, background fluorescence was subtracted, and the YFP/CFP ratio for each pixel of the image was calculated using ImageJ. FRET response ratios were visualized as a blue-green-red color map.

Cell Response to Dynamically Patterned EGFP-EGF.

EGFP-EGF-oNB—$N_3$ (25 μM) was conjugated (25° C., 1 hr) to PEG-tetraBCN ($M_n$~20,000 Da, 4 mM). EGFP-EGF-modified hydrogels (5 μL) were formed (1 hr) between Rain-X®-treated glass slides with silicone rubber spacers (McMaster-Carr, 0.5 mm thick) with cell-adhesive and matrix metalloproteinase-degradable crosslinker $N_3$-GGRGDSPGGPQGIWGQGK($N_3$)—$NH_2$ [SEQ ID No.: 13] (8 mM). After removal from glass slide chamber, hydrogels were exposed to masked collimated UV light (λ=365 nm, 10 min, 10 mW cm$^{-2}$) through a slitted photomask containing 400 μm wide line features and soaked in PBS overnight. Hydrogels were swollen (1 hr) in DMEM containing FBS (10%) prior to cell seeding. A431 cells (1×10$^7$ cells mL$^{-1}$) were added to the top of hydrogels as a droplet (10 μL) and allowed to attach (1 hr, 37° C.) prior to media addition. Hydrogels were swollen in DMEM containing FBS (10%) and penicillin/streptomycin (1%) overnight prior to imaging (condition 0). Hydrogel media was supplemented with bovine serum albumin (BSA, 0.1%) and cells maintained in culture (37° C., 5% $CO_2$). Three days after cell seeding, a portion of the hydrogels were exposed to a second round of photopatterning; one half of each treated hydrogel was exposed to UV light ($\lambda$=365 nm, 10 min, 10 mW $cm^{-2}$) while the other half was left unexposed. In all cases, hydrogels were maintained in DMEM containing FBS (10%), penicillin/streptomycin (1%), and BSA (0.1%) for an additional three days prior to analysis (conditions ② and ③). At the end of each treatment condition, cells were fixed in paraformaldehyde (1%, 30 min), stained with DAPI (0.15 µg/mL, 30 min), and visualized via fluorescence microscopy. Image analysis was performed for each condition using ImageJ, quantifying the normalized intensity profile for EGFP, nuclei, and optical transmission across the hydrogel perpendicular to photopatterned lines. Whole-gel images were performed on an Epson Perfection 4490 Photo document scanner.

Encapsulated Cell Response to Subcellular Photoreleased EGFP EGF.

A431 cells ($2\times10^6$ cells $ml^{-1}$) were encapsulated in SPAAC hydrogels (5 µL) containing EGFP-EGF-oNB—$N_3$ (125 nM) and $N_3$-GRGDS-$NH_2$ peptide (1 mM) affixed to an azide-functionalized slide. The cells were cultured for 48 hr in DMEM supplemented with FBS (10%) and penicillin/streptomycin (1%) before transferring to phenol red-free DMEM containing FBS (10%) and penicillin/streptomycin (1%). Protein photorelease was performed via multiphoton laser scanning lithography (Olympus FV1000 MPE BX61 Multi-photon Microscope, 20× objective, 5× zoom, $\lambda$=740 nm, 25% laser power, 16 scan repeats, z-interval=2.5 confined to a 40 µm×30 µm×5 µm subvolume bisecting an individual cell. ImageJ was used to calculate the difference in EGFP fluorescence pixel intensity accompanying photorelease.

Statistics: Two-tailed t-tests assuming equal variance were performed to determine p values and statistical significance.

Example 3. Photo-Cleavable Linkers

Example 3A: Photocleavable Protein PhoCl

In this Example, a modular and scalable method for the creation of monodisperse genetically encoded protein fusions for immobilization into cytocompatible hydrogels is presented. A unique photo-cleavable protein capable of undergoing intramolecular β-elimination upon exposure to visible 400 nm violet light was used to tether and release bioactive proteins from hydrogels. Protein engineering and chemoenzymatic protein modification techniques were used to provide homogeneous monofunctionalized azide-tagged fusion proteins. These site-specifically modified photosensitive proteins are convenient to visualize, undergo a unique photochemical reaction, and can be patterned into biomaterials using commonly available light sources. The fusions retain their activity and are able to dictate complex biological functions such as receptor binding, vesicle formation, and cellular proliferation. This method permits a broadly applicable technique for the creation of site-specifically modified photocleavable fusion proteins for spatiotemporally defined protein immobilization in biomaterials.

Photo-Cleavable protein (PhoCl) that has the unique ability to break an internal covalent bond upon exposure to visible ($\lambda$=400 nm) light. This protein undergoes β-elimination upon exposure to violet light that results in cleavage of the polypeptide backbone of the protein. This Example presents multi-functional protein fusions, with a reactive domain for protein immobilization, the PhoCl domain for photocleavage and visualization via fluorescence microscopy, and a modular fusion partner domain to leverage the endless functionalities of engineered and natural proteins.

To install a reactive handle onto our PhoCl fusion proteins, chemoenzymatic protein modification techniques were used to add a functional handle site-specifically and quantitatively onto the N-terminus. The N-myristoltransferase (NMT) enzyme was used due to its ability to co-translationally append an azide-functionalized myristic acid analog onto the N-terminus of the growing polypeptide chain. Azide groups are widely used in "click" chemistries due to their biorthogonal nature and cytocompatible reaction conditions. By coexpressing PhoCl fusion proteins with a plasmid encoding NMT and a methionine aminopeptidase in E. coli, expressed proteins could be modified site-specifically and quantitatively simply through the concurrent addition of 12-azidododecanoic acid (12-ADA) and isopropyl β-D-1-thiogalactopyranoside (IPTG) during protein expression. SDS-PAGE and mass spectrometry revealed a singly modified pure (<95%) protein population after nickel-nitrolotriacetic acid (Ni-NTA) purification with no additional need for post-translational modification or conjugation steps.

Utilizing this protein expression and modification scheme, a library of azide-functionalized PhoCl fusion proteins were synthesized from an array of different protein categories: fluorescent (mRuby, sfGFP, mCerulean), enzymatic (beta-lactamase, bla), and a growth factor (epidermal growth factor, EGF). To ensure that the 12-ADA installation and protein fusions partners would not hinder PhoCl's ability to undergo intramolecular bond scission, PhoCl cleavage was quantified for two different classes of proteins using two independent methods. First, the green fluorescence of the PhoCl domain in PhoCl-bla was monitored as a function of increasing violet light exposure. To decouple photocleavage from any potential photobleaching, SDS-PAGE was performed on intact and cleaved PhoCl-mRuby to look for cleavage products. For both quantification methods, the proteins cleaved with predictable kinetics ($t_{1/2}$~5 minutes, mean 4.68 minutes 95% CI 3.55-6.87 minutes for the fluorescence based approach, mean 4.70 95% CI 3.22-8.608 for SDS-PAGE) upon exposure to 10 mW $cm^{-2}$ violet light. Finally, whole protein mass spectrometry (ESI LC/MS) was performed before and after photocleavage to validate that cleavage was occurring at the expected amino acid. Mass spectrometry revealed a singly modified protein species that decayed into the anticipated cleavage products upon exposure to violet light.

The activity of fusion partners to Pho-Cl were also tested. Fluorescent protein fusions retained their spectral properties. Beta-lactamase activity was measured through cleavage of a nitrocefin, a compound that undergoes a color change upon beta-lactam cleavage. The activity of the enzyme was measured before and after photocleavage to determine the effect of fusing the azide containing PhoCl domain to the beta-lactamase domain. The enzymatic activity was completely retained after fusion with the PhoCl domain.

Although enzymatic cleavage of a substrate proved successful in a PhoCl fusion, biological activity was also demonstrated for the recombinant proteins. The ability of PhoCl-EGF to retain the key signaling activity of native EGF, particularly the growth factor's ability to bind its receptor and undergo internalization, was investigated. A431 cells, an epidermal cell line that overexpressed EGFR, was cultured and treated with PhoCl-EGF. After 15 minutes incubation at room temperature, cells were fixed, stained with DAPI, and imaged. Fusion protein localization was tracked via the fluorescence of the PhoCl domain. A431 cells incubated with PhoCl-EGF showed strong membrane staining and vesicle formation, both indicators of canonical EGF signaling. To further validate the biological potency of PhoCl-EGF, downstream biological effects were also tested. Culturing HeLa cells in media supplemented with PhoCl-EGF increased cell proliferation as compared to serum free controls. This effect was observed before and after light exposure, demonstrating that the EGF domain lead to downstream signal transduction even as a fusion with the PhoCl domain.

Next, bioinert optically clear hydrogel scaffolds were formed using Strain-Promoted Azide Alkyne Cycloaddition (SPAAC) between tetra-(1R,8S,9s)-Bicyclo[6.1.0]non-4-yn-9-ylmethyl (BCN) functionalized PEG monomers and di-azide functionalized crosslinkers leading to step growth polymerization creating mechanically robust gels.

To demonstrate the utility of the reactive azide moiety, SPAAC was used to sequester proteins within hydrogel depots for the light-triggered spatiotemporal release of active proteins from biomaterials. First, azide-functionalized PhoCl-bla was incorporated during gelation to create sequestered enzyme covalently immobilized within the hydrogel network. After removal of unbound protein by washing with PBS, the immobilized protein was released by exposing the gels to violet light. Bla activity in the gel supernatant was then assessed via the nitrocefin assay to quantify enzyme release from the gels. Supernatants from gels exposed to light degraded nitrocefin, demonstrating the release of active protein while gels left in the dark showed little non-specific protein release. This indicates the potential for hydrogels to be used as depots for targeted therapeutic release. This experiment was also performed for PhoCl-EGF, where HeLa cells cultured with PhoCl-EGF immobilized gels showed increased proliferation following light exposure.

As PhoCl cleavage can be spatiotemporally controlled using light, its versatility in creating photopatterned biomaterials was demonstrated. As a proof of concept, PhoCl-sfGFP, PhoCl-mRuby, and PhoCl-mCerulean (6 µm) were incorporated into PEG hydrogels during gelation. Gels were then exposed to masked violet light ($\lambda$=400 nm, 30 minutes, 10 mw/cm$^2$) and released proteins were allowed to diffuse out before imaging. In each case, the fluorescence from the PhoCl domain co-localized with the fluorescent fusion partner. This proves to be a convenient tool for tracking areas of protein immobilization when the fusion partner itself is not fluorescent. Patterning showed micron-scale resolution over long time scales, with patterns retaining their fidelity at least up to 2 weeks post patterning.

In addition to creating step-wise regions of immobilized protein, biochemical gradients can also be useful in biological experiments. To create PhoCl-immobilized gradients a syringe pump was used to move an opaque photomask across the surface of a gel during the course of light exposure ($\lambda$=400 nm, 10 mw/cm$^2$). By varying the speed the photomask moves across the hydrogel, the slope of the gradient can be modulated. As in the cleavage quantification experiments performed in solution, immobilized PhoCl also proved to cleave with a half-life of ~5 minutes (mean 4.58 minutes, 95% CI 3.47-6.78 minutes). This precise control over protein immobilization represents is useful for the creation of protein-patterned biomaterials.

While PhoCl cleavage and patterned biomaterials can be created using an LED light source and photomasks, the broad applicability of this approach was demonstrated by using argon laser line ($\lambda$=405 nm) on a Leica SP8× confocal microscope, commonly utilized to visualize DAPI, to generate patterns and gradients of immobilized proteins within the hydrogel. Regions of interest (ROIs) were drawn using the Leica software to selectively expose only those subvolumes to violet light. This resulted in the generation of arbitrarily patterned biomaterials within minutes. Tethered proteins could be completely released under mild laser conditions (5% laser power, 64 scans). Protein gradients could be generated by varying the scan number within a region of interest, leading to discrete gradients in protein concentration with micron scale resolution. As a potentially useful quirk of the system, PhoCl briefly displays red fluorescence subsequent to photocleavage, and this fluorescence change could be visualized when patterning on the confocal.

Finally, the ability of immobilized PhoCl-EGF to direct cell fate within hydrogels was investigated. HeLa cells were encapsulated within the SPAAC based gels containing either 4 µM PhoCl-EGF or 4 µM PhoCl-mRuby and an MMP degradable and RGD adhesive peptide crosslinker. One day post encapsulation, gels were exposed to 30 minutes of masked violet light, and the cells were allowed to grow for 14 days with media changes every 2-3 days. Cells were then fixed in 1% paraformaldehyde and nuclei were stained with DAPI. The cell density and spheroid area in patterned and unpatterned regions were quantified using ImageJ. Areas with immobilized PhoCl-EGF showed larger spheroid growth and more cell density than regions containing PhoCl-mRuby or no EGF. Thus, cells remain viable and are able to proliferate in PhoCl-immobilized hydrogels, and that PhoCl fusion proteins can be used to visualize and influence cell response in protein patterned biomaterials.

Thus, in this Example, a facile method for the production of site-specifically modified bioactive proteins for photoreleasable tethering into biomaterials was demonstrated. PhoCl fusion proteins showed co-translational incorporation of azide functionalized myristic acid and cleaved upon exposure to cytocompatible violet light. PhoCl fusion proteins retained their activity, enabling the creation of protein constructs with modular functionality. Proteins could be immobilized within hydrogels, visualized via the fluorescent properties of PhoCl, and released on demand by exposing the gels to light. By controlling the location, duration, and time of light exposure, high resolution protein patterns and gradients were formed within PEG based hydrogels. Finally, immobilized PhoCl fusion proteins retained bioactivity and showed the ability to guide cell fate in 3D cell culture platforms.

Plasmid Generation:

PhoCl Plasmid Construction:

A gene block containing the PhoCl domain with a 5' NdeI site and a 3' HindIII site was purchased from Integrated DNA Technologies. Polymerase chain reaction (PCR) was used to amplify gene sequences of interest and introduce relevant restriction sites (5' HindIII and 3' XhoI) for ligation with the pET21 expression plasmid (Novagen) and the 3' end of the PhoCl sequence.

Restriction enzymes (New England BioLabs) digested (4 hr, 37° C.) the pET21 plasmid (NdeI and XhoI), PhoCl gene sequence (NdeI and HindII), and PCR products (HindIII and XhoI), and the digested products were purified by extraction following electrophoretic separation (0.8% agarose). A double ligation was used to insert the PhoCl and POI genes into the pET21 plasmid (T4 DNA ligase, 16 hr, 16° C.). The plasmid was transformed into chemically competent Top10

E. coli (Thermo Fisher) by heat shock (42° C., 45 seconds), and plated onto agar plates (10 g Tryptone, 5 g Yeast Extract, 10 g NaCl, 15 g agar, 1 L dH$_2$O) containing ampicillin (100 µg mL-1). Colonies were subsequently grown overnight in Miller's Lysogeny Broth (LB, 5 mL) containing ampicillin (100 µg mL$^{-1}$). Plasmids were purified using a QIAprep Spin Miniprep Kit (Qiagen), and sequenced using a SimpleSeq DNA Sequencing Kit (Thermo Fisher). Plasmids corresponding to the construct of interest were purified and subsequently cotransformed into chemically competent BL21(DE3) E. coli (Promega) along with the NMT1 Met/AP plasmid (a gift from the Kahn lab at Emory) via heat shock (42° C., 45 seconds) and plated onto agar plates containing both ampicillin (100 µg mL$^{-1}$) and kanamycin (50 µg mL$^{-1}$). Single colonies were selected for subsequent protein expression.

Synthesis of 12-ADA 12-azidododecanoic acid (12-ADA) was synthesized following a known synthetic route with minor modifications. Briefly, 12-bromododecanoic acid (1,219 mg, 4.617 mmol, NaN3 (853 mg, 13.1 mmol, 3×), and NaI (65.4 mg, 0.436 mmol, 0.1×) were dissolved into DMF (25 mL). The mixture was stirred overnight at room temperature, diluted with ethyl acetate (40 mL) and quenched with HCl (1 M, ~20 mL) until pH 3-4. The organic phase was washed with brine (20 mL, 3×), dried over Na2SO4, and concentrated to yield a pale yellow oil (0.9488 g, 90% yield). Product (denoted 12-ADA) was used as pure with no additional purification. 1H NMR (500 MHz, CDCl3) δ 11.22 (br s, 1H), 3.25 (t, J=7.0 Hz, 2H), 2.35 (t, J=7.5 Hz, 2H), 1.69-1.54 (m, 4H), 1.41-1.22 (m, 14H); 13C NMR (126 MHz, CDCl3) δ 179.67, 51.49, 33.96, 29.43 (2C), 29.36, 29.20, 29.13, 29.03, 28.84, 26.71, 24.66; HRMS (EI+): calculated for C12H24N3O2+[M+1H+], 242.1868; found 242.1859 (Δ=−3.9 ppm). These spectral data matched those previously reported.

Protein Expression and Purification:

LB buffer (500 mL) supplemented with ampicillin (100 µg mL$^{-1}$) and kanamycin (50 µg mL$^{-1}$) was inoculated with an overnight cell culture (10 mL) and incubated (37° C.) with agitation (250 rev min-1). After reaching an optical density at λ=600 nm of 0.6, isopropyl β-D-1-thiogalactopyranoside (final concentration of 0.5 mM) and 12-azidododecanoic acid (final concentration of 1 mM) were added, and expression was continued overnight under reduced temperature (18° C.). Cells were harvested via centrifugation (4,000 g, 20 min). The cell pellet was resuspended in lysis buffer (40 mL, 20 mM Tris, 50 mM NaCl, 10 mM imidazole, 1 mM phenylmethylsulfonyl fluoride) and sonicated on ice (6 cycles of 3 minutes at 30% amplitude 33% duty cycle and 3 min resting). Soluble and insoluble fractions were separated via centrifugation (5,000 g, 20 min). Clarified lysate was applied to Ni-NTA resin (5 mL) and incubated under mild agitation (4° C., 1 hr). The flow-through was discarded, and the resin was washed with wash buffer (20 mM Tris, 50 mM NaCl, 20 mM imidazole, 20 mL, 5×). The protein was eluted with elution buffer (20 mM Tris, 50 mM NaCl, 250 mM imidazole 5 mL, 10×) and collected. The protein solution was dialyzed for 24 hours against Tris buffer (20 mM Tris, 50 mM NaCl, 3×20 fold excess dialysate to sample) using ThermoFisher SnakeSkin Dialysis Tubing (molecular weight cut-off, MWCO~10 kDa) to remove any residual imidazole and concentrated using an Amicon centrifugal spin column (MWCO~10 kDa). Typical yields for purified proteins were ~10-20 mg/L of cell culture.

Beta-Lactamase Activity Assay 10 ng PhoCl-bla or 50 uL supernatant from 5 µl PhoCl-bla immobilized hydrogels were added to nitrocefin (100 µL in PBS, 0.25 mg/mL) in a clear 96 well plate. The plate was then immediately put in a plate reader maintained at 37° C. and the absorbance at 482 nm was measured every 30 seconds for 30 minutes. The initial rate of nitrocefin cleavage for the first 5 minutes of the experiment was taken as the activity of the enzyme.

Gel Formation

PEG-tetraBicyclononyne (BCN) (Mn~20,000 Da, 4 mM) was pre-reacted with azide labeled PhoCl fusion proteins for a minimum of 30 minutes. The reaction was centrifuged (10,000 rpm, 20 s) to remove aggregated protein from the solution. $N_3$—PEG-$N_3$ (Mn~3,500 Da, 8 mM) was added, and network formation was allowed to proceed for 1 hour between Rain-X®-treated glass slides with silicone rubber spacers (McMaster-Carr, 0.5 mm thick). The slides were separated, and gels were equilibrated overnight in PBS prior to use.

Photomask Photopatterning

PhoCl-fusion protein containing gels were exposed to collimated violet light (λ=400 nm, 10 mW cm$^2$, 30 min) through a patterned chrome photomask (Photo Sciences, Inc.). Released proteins were allowed to diffuse out, and the gels were incubated in PBS overnight. Gels were then visualized using a Leica SP8X confocal microscope. For the generation of biochemical gradients, an opaque photomask moved across the surface of the gel during light exposure using a syringe pump moving at a fixed rate. The plate was set to move at a given speed (0.4 mm/min or 1.2 mm/min) while violet light (λ=400 nm, 10 mW cm$^{-2}$) shown from above.

Cell Culture and Encapsulation

HeLa and A431 cells were maintained in a Sanyo inCusaFe® MCO-17AC incubator at 37° C. and 5% $CO_2$ and fed with in Dulbecco's Modified Eagle Medium (DMEM) (Life Technologies) supplemented with fetal bovine serum (FBS, 10%) and Penicillin/Streptomycin (P/S, 1%) every 2-3 days. For HeLa cell encapsulation, HeLa cells were suspended using Trypsin, pelleted (125 g, 5 minutes), and resuspended in DMEM with 10% FBS at 2×10$^7$ cells/mL. PEG-tetraBCN (3 mM) pre-reacted with PhoCl-EGF (4 µm) for 1 hour was mixed with cell suspension and an MMP degradable and cell adhesive peptide ($N_3$-MMPRGD-$M_3$, 6 mM) to give a final cell concentration of 1×10$^7$ cells/mL and 5 µL gels were allowed to form between Rain-X®-treated glass slides with silicone rubber spacers (McMaster-Carr, 0.5 mm thick) for 1 hour at 37° C. The gels were transferred to a 24 well dish and maintained in 500 µL DMEM containing 10% FBS. And 1% P/S. For photopatterning in the presences of cells, the media was replaced with PBS containing $Ca^{2+}$ and $Mg^{2+}$ for 30 minutes prior to light exposure. Cell-laden hydrogels were maintained in 500 µL DMEM containing 10% FBS with media swaps every 2-3 days for 14 days.

A431 Membrane Staining

A431 cells were passaged and plated on chambered coverglass slides at 1.5×10$^3$ cells/cm$^2$ and allowed to attach overnight in DMEM supplemented with 10% FBS and 1% P/S. PhoCl-EGF (1 µm) was then added and the cells were incubated at room temperature for 15 minutes. Cells were then washed 2× with PBS before fixing in 1% paraformaldehyde (30 minutes) and staining with DAPI (0.15 µg/mL, 30 minutes) before imaging on a Leica SP8x confocal microscope.

Sequencing for PhoCl Constructs
Underlined text corresponds to Rs1 His6×
Italicized text corresponds to the PhoCl domain
Unformatted text corresponds to the protein of interest Rs1-His₆ₓ-PhoCl-sfGFP
[SEQ ID No.: 14]
<u>ATGGGAAATGAGGCGTCGTATCCGTTACACCATCACCATCATCAC</u>ATGGT
TATCCCGGACTACTTCAAACAGTCTTTCCCGGAAGGTTACTCTTGGGAAC
GTTCTATGACCTACGAAGACGGTGGTATCTGCATCGCTACCAACGACATC
ACCATGGAAGGTGACTCTTTCATCAACAAAATCCACTTCAAAGGTACCAA
CTTCCCGCCGAACGGTCCGGTTATGCAGAAACGTACCGTTGGTTGGGAAG
CTAGTACCGAAAAAATGTACGAACGTGACGGTGTTCTGAAAGGTGACGTT
AAAATGAAACTGCTGCTGAAAGGTGGTGGTCACTACCGTTGCGACTACCG
TACCACCTACAAAGTTAAACAGAAACCGGTTAAACTGCCGGACTACCACT
TCGTTGACCACCGTATCGAAATCCTGTCTCACGACAAAGACTACAACAAA
GTTAAACTGTACGAACACGCTGTTGCTCGTAACTCTACCGACTCTATGGA
CGAACTGTACAAAGGTGGTTCTGGTGGTATGGTTTCTAAAGGTGAAGAAA
CCATCACCTCTGTTATCAAACCGGACATGAAAAACAAACTGCGTATGGAA
GGTAACGTTAACGGTCACGCTTTCGTTATCGAAGGTGAAGGTTCTGGTAA
ACCGTTCGAAGGTATCCAGACCATCGACCTGGAAGTTAAAGAAGGTGCTC
CGCTGCCGTTCGCTTACGACATCCTGACCACCGCTTTCCACTACGGTAAC
CGTGTTTTCACCAAATACCCGCGTGGTGGTGGTAAGCTTATGCGTAAAGG
CGAAGAGCTGTTCACTGGTGTCGTCCCTATTCTGGTGGAACTGGATGGTG
ATGTCAACGGTCATAAGTTTTCCGTGCGTGGCGAGGGTGAAGGTGACGCA
ACTAATGGTAAACTGACGCTGAAGTTCATCTGTACTACTGGTAAACTGCC
GGTACCTTGGCCGACTCTGGTAACGACGCTGACTTATGGTGTTCAGTGCT
TTGCTCGTTATCCGGACCACATGAAGCAGCATGACTTCTTCAAGTCCGCC
ATGCCGGAAGGCTATGTGCAGGAACGCACGATTTCCTTTAAGGATGACGG
CACGTACAAAACGCGTGCGGAAGTGAAATTTGAAGGCGATACCCTGGTAA
ACCGCATTGAGCTGAAAGGCATTGACTTTAAAGAAGACGGCAATATCCTG
GGCCATAAGCTGGAATACAATTTTAACAGCCACAATGTTTACATCACCGC
CGATAAACAAAAAAATGGCATTAAAGCGAATTTTAAAATTCGCCACAACG
TGGAGGATGGCAGCGTGCAGCTGGCTGATCACTACCAGCAAAACACTCCA
ATCGGTGATGGTCCTGTTCTGCTGCCAGACAATCACTATCTGAGCACGCA
AAGCGTTCTGTCTAAAGATCCGAACGAGAAACGCGATCACATGGTTCTGC
TGGAGTTCGTAACCGCAGCGGGCATCACGCATGGTATGGATGAACTGTAC
AAATAA Rs1-His₆ₓ-PhoCl-mRuby
[SEQ ID No.: 15]
<u>ATGGGAAATGAGGCGTCGTATCCGTTACACCATCACCATCATCAC</u>ATGGT
TATCCCGGACTACTTCAAACAGTCTTTCCCGGAAGGTTACTCTTGGGAAC
GTTCTATGACCTACGAAGACGGTGGTATCTGCATCGCTACCAACGACATC
ACCATGGAAGGTGACTCTTTCATCAACAAAATCCACTTCAAAGGTACCAA
CTTCCCGCCGAACGGTCCGGTTATGCAGAAACGTACCGTTGGTTGGGAAG
CTAGTACCGAAAAAATGTACGAACGTGACGGTGTTCTGAAAGGTGACGTT
AAAATGAAACTGCTGCTGAAAGGTGGTGGTCACTACCGTTGCGACTACCG
TACCACCTACAAAGTTAAACAGAAACCGGTTAAACTGCCGGACTACCACT
TCGTTGACCACCGTATCGAAATCCTGTCTCACGACAAAGACTACAACAAA
GTTAAACTGTACGAACACGCTGTTGCTCGTAACTCTACCGACTCTATGGA
CGAACTGTACAAAGGTGGTTCTGGTGGTATGGTTTCTAAAGGTGAAGAAA
CCATCACCTCTGTTATCAAACCGGACATGAAAAACAAACTGCGTATGGAA
GGTAACGTTAACGGTCACGCTTTCGTTATCGAAGGTGAAGGTTCTGGTAA
ACCGTTCGAAGGTATCCAGACCATCGACCTGGAAGTTAAAGAAGGTGCTC
CGCTGCCGTTCGCTTACGACATCCTGACCACCGCTTTCCACTACGGTAAC
CGTGTTTTCACCAAATACCCGCGTGGTGGTGGTAAGCTTGTTTCTAAAGG
TGAAGAACTGATCAAAGAAAACATGCGTATGAAAGTTGTTATGGAAGGTT
CTGTTAACGGTCACCAGTTCAAATGCACCGGTGAAGGTGAAGGTCGTCCG
TACGAAGGTGTTCAGACCATGCGTATCAAAGTTATCGAAGGTGGTCCGCT
GCCGTTCGCTTTCGACATCCTGGCTACCTCTTTCATGTACGGTTCTCGTA
CCTTCATCAAATACCCGGCTGACATCCCGGACTTCTTCAAACAGTCTTTC
CCGGAAGGTTTCACCTGGGAACGTGTTACCCGTTACGAAGACGGTGGTGT
TGTTACCGTTACCCAGGACACCTCTCTGGAAGACGGTGAACTGGTTTACA
ACGTTAAAGTTCGTGGTGTTAACTTCCCGTCTAACGGTCCGGTTATGCAG
AAAAAAACCAAAGGTTGGGAACCGAACACCGAAATGATGTACCCGGCTGA
CGGTGGTCTGCGTGGTTACACCGACATCGCTCTGAAAGTTGACGGTGGTG
GTCACCTGCACTGCAACTTCGTTACCACCTACCGTTCTAAAAAAACCGTT
GGTAACATCAAAATGCCGGGTGTTCACGCTGTTGACCACCGTCTGGAACG
TATCGAAGAATCTGACAACGAAACCTACGTTGTTCAGCGTGAAGTTGCTG
TTGCTAAATACTCTAACCTGGGTGGTGGTATGGACGAACTGTACAAATAA Rs1-His₆ₓ-PhoCl-Beta-Lactamase
[SEQ ID No.: 16]
<u>ATGGGAAATGAGGCGTCGTATCCGTTACACCATCACCATCATCAC</u>ATGGT
TATCCCGGACTACTTCAAACAGTCTTTCCCGGAAGGTTACTCTTGGGAAC
GTTCTATGACCTACGAAGACGGTGGTATCTGCATCGCTACCAACGACATC
ACCATGGAAGGTGACTCTTTCATCAACAAAATCCACTTCAAAGGTACCAA
CTTCCCGCCGAACGGTCCGGTTATGCAGAAACGTACCGTTGGTTGGGAAG
CTAGTACCGAAAAAATGTACGAACGTGACGGTGTTCTGAAAGGTGACGTT
AAAATGAAACTGCTGCTGAAAGGTGGTGGTCACTACCGTTGCGACTACCG
TACCACCTACAAAGTTAAACAGAAACCGGTTAAACTGCCGGACTACCACT
TCGTTGACCACCGTATCGAAATCCTGTCTCACGACAAAGACTACAACAAA
GTTAAACTGTACGAACACGCTGTTGCTCGTAACTCTACCGACTCTATGGA
CGAACTGTACAAAGGTGGTTCTGGTGGTATGGTTTCTAAAGGTGAAGAAA
CCATCACCTCTGTTATCAAACCGGACATGAAAAACAAACTGCGTATGGAA
GGTAACGTTAACGGTCACGCTTTCGTTATCGAAGGTGAAGGTTCTGGTAA
ACCGTTCGAAGGTATCCAGACCATCGACCTGGAAGTTAAAGAAGGTGCTC -continued

CGCTGCCGTTCGCTTACGACATCCTGACCACCGCTTTCCACTACGGTAAC

CGTGTTTTCACCAAATACCCGCGTGGTGGTGGTAAGCTTATGCACCCTGA

AACGCTGGTGAAAGTAAAANATGCTGAAGATCAGTTGGGTGCACGAGTGG

GTTACATCGAACTGGATCTCAACAGCGGTAAGATCCTTGAGAGTTTTCGC

CCCGAAGAACGTTTTCCAATGATGAGCACTTTTAAAGTTCTGCTATGTGG

CGCGGTATTATCCCGTGTTGACGCCGGGCAAGAGCAACTCGGTCGCCGCA

TACACTATTCTCAGAATGACTTGGTTGAGTACTCACCAGTCACAGAAAAG

CATCTTACGGATGGCATGACAGTAAGAGAATTATGCAGTGCTGCCATAAC

CATGAGTGATAACACTGCGGCCAACTTACTTCTGACAACGATCGGAGGAC

CGAAGGAGCTAACCGCTTTTTTGCACAACATGGGGGATCATGTAACTCGC

CTTGATCGTTGGGAACCGGAGCTGAATGAAGCCATACCAAACGACGAGCG

TGACACCACGATGCCTGCAGCAATGGCAACAACGTTGCGCAAACTATTAA

CTGGCGAACTACTTACTCTAGCTTCCCGGCAACAATTAATAGACTGGATG

GAGGCGGATAAAGTTGCAGGACCACTTCTGCGCTCGGCCCTTCCGGCTGG

CTGGTTTATTGCTGATAAATCTGGAGCCGGTGAGCGTGGGTCTCGCGGTA

TCATTGCAGCACTGGGGCCAGATGGTAAGCCCTCCCGTATCGTAGTTATC

TACACGACGGGGAGTCAGGCAACTATGGATGAACGAAATAGACAGATCGC

TGAGATAGGTGCCTCACTGATTAAGCATTGGTAA

Rs1-His$_{6x}$-PhoCl-EGF

[SEQ ID No.: 17]

<u>ATGGGAAATGAGGCGTCGTATCCGTTACACCATCACCATCATCAC</u>ATGGT

TATCCCGGACTACTTCAAACAGTCTTTCCCGGAAGGTTACTCTTGGGAAC

GTTCTATGACCTACGAAGACGGTGGTATCTGCATCGCTACCAACGACATC

ACCATGGAAGGTGACTCTTTCATCAACAAAATCCACTTCAAAGGTACCAA

CTTCCCGCCGAACGGTCCGGTTATGCAGAAACGTACCGTTGGTTGGGAAG

CTAGTACCGAAAAAATGTACGAACGTGACGGTGTTCTGAAAGGTGACGTT

AAAATGAAACTGCTGCTGAAAGGTGGTGGTCACTACCGTTGCGACTACCG

TACCACCTACAAAGTTAAACAGAAACCGGTTAAACTGCCGGACTACCACT

TCGTTGACCACCGTATCGAAATCCTGTCTCACGACAAAGACTACAACAAA

GTTAAACTGTACGAACACGCTGTTGCTCGTAACTCTACCGACTCTATGGA

CGAACTGTACAAAGGTGGTTCTGGTGGTATGGTTTCTAAAGGTGAAGAAA

CCATCACCTCTGTTATCAAACCGGACATGAAAAACAAACTGCGTATGGAA

GGTAACGTTAACGGTCACGCTTTCGTTATCGAAGGTGAAGGTTCTGGTAA

ACCGTTCGAAGGTATCCAGACCATCGACCTGGAAGTTAAAGAAGGTGCTC

CGCTGCCGTTCGCTTACGACATCCTGACCACCGCTTTCCACTACGGTAAC

CGTGTTTTCACCAAATACCCGCGTGGTGGTGGTAAGCTTATGAACAGCGA

CAGCGAGTGCCCACTGAGCCACGACGGCTACTGCCTGCACGACGGCGTGT

GCATGTACATCGAGGCCCTGGACAAGTACGCCTGCAACTGCGTCGTGGGC

TACATCGGCGAGCGGTGCCAGTACCGGGACCTGAAGTGGTGGGAGCTGAG

ACTAA

Rs1-His$_{6x}$-PhoCl-Cerulean

[SEQ ID No.: 18]

<u>ATGGGAAATGAGGCGTCGTATCCGTTACACCATCACCATCATCAC</u>ATGGT

TATCCCGGACTACTTCAAACAGTCTTTCCCGGAAGGTTACTCTTGGGAAC

GTTCTATGACCTACGAAGACGGTGGTATCTGCATCGCTACCAACGACATC

ACCATGGAAGGTGACTCTTTCATCAACAAAATCCACTTCAAAGGTACCAA

CTTCCCGCCGAACGGTCCGGTTATGCAGAAACGTACCGTTGGTTGGGAAG

CTAGTACCGAAAAAATGTACGAACGTGACGGTGTTCTGAAAGGTGACGTT

AAAATGAAACTGCTGCTGAAAGGTGGTGGTCACTACCGTTGCGACTACCG

TACCACCTACAAAGTTAAACAGAAACCGGTTAAACTGCCGGACTACCACT

TCGTTGACCACCGTATCGAAATCCTGTCTCACGACAAAGACTACAACAAA

GTTAAACTGTACGAACACGCTGTTGCTCGTAACTCTACCGACTCTATGGA

CGAACTGTACAAAGGTGGTTCTGGTGGTATGGTTTCTAAAGGTGAAGAAA

CCATCACCTCTGTTATCAAACCGGACATGAAAAACAAACTGCGTATGGAA

GGTAACGTTAACGGTCACGCTTTCGTTATCGAAGGTGAAGGTTCTGGTAA

ACCGTTCGAAGGTATCCAGACCATCGACCTGGAAGTTAAAGAAGGTGCTC

CGCTGCCGTTCGCTTACGACATCCTGACCACCGCTTTCCACTACGGTAAC

CGTGTTTTCACCAAATACCCGCGTGGTGGTGGTAAGCTTATGGTGAGCAA

GGGCGAGGAGCTGTTCACCGGGGTGGTGCCCATCCTGGTCGAGCTGGACG

GCGACGTAAACGGCCACAAGTTCAGCGTGTCCGGCGAGGGCGAGGGCGAT

GCCACCTACGGCAAGCTGACCCTGAAGTTCATCTGCACCACCGGCAAGCT

GCCCGTGCCCTGGCCCACCCTCGTGACCACCCTGACCTGGGGCGTGCAGT

GCTTCGCCCGCTACCCCGACCACATGAAGCAGCACGACTTCTTCAAGTCC

GCCATGCCCGAAGGCTACGTCCAGGAGCGCACCATCTTCTTCAAGGACGA

CGGCAACTACAAGACCCGCGCCGAGGTGAAGTTCGAGGGCGACACCCTGG

TGAACCGCATCGAGCTGAAGGGCATCGACTTCAAGGAGGACGGCAACATC

CTGGGGCACAAGCTGGAGTACAACGCCATCAGCGACAACGTCTATATCAC

CGCCGACAAGCAGAAGAACGGCATCAAGGCCAACTTCAAGATCCGCCACA

ACATCGAGGACGGCAGCGTGCAGCTCGCCGACCACTACCAGCAGAACACC

CCCATCGGCGACGGCCCCGTGCTGCTGCCCGACAACCACTACCTGAGCAC

CCAGTCCAAGCTGAGCAAAGACCCCAACGAGAAGCGCGATCACATGGTCC

TGCTGGAGTTCGTGACCGCCGCCGGGATCACTCTCGGCATGGACGAGCTG

TACAAGTAA

Rs1-His$_{6x}$-PhoCl-mCherry

[SEQ ID No.: 19]

<u>ATGGGAAATGAGGCGTCGTATCCGTTACACCATCACCATCATCAC</u>ATGGT

TATCCCGGACTACTTCAAACAGTCTTTCCCGGAAGGTTACTCTTGGGAAC

GTTCTATGACCTACGAAGACGGTGGTATCTGCATCGCTACCAACGACATC

ACCATGGAAGGTGACTCTTTCATCAACAAAATCCACTTCAAAGGTACCAA

CTTCCCGCCGAACGGTCCGGTTATGCAGAAACGTACCGTTGGTTGGGAAG

CTAGTACCGAAAAAATGTACGAACGTGACGGTGTTCTGAAAGGTGACGTT

AAAATGAAACTGCTGCTGAAAGGTGGTGGTCACTACCGTTGCGACTACCG

-continued
```
TACCACCTACAAAGTTAAACAGAAACCGGTTAAACTGCCGGACTACCACT

TCGTTGACCACCGTATCGAAATCCTGTCTCACGACAAAGACTACAACAAA

GTTAAACTGTACGAACACGCTGTTGCTCGTAACTCTACCGACTCTATGGA

CGAACTGTACAAAGGTGGTTCTGGTGGTATGGTTTCTAAAGGTGAAGAAA

CCATCACCTCTGTTATCAAACCGGACATGAAAAACAAACTGCGTATGGAA

GGTAACGTTAACGGTCACGCTTTCGTTATCGAAGGTGAAGGTTCTGGTAA

ACCGTTCGAAGGTATCCAGACCATCGACCTGGAAGTTAAAGAAGGTGCTC

CGCTGCCGTTCGCTTACGACATCCTGACCACCGCTTTCCACTACGGTAAC

CGTGTTTTCACCAAATACCCGCGTGGTGGTGGTAAGCTTATGGTTTCCAA

GGGCGAAGAAGACAACATGGCGATCATCAAAGAATTTATGCGTTTTAAAG

TTCACATGGAAGGTTCTGTTAACGGTCATGAGTTCGAAATTGAAGGTGAG

GGTGAAGGTCGCCCGTACGAAGGTACCCAGACCGCGAAACTGAAAGTTAC

CAAAGGTGGTCCGCTGCCGTTCGCGTGGGACATCCTCAGCCCGCAGTTCA

TGTACGGTTCTAAAGCGTACGTTAAACATCCGGCGGACATTCCAGACTAC

CTCAAACTCTCTTTCCCTGAAGGTTTCAAATGGGAACGTGTTATGAACTT

CGAGGACGGTGGTGTTGTCACCGTTACCCAGGACTCTTCTCTGCAGGACG

GCGAGTTCATCTACAAGGTCAAACTGCGTGGCACCAACTTCCCGTCTGAC

GGTCCGGTTATGCAGAAAAAAACCATGGGTTGGGAAGCGTCTTCTGAACG

TATGTACCCGGAAGATGGTGCGCTGAAAGGCGAAATCAAACAGCGTCTGA

AGCTCAAAGACGGCGGTCACTACGACGCGGAGGTTAAAACCACCTACAAA

GCGAAAAAGCCGGTTCAACTGCCGGGTGCGTACAACGTTAATATCAAGCT

GGACATCACCTCTCACAACGAAGACTACACCATCGTTGAACAGTACGAAC

GTGCGGAAGGCCGTCACTCTACCGGTGGTATGGACGAACTGTACAAGTAA
```

Photocleavage Kinetics of PhoCl

Rs1-His$_{6x}$-PhoCl-mCherry at ~1 mg/ml was exposed to 405 nm light at 10 mw/cm$^2$ for varying lengths of time. The samples were then loaded onto SDS page where the intact protein can be separated from the cleaved protein and visualized by the change in size. The intact protein is ~56 kDa, while cleaved PhoCl and mCherry appear as bands around 26 and 30 kDa respectively. The photocleavage could be tracked by observing the proportion of intact to cleaved proteins. After 1 hour, there were diminishing returns for photocleavage vs irradiation times, so this time point was chosen for subsequent patterning experiments.

PhoCl Aggregation

Gel precursor solution was pre-reacted with N$_3$-PhoCl-sfGFP for 4 hours and then either centrifuged at 10,000 g for 10 minutes (left) or directly used for gelation (right) and imaged 24 hours later. Upon centrifugation, there was a clear precipitate of aggregated proteins which are evident as bright specs of light in the hydrogel that did not undergo centrifugation. Once conjugated to the hydrogel, these protein aggregates did not appear even after extended incubation times (~1 week) at room temperature.

Photolithographic Patterning of PhoCl-Fluorescent Protein Fusions

5 μL hydrogels were formed with either 30 μm N$_3$-PhoCl-eGFP (a) or 30 μm N$_3$-PhoCl-mCerulean (b and c) and exposed to patterned 405 nm light at 10 mw/cm$^2$ for 1 hour. The photocleaved protein was allowed to diffuse out overnight in 1 mL of Phosphate Buffered Saline (PBS). Residual tethered PhoCl maintains its green fluorescence, highlighting areas where conjugated protein remain. Dark regions correspond to areas where PhoCl was cleaved and the liberated protein diffused away.

Confocal Patterning of PhoCl-EGFP

Hydrogels containing immobilized PhoCl-eGFP were patterned using confocal microscopy (405 nm argon laser, 5% laser power, 64 scans) and immediately imaged in the green (a) and red channels (b). The region exposed to 405 nm light shows depletion of sfGFP fluorescence, and the appearance of red fluorescence that is associated with PhoCl cleavage.

Confocal Patterning of PhoCl-mCerulean

Gels containing immobilized PhoCl-mCerulean were patterned using the FRAP module of a Leica-SP8x microscope in order to localize photocleavage to arbitrary regions. 5% laser power at 64 scans with 405 nm light was used, and the hydrogels were immediately imaged in the green, red, and blue channels. The hydrogels showed the expected depletion of intact PhoCl and mCerulean in the patterned regions, and the appearance of red fluorescence associated with PhoCl cleavage.

Gel Release Study of PhoCl-sfGFP Hydrogels

10 μL hydrogels containing 15 μm PhoCl-sfGFP were either exposed to 405 nm light at 10 mw/cm$^2$ for 1 hour or left in the dark, and then fluorescent measurements were taken (488 nm excitation, 510 nm emission) at the given time points. Hydrogels that were exposed to light showed greater supernatant fluorescence, corresponding to sfGFP being liberated from the hydrogel matrix.

Example 3B. LOVTRAP for Fully Reversible Biochemical Patterning

While combining oxime ligation with ortho-nitrobenzyl ester (oNB) photocleavage allows for the addition and removal of proteins from a hydrogel, the process is not completely reversible. Once the oNB bond is cleaved, the liberated functional group is not amenable to further photochemistries. To overcome these limitations, an attractive alternative is to use non-covalent protein-protein interactions whose affinities can be altered upon exposure to light. This conformational change need not involve the breaking or formation of covalent bonds, therefore the process can be fully reversible. As light exposure can be easily spatially and temporally defined, a protein that changes binding affinity in response to light would be useful for fully reversible photopatterning.

Protein-protein interactions can be studied by a variety of techniques. Binding affinity has long been understood to depend on structure, with one well-characterized example being the G-protein coupled receptors (GPCRs), a highly-conserved family of proteins containing seven transmembrane-spanning domains. GPCRs undergo a conformational change upon binding an extracellular ligand that results in association with an intracellular G-protein to transduce signals across the cell membrane. These sorts of interactions hold promise for their potential to bind biochemical cues within hydrogels as they can be dynamic and quite powerful, reaching binding affinities with dissociation constants in the sub-nanomolar range.

Several interesting candidate proteins exist which undergo reversible conformational changes upon exposure to light. For example, *Arabidopsis thaliana* protein Phytochrome B (PhyB) undergoes a conformational change upon exposure to red light that promotes its binding with Phytochrome Interaction Factor 3 (PIF3). PhyB normally undergoes thermal relaxation in the dark, or the dark state reversion can be initiated by exposure to infrared light. However, PhyB requires the exogenous addition of phycocyanobilin to act as a chromophore in order for it to function. For this reason, another light-sensitive protein Light-Oxygen-Voltage-Sensing-Domain 2 (LOV2) was chosen, whose cofactor, flavin mononucleotide, is naturally expressed by *E. coli*. This method simplifies the expression and purification steps, and is adaptable to applications in other expression vectors.

LOV2 undergoes a conformational change in the Jα domain upon exposure to blue light (~470 nm) that leads to partial unfolding of the Jα helix. Recently, a variety of binding partners have been engineered whose binding affinity is dependent upon the conformational state of the Jα helix. Termed "LOVTRAP" a binding partner, termed Zdark (Zdk), has been used in optogenetics experiments to cycle recruitment to the mitochondria of LOV2-fusion proteins with a Zdk bound mitochondrial membrane protein. There is a 150-fold difference in binding affinity of Zdk with the LOV2 Jα helix between the light and dark states, meaning that there should be good contrast in the amount of bound protein between the light and dark states of LOV2. Hypothesizing that both of these proteins can be expressed in *E. coli* without the addition of exogenous chromophores, Zdk fusion proteins and an azide-tagged LOV2 were recombinantly expressed. An additional advantage of the LOVTRAP system is that LOV2 is sensitive to 470 nm blue light, well outside of the UV region that could be damaging to cellular DNA. As an added benefit, blue light has increased penetration into tissues, allowing for potential future applications in drug delivery.

In order to demonstrate the ability of LOVTRAP to be used as a technique for fully reversible photopatterning of biomaterials, the following steps can be carried out:
1. Recombinantly express and purify LOV2-Jα and Zdk fusion proteins;
2. Immobilize LOV2-Jα within a hydrogel matrix;
3. Show that immobilized LOV-Jα is able to bind Zdk fusion proteins, and that the extent of binding can be modulated via light; and
4. Reversibly pattern hydrogels using light to create dynamic biochemical gradients.

To minimize the size of the fusion partners with the protein of interest, the smaller Zdk domain (~7 kDa) was chosen for the fusion protein. As the C-terminal Jα helix is critical for Zdk binding, Lov2 was expressed with an N-terminal RS1 sequence for N-myristoyltransferase (NMT) modification and a polyhistidine tag immediately downstream for purification. A gene encoding RS1-His$_{6x}$-LOV2-Jα was cloned into the PET21-a(+) plasmid and successfully expressed in BL21(DE3) *E. coli* and verified via mass spectrometry. C-terminal Zdk fusions with eGFP, mCerulean, mCherry, Beta-lactamase, and EGF were also produced and recovered with excellent yield, up to 80 mg/L of cell culture for the fluorescent proteins.

Next, azide-functionalized LOV2 was immobilized into PEG hydrogels at 10 mg/mL. Basic modeling was performed based on the dissociation constants of the light and dark states of LOV2 with Zdk in order to optimize the amount of Zdk-fused protein to add. mCherry-Zdk was swelled into either blank PEG hydrogels or ones containing immobilized LOV2. Hydrogels which were conjugated with LOV2 retained more fluorescence than control hydrogels after an overnight wash step in PBS.

The ability of light to induce dissociation of the LOV2-Zdk complex was tested by exposing hydrogels containing LOV2 and mCherry-Zdk to patterned 470 nm light. Interestingly, even extremely low exposure intensities (0.1 mW/cm$^2$ intermittent light exposure, 5 seconds on 55 seconds off for 1 hour) led to the generation of patterned hydrogels. Lov2 containing hydrogels were also successfully patterned on a confocal microscope using a 470 nm laser line. This points to the great sensitivity of LOV2 to undergo photoinduced conformational change.

To determine whether the patterning could be performed reversibly, sfGFP-Zdk was purified and swelled into patterned mCherry-Zdk hydrogels. sfGFP-Zdk enriched in areas depleted of mCherry-ZDK, suggesting that the LOV2 binding sites were already saturated with mCherry-ZDK, and that here were no additional LOV2-Jα sites available for binding. Subsequent rounds of photopatterning can be performed to see how many times the system can be cycled.

Sequencing Data

The RS1 sequence for NMT modification is underlined.
The polyhistidine tag for Ni-NTA purification is italicized.
The Zdk binding motif is shown in bold.
The protein of interest is shown in unformatted text.

RS1-His$_{6x}$-LOV2

[SEQ ID No.: 20]
<u>ATGGGAAATGAGGCGTCGTATCCGTTA*CACCATCACCATCATCACCTGGC*</u>

TACCACCCTGGAACGTATCGAAAAAAACTTCGTTATCACCGACCCGCGTC

TGCCGGACAACCCGATCATCTTCGCTTCTGACTCTTTCCTGCAGCTGACC

GAATACTCTCGTGAAGAAATCCTGGGTCGTAACTGCCGTTTCCTGCAGGG

TCCGGAAACCGACCGTGCTACCGTTCGTAAAATCCGTGACGCTATCGACA

ACCAGACCGAAGTTACCGTTCAGCTGATCAACTACACCAAATCTGGTAAA

AAATTCTGGAACCTGTTCCACCTGCAGCCGATGCGTGACCAGAAAGGTGA

CGTTCAGTACTTCATCGGTGTTCAGCTGGACGGTACCGAACACGTTCGTG

ACGCTGCTGAACGTGAAGGTGTTATGCTGATCAAAAAAACCGCTGAAAAC

ATCGACGAAGCTGCTAAAGAACTG

His$_{6x}$-mCherry-Zdk

[SEQ ID No.: 21]
*ATGCACCATCACCATCATCAC*ATGGTTTCCAAGGGCGAAGAAGACAACAT

GGCGATCATCAAAGAATTTATGCGTTTTAAAGTTCACATGGAAGGTTCTG

TTAACGGTCATGAGTTCGAAATTGAAGGTGAGGGTGAAGGTCGCCCGTAC

GAAGGTACCCAGACCGCGAAACTGAAAGTTACCAAAGGTGGTCCGCTGCC

GTTCGCGTGGGACATCCTCAGCCCGCAGTTCATGTACGGTTCTAAAGCGT

ACGTTAAACATCCGGCGGACATTCCAGACTACCTCAAACTCTCTTTCCCT

GAAGGTTTCAAATGGGAACGTGTTATGAACTTCGAGGACGGTGGTGTTGT

CACCGTTACCCAGGACTCTTCTCTGCAGGACGGCGAGTTCATCTACAAGG

TCAAACTGCGTGGCACCAACTTCCCGTCTGACGGTCCGGTTATGCAGAAA

AAAACCATGGGTTGGGAAGCGTCTTCTGAACGTATGTACCCGGAAGATGG

TGCGCTGAAAGGCGAAATCAAACAGCGTCTGAAGCTCAAAGACGGCGGTC

ACTACGACGCGGAGGTTAAAACCACCTACAAAGCGAAAAAGCCGGTTCAA

CTGCCGGGTGCGTACAACGTTAATATCAAGCTGGACATCACCTCTCACAA

CGAAGACTACACCATCGTTGAACAGTACGAACGTGCGGAAGGCCGTCACT

CTACCGGTGGTATGGACGAACTGTACAAGAAGCTT**GGTGGTTCTGGTGGT
AGCATGGTGGATAACAAATTCAATAAAGAAAAGACGCGTGCCGGTGCGGA
AATCCATTCTCTGCCAAACCTGAATGTTGAGCAGAAGTTTGCCTTCATCG
TGAGCCTGTTTGATGATCCATCTCAGAGCGCCAATCTGCTGGCCGAAGCC
AAAAAACTGAACGATGCCCAGGCCCCAAAATAA**

His$_{6x}$-sfGFP-Zdk

[SEQ ID No.: 22]

ATG*CACCATCACCATCATCACATG*CGTAAAGGCGAAGAGCTGTTCACTGG
TGTCGTCCCTATTCTGGTGGAACTGGATGGTGATGTCAACGGTCATAAGT
TTTCCGTGCGTGGCGAGGGTGAAGGTGACGCAACTAATGGTAAACTGACG
CTGAAGTTCATCTGTACTACTGGTAAACTGCCGGTACCTTGGCCGACTCT
GGTAACGACGCTGACTTATGGTGTTCAGTGCTTTGCTCGTTATCCGGACC
ACATGAAGCAGCATGACTTCTTCAAGTCCGCCATGCCGGAAGGCTATGTG
CAGGAACGCACGATTTCCTTTAAGGATGACGGCACGTACAAAACGCGTGC
GGAAGTGAAATTTGAAGGCGATACCCTGGTAAACCGCATTGAGCTGAAAG
GCATTGACTTTAAAGAAGACGGCAATATCCTGGGCCATAAGCTGGAATAC
AATTTTAACAGCCACAATGTTTACATCACCGCCGATAAACAAAAAAATGG
CATTAAAGCGAATTTTAAAATTCGCCACAACGTGGAGGATGGCAGCGTGC
AGCTGGCTGATCACTACCAGCAAAACACTCCAATCGGTGATGGTCCTGTT
CTGCTGCCAGACAATCACTATCTGAGCACGCAAAGCGTTCTGTCTAAAGA
TCCGAACGAGAAACGCGATCACATGGTTCTGCTGGAGTTCGTAACCGCAG
CGGGCATCACGCATGGTATGGATGAACTGTACAAAAAGCTT**GGTGGTTCT
GGTGGTAGCATGGTGGATAACAAATTCAATAAAGAAAAGACGCGTGCCGG
TGCGGAAATCCATTCTCTGCCAAACCTGAATGTTGAGCAGAAGTTTGCCT
TCATCGTGAGCCTGTTTGATGATCCATCTCAGAGCGCCAATCTGCTGGCC
GAAGCCAAAAAACTGAACGATGCCCAGGCCCCAAAATAA**

His$_{6x}$-mCerulean-Zdk

[SEQ ID No.: 23]

ATG*CACCATCACCATCATCACATG*GTGAGCAAGGGCGAGGAGCTGTTCAC
CGGGGTGGTGCCCATCCTGGTCGAGCTGGACGGCGACGTAAACGGCCACA
AGTTCAGCGTGTCCGGCGAGGGCGAGGGCGATGCCACCTACGGCAAGCTG
ACCCTGAAGTTCATCTGCACCACCGGCAAGCTGCCCGTGCCCTGGCCCAC
CCTCGTGACCACCCTGACCTGGGGCGTGCAGTGCTTCGCCCGCTACCCCG
ACCACATGAAGCAGCACGACTTCTTCAAGTCCGCCATGCCCGAAGGCTAC
GTCCAGGAGCGCACCATCTTCTTCAAGGACGACGGCAACTACAAGACCCG
CGCCGAGGTGAAGTTCGAGGGCGACACCCTGGTGAACCGCATCGAGCTGA
AGGGCATCGACTTCAAGGAGGACGGCAACATCCTGGGGCACAAGCTGGAG
TACAACGCCATCAGCGACAACGTCTATATCACCGCCGACAAGCAGAAGAA
CGGCATCAAGGCCAACTTCAAGATCCGCCACAACATCGAGGACGGCAGCG
TGCAGCTCGCCGACCACTACCAGCAGAACACCCCCATCGGCGACGGCCCC
GTGCTGCTGCCCGACAACCACTACCTGAGCACCCAGTCCAAGCTGAGCAA
AGACCCCAACGAGAAGCGCGATCACATGGTCCTGCTGGAGTTCGTGACCG
CCGCCGGGATCACTCTCGGCATGGACGAGCTGTACAAGAAGCTT**GGTGGT
TCTGGTGGTAGCATGGTGGATAACAAATTCAATAAAGAAAAGACGCGTGC
CGGTGCGGAAATCCATTCTCTGCCAAACCTGAATGTTGAGCAGAAGTTTG
CCTTCATCGTGAGCCTGTTTGATGATCCATCTCAGAGCGCCAATCTGCTG
GCCGAAGCCAAAAAACTGAACGATGCCCAGGCCCCAAAATAA**

His$_{6x}$-Beta-lactamase-Zdk

[SEQ ID No.: 24]

ATG*CACCATCACCATCATCACATG*CACCCTGAAACGCTGGTGAAAGTAAA
ANATGCTGAAGATCAGTTGGGTGCACGAGTGGGTTACATCGAACTGGATC
TCAACAGCGGTAAGATCCTTGAGAGTTTTCGCCCCGAAGAACGTTTTCCA
ATGATGAGCACTTTTAAAGTTCTGCTATGTGGCGCGGTATTATCCCGTGT
TGACGCCGGGCAAGAGCAACTCGGTCGCCGCATACACTATTCTCAGAATG
ACTTGGTTGAGTACTCACCAGTCACAGAAAAGCATCTTACGGATGGCATG
ACAGTAAGAGAATTATGCAGTGCTGCCATAACCATGAGTGATAACACTGC
GGCCAACTTACTTCTGACAACGATCGGAGGACCGAAGGAGCTAACCGCTT
TTTTGCACAACATGGGGGATCATGTAACTCGCCTTGATCGTTGGGAACCG
GAGCTGAATGAAGCCATACCAAACGACGAGCGTGACACCACGATGCCTGC
AGCAATGGCAACAACGTTGCGCAAACTATTAACTGGCGAACTACTTACTC
TAGCTTCCCGGCAACAATTAATAGACTGGATGGAGGCGGATAAAGTTGCA
GGACCACTTCTGCGCTCGGCCCTTCCGGCTGGCTGGTTTATTGCTGATAA
ATCTGGAGCCGGTGAGCGTGGGTCTCGCGGTATCATTGCAGCACTGGGGC
CAGATGGTAAGCCCTCCCGTATCGTAGTTATCTACACGACGGGGAGTCAG
GCAACTATGGATGAACGAAATAGACAGATCGCTGAGATAGGTGCCTCACT
GATTAAGCATTGGAAGCTT**GGTGGTTCTGGTGGTAGCATGGTGGATAACA
AATTCAATAAAGAAAAGACGCGTGCCGGTGCGGAAATCCATTCTCTGCCA
AACCTGAATGTTGAGCAGAAGTTTGCCTTCATCGTGAGCCTGTTTGATGA
TCCATCTCAGAGCGCCAATCTGCTGGCCGAAGCCAAAAAACTGAACGATG
CCCAGGCCCCAAAATAA**

His$_{6x}$-EGF-Zdk

[SEQ ID No.: 25]

ATG*CACCATCACCATCATCACATG*AACAGCGACAGCGAGTGCCCACTGAG
CCACGACGGCTACTGCCTGCACGACGGCGTGTGCATGTACATCGAGGCCC
TGGACAAGTACGCCTGCAACTGCGTCGTGGGCTACATCGGCGAGCGGTGC
CAGTACCGGGACCTGAAGTGGTGGGAGCTGAGACTAAGCTT**GGTGGTTCT
GGTGGTAGCATGGTGGATAACAAATTCAATAAAGAAAAGACGCGTGCCGG
TGCGGAAATCCATTCTCTGCCAAACCTGAATGTTGAGCAGAAGTTTGCCT
TCATCGTGAGCCTGTTTGATGATCCATCTCAGAGCGCCAATCTGCTGGCC
GAAGCCAAAAAACTGAACGATGCCCAGGCCCCAAAATAA**

Modeling of Zdk to LOV2 Ratio to Optimize Contrast

As the binding affinities of Zdk to LOV2 in the light and dark states are known, it is possible to calculate the % of protein added that remains bound in light exposed and dark regions of the hydrogel. Adding too little Zdk to the system means that even in light exposed regions there was still enough binding affinity to bind all of the Zdk. Adding excessive amounts of Zdk flooded the system so that the amount of protein remaining in solution diminished the signal of bound vs. unbound Zdk. Adding 0.75 Zdk fusion proteins for every 1 LOV2 moiety gave the optimal contrast in patterning.

Bulk Hydrogel Fluorescence of LOV2 Immobilized Hydrogels with mCherry-Zdk

Hydrogels containing either 10 mg/mL immobilized LOV2 (a) or control hydrogels (b) were put into a solution of 30 μM mCherry-Zdk for 8 hours before washing with PBS overnight. The resulting hydrogels were imaged on a fluorescent microscope. The hydrogels containing immobilized LOV2 retained approximately 2 fold more mCherry-Zdk than the control hydrogels.

Patterned mCherry-Zdk in LOV2 Hydrogels

Hydrogels containing 10 mg/mL LOV2 and 30 um mCherry were exposed to 0.1 mw/cm$^2$ intermittent 5 seconds on 55 seconds off 470 nm blue light in a 400 μm line pattern for 1 hour. The resulting hydrogel was imaged on a fluorescent microscope and the line pattern could clearly be seen.

LOV2 Hydrogels Patterned Via Confocal Microscopy

Hydrogels containing 10 mg/mL LOV2 or blank and 30 μM Cherry were exposed to 470 nm laser light (1% laser power, 8 scans right 64 scans left). Hydrogels containing LOV2 showed release in the area exposed to laser light. Control hydrogels containing only nonspecifically adsorbed mCherry showed no patterning even with higher scan numbers, indicating that the decreased fluorescence was not a photobleaching event and was indeed release.

Backfilling of Patterned LOV2 Hydrogels

Gels containing immobilized LOV2 were either swelled with 30 μM mCherry-Zdk (a) or sfGFP-Zdk (b), then exposed to light (0.1 mw/cm$^2$ intermittent 5 seconds on 55 seconds off 470 nm blue light for 1 hour) in circles of decreasing radius (outlined with white circles) then backfilled by soaking in a solution containing either 30 μM sfGFP-Zdk (a) or mCherry-Zdk (b), and imaged on a fluorescent microscope. The initial fluorescent protein was depleted in irradiated areas, and the subsequent protein was enriched in those areas. Scale bar is 100 μm.

Photobleaching of LOV2

Gels containing immobilized LOV2 were swelled with 30 μM mCherry-Zdk then exposed to light (1 mw/cm$^2$ 2 hours) in circles of decreasing radius then backfilled by soaking in a solution containing 30 μM sfGFP, and imaged on a fluorescent microscope in the red (a) and green (b) channels. Both fluorescent proteins were depleted in irradiated areas, suggesting that LOV2 in the areas exposed to higher intensities of 470 nm light lost its ability to bind Zdk fusion proteins. Scale bar is 100 μm.

Expression and Ni-NTA Purification of Polyhistidine Tagged Proteins

LB (500 mL) supplemented with ampicillin (100 μg mL$^{-1}$) was inoculated with an overnight cell culture (10 mL) and incubated (37° C.) with agitation (250 rev min$^{-1}$). After reaching an optical density at λ=600 nm of 0.6, isopropyl β-D-1-thiogalactopyranoside was added (final concentration of 0.5 mM) and expression was continued overnight under reduced temperature (18° C.).

Cells were harvested via centrifugation (7,000 g, 10 min). The cell pellet was resuspended in lysis buffer (40 mL, 20 mM Tris, 50 mM NaCl, 10 mM imidazole, 1 mM phenylmethylsulfonyl fluoride) and sonicated on ice (6 cycles of 3 minutes at 30% amplitude 33% duty cycle and 3 min resting). Soluble and insoluble fractions were separated via centrifugation (5,000 g, 20 min).

Clarified lysate was applied to Ni-NTA resin (2.5 mL) and incubated under mild agitation (4° C., 1 hr). The flow-through was discarded, and the resin was washed with wash buffer (20 mM Tris, 50 mM NaCl, 20 mM imidazole, 20 mL, 5×) then eluted in elution buffer (20 mM Tris, 50 mM NaCl, 250 mM imidazole 1 mL, 20×).

The elution fractions were collected and dialyzed against tris buffer (20 mM Tris, 50 mM NaCl, 4 L) using ThermoFisher SnakeSkin Dialysis Tubing (molecular weight cut-off, MWCO~10 kDa) to remove imidazole and concentrated using an Amicon centrifugal spin column (MWCO~10 kDa).

Expression, 12-Azadodecanoic Acid Labelling, and Ni-NTA Purification of Polyhistidine Tagged Proteins LB (500 mL) supplemented with ampicillin (100 μg mL$^{-1}$) and kanamycin (50 μg mL$^{-1}$) was inoculated with an overnight cell culture (10 mL) that has been cotransformed with the plasmid of interest and the NMT-Met/AP plasmid and incubated (37° C.) with agitation (250 rev min$^{-1}$). After reaching an optical density at λ=600 nm of 0.6, isopropyl β-D-1-thiogalactopyranoside was added (final concentration of 0.5 mM) and 50 μM 12-azidododecanoic acid were added and expression was continued overnight under reduced temperature (18° C.).

Cells were harvested via centrifugation (7,000 g, 10 min). The cell pellet was resuspended in lysis buffer (40 mL, 20 mM Tris, 50 mM NaCl, 10 mM imidazole, 1 mM phenylmethylsulfonyl fluoride) and sonicated on ice (6 cycles of 3 minutes at 30% amplitude 33% duty cycle and 3 min resting). Soluble and insoluble fractions were separated via centrifugation (5,000 g, 20 min).

Clarified lysate was applied to Ni-NTA resin (2.5 mL) and incubated under mild agitation (4° C., 1 hr). The flow-through was discarded, and the resin was washed with wash buffer (20 mM Tris, 50 mM NaCl, 20 mM imidazole, 20 mL, 5×) then eluted in elution buffer (20 mM Tris, 50 mM NaCl, 250 mM imidazole 1 mL, 20×).

The elution fractions were collected and dialyzed against tris buffer (20 mM Tris, 50 mM NaCl, 4 L) using ThermoFisher SnakeSkin Dialysis Tubing (molecular weight cut-off, MWCO~10 kDa) to remove imidazole and concentrated using an Amicon centrifugal spin column (MWCO~10 kDa).

Synthesis of 12-azidododecanoic acid (12-ADA)

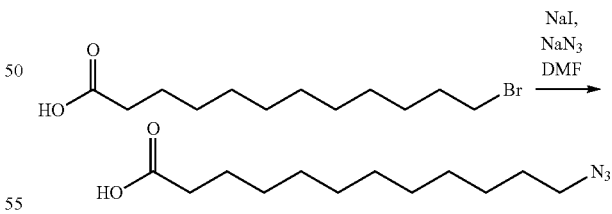

12-bromododecanoic acid (12189 mg, 4.617 mmol, 1×), NaN$_3$ (850 mg, 13.1 mmol, 3×) and NaI (64.2 mg, 0.436 mmol, 0.1×) were dissolved into dimethylformamide (10 mL). The mixture formed a white slurry and was stirred overnight at RT, diluted with ethyl acetate (40 mL) and quenched with HCl (1 M, added 5 mL increments until slurry was fully dissolved, 25 mL total). The aqueous layer was removed via separation funnel, followed by brine washing (20 mL, 3×). The organic layer was then dried with ~2 g Na$_2$SO$_4$ and transferred to a rotary evaporator to yield a faintly yellow liquid (0.898 g, 90% yield).

Nitrocefin Assay

Each sample of beta-lactamase to be tested (10 ng in 10 μL PBS) was added to a well of a 96 well dish in triplicate. Nitrocefin (2 mM) in PBS (100 μL) was added using a multichannel pipette. The plate was immediately moved into a plate reader, and sample absorbance ($\lambda_{abs}$=386 nm and $\lambda_{abs}$=482 nm) was measured every 30 seconds 37° C.

Conjugation of Azide-Tagged Proteins into Hydrogels

Azide-tagged proteins (either via NMT or sortase) were prereacted with PEG-tetraBCN monomer (8 mM) for at least 4 hours with shaking. The solution was then centrifuged at 10,000 g for 10 minutes, and the supernatant taken and added to $N_3$—PEG-$N_3$ (Mn~3,500 Da, 8 mM) in. Network formation was allowed to proceed for 1 hour between Rain-X®-treated glass slides with silicone rubber spacers (McMaster-Carr, 0.5 mm thick). The slides were separated, and hydrogels were equilibrated overnight in PBS prior to use.

Example 4. Logic-Based Delivery of Site-Specifically Modified Proteins from Environmentally Responsive Hydrogel Biomaterials The controlled presentation of proteins from and within materials remains of significant interest for many bioengineering applications. Though "smart" platforms offer control over protein release in response to a single external cue, no strategy has been developed to trigger delivery in response to user-specified combinations of environmental inputs, nor to independently control the release of multiple species from a homogenous material. In this work, we introduce a modular semisynthetic scheme to govern the release of site-specifically modified proteins from hydrogels following Boolean logic. A sortase-mediated transpeptidation reaction was used to generate recombinant proteins C-terminally tethered to hydrogels through environmentally sensitive degradable linkers. By varying the connectivity of multiple stimuli-labile moieties within these customizable linkers, we exhaustively demonstrate YES/OR/AND control of protein release in response to one and two-input combinations involving enzyme, reductant, and light. Tethering of multiple proteins each through a different stimuli-sensitive linker permits their independent and sequential release from a common material. These methodologies can be used for tissue engineering and therapeutic delivery.

Presented in this Example is a robust synthetic strategy that affords user-programmable release of site-specifically modified proteins from hydrogels. By tethering proteins of interest to hydrogel networks through degradable linkers of defined molecular architecture, Boolean YES/OR/AND logic-based control over protein release in response to complex sets of inputs can be achieved. This approach yields biomacromolecular delivery only when user-specified combinations of external cues are present, permitting the sequential and independent triggered release of multiple proteins from hydrogel biomaterials.

On-demand protein release experiments were performed using poly(ethylene glycol) (PEG)-based hydrogels. PEG is an inert hydrophilic polymer that exhibits low biofouling and is useful in preventing non-specific adsorption to hydrogels that could inhibit protein delivery. A strain-promoted azide-alkyne cycloaddition (SPAAC) reaction between a four-arm PEG tetrabicyclononyne (PEG-tetraBCN) and a linear PEG diazide ($N_3$—PEG-$N_3$) was used to generate near-ideal step-growth polymer networks. SPAAC is the most common biocompatible click reaction; we have previously exploited SPAAC's excellent reaction selectivity to form hydrogels in the presence of living cells and serum-containing culture medium. Azide-functionalized proteins that are included within the hydrogel formulation at physiologically relevant concentrations (<100 μM) are homogenously tethered throughout the network with minimal impact on material mechanical properties.

To introduce azido functionality onto proteins of interest in a site-specific manner, thereby yielding a monodisperse population with uniform bioactivity, a sortase-mediated reaction was used. *Staphylococcus aureus* sortase A is a calcium-assisted transpeptidase that recognizes the C-terminal sorting signal "LPXTG", forming an acyl-enzyme intermediate with the protein while simultaneously displacing the C-terminal portion of the sorting signal's threonine residue. The thioester of the acyl-enzyme intermediate can be nucleophilically displaced with a polyglycine probe, covalently modifying the C-terminus while regenerating the sortase A enzyme. "Sortagging" was implemented through the Sortase-Tag Enhanced Protein Ligation (STEPL) technique (FIG. 22A). In STEPL, *E. coli* is used to recombinantly express a single fusion protein construct containing the protein of interest, the sorting sequence LPETG [SEQ ID No.: 9], a $(GGS)_5$ flexible linker [SEQ ID No.: 12], sortase A, and a 6×His-Tag. Upon addition of calcium and a customizable probe containing an N-terminal polyglycine moiety, an intramolecular sortagging event ligates the probe to the protein of interest and cleaves the 6×His-functionalized sortase. When this reaction is performed during immobilized metal affinity chromatography of the protein, sortase A remains bound to the Ni-NTA column, enabling site-specific protein labeling and purification in a single step.

Taking advantage of its unique ability to install non-natural functionalities onto the C-terminus of recombinant proteins, STEPL was used to introduce both an azide necessary for hydrogel tethering and a modular degradable sequence to regulate triggered protein release. In Example 2, programmable hydrogel biomaterials were described that degrade in response to precise combinations of external stimuli specified through the controlled arrangement of degradable groups within material crosslinkers. Here, the biocomputational scheme was extended to control the release of site-specifically modified proteins via linkers that cleave in response to user-defined input combinations governed by Boolean YES/OR/AND logic. The linker between the protein and azide can function as a YES-gate for controlling protein release when it contains a single degradable moiety, an OR-gate (denoted with logic symbol v) when two unique degradable moieties are included in series, and as an AND-gate (denoted by logic symbol ∧) when two unique degradable moieties are present in parallel. To formulate linkers containing an N-terminal polyglycine moiety for sortagging and a C-terminal azide for hydrogel conjugation, precisely connected through multiple labile groups with defined topology, linkers were created using peptide chemistry.

Figure 22E:
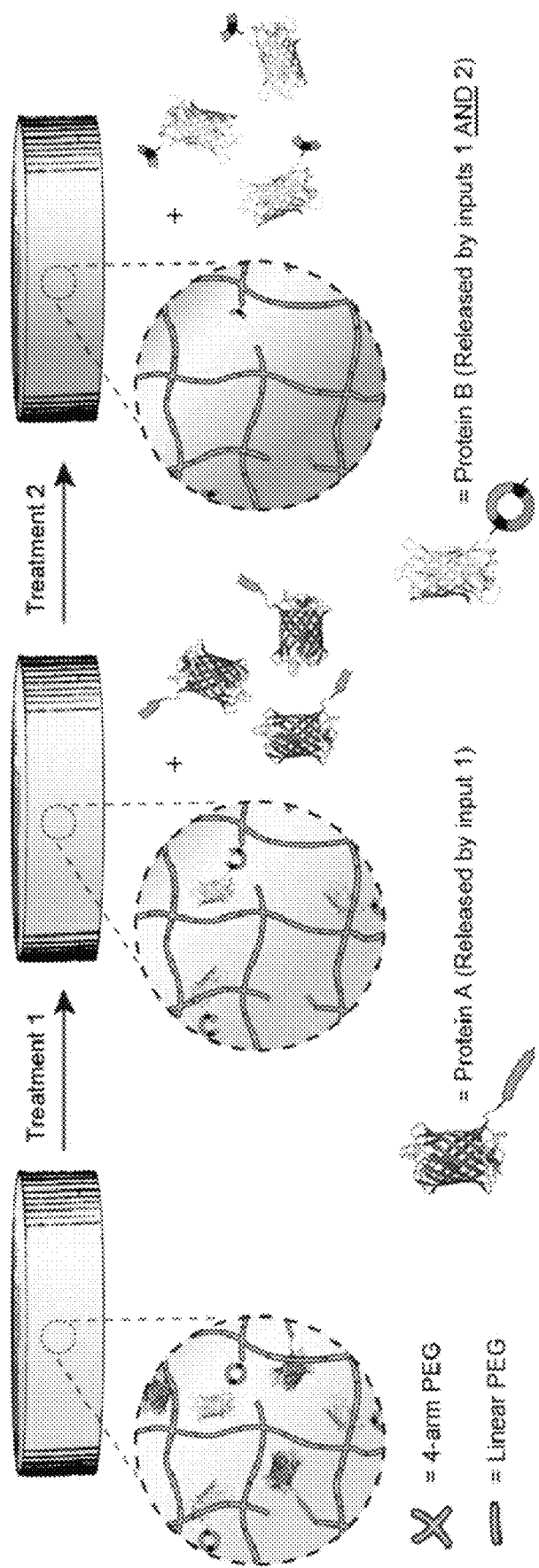
Figure 24:
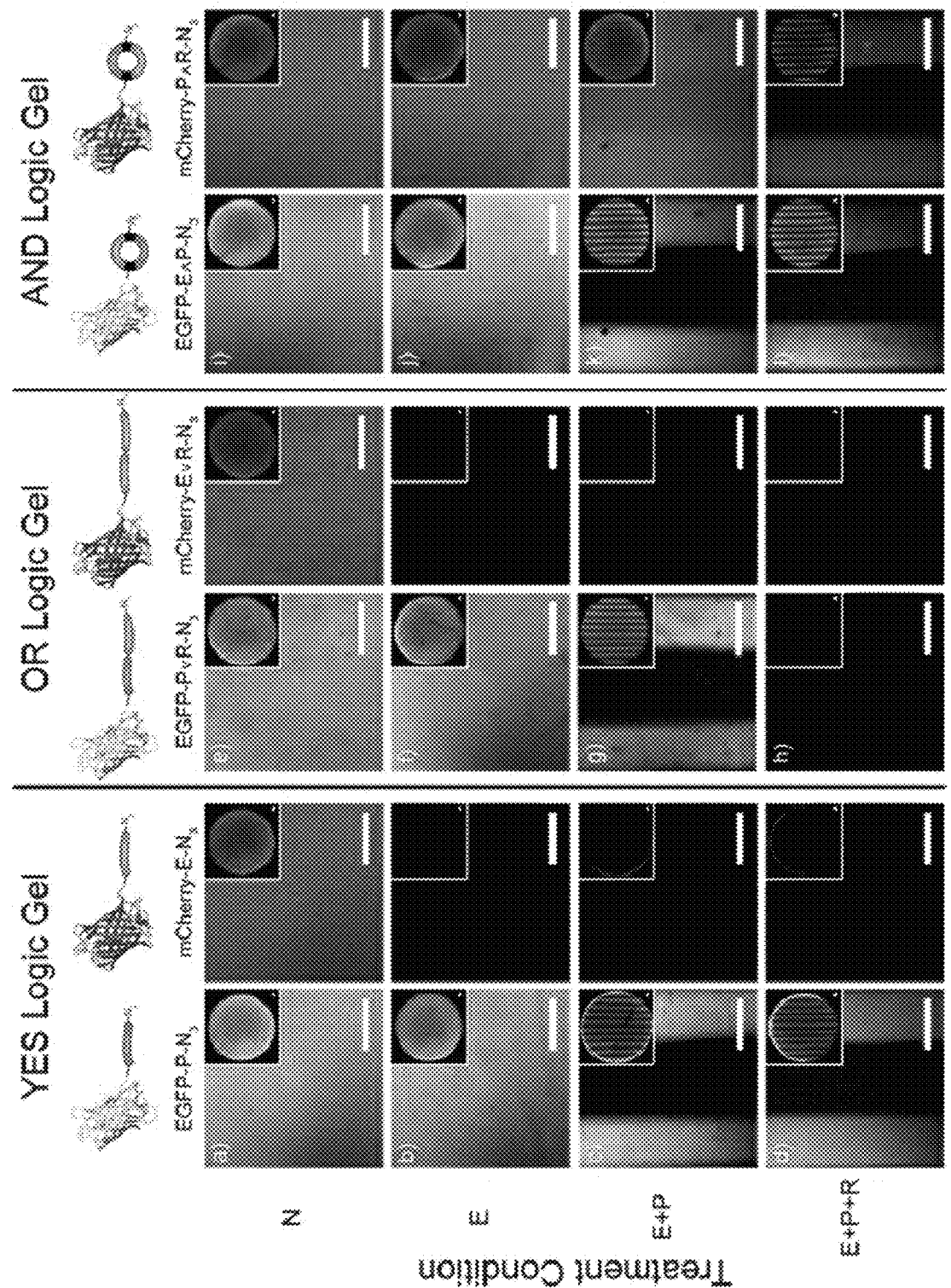
FIG. 24 is related to sequential and spatiotemporally varied release of EGFP and mCherry from a single hydrogel in response to environmental cues. (a-d) YES-based logical release of EGFP-P—N$_3$ and mCherry-E-N$_3$; (e-h) OR-based logical release of EGFP-P\/R—N$_3$ and mCherry-E\/R—N$_3$; (i-l) AND-based logical release of EGFP-E/\P—N$_3$ and mCherry-P/\R—N$_3$ prior to treatment (N) and upon sequential enzyme (E), masked light exposure (P), and reductive (R) treatments. Hydrogels were imaged using fluorescent microscopy. Left and right images for each condition respectively correspond to the fluorescence of EGFP (light gray) and mCherry (dark gray) within the same hydrogel. Insets depict full hydrogel. Scale bars=400

To assess this approach for modular logic-based protein release, three distinct stimuli-labile moieties (FIGS. 22B-22D) were selected: (1) the proteolytically degradable peptide sequence, GPQGVWGQ [SEQ ID No.: 7], which is cleaved by matrix metalloproteinase (MMP) enzymes; (2) disulfide bonds, which are reduced by tris(2-carboxyethyl) phosphine (TCEP) and other reducing agents; and (3) an ortho-nitrobenzyl ether (oNB) group, which undergoes irreversible photoscission upon exposure to near-UV light ($\lambda$=365 nm). Since each degradable moiety is susceptible to a different class of external stimulus (i.e., enzyme, chemical environment, light), orthogonal control over chemical cleavage was expected (FIG. 22E).

The enzyme- (E), reductive- (R), and light- (P) degradable moieties were used to construct nine distinct linkers for C-terminal protein modification by STEPL that collectively spanned every permutation of YES-, OR-, and AND-gated responses involving the E, R, and P inputs. Each linker contained a stimuli-degradable region flanked by an N-terminal polyglycine moiety (GGGG) for sortagging and a C-terminal azide ($N_3$) for hydrogel tethering. All peptide linkers were synthesized using solid-phase peptide synthesis, purified, and characterized by mass spectrometry.

Logic-based degradable linkers were installed onto the C-terminus of several recombinant proteins of interest using STEPL. While this method can be used to modify virtually any monomeric protein species, initial efforts focused on Enhanced Green Fluorescent Protein (EGFP), whose fluorescence provides a convenient way to visualize and quantify protein release from hydrogels. Each of the nine degradable polyglycine probes were sortagged onto EGFP. All proteins were isolated with quantitative terminal functionalization in excellent purity as confirmed by mass spectrometry.

To characterize protein release in response to different combinations of environmental stimuli, each of the nine EGFP variants were individually tethered into PEG-based hydrogels. Release of each EGFP variant was quantified for all eight possible input combinations of enzyme, reductant, and light using the supernatant fluorescence corresponding to EGFP (FIGS. 23A-23C). The YES logic-based systems (EGFP-E-$N_3$, EGFP-R—$N_3$, EGFP-P—$N_3$) behaved as engineered, releasing protein in conditions containing the programmed cue with a ~10-fold greater selectivity than conditions that did not. This high selectivity demonstrates chemical orthogonality amongst the three input/substrate pairs. The OR logic-based systems (EGFP-E$\lor$R—$N_3$, EGFP-P$\lor$R—$N_3$, EGFP-E$\lor$P—$N_3$) also behaved as expected, releasing protein in the presence of either programmed cue. The AND logic-based systems (EGFP-E$\land$R—$N_3$, EGFP-P$\land$R—$N_3$, and EGFP-E$\land$P—$N_3$) all offered protein release only when both requisite environmental cues were present. It is believed that these AND-based materials represent the first systems that require more than one input to release a protein payload from a hydrogel. The modularity of the approach is notable, where the same protein can be readily sortagged with different species to yield a wide variety of user-defined responsiveness to combinations of environmental factors.

Leveraging the precise control that this approach affords over the environmentally triggered release, the independent and differential release of multiple proteins from the same material was demonstrated. Hydrogels were formulated with both EGFP and a red fluorescent protein, mCherry (also synthesized and modified by STEPL), uniformly tethered via different logically degradable linkages. These materials were sequentially treated with enzyme, masked UV light (400 μm line patterns), and reductant; after each step, fluorescent microscopy was used to visualize the spatial presentation of each hydrogel-bound protein (FIGS. 24A-24L). When a hydrogel containing YES logical proteins EGFP-P—$N_3$ and mCherry-E-$N_3$ was treated with enzyme, mCherry was fully released while EGFP remained attached to the hydrogel. Subsequent exposure to masked light induced patterned EGFP release. EGFP remained in the photopatterned configuration upon reductive treatment. Next, a second hydrogel containing the OR logic-based proteins EGFP-P$\lor$R—$N_3$ and mCherry-E$\lor$R—$N_3$ was exposed to enzyme, inducing the full release of mCherry while not affecting EGFP presentation. Exposure to masked UV light resulted in selective EGFP release in a photopatterned line configuration; subsequent exposure to a reductant fully released EGFP. Finally, a third hydrogel containing AND logically tethered proteins EGFP-E$\land$P—$N_3$ and mCherry-P$\land$R-$N_3$ was exposed to enzyme and displayed no protein release. Subsequent treatment with masked UV light induced EGFP release in exposed regions but did not elicit mCherry release. Upon reductive treatment, EGFP presentation was unchanged while mCherry was released from the previously light-exposed regions, inducing the development of the interspaced line pattern. In every case, the observed environmentally triggered protein release matched the engineered response, highlighting this platform's unique ability to permit programmable, independently triggered delivery of multiple proteins from a single material.

Figure 25A:
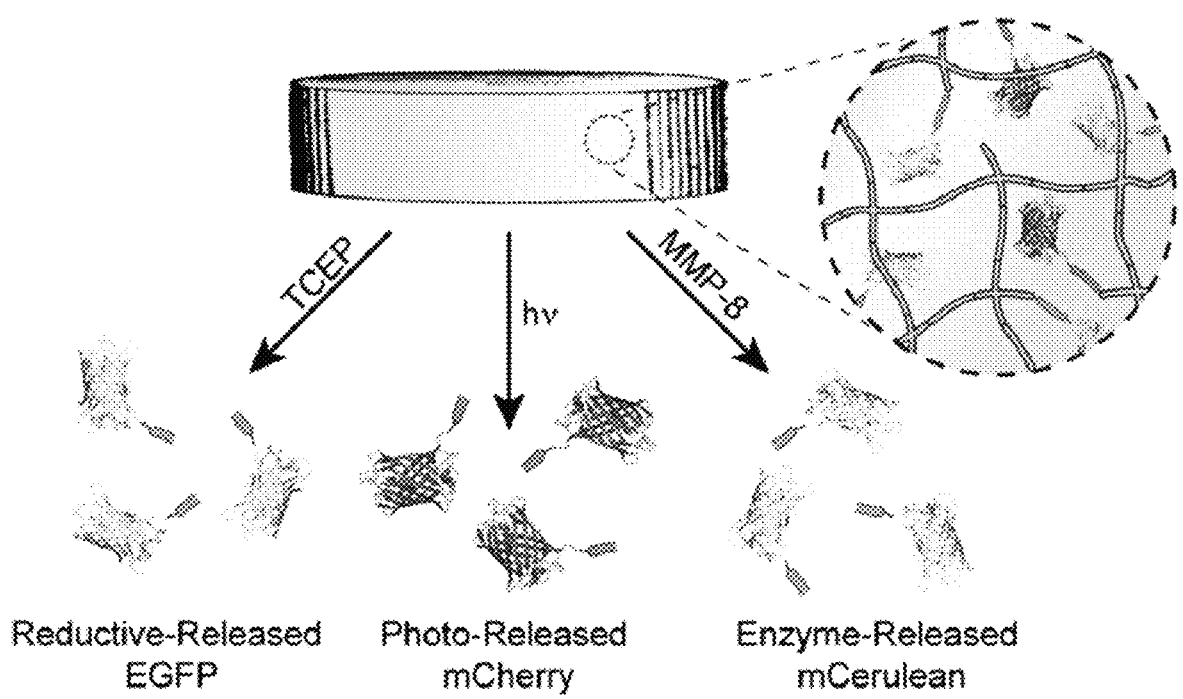
FIGS. 25A and 25B are related to the independently triggered release of three distinct proteins from a single hydrogel.
Figure 25B:
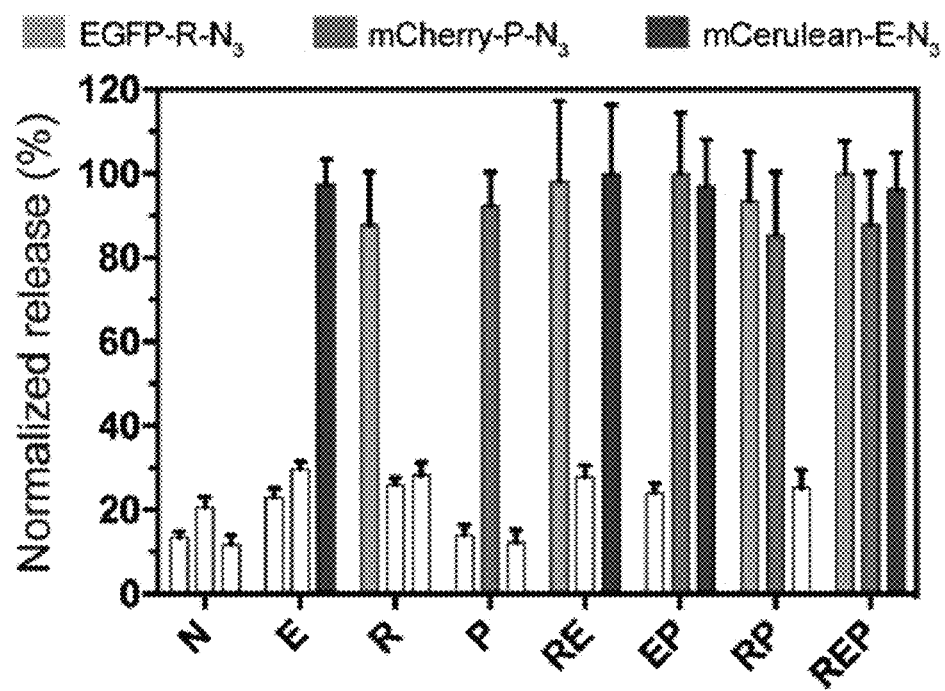

To demonstrate independent control of three biomacromolecules from the same material, hydrogels were formulated with three distinct fluorescent proteins tethered through different YES-logic degradable linkers: EGFP-R—$N_3$, mCherry-P—$N_3$, and a blue fluorescent protein construct, mCerulean-E-$N_3$ (also synthesized and modified by STEPL). Spectrally separated excitation and emissions for these fluorophores enabled independent quantification of each species following hydrogel treatments. As expected, proteins were released only in the presence of the input corresponding to their linker (FIGS. 25A-25B). It is believed this is the first approach for independent programmable control over the environmentally triggered delivery of multiple proteins from a single material.

Thus, in this Example, a robust strategy to program release of site-specifically modified proteins from hydrogels in response to user-defined environmental signals is demonstrated. A unique sortase-mediated transpeptidation reaction was used to quantitatively functionalize the C-termini of a variety of proteins with degradable linkers that tether species to hydrogels. Nine unique linkers exhaustively spanning each Boolean YES-, OR-, and AND-gated response to three distinct input classes (i.e., enzyme, light, reductive environments) enabled triggered protein release in accordance with the engineered logical function. It is believed that this is the first biomaterial systems that require more than one external cue to release a protein payload and the systems allow the independently triggered release of multiple proteins from a single homogenous material.

Synthesis of Logical Peptide Linkers for Sortagging

Peptides were synthesized via standard Fmoc solid-phase peptide synthesis and further modified with solution-phase reactions. Intramolecular peptide stapling was introduced via either oxidative disulfide formation or by copper(I)-catalyzed azide-alkyne cycloaddition. Peptides were purified using reversed-phase high-pressure liquid chromatography (RP-HPLC) on a silica C18 column. Purity was confirmed by matrix-assisted laser desorption/ionization time of flight mass spectrometry.

STEPL-Based Sortagging for C-Terminal Protein Labeling:

Each fusion protein containing: the protein of interest (i.e., EGFP, mCherry, mCerulean), sorting sequence LPETG, (GGS)$_5$ flexible linker, sortase A, and a 6×His-Tag, was expressed in BL21(DE3) *E. coli*. Cells were lysed via sonication, and the 6×His-tagged fusion protein was immobilized on Ni-NTA. To promote the STEPL reaction, sortaggable peptide (10×) and calcium chloride (0.1 mM) were added to the Ni-NTA resin and reacted at 37° C. for 4 hours with mild agitation. The flow-through containing the sortagged protein was collected and purified via centrifugal membrane filtration.

Logic-Based Protein Release in Response to Environmental Stimuli:

Hydrogels (10 µL) were formulated from PEG-tetraBCN ($M_n$~20,000 Da, 2 mM), $N_3$—PEG-$N_3$ ($M_n$~3,500 Da, 4 mM), and sortagged azide-functionalized logical proteins (0.1 mM total, equal concentration of all proteins) in MMP buffer (50 mM Tris, 200 mM NaCl, 5 mM $CaCl_2$, 1 µM $ZnCl_2$, pH=7.5). The protein and PEG-tetraBCN were pre-reacted for 4 hours prior to mixing with $N_3$-PEG-$N_3$. After one hour, formed hydrogels were washed in MMP buffer to remove unconjugated protein.

All treatments were performed at 4° C. in MMP buffer (100 µL). Samples receiving the reductive input were treated with TCEP. HCl (2 µL, 100 mM in MMP buffer) and incubated overnight. Excess TCEP was quenched with hydroxyethyl disulfide (5 µL, 100 mM in MMP buffer). Samples receiving the enzyme input were treated with MMP-8 (2.5 µL, 0.4 mg mL$^{-1}$ in MMP buffer) overnight. Samples receiving the light input were exposed to UV light ($\lambda$=365 nm, 20 mW cm$^{-2}$, 10 minutes) and all samples were incubated overnight. Protein release was quantified by measuring the fluorescence corresponding to EGFP ($\lambda$=475 nm, $\lambda_{em}$=510 nm), mCherry ($\lambda$=575 nm, $\lambda_{em}$=610 nm), and mCerulean ($\lambda$=433 nm, $\lambda_{em}$=475 nm) in the supernatant.

Chemical reagents and solvents were purchased from either Sigma-Aldrich or Fisher Scientific and used without further purification. Distilled water (dH$_2$O) was obtained from a U.S. Filter Corporation Reverse Osmosis system equipped with a desalination membrane. All chemical reactions were performed under inert nitrogen atmosphere in flame-dried glassware and were stirred with Teflon-coated magnetic stir bars. Solvent was removed under reduced pressure with a Buchi Rotovap R-3 by using either V-700 vacuum pump or Welch 1400 high vacuum pump. All peptides were synthesized using Fmoc-based, microwave-assisted, solid-phase peptide synthesis methodology on a CEM Liberty 1. All peptides were purified by semi-preparative reverse-phase high pressure liquid chromatography (RP-HPLC) performed on Dionex Ultimate 3000 equipped with RS multiple variable wavelength detector, automated fraction collector, and C18 column. Peptide characterization was performed by using Matrix-assisted laser desorption/ionization time of flight (MALDI-TOF) on Bruker AutoFlex II. Lyophilization was performed on a Labconco FreeZone 2.5 Plus freeze-dryer equipped with Labconco rotary vane 117 vacuum pump. Lumen Dynamics OmniCure S1500 Spot UV curing system was used for photochemical cleavage reactions, where light intensity was determined using a Cole-Palmer radiometer (Series 9811-50, $\lambda$=365 nm). All cell cultures were maintained in Thermo-Fisher Scientific MaxQ 4000 Benchtop Orbital Shaker-Incubator. Cells were lysed using Fisher Scientific Sonic Dismembrator (Model 505). Protein concentrations were measured on Thermo-Scientific NanoDrop 2000 Spectrophotometer. Protein mass characterization was performed on SYNAPT G2-Si Mass Spectrometer equipped with a liquid chromatography column (LC-MS). Fluorescence measurement data was acquired from SpectraMax M5 spectrometer. Fluorescence microscopy was performed on Leica SP8X confocal microscope. The synthesis of 2,5-dioxopyrrolidin-1-yl 4-azidobutanoate ($N_3$-0 Su), 2,5-dioxopyrrolidin-1-yl 4-(4-(1-((4-azidobutanoyl)oxy)ethyl)-2-methoxy-5-nitrophenoxy) butanoate ($N_3$-oNB-OSu), PEG-tetraBCN, and $N_3$—PEG-$N_3$ were performed as reported in literature. Fmoc-Lys($N_3$)—OH was synthesized as previously reported.

Synthesis of Enzymatically-Degradable, Sortaggable Peptide (GGGG-E-$N_3$, E is Enzyme)

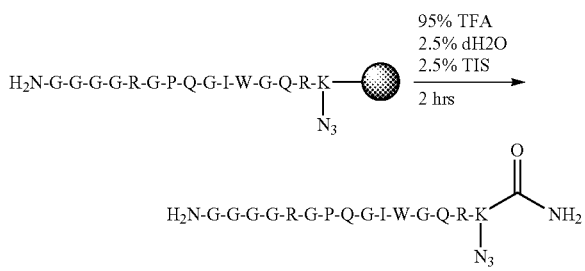

H-GGGGRGPQGIWGQRK($N_3$)—NH$_2$ [SEQ ID No.: 26] was synthesized on rink amide resin (0.25 mmol scale) via standard Fmoc-based, microwave-assisted, solid-phase peptide synthesis methodologies; Fmoc-Lys($N_3$)—OH was utilized to introduce azide functionality at the C-terminus. The peptide was deprotected and cleaved from resin by treatment with trifluoroacetic acid (TFA)/triisopropylsilane (TIS)/dH$_2$O (95:2.5:2.5, 15 mL) for 2 hours. Following cleavage, the peptide was precipitated in and washed with ice-cold diethyl ether (2×), purified by RP-HPLC operating with 55 min gradient (5-100%) of acetonitrile in water containing TFA (0.1%), and lyophilized to obtain the final peptide (H-GGGGRGPQGIWGQRK($N_3$)—NH$_2$, [SEQ ID No.: 26] denoted GGGG-E-$N_3$, and represented graphically as GGGG-enzyme-$N_3$) as a white solid (97.6 mg, 0.0613 mmol, 24.5% yield). Peptide purity was confirmed by MALDI-TOF mass spectroscopy: calculated [M+$^1$H]$^+$, 1592.70, observed 1592.46.

Synthesis of Reduction-Degradable, Sortaggable Peptide (GGGG-R—$N_3$) [SEQ ID No.: 2]

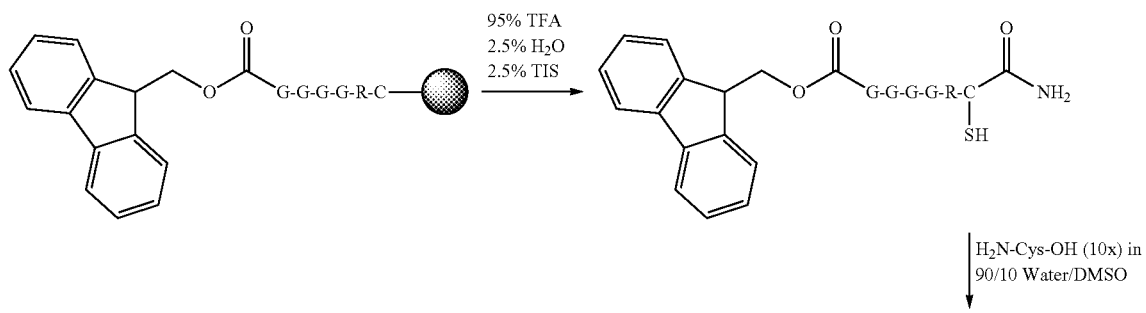

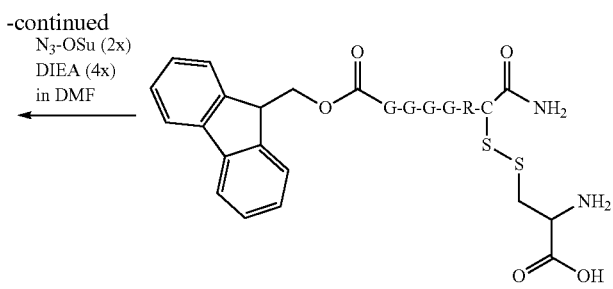

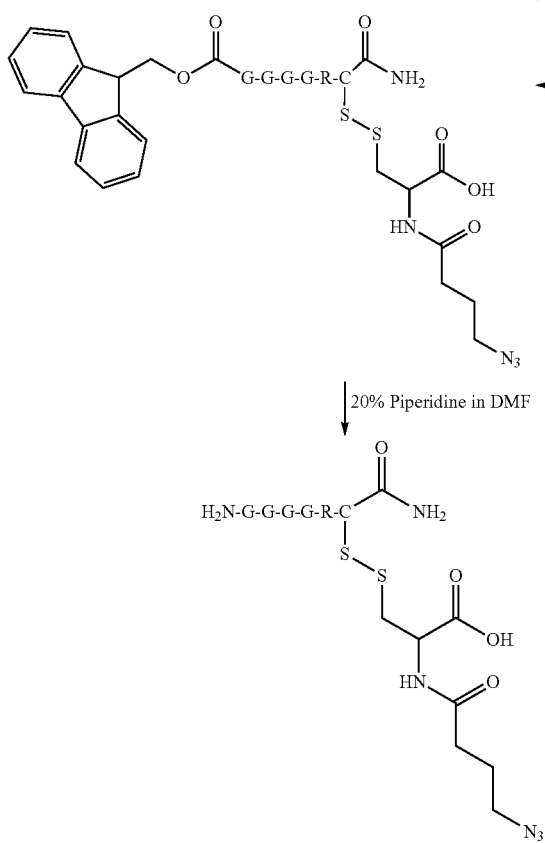

Fmoc-GGGGRC-NH$_2$ [SEQ ID No.: 27] was synthesized on rink amide resin (0.25 mmol scale) via standard Fmoc-based, microwave-assisted, solid-phase peptide synthesis methodologies. The peptide was deprotected and cleaved from resin by treatment with TFA/TIS/dH$_2$O (95:2.5:2.5, 15 mL) for 2 hours. Following cleavage, the peptide was precipitated in and washed with ice-cold diethyl ether (2×), purified by RP-HPLC operating with 43.4 min gradient (20-100%) of acetonitrile in water containing TFA (0.1%), and lyophilized to obtain the intermediate peptide as a white solid. The intermediate peptide (50 mg, 0.069 mmol, 27.6% yield) and H-Cys-OH (84 mg, 0.69 mmol, 10×) were dissolved dH$_2$O/DMSO (9:1) and reacted at room temperature for 48 hrs. The solution was concentrated by rotary evaporation, dissolved in dH$_2$O, purified by RP-HPLC with 43.4 min gradient (20-100%) of acetonitrile in water containing TFA (0.1%), and lyophilized to give the intermediate peptide (Fmoc-GGGGRC(H—C—OH)—NH$_2$ [SEQ ID No.: 28] with cysteines linked via disulfide bond) as a white solid. The intermediate peptide (8.2 mg, 0.0097 mmol, 14% yield) was reacted overnight with N$_3$—OSu (4.38 mg, 0.0194 mmol, 2×) and DIEA (5.01 mg, 0.039 mmol, 4×) in minimal DMF to introduce azide functionality onto the peptide. The reaction mixture was purified by RP-HPLC with 43.4 min gradient (20-100%) of acetonitrile in water containing TFA (0.1%), and the product fraction was lyophilized to obtain the intermediate peptide, Fmoc-GGGGRC(N$_3$—C—OH)—NH$_2$ with cysteines linked via disulfide bond (9 mg, 0.0094 mmol, 97% yield). The N-terminal Fmoc group was cleaved by incubating the peptide in piperidine (20%) in DMF (9 mL) for 10 mins. The deprotection reaction mixture was concentrated via rotary evaporation, purified by RP-HPLC operating with 55 min gradient (5-100%) of acetonitrile in water containing TFA (0.1%), and lyophilized to obtain the final product (H-GGGGRC(N$_3$—C—OH)—NH$_2$ [SEQ ID No.: 29] with cysteines linked via disulfide bond, denoted GGGG-R—N$_3$, and represented graphically as GGGG-Reductive-N$_3$) as a white solid (1.5 mg, 0.002 mmol, 21.3% yield). Peptide purity was confirmed by MALDI-TOF mass spectroscopy: calculated [M+$^1$H]$^+$, 734.97, observed 735.33.

Synthesis of Photo-Degradable, Sortaggable Peptide (GGGG-P—N$_3$)

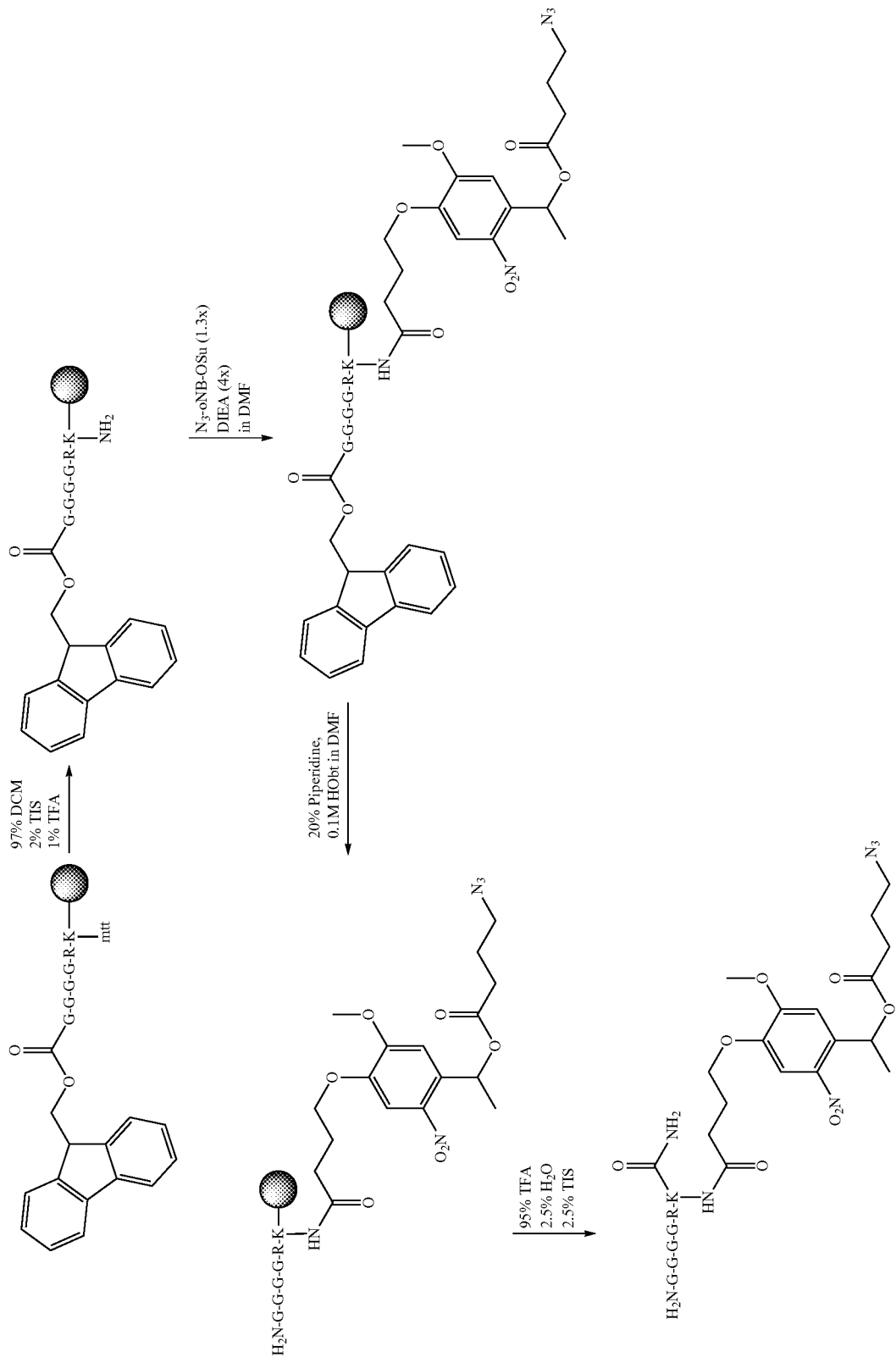

Fmoc-GGGGRK(Mtt)-NH$_2$ [SEQ ID No.: 30] was synthesized on rink amide resin (0.25 mmol scale) via standard Fmoc-based, microwave-assisted, solid-phase peptide synthesis methodologies. The acid-labile N-methyltrityl (Mtt) moiety protecting the ε-amino group of the lysine side chain was removed by treatment with DCM/TIS/TFA (97:2:1, 9×15 mL, 10 min each). The resin-bound peptide was reacted overnight with N$_3$-oNB-OSu (165 mg, 0.325 mmol, 1.3×) and DIEA (129.25 mg, 1 mmol, 4×) in minimal DMF to introduce oNB and azido functionality onto the ε-amino group of the lysine side chain. Fmoc deprotection was achieved on resin by treatment with piperidine (20%) and 1-hydroxybenzotriazole (HOBt, 0.1 M) in DMF (2×15 mL, 10 mins each). The peptide was deprotected and cleaved from resin by treatment with TFA/TIS/dH$_2$O (95:2.5:2.5, 15 mL) for 2 hours. Following cleavage, the peptide was precipitated in and washed with ice-cold diethyl ether (2×), purified by RP-HPLC operating with 55 min gradient (5-100%) of acetonitrile in water containing TFA (0.1%), and lyophilized to obtain the final product (H-GGGGRK (oNB—N$_3$)—NH$_2$ [SEQ ID No.: 31], denoted GGGG-P—N$_3$, and represented graphically as GGGG-Photo-N$_3$) as a yellow solid (41.1 mg, 0.45 mmol, 17.83% yield). Peptide purity was confirmed by MALDI-TOF mass spectroscopy: calculated [M+$^1$H]$^+$, 921.96, observed 921.47.

Synthesis of Enzyme-OR-Reductive-Degradable, Sortaggable Peptide (GGGG-E\/R—N$_3$)

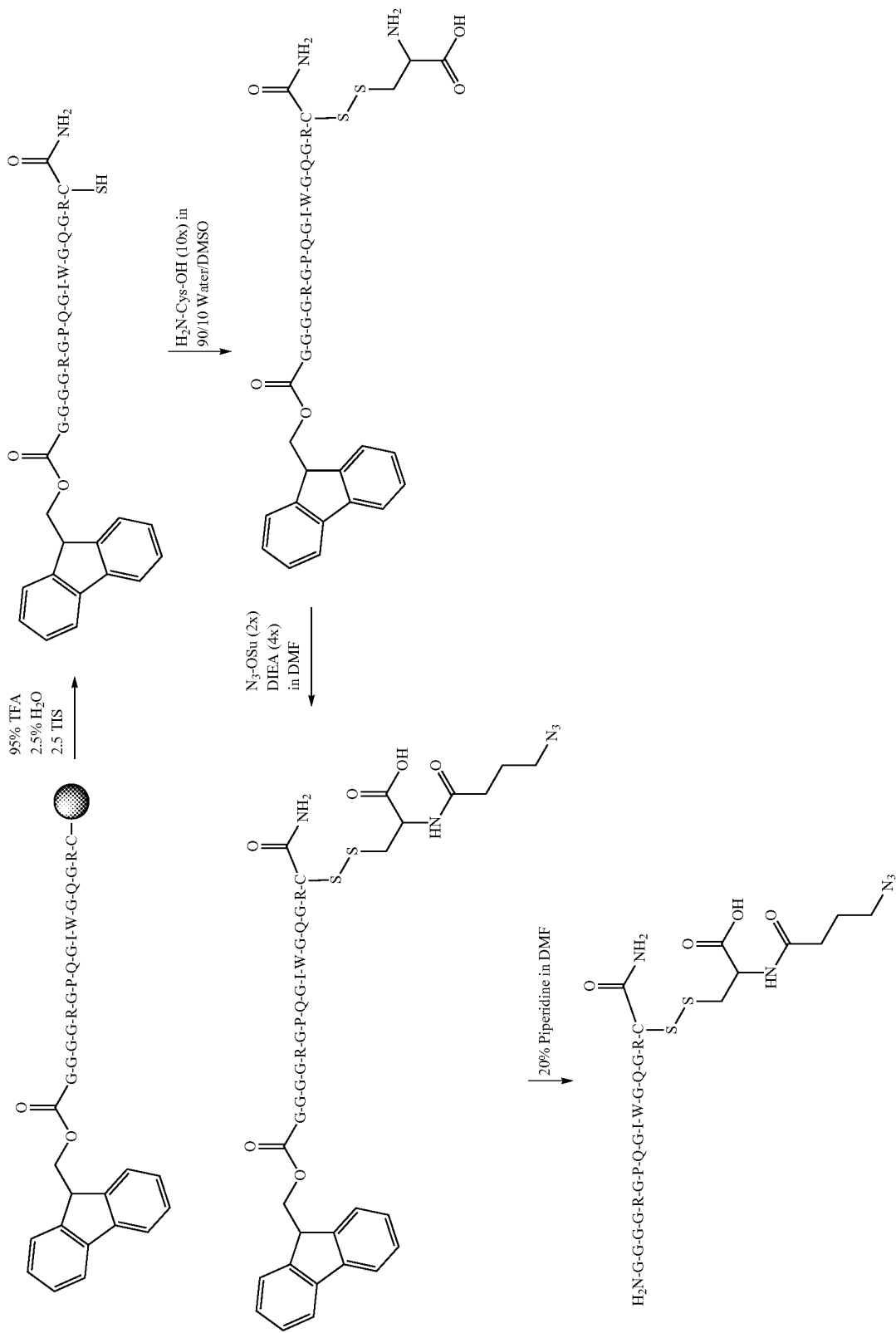

Fmoc-GGGGRGPQGIWGQGRC-NH$_2$ [SEQ ID No.: 32] was synthesized on rink amide resin (0.25 mmol scale) via standard Fmoc-based, microwave-assisted, solid-phase peptide synthesis methodologies. The peptide was deprotected and cleaved from resin by treatment with TFA/TIS/dH$_2$O (95:2.5:2.5, 15 mL) for 2 hours. Following cleavage, the peptide was precipitated in and washed with ice-cold diethyl ether (2×), purified by RP-HPLC operating with 55 min gradient (5-100%) of acetonitrile in water containing TFA (0.1%), and lyophilized to obtain the intermediate peptide as a white solid (52 mg, 0.0295 mmol, 11.8% yield). The intermediate peptide and H-Cys-OH (35.71 mg, 0.295 mmol, 10×) were dissolved in dH$_2$O/DMSO (9:1, 10 mL) and reacted at room temperature for 48 hrs. The solution was concentrated by rotary evaporation, dissolved in dH$_2$O, purified by RP-HPLC with 43.4 min gradient (20-100%) of acetonitrile in water containing TFA (0.1%), and lyophilized to give the intermediate peptide (Fmoc-GGG-GRGPQGIWGQGRC(NH$_2$—C—OH)—NH$_2$ [SEQ ID No.: 33] with cysteines linked via disulfide bond) as a white solid (38 mg, 0.0202 mmol, 68.5% yield). The intermediate peptide was reacted overnight with N$_3$—OSu (9.1294 mg, 0.0403 mmol, 2×) and DIEA (10.42 mg, 0.087 mmol, 4×) in minimal DMF to introduce azide functionality onto the peptide. The reaction mixture was purified by RP-HPLC with 43.4 min gradient (20-100%) of acetonitrile in water containing TFA (0.1%), and the product fraction was lyophilized to obtain the intermediate peptide (Fmoc-GGG-GRGPQGIWGQGRC(N$_3$—C—OH)—NH$_2$ [SEQ ID No.: 34] with cysteines linked via disulfide bond) as a white solid (25 mg, 0.0125 mmol, 61.8% yield). The N-terminal Fmoc group was cleaved by incubating the peptide in piperidine (20%) in DMF (25 mL) for 10 mins. The deprotection reaction mixture was concentrated via rotary evaporation, purified by RP-HPLC operating with 55 min gradient (5-100%) of acetonitrile in water containing TFA (0.1%), and lyophilized to obtain the final product (H-GGG-GRGPQGIWGQGRC(N$_3$—C—OH)—NH$_2$ [SEQ ID No.: 35] with cysteines linked via disulfide bond, denoted GGGG-E\/R—N$_3$, and represented graphically as GGGG-Enzyme-Reductive-N$_3$) as a white solid (14.5 mg, 0.0082 mmol, 65% yield). Peptide purity was confirmed by MALDI-TOF mass spectroscopy: calculated [M+$^1$H]$^+$, 1771.8; observed 1771.6.

Synthesis of Reductive-OR-Photo-Degradable, Sortaggable Peptide (GGGG-P\/R—N$_3$)

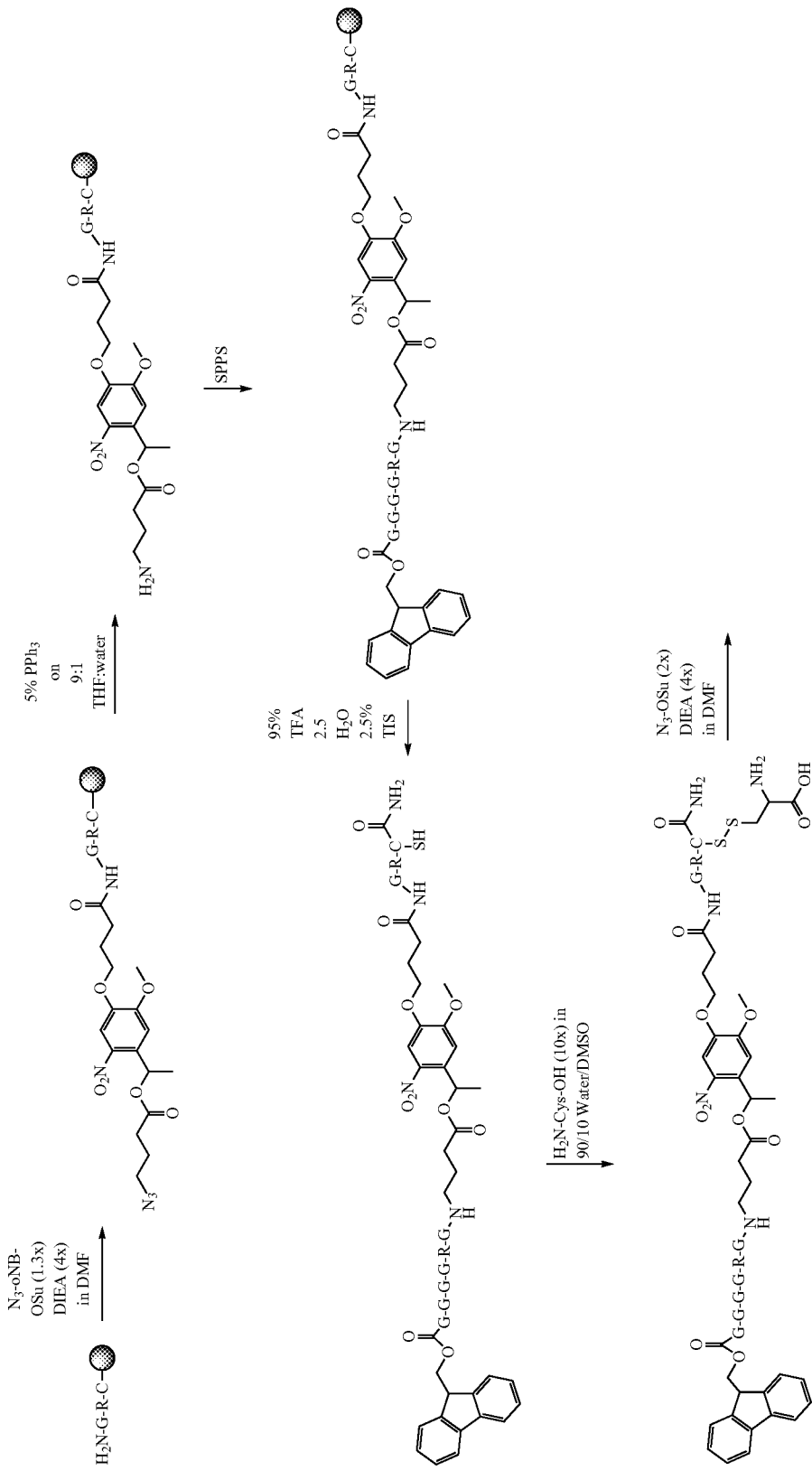

-continued
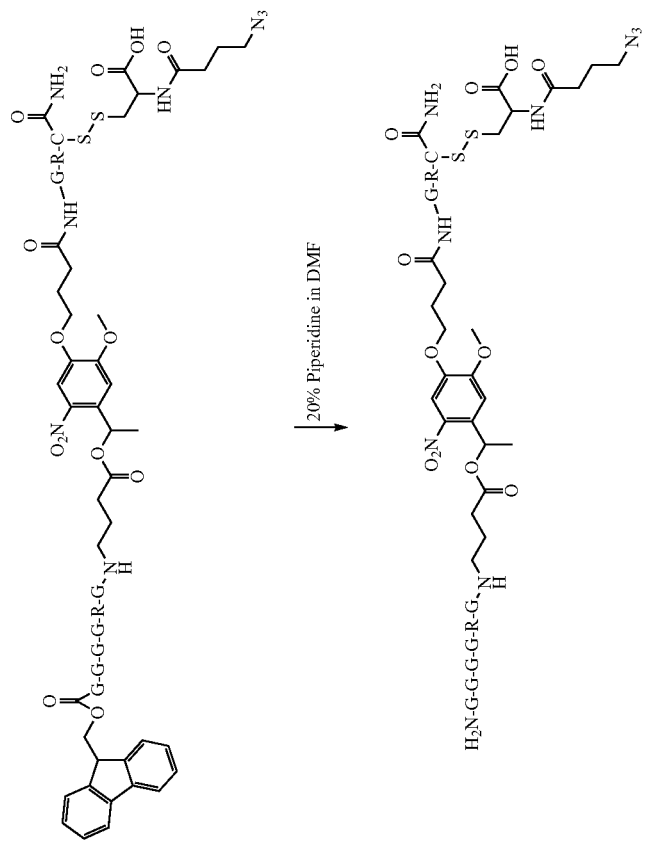

H-GRC-NH$_2$ was synthesized on rink amide resin (0.25 mmol scale) via standard Fmoc-based, microwave-assisted, solid-phase peptide synthesis methodologies. The resin-bound peptide was reacted overnight with N$_3$-oNB-OSu (165 mg, 0.325 mmol, 1.3×) and DIEA (129.25 mg, 1 mmol, 4×) in minimal DMF to introduce oNB and azido functionality onto the peptide N-terminus. The N-terminal azide was reduced to an amine by Staudinger reduction; the resin-bound peptide was washed THF/dH$_2$O (90:10, 3×20 mL) and reacted overnight with 5 wt % triphenylphosphine in THF/dH$_2$O (90/10, 30 mL). The peptide Fmoc-GGGGRG [SEQ ID No.: 36] was appended to the N-terminus via standard microwave-assisted solid-phase peptide synthesis methodology. The peptide was deprotected and cleaved from resin by treatment with TFA/TIS/dH$_2$O (95:2.5:2.5, 15 mL) for 2 hours. Following cleavage, the peptide was precipitated in and washed with ice-cold diethyl ether (2×), purified by RP-HPLC operating with 43.4 min gradient (20-100%) of acetonitrile in water containing TFA (0.1%), and lyophilized to obtain the intermediate peptide (Fmoc-GGG-GRG-oNB-GRC-NH$_2$) [SEQ ID No.: 37] as a yellow solid (75 mg, 0.055 mmol, 22% yield). The intermediate peptide and H-Cys-OH (66.64 mg, 0.55 mmol, 10×) were dissolved in dH$_2$O/DMSO (9:1, 10 mL) and reacted at room temperature for 48 hrs. The solution was concentrated by rotary evaporation, dissolved in dH$_2$O, purified by RP-HPLC with 43.4 min gradient (20-100%) of acetonitrile in water containing TFA (0.1%), and lyophilized to give the intermediate peptide (Fmoc-GGGGRG-oNB-GR<u>C</u>(H—<u>C</u>—OH)—NH$_2$ [SEQ ID No.: 38] with cysteines linked via disulfide bond) as a yellow solid (43.33 mg, 0.0292 mmol, 53.1% yield). The intermediate peptide was reacted overnight with N$_3$—OSu (13.22 mg, 0.584 mmol, 2×) and DIEA (15.13 mg, 0.117 mmol, 4×) in minimal DMF to introduce azide functionality onto the peptide. The reaction mixture was purified by RP-HPLC with 43.4 min gradient (20-100%) of acetonitrile in water containing TFA (0.1%), and the product fraction was lyophilized to obtain the intermediate peptide (Fmoc-GGGGRG-oNB-GR<u>C</u>(N$_3$—<u>C</u>—OH)—NH$_2$ with cysteines linked via disulfide bond) as a yellow solid (38.6 mg, 0.0242 mmol, 82.9% yield). The N-terminal Fmoc group was cleaved by incubating the peptide in piperidine (20%) in DMF (40 mL) for 10 mins. The deprotection reaction mixture was concentrated via rotary evaporation, purified by RP-HPLC operating with 55 min gradient (5-100%) of acetonitrile in water containing TFA (0.1%), and lyophilized to obtain the final product (H-GGGGRG-oNB-GR<u>C</u>(N$_3$—<u>C</u>—OH)—NH$_2$ [SEQ ID No.: 39] with cysteines linked via disulfide bond, denoted GGGG-P\/R—N$_3$, and represented graphically as GGGG-Photo-Reductive-N$_3$) as a yellow solid (7.86 mg, 0.0057 mmol, 20% yield). Peptide purity was confirmed by MALDI-TOF mass spectroscopy: calculated [M+$^1$H]$^+$, 1371.65; observed 1371.52.

Synthesis of Enzyme-OR-Photo-Degradable, Sortaggable Peptide (GGGG-E\/P—N$_3$)

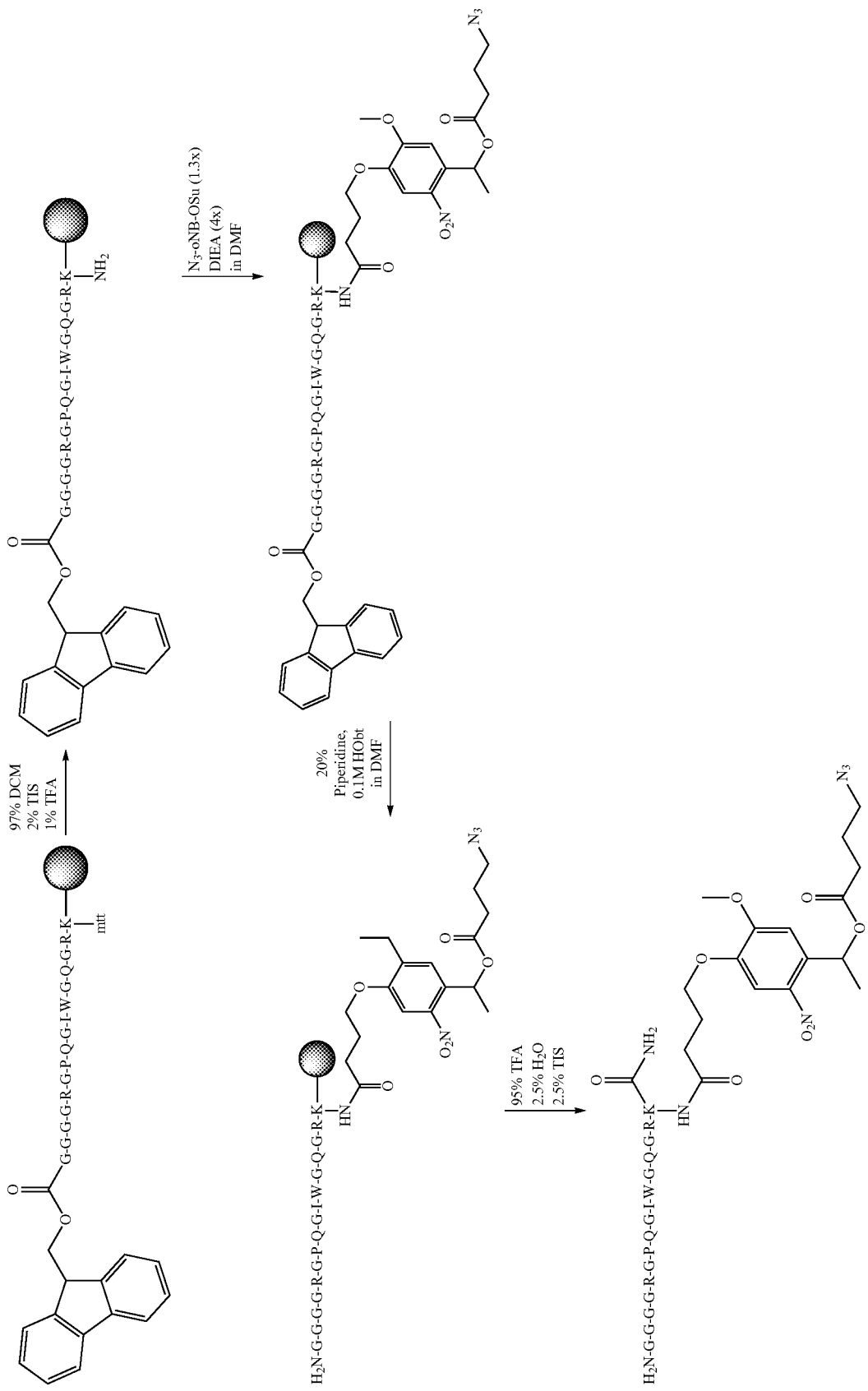

Fmoc-GGGGRGPQGIWGQGRK(Mtt)-NH$_2$ [SEQ ID No.: 40] was synthesized on rink amide resin (0.25 mmol scale) via standard Fmoc-based, microwave-assisted, solid-phase peptide synthesis methodologies. The highly acid labile N-methyltrityl (Mtt) protection group on ε-amino group of the Lysine side chain was removed via treatment with Dichloromethane/triisopropylsilane/trifluoroacetic acid (97:2:1, 9×15 mL, 10 min each). The resin-bound peptide was reacted overnight with N$_3$-oNB-OSu (165 mg, 0.325 mmol, 1.3×) and DIEA (129.25 mg, 1 mmol, 4×) in minimal DMF to introduce oNB and azido functionality onto the ε-amino group of the Lysine side chain. The Fmoc deprotection was achieved on resin by treatment with a solution of piperidine (20%) and HOBt (0.1 M) in DMF (2×15 mL) for 10 mins. The peptide was deprotected and cleaved from resin by treatment with TFA/TIS/dH$_2$O (95:2.5:2.5, 15 mL) for 2 hours. Following cleavage, the peptide was precipitated in and washed with ice-cold diethyl ether (2×), purified by RP-HPLC operating with 55 min gradient (5-100%) of acetonitrile in water containing TFA (0.1%), and lyophilized to obtain the final product (H-GGGGRGPQGIWGQGRK(oNB—N$_3$)—NH$_2$ [SEQ ID No.: 41], denoted GGGG-E\/P—N$_3$, represented graphically as GGGG-Enzyme-Photo-N$_3$) as a yellow solid (31.5 mg, 0.016 mmol, 6.4% yield). Peptide purity was confirmed by MALDI-TOF mass spectroscopy: calculated [M+$^1$H]$^+$, 1958.2, observed 1958.5.

Synthesis of Enzyme-AND-Reductive-Degradable, Sortaggable Peptide (GGGG-E/\R—N$_3$)

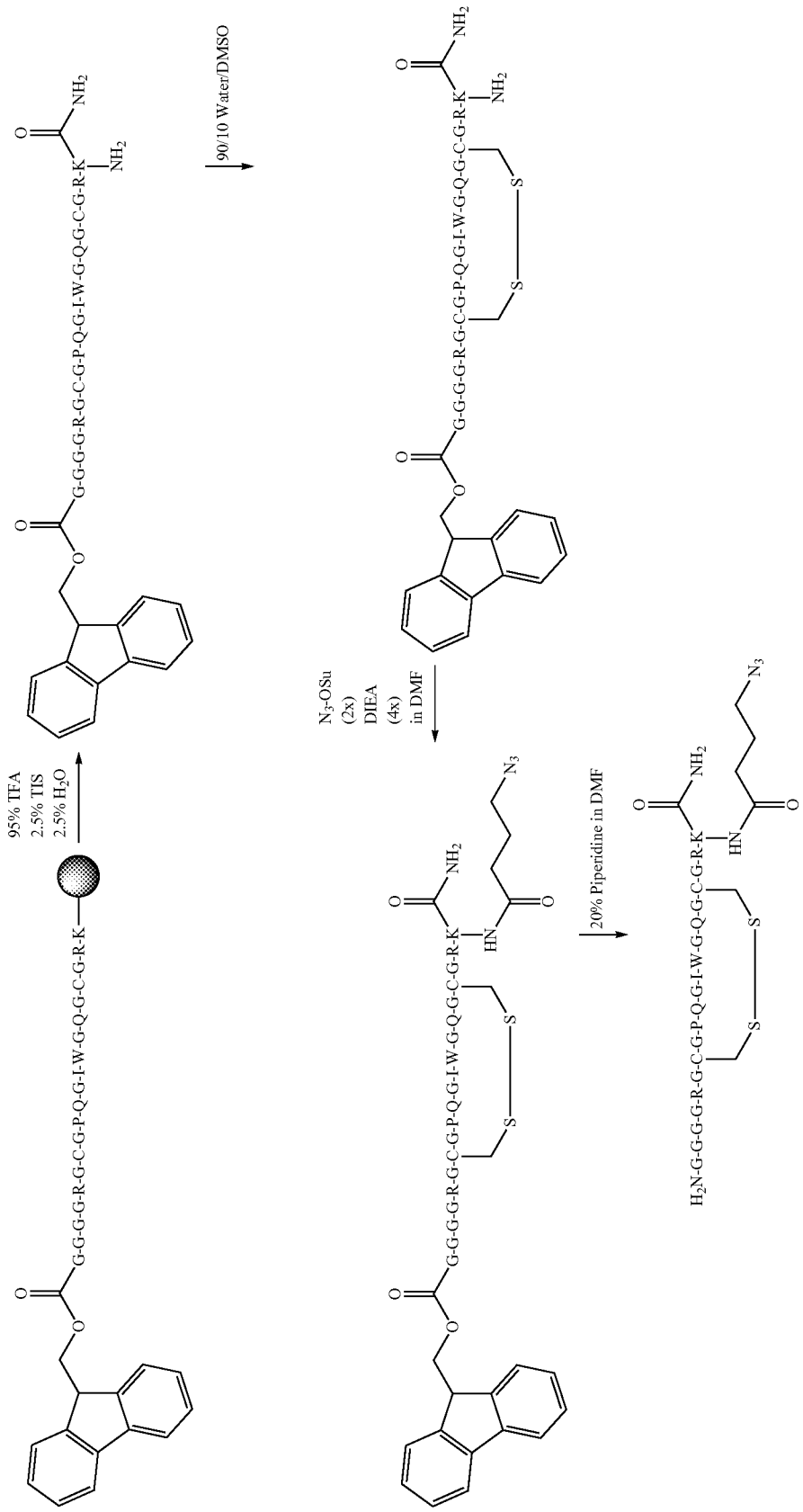

Fmoc-GGGGRGCGPQGIWGQGQGCGRK-NH$_2$ [SEQ ID No.: 42] was synthesized on rink amide resin (0.25 mmol scale) via standard Fmoc-based, microwave-assisted, solid-phase peptide synthesis methodologies. The peptide was deprotected and cleaved from resin by treatment with TFA/TIS/dH$_2$O (95:2.5:2.5, 15 mL) for 2 hours. Following cleavage, the peptide was precipitated in and washed with ice-cold diethyl ether (2×), purified by RP-HPLC operating with 43.4 min gradient (20-100%) of acetonitrile in water containing TFA (0.1%), and lyophilized to obtain the intermediate peptide (Fmoc-GGGGRGCGPQGIWGQGQGCGRK-NH$_2$ [SEQ ID No.: 42]) as a white solid (126.5 mg, 0.059 mmol, 23.9% yield). The peptide was stapled via formation of an intramolecular disulfide bridge between the cysteine residues of the peptide; the intermediate peptide (1 mM) was dissolved in a dH$_2$O/DMSO (90:10, 63 mL) solution and reacted at room temperature with no agitation for 48 hours. The stapled peptide was concentrated by rotary evaporation, dissolved in dH$_2$O, purified by RP-HPLC with 43.4 min gradient (20-100%) of acetonitrile in water containing TFA (0.1%), and lyophilized to give the intermediate peptide (Fmoc-GGGGRGCGPQGIWGQGQGCGRK-NH$_2$ [SEQ ID No.: 42], stapled intramolecularly via cysteine-cysteine disulfide bond) as a white solid (47.6 mg, 0.0226 mmol, 37.7% yield). The intermediate peptide was reacted overnight with N$_3$—OSu (10.11 mg, 0.044 mmol, 2×) and DIEA (11.55 mg, 0.089 mmol, 4×) in minimal DMF to introduce azide functionality onto the peptide. The reaction mixture was purified by RP-HPLC operating with 43.4 min gradient (20-100%) of acetonitrile in water containing TFA (0.1%), and lyophilized to obtain the intermediate peptide (Fmoc-GGGGRGCGPQGIWGQGQGCGRK(N$_3$)—NH$_2$ [SEQ ID No.: 43], stapled intramolecularly via cysteine-cysteine disulfide bond) as a white solid (34.4 mg, 0.0155 mmol, 68.6%). The N-terminal Fmoc group was cleaved by incubating the peptide in piperidine (20%) in DMF (30 mL) for 10 mins. The deprotection reaction mixture was concentrated via rotary evaporation, purified by RP-HPLC operating with 55 min gradient (5-100%) of acetonitrile in water containing TFA (0.1%), and lyophilized to obtain the final product (H-GGGGRGCGPQGIWGQGQGCGRK(N$_3$)—NH$_2$ [SEQ ID No.: 44] stapled intramolecularly via cysteine-cysteine disulfide bond, denoted GGGG-E/\R—N$_3$, and represented graphically as GGGG-Enzyme and Reductive-N$_3$, where Enzyme and Reduced are in the form of a circle bridging GGGG- and —N$_3$, with Enzyme on the upper semicircle and Reductive on the lower semicircle between GGGG- and —N$_3$) as white a solid (8.3 mg, 0.0042 mmol, 27% yield). Peptide purity was confirmed by MALDI-TOF mass spectroscopy: calculated [M+$^1$H]$^+$, 1997.13; observed 1996.9.

Synthesis of Reductive-AND-Photo-Degradable, Sortaggable Peptide (GGGG-P/\R—N$_3$)

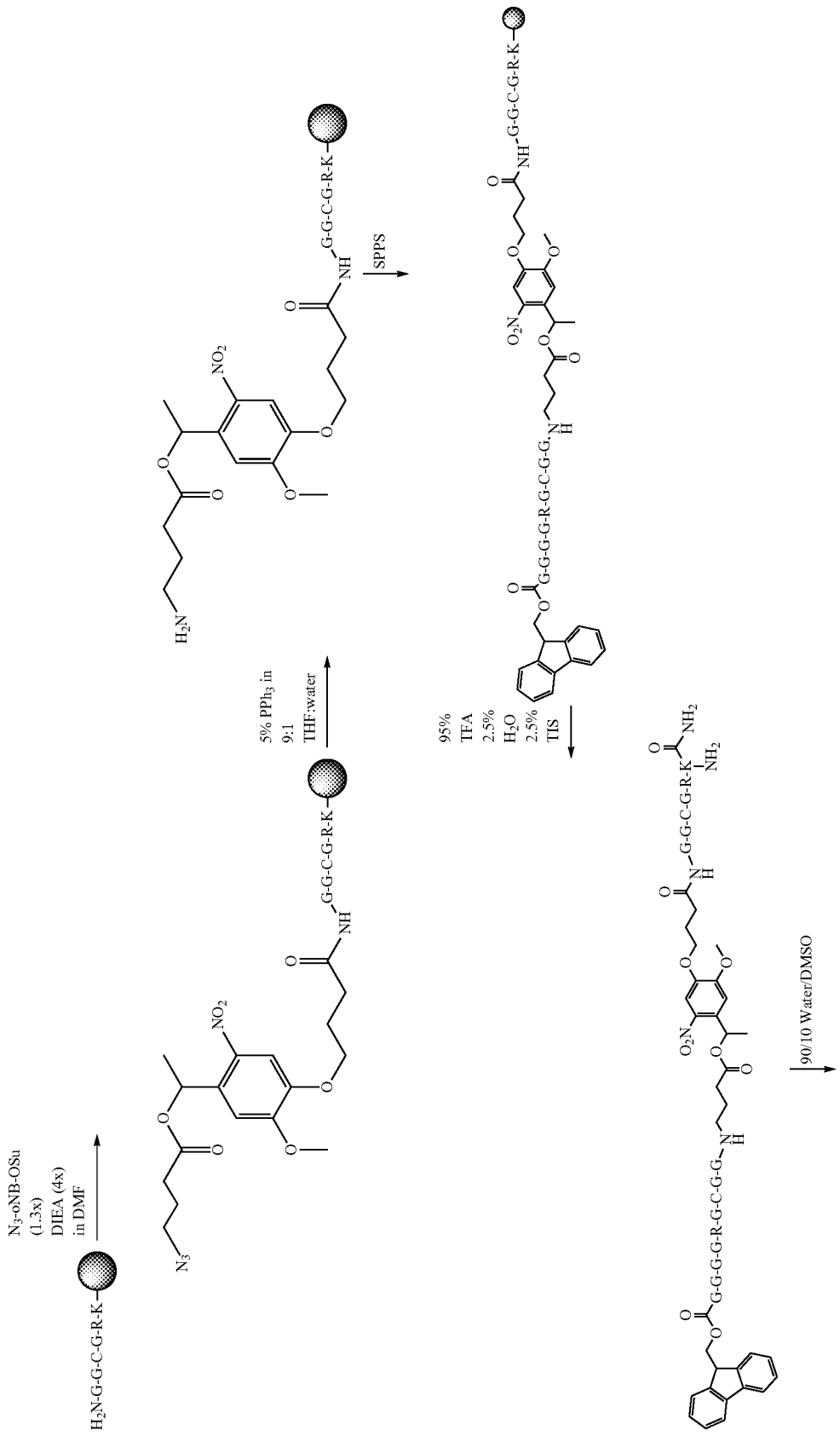

-continued
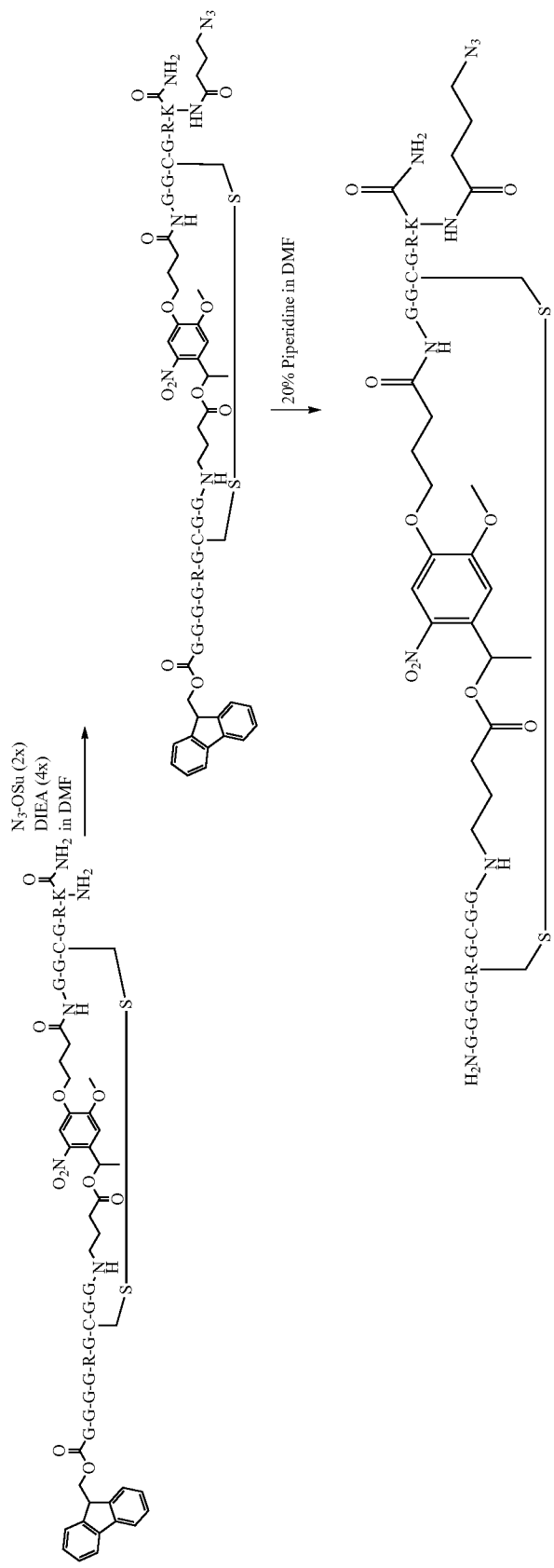

H-GCGRK-NH$_2$ [SEQ ID No.: 45] was synthesized on rink amide resin (0.25 mmol scale) via standard Fmoc-based, microwave-assisted, solid-phase peptide synthesis methodologies. The resin-bound peptide was reacted overnight with N$_3$-oNB-OSu (165 mg, 0.325 mmol, 1.3×) and DIEA (129.25 mg, 1 mmol, 4×) in minimal DMF to introduce oNB and azido functionality onto the N-terminus. The N-terminal azide was reduced to an amine by Staudinger reduction; the resin-bound peptide was washed THF/dH$_2$O (90:10, 3×20 mL) and reacted overnight with 5 wt % triphenylphosphine in THF/dH$_2$O (90:10, 30 mL). Fmoc-GGGGRGCG-OH [SEQ ID No.: 46] was appended to the N-terminus via standard microwave-assisted solid-phase peptide synthesis methodology. The peptide was deprotected and cleaved from resin by treatment with TFA/TIS/dH$_2$O (95:2.5:2.5, 15 mL) for 2 hours. Following cleavage, the peptide was precipitated in and washed with ice-cold diethyl ether (2×), purified by RP-HPLC operating with 43.4 min gradient (20-100%) of acetonitrile in water containing TFA (0.1%), and lyophilized to obtain the intermediate peptide (Fmoc-GGGGRGCG-oNB-GCGRK-NH$_2$ [SEQ ID No.: 47]) as a yellow solid (100 mg, 0.055 mmol, 22% yield). The peptide was stapled via formation of an intramolecular disulfide bridge between the cysteine residues of the peptide; the intermediate peptide (1 mM) was dissolved in a dH$_2$O/DMSO (90:10, 55 mL) solution and reacted at room temperature with no agitation for 48 hours. The stapled peptide was concentrated by rotary evaporation, dissolved in dH$_2$O, purified by RP-HPLC with 43.4 min gradient (20-100%) of acetonitrile in water containing TFA (0.1%), and lyophilized to give the intermediate peptide (Fmoc-GGGGRGCG-oNB-GCGRK-NH$_2$ [SEQ ID No.: 47], stapled intramolecularly via cysteine-cysteine disulfide bond) as a yellow solid (60 mg, 0.0329 mmol, 59.8% yield). The intermediate peptide was reacted overnight with N$_3$—OSu (10.5 mg, 0.464 mmol, 2×) and DIEA (11.98 mg, 0.093 mmol, 4×) in minimal DMF to introduce azide functionality onto the peptide. The reaction mixture was purified by RP-HPLC operating with 43.4 min gradient (20-100%) of acetonitrile in water containing TFA (0.1%), and lyophilized to obtain the intermediate peptide (Fmoc-GGGGRGCG-oNB-GCGRK(N$_3$)—NH$_2$ [SEQ ID No.: 48], stapled intramolecularly via cysteine-cysteine disulfide bond) as a yellow solid (44 mg, 0.0227 mmol, 50%). The N-terminal Fmoc group was cleaved by incubating the peptide in piperidine (20%) in DMF (10 mL) for 10 mins. The deprotection reaction mixture was concentrated via rotary evaporation, purified by RP-HPLC operating with 55 min gradient (5-100%) of acetonitrile in water containing TFA (0.1%), and lyophilized to obtain the final product (H-GGGGRGCG-oNB-GCGRK(N$_3$)—NH$_2$ [SEQ ID No.: 49] stapled intramolecularly via cysteine-cysteine disulfide bond, denoted GGGG-P/\R—N$_3$, and represented graphically as GGGG-Photo and Reductive-N$_3$, where Photo and Reduced are in the form of a circle bridging GGGG- and —N$_3$, with Photo on the upper semicircle and Reductive on the lower semicircle between GGGG- and —N$_3$) as a yellow solid (6.3 mg, 0.0037 mmol, 16.3% yield). Peptide purity was confirmed by MALDI-TOF mass spectroscopy: calculated [M+$^1$H]$^+$, 1709.9; observed 1709.6

Synthesis of Enzyme-AND-Photo-Degradable, Sortaggable Peptide (GGGG-E/\P—N$_3$)

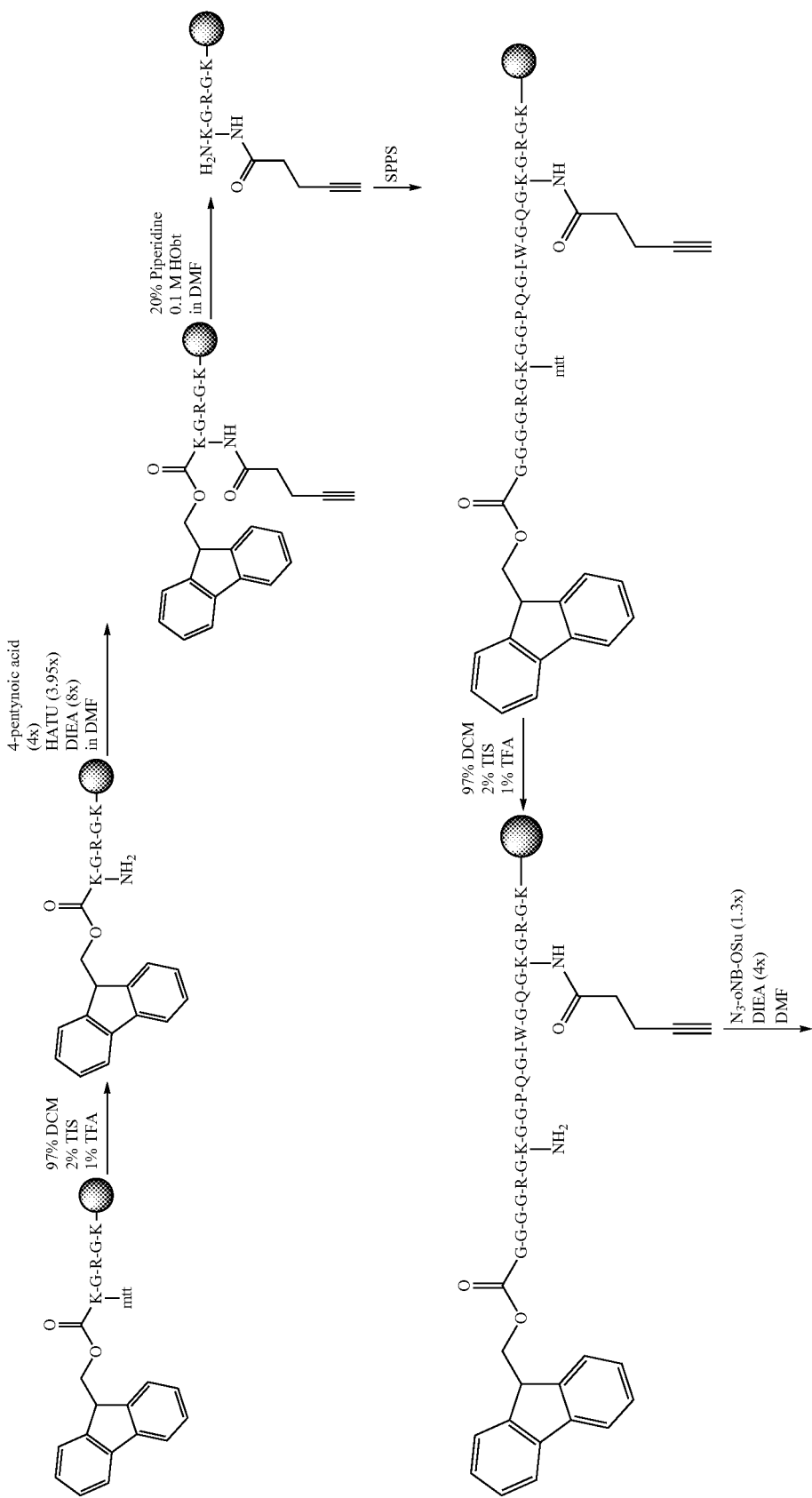

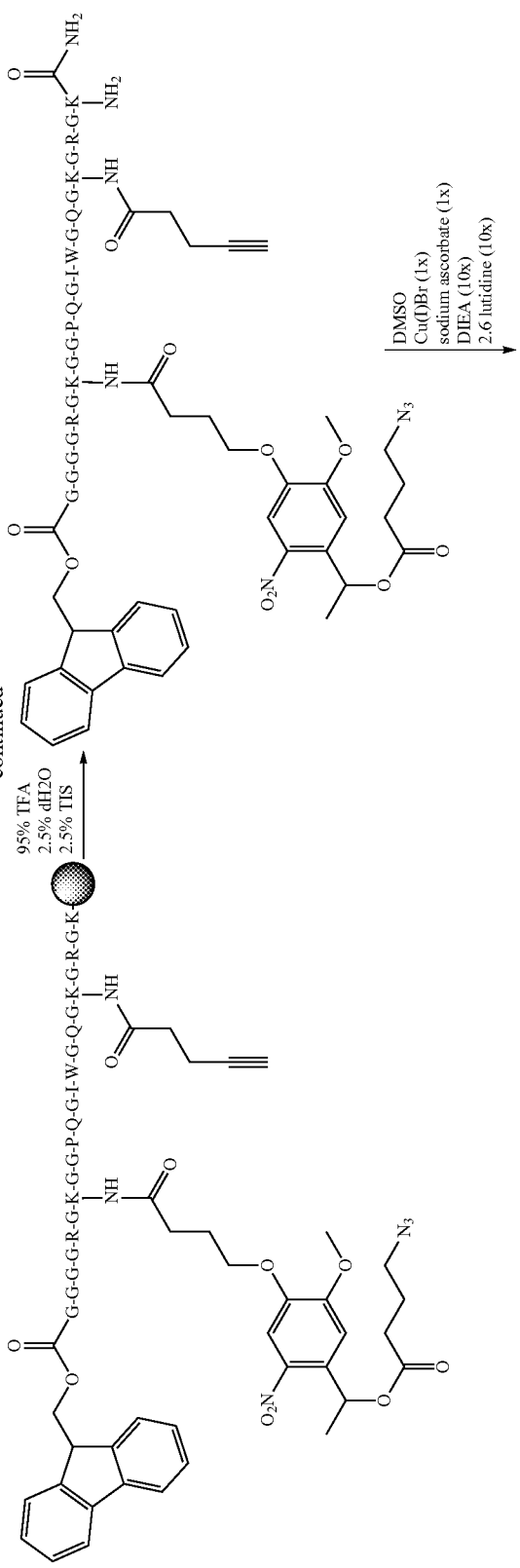
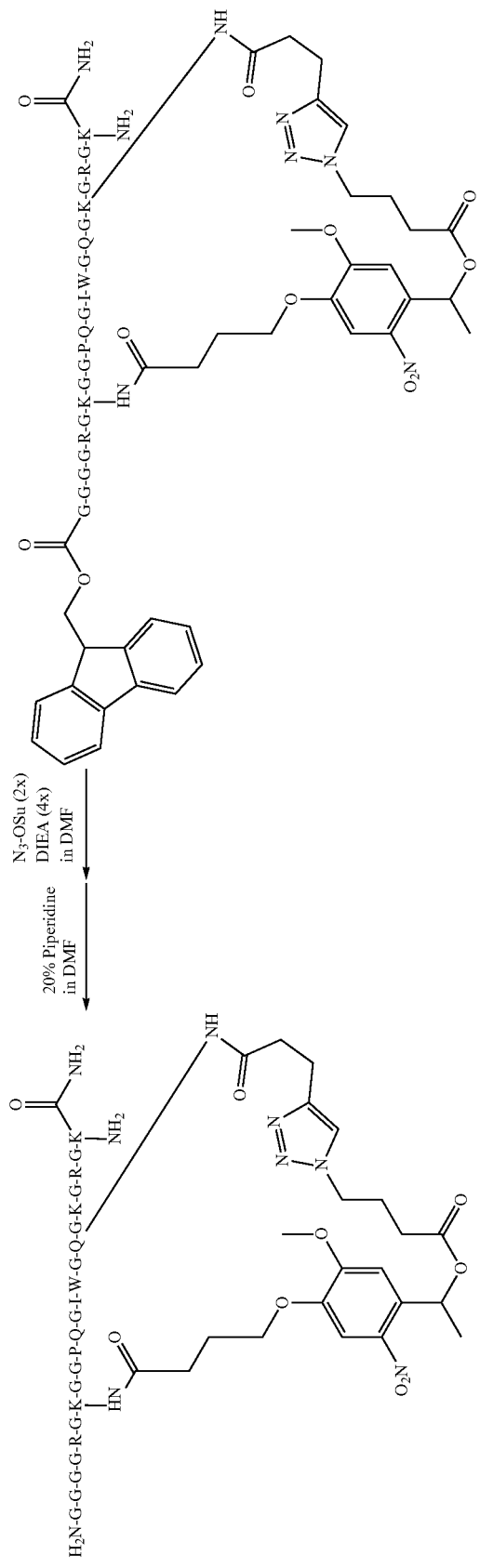

Fmoc-K(Mtt)GRK-NH₂ [SEQ ID No.: 50] was synthesized on rink amide resin (0.25 mmol scale) via standard Fmoc-based, microwave-assisted, solid-phase peptide synthesis methodologies. The highly acid labile N-methyltrityl (Mtt) protection group on ε-amino group of the Lysine side chain was removed via treatment with Dichloromethane/triisopropylsilane/trifluoroacetic acid (97:2:1, 9×15 mL, 10 min each). HATU coupling was used to functionalize ε-amino group of the Lysine side chain with an alkyne; 4-pentynoic acid (98.1 mg, 1 mmol, 4×) was pre-activated upon reaction with HATU (0.376 g, 0.99 mmol, 3.95×) and DIEA (260.7 mg, 2 mmol, 8×) in minimal DMF for 5 minutes and then reacted with the resin for 90 minutes. The Fmoc protecting group on the N-terminus of the peptide was cleaved on resin by treatment with a solution of piperidine (20%) and HOBt (0.1 M) in DMF (2×15 mL, 10 mins each). The peptide Fmoc-GGGGRGK(Mtt)GGPQGIWGQG [SEQ ID No.: 51] was appended to the N-terminus via standard microwave-assisted solid-phase peptide synthesis methodology. The N-methyltrityl (Mtt) protection group on ε-amino group of the Lysine side chain was removed via treatment with Dichloromethane/triisopropylsilane/trifluoroacetic acid (97:2:1, 9×15 mL, 10 min each). The resin-bound peptide was reacted overnight with N₃-oNB-OSu (165 mg, 0.325 mmol, 1.3×) and DIEA (129.25 mg, 1 mmol, 4×) in minimal DMF to introduce oNB and azido functionality onto the ε-amino group of the Lysine side chain. The peptide was deprotected and cleaved from resin by treatment with TFA/TIS/dH₂O (95:2.5:2.5, 15 mL) for 2 hours. Following cleavage, the peptide was precipitated in and washed with ice-cold diethyl ether (2×), purified by RP-HPLC operating with 43.4 min gradient (20-100%) of acetonitrile in water containing TFA (0.1%), and lyophilized to obtain the intermediate peptide (Fmoc-GGGGRGK(oNB—N₃)GGPQGIWGQGK(yne)GRK-NH₂) [SEQ ID No.: 52] as a yellow solid (85 mg, 0.0316 mmol, 12.7% yield). The alkyne and azide functionalities present on the peptide side chains were stapled together via CuAAC (copper(I)-catalyzed azide-alkyne cycloaddition) click reaction; the linear peptide (1 mM) was dissolved in nitrogen-purged DMSO (32 mL) containing cooper(I) bromide (4.53 mg, 0.032 mmol, 1 eq), sodium ascorbate (6.19 mg, 0.032 mmol, 1 eq) in water (316 µL), lutidine (32.23 mg, 0.316 mmol, 10 eq), and DIEA (40.84 mg, 0.316 mmol, 10 eq); this mixture was allowed to react under nitrogen at room temperature overnight, concentrated via rotary evaporation, passed through ion exchange column (Dowex, M4195 resin, 5 g), and lyophilized. The stapled product was purified by RP-HPLC operating with 43.4 min gradient (20-100%) of acetonitrile in water containing TFA (0.1%), and lyophilized to obtain the intermediate peptide (Fmoc-GGGGRGK(oNB—N₃)GGPQGIWGQK(yne)GRK-NH₂ [SEQ ID No.: 52], stapled intramolecularly via triazole linkage between the alkyne and oNB—N₃ side chains) as a yellow solid (7.8 mg, 2.9 µmol, 9.18% yield). The intermediate peptide was reacted overnight with N₃—OSu (1.31 mg, 0.0058, 2×) and DIEA (1.498 mg, 0.0116 mmol, 4×) in minimal DMF to introduce azide functionality onto the peptide. The reaction mixture was purified by RP-HPLC operating with 43.4 min gradient (20-100%) of acetonitrile in water containing TFA (0.1%), and lyophilized to obtain the intermediate peptide (Fmoc-GGGGRGK(oNB—N₃)GGPQGIWGQGK(yne)GRK(N₃)—NH₂ [SEQ ID No.: 53], stapled intramolecularly via triazole linkage between the alkyne and oNB—N₃ side chains) as a yellow solid (8 mg, 2.85 µmol, 98% yield). The N-terminal Fmoc group was cleaved by incubating the peptide in piperidine (20%) in DMF (8 mL) for 10 mins. The deprotection reaction mixture was concentrated via rotary evaporation, purified by RP-HPLC operating with 55 min gradient (5-100%) of acetonitrile in water containing TFA (0.1%), and lyophilized to obtain the final product (H-GGG-GRGK(oNB-N₃)GGPQGIWGQGK(yne)GRK(N₃)—NH₂ [SEQ ID No.: 54], stapled intramolecularly via triazole linkage between the alkyne and oNB—N₃ side chains, denoted GGGG-E/\P—N₃, and represented graphically as GGGG-Enzyme and Photo-N₃, where Enzyme and Photo are in the form of a circle bridging GGGG- and —N₃, with Enzyme on the upper semicircle and Photo on the lower semicircle between GGGG- and —N₃) as a solid (3.6 mg, 1.4 µmol, 49% yield). Peptide purity was confirmed by MALDI-TOF mass spectroscopy: calculated [M+$^1$H]$^+$, 2577.7; observed 2577.5.

Protein Expression and Protein-Peptide Conjugation.
Protein Expression and Ni-NTA Immobilization The pSTEPL-POI construct was transformed into BL21 (DE3) line. A starter culture (20 mL) was grown overnight in LB containing ampicillin (0.1 mg/mL). The starter culture was used to inoculate LB (480 mL) containing ampicillin (0.1 mg/mL). The culture was grown to an OD600 of 0.4-0.6 before induction with Isopropyl β-D-1-thiogalactopyranoside (0.5 mM, IPTG). The culture was grown overnight at 25° C. The cells were centrifuged (4000×g, 10 mins) to obtain a pellet. The cells were re-suspended in STEPL Lysis Buffer (20 mM Tris-base, 50 mM NaCl, 10 mM imidazole, pH 7.5) containing phenylmethanesulfonyl fluoride (1 mM, PMSF) as a protease inhibitor. The cells were lysed using sonication; the cell suspension was kept on ice and subjected to short sonication burst cycles (1 sec pulse, 2 sec pause) with total sonication time 6 minutes. After sonication, the lysate was clarified by centrifugation (4000×g, 10 minutes) and loaded onto Ni-NTA resin. The resin was washed with STEPL wash buffer (20 mM Tris-base, 50 mM NaCl, 20 mM imidazole, pH 7.5) to remove non-specifically bound proteins.

POI-Peptide Conjugation by STEPL Reaction

Ni-NTA column was loaded with EGFP as described. Sortaggable peptide was dissolved in STEPL buffer (5 mL) containing calcium chloride (0.1 mM, Ca$^{2+}$) and added to the column. To promote STEPL reaction, the column was reacted at 37° C. for 4 hours under gently agitation, resulting to the modification and subsequent displacement of POI with sortaggable peptide. After the STEPL reaction, the column flow through, containing the protein-peptide construct, was collected. Centrifugal membrane filter (Amicon Ultra-4, MW cutoff: 10 kDa) were used to simultaneously concentrate and further purify the protein-peptide construct.

Synthesis of Enzyme-Responsive EGFP Pendant (EGFP-E-N₃)

EGFP was expressed as a STEPL construct and loaded on the Ni-NTA column.

Sortaggable peptide GGGG-E-N₃ was conjugated onto EGFP by STEPL. Protein purity was confirmed by LC-MS: calculated [M], 29179.7; observed 29179.5.

Synthesis of Reductive-Responsive EGFP Pendant (EGFP-R—N₃)

EGFP was expressed as a STEPL construct and loaded on the Ni-NTA column. Sortaggable peptide GGGG-R—N₃ was conjugated onto EGFP by STEPL. Protein purity was confirmed by LC-MS: calculated [M], 28321.97; observed 28322.

Synthesis of Photo-Responsive EGFP Pendant (EGFP-P—$N_3$)

EGFP was expressed as a STEPL construct and loaded on the Ni-NTA column. Sortaggable peptide GGGG-P—$N_3$ was conjugated onto EGFP by STEPL. Protein purity was confirmed by LC-MS: calculated [M], 28508.96; observed 28509.

Synthesis of Enzyme-OR-Reductive-Responsive EGFP Pendant (EGFP-E\/R—$N_3$)

EGFP was expressed as a STEPL construct and loaded on the Ni-NTA column. Sortaggable peptide GGGG-E\/R—$N_3$ was conjugated onto EGFP by STEPL. Protein purity was confirmed by LC-MS: calculated [M], 29358.8; observed 29358.5.

Synthesis of Photo-OR-Reductive-Responsive EGFP Pendant (EGFP-P\/R—$N_3$)

EGFP was expressed as a STEPL construct and loaded on the Ni-NTA column. Sortaggable peptide GGGG-P\/R—$N_3$ was conjugated onto EGFP by STEPL. Protein purity was confirmed by LC-MS: calculated [M], 28958.65; observed 28958.

Synthesis of Enzyme-OR-Photo-Responsive EGFP Pendant (EGFP-E\/P—$N_3$)

EGFP was expressed as a STEPL construct and loaded on the Ni-NTA column. Sortaggable peptide GGGG-E\/P—$N_3$ was conjugated onto EGFP by STEPL. Protein purity was confirmed by LC-MS: calculated [M], 29545.2; observed 29545.5.

Synthesis of Enzyme-AND-Reductive-Responsive-EGFP Pendant (EGFP-E/\R—$N_3$)

EGFP was expressed as a STEPL construct and loaded on the Ni-NTA column. Sortaggable peptide GGGG-E/\R—$N_3$ was conjugated onto EGFP by STEPL. Protein purity was confirmed by LC-MS: calculated [M], 29584.13; observed 29583.5.

Synthesis of Photo-AND-Reductive-Responsive-EGFP Pendant (EGFP-P/\R—$N_3$)

EGFP was expressed as a STEPL construct and loaded on the Ni-NTA column. Sortaggable peptide GGGG-P/\R—$N_3$ was conjugated onto EGFP by STEPL. Protein purity was confirmed by LC-MS: calculated [M], 29296.9; observed 29296.5.

Synthesis of Enzyme-AND-Photo-Responsive EGFP Pendant (EGFP-E/\P—$N_3$)

EGFP was expressed as a STEPL construct and loaded on the Ni-NTA column. Sortaggable peptide GGGG-E/\P—$N_3$ was conjugated onto EGFP by STEPL. Protein purity was confirmed by LC-MS: calculated [M], 30165.7; observed 30165.

Synthesis of Enzyme-Responsive mCherry Pendant (mCherry-E-$N_3$)

mCherry was expressed as a STEPL construct and loaded on the Ni-NTA column. Sortaggable peptide GGGG-E-$N_3$ was conjugated onto mCherry by STEPL. Protein purity was confirmed by LC-MS: calculated [M], 28959.9; observed 28958.5.

Synthesis of Enzyme-OR-Reductive-Responsive-mCherry Pendant (mCherry-E\/R—$N_2$)

EGFP was expressed and loaded on the Ni-NTA column. Sortaggable peptide GGGG-E\/R—$N_3$ was conjugated onto mCherry by STEPL. Protein purity was confirmed by LC-MS: calculated [M], 29140.9; observed 29137.5.

Synthesis of Reductive-AND-Photo-Responsive-mCherry Pendant (mCherry-P/\R—$N_3$)

mCherry was expressed as a STEPL construct and loaded on the Ni-NTA column. Sortaggable peptide GGGG-P/\R—$N_3$ was conjugated onto mCherry by STEPL. Protein purity was confirmed by LC-MS: calculated [M], 29079.0; observed 29075.5.

Synthesis of Enzyme-Responsive mCerulean Pendant (mCerulean-E-$N_3$)

mCerulean was expressed as a STEPL construct and loaded on the Ni-NTA column. Sortaggable peptide GGGG-E-$N_3$ was conjugated onto mCerulean by STEPL. Protein purity was confirmed by LC-MS: calculated [M], 29179.7; observed 29179.5.

Relating Protein Concentration to Fluorescence

The EGFP calibration curve was obtained for peptide-protein conjugate (EGFP-E-$N_3$) dissolved in MMP buffer (50 mM Tris, 200 mM NaCl, 5 mM $CaCl_2$, 1 µM $ZnCl_2$, pH=7.5). Fluorescence measurements ($\lambda_{excitation}$=475 nm, $\lambda_{emission}$=510 nm) were performed in triplicate.

The mCherry calibration curve was obtained for peptide-protein conjugate (mCherry-P—$N_3$) dissolved in MMP buffer. Fluorescence measurements ($\lambda_{excitation}$=575 nm, $\lambda_{emission}$=610 nm) were performed in triplicate.

The mCerulean calibration curve was obtained for peptide-protein conjugate (mCerulean-E-$N_3$) dissolved in MMP buffer. Fluorescence measurements ($\lambda_{excitation}$=433 nm, $\lambda_{emission}$=475 nm) were performed in triplicate.

In all cases, a linear relationship between protein concentration and fluorescence was observed over the measured range.

While illustrative embodiments have been illustrated and described, it will be appreciated that various changes can be made therein without departing from the spirit and scope of the disclosure.

The embodiments of the invention in which an exclusive property or privilege is claimed are defined as follows:

1. A crosslinked protein-polymer hydrogel that is stimuli-responsive, comprising:
a crosslinked polymer network formed by reacting a monomer and a stimuli-responsive fusion protein, the crosslinked polymer network having branched polymer building blocks covalently bonded to each other by the stimuli-responsive fusion proteins;
wherein the stimuli-responsive fusion proteins comprise a stimuli-responsive protein covalently bonded to the crosslinked polymer network and covalently bonded to a second protein that is a protein binding partner to the stimuli-responsive protein, wherein the second protein is also covalently bonded to the crosslinked polymer network; and
wherein the stimuli-responsive crosslinked polymer network is configured to reversibly soften upon an exposure of the fusion protein to a light of a predetermined wavelength, the exposure resulting in a reversible dissociation of the stimuli-responsive protein from the protein binding partner, while maintaining a covalent bond, wherein the reversible dissociation increases an end-to-end length of the fusion protein to provide a softened hydrogel state of the crosslinked protein-polymer hydrogel, wherein the stimuli responsive protein is LOV2 and the protein binding partner is Jα or Zdk1, or wherein the stimuli responsive protein is PIF and the protein binding partner is Phy.

2. The crosslinked protein-polymer hydrogel of claim 1, wherein the monomer is selected from ethylene glycol, NIPAM, lactic acid, glycolic acid, styrene, or vinyl alcohol repeating units.

3. The crosslinked protein-polymer hydrogel of claim 1, wherein the stimuli-responsive protein is covalently bonded to the branched polymer building block via a reaction selected from azide-alkyne cycloaddition, oxime ligation, hydrazide formation, thiol-maleimide, michael-type addition, thiol-ene, thiol-yne, SPANC, SPAAC, CuAAC, staudinger ligation, tetrazine-cyclooctene, diels-alder, inverse electron-demand diels-alder, native chemical ligation, cinnamate/coumarin/anthracine dimerization, amide formation through amine reacting with activated ester, and enzymatic crosslinking.

4. A cell-culturing article, comprising the crosslinked protein-polymer hydrogel of claim 1.

5. A drug delivery device, comprising the crosslinked protein-polymer hydrogel of claim 1.

6. A method of mimicking a cellular environment, comprising:
(a) exposing a crosslinked protein-polymer hydrogel of claim 1 to a predetermined stimulus to provide a mechanical response in the crosslinked protein-polymer hydrogel;
(b) withdrawing the stimulus to reverse the mechanical response in the crosslinked protein-polymer hydrogel; and
(c) repeating (a) and (b) one or more times to provide a cyclic reversible mechanical response in the crosslinked protein-polymer hydrogel.

7. The crosslinked protein-polymer hydrogel of claim 1, wherein the light is visible light.

8. The crosslinked protein-polymer hydrogel of claim 7, wherein the light is blue light and wherein the predetermined wavelength is less than 500 nm.

9. The crosslinked protein-polymer hydrogel of claim 1, wherein the light is infrared light.

* * * * *

SEQUENCE LISTING

<160> NUMBER OF SEQ ID NOS: 54

<210> SEQ ID NO 1
<211> LENGTH: 8
<212> TYPE: PRT

```
<213> ORGANISM: Artificial sequence
<220> FEATURE:
<223> OTHER INFORMATION: Synthetic

<400> SEQUENCE: 1

Gly Asn Glu Ala Ser Tyr Pro Leu
1               5

<210> SEQ ID NO 2
<211> LENGTH: 4
<212> TYPE: PRT
<213> ORGANISM: Artificial sequence
<220> FEATURE:
<223> OTHER INFORMATION: Synthetic

<400> SEQUENCE: 2

Gly Gly Gly Gly
1

<210> SEQ ID NO 3
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: K at position 7 is modified (N3)-NH2

<400> SEQUENCE: 3

Gly Gly Gly Gly Asp Asp Lys
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: K at position 7 is modified (CHO)-NH2

<400> SEQUENCE: 4

Gly Gly Gly Gly Asp Asp Lys
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: K at position 7 is modified (ortho-nitrobenzyl-
      N3)-NH2

<400> SEQUENCE: 5

Gly Gly Gly Gly Asp Asp Lys
1               5

<210> SEQ ID NO 6
<211> LENGTH: 7
<212> TYPE: PRT
<213> ORGANISM: Artificial sequence
```

```
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: G at position 4 is modified ortho-nitrobenzyl
<220> FEATURE:
<221> NAME/KEY: MISC_FEATURE
<222> LOCATION: (7)..(7)
<223> OTHER INFORMATION: K at position 7 is modified (CHO)-NH2

<400> SEQUENCE: 6

Gly Gly Gly Gly Asp Asp Lys
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic

<400> SEQUENCE: 7

Gly Pro Gln Gly Ile Trp Gly Gln
1               5

<210> SEQ ID NO 8
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 8

Leu Pro Xaa Thr Gly
1               5

<210> SEQ ID NO 9
<211> LENGTH: 5
<212> TYPE: PRT
<213> ORGANISM: Artificial sequence
<220> FEATURE:
<223> OTHER INFORMATION: Synthetic

<400> SEQUENCE: 9

Leu Pro Glu Thr Gly
1               5

<210> SEQ ID NO 10
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: K at position 5 is modified (N3)-NH2

<400> SEQUENCE: 10

Gly Gly Gly Gly Lys
1               5

<210> SEQ ID NO 11
<211> LENGTH: 5
```

```
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: S at position 5 is modified NH2

<400> SEQUENCE: 11

Gly Arg Gly Asp Ser
1               5

<210> SEQ ID NO 12
<211> LENGTH: 15
<212> TYPE: PRT
<213> ORGANISM: Artificial sequence
<220> FEATURE:
<223> OTHER INFORMATION: Synthetic

<400> SEQUENCE: 12

Gly Gly Ser Gly Gly Ser Gly Gly Ser Gly Gly Ser Gly Gly Ser
1               5                   10                  15

<210> SEQ ID NO 13
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: K at position 18 is modified (N3)-NH2

<400> SEQUENCE: 13

Gly Gly Arg Gly Asp Ser Pro Gly Gly Pro Gln Gly Ile Trp Gly Gln
1               5                   10                  15
Gly Lys

<210> SEQ ID NO 14
<211> LENGTH: 1506
<212> TYPE: DNA
<213> ORGANISM: Artificial sequence
<220> FEATURE:
<223> OTHER INFORMATION: Synthetic

<400> SEQUENCE: 14
atgggaaatg aggcgtcgta tccgttacac catcaccatc atcacatggt tatcccggac      60
tacttcaaac agtctttccc ggaaggttac tcttgggaac gttctatgac ctacgaagac     120
ggtggtatct gcatcgctac caacgacatc accatggaag tgactctttt catcaacaaa     180
atccacttca aggtaccaa cttcccgccg aacggtccgg ttatgcagaa acgtaccgtt      240
ggttgggaag ctagtaccga aaaaatgtac gaacgtgacg tgttctgaa aggtgacgtt      300 aaaatgaaac tgctgctgaa aggtggtggt cactaccgtt cgactaccg taccacctac      360 aaagttaaac agaaaccggt taaactgccg gactaccact tcgttgacca ccgtatcgaa     420
atcctgtctc acgacaaaga ctacaacaaa gttaaactgt acgaacacgc tgttgctcgt     480
aactctaccg actctatgga cgaactgtac aaaggtggtt ctggtggtat ggtttctaaa     540
ggtgaagaaa ccatcacctc tgttatcaaa ccggacatga aaacaaaact gcgtatggaa     600
ggtaacgtta acggtcacgc tttcgttatc gaaggtgaag ttctggtaa accgttcgaa      660 ggtatccaga ccatcgacct ggaagttaaa gaaggtgctc cgctgccgtt cgcttacgac     720
```

```
atcctgacca ccgctttcca ctacggtaac cgtgttttca ccaaataccc gcgtggtggt    780
ggtaagctta tgcgtaaagg cgaagagctg ttcactggtg tcgtccctat tctggtggaa    840
ctggatggtg atgtcaacgg tcataagttt tccgtgcgtg gcgagggtga aggtgacgca    900
actaatggta aactgacgct gaagttcatc tgtactactg gtaaactgcc ggtaccttgg    960
ccgactctgg taacgacgct gacttatggt gttcagtgct ttgctcgtta tccggaccac   1020
atgaagcagc atgacttctt caagtccgcc atgccggaag ctatgtgca ggaacgcacg   1080 atttccttta aggatgacgg cacgtacaaa acgcgtgcgg aagtgaaatt tgaaggcgat   1140
accctggtaa accgcattga gctgaaaggc attgacttta agaagacgg caatatcctg   1200 ggccataagc tggaatacaa ttttaacagc cacaatgttt acatcaccgc cgataaacaa   1260
aaaaatggca ttaaagcgaa ttttaaaatt cgccacaacg tggaggatgg cagcgtgcag   1320
ctggctgatc actaccagca aaacactcca atcggtgatg gtcctgttct gctgccagac   1380
aatcactatc tgagcacgca aagcgttctg tctaaagatc cgaacgagaa acgcgatcac   1440
atggttctgc tggagttcgt aaccgcagcg ggcatcacgc atggtatgga tgaactgtac   1500
aaataa                                                               1506

<210> SEQ ID NO 15
<211> LENGTH: 1500
<212> TYPE: DNA
<213> ORGANISM: Artificial sequence
<220> FEATURE:
<223> OTHER INFORMATION: Synthetic

<400> SEQUENCE: 15
atgggaaatg aggcgtcgta tccgttacac catcaccatc atcacatggt tatcccggac     60
tacttcaaac agtctttccc ggaaggttac tcttgggaac gttctatgac ctacgaagac    120
ggtggtatct gcatcgctac caacgacatc accatggaag gtgactcttt catcaacaaa    180
atccacttca aggtaccaa cttcccgccg aacggtccgg ttatgcagaa acgtaccgtt    240
ggttgggaag ctagtaccga aaaaatgtac gaacgtgacg gtgttctgaa aggtgacgtt    300
aaaatgaaac tgctgctgaa aggtggtggt cactaccgtt gcgactaccg taccacctac    360
aaagttaaac agaaaccggt taaactgccg gactaccact tcgttgacca ccgtatcgaa    420
atcctgtctc acgacaaaga ctacaacaaa gttaaactgt acgaacacgc tgttgctcgt    480
aactctaccg actctatgga cgaactgtac aaaggtggtt ctggtggtat ggtttctaaa    540
ggtgaagaaa ccatcaccct ctgttatcaaa ccggacatga aaacaaaact gcgtatggaa    600
ggtaacgtta acggtcacgc tttcgttatc gaaggtgaag gttctggtaa ccgttcgaa    660 ggtatccaga ccatcgacct ggaagttaaa gaaggtgctc cgctgccgtt cgcttacgac    720
atcctgacca ccgcttttcca ctacggtaac cgtgttttca ccaaataccc gcgtggtggt    780
ggtaagcttg tttctaaagg tgaagaactg atcaaagaaa acatgcgtat gaaagttgtt    840
atggaaggtt ctgttaacgg tcaccagttc aaatgcaccg gtaaggtga aggtcgtccg    900 tacgaaggtg ttcagaccat gcgtatcaaa gttatcgaag tggtccgct gccgttcgct    960 ttcgacatcc tggctacctc tttcatgtac ggttctcgta ccttcatcaa ataccggct   1020 gacatcccgg acttcttcaa acagtctttc ccggaaggtt tcacctggga acgtgttacc   1080
cgttacgaag acggtggtgt tgttaccgtt acccaggaca cctctctgga agacggtgaa   1140
ctggtttaca acgttaaagt tcgtggtgtt aacttcccgt ctaacggtcc ggttatgcag   1200
```

| | |
|---|---|
| aaaaaaaacca aaggttggga accgaacacc gaaatgatgt acccggctga cggtggtctg | 1260 |
| cgtggttaca ccgacatcgc tctgaaagtt gacggtggtg gtcacctgca ctgcaacttc | 1320 |
| gttaccacct accgttctaa aaaaaccgtt ggtaacatca aaatgccggg tgttcacgct | 1380 |
| gttgaccacc gtctggaacg tatcgaagaa tctgacaacg aaacctacgt tgttcagcgt | 1440 |
| gaagttgctg ttgctaaata ctctaacctg gtggtggta tggacgaact gtacaaataa | 1500 |

<210> SEQ ID NO 16
<211> LENGTH: 1584
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (820)..(820)
<223> OTHER INFORMATION: n is a, c, g, or t

<400> SEQUENCE: 16

| | |
|---|---|
| atgggaaatg aggcgtcgta tccgttacac catcaccatc atcacatggt tatcccggac | 60 |
| tacttcaaac agtcttttccc ggaaggttac tcttgggaac gttctatgac ctacgaagac | 120 |
| ggtggtatct gcatcgctac caacgacatc accatgaag gtgactcttt catcaacaaa | 180 |
| atccacttca aggtaccaa cttcccgccg aacggtccgg ttatgcagaa acgtaccgtt | 240 |
| ggttgggaag ctagtaccga aaaaatgtac gaacgtgacg tgttctgaa aggtgacgtt | 300 |
| aaaatgaaac tgctgctgaa aggtggtggt cactaccgtt gcgactaccg taccacctac | 360 |
| aaagttaaac agaaaccggt taaactgccg gactaccact cgttgacca ccgtatcgaa | 420 |
| atcctgtctc acgacaaaga ctacaacaaa gttaaactgt acgaacacgc tgttgctcgt | 480 |
| aactctaccg actctatgga cgaactgtac aaaggtggtt ctggtggtat ggtttctaaa | 540 |
| ggtgaagaaa ccatcaccctc tgttatcaaa ccggacatga aaaacaaact gcgtatggaa | 600 |
| ggtaacgtta acgtcacgc tttcgttatc gaaggtgaag gttctggtaa accgttcgaa | 660 |
| ggtatccaga ccatcgacct ggaagttaaa gaaggtgctc cgctgccgtt cgcttacgac | 720 |
| atcctgacca ccgcttttcca ctacggtaac cgtgttttca ccaaataccc gcgtggtggt | 780 |
| ggtaagctta tgcaccctga aacgctggtg aaagtaaaan atgctgaaga tcagttgggt | 840 |
| gcacgagtgg gttacatcga actggatctc aacagcggta agatccttga gagttttcgc | 900 |
| cccgaagaac gttttccaat gatgagcact tttaaagttc tgctatgtgg cgcggtatta | 960 |
| tcccgtgttg acgccgggca agagcaactc ggtcgccgca tacactattc tcagaatgac | 1020 |
| ttggttgagt actcaccagt cacagaaaag catcttacgg atggcatgac agtaagagaa | 1080 |
| ttatgcagtg ctgccataac catgagtgat aacactgcgg ccaacttact tctgacaacg | 1140 |
| atcggaggac cgaaggagct aaccgctttt ttgcacaaca tggggatca tgtaactcgc | 1200 |
| cttgatcgtt gggaaccgga gctgaatgaa gccataccaa acgacgagcg tgacaccacg | 1260 |
| atgcctgcag caatggcaac aacgttgcgc aaactattaa ctggcgaact acttactcta | 1320 |
| gcttcccggc aacaattaat agactggatg gaggcggata agttgcagg accacttctg | 1380 |
| cgctcggccc ttccggctgg ctggtttatt gctgataaat ctggagccgg tgagcgtggg | 1440 |
| tctcgcggta tcattgcagc actggggcca gatggtaagc cctcccgtat cgtagttatc | 1500 |
| tacacgacgg ggagtcaggc aactatggat gaacgaaata gacagatcgc tgagataggt | 1560 |
| gcctcactga ttaagcattg gtaa | 1584 |

<210> SEQ ID NO 17
<211> LENGTH: 955
<212> TYPE: DNA
<213> ORGANISM: Artificial sequence
<220> FEATURE:
<223> OTHER INFORMATION: Synthetic

<400> SEQUENCE: 17

```
atgggaaatg aggcgtcgta tccgttacac catcaccatc atcacatggt tatcccggac      60
tacttcaaac agtctttccc ggaaggttac tcttgggaac gttctatgac ctacgaagac     120
ggtggtatct gcatcgctac caacgacatc accatggaag gtgactcttt catcaacaaa     180
atccacttca aagtaccaa cttcccgccg aacggtccgg ttatgcagaa acgtaccgtt      240
ggttgggaag ctagtaccga aaaatgtac gaacgtgacg gtgttctgaa aggtgacgtt      300
aaaatgaaac tgctgctgaa aggtggtggt cactaccgtt gcgactaccg taccacctac     360
aaagttaaac agaaaccggt taaactgccg gactaccact tcgttgacca ccgtatcgaa     420
atcctgtctc acgacaaaga ctacaacaaa gttaaactgt acgaacacgc tgttgctcgt     480
aactctaccg actctatgga cgaactgtac aaaggtggtt ctggtggtat ggtttctaaa     540
ggtgaagaaa ccatcaccct cgttatcaaa ccggacatga aaacaaact gcgtatggaa      600
ggtaacgtta acggtcacgc tttcgttatc gaaggtgaag gttctggtaa accgttcgaa     660
ggtatccaga ccatcgacct ggaagttaaa gaaggtgctc cgctgccgtt cgcttacgac     720
atcctgacca ccgcttttcca ctacggtaac cgtgttttca ccaaataccc gcgtggtggt     780
ggtaagctta tgaacagcga cagcgagtgc ccactgagcc acgacggcta ctgcctgcac     840
gacggcgtgt gcatgtacat cgaggccctg gacaagtacg cctgcaactg cgtcgtgggc     900
tacatcggcg agcggtgcca gtaccggac ctgaagtggt gggagctgag actaa          955
```

<210> SEQ ID NO 18
<211> LENGTH: 1509
<212> TYPE: DNA
<213> ORGANISM: Artificial sequence
<220> FEATURE:
<223> OTHER INFORMATION: Synthetic

<400> SEQUENCE: 18

```
atgggaaatg aggcgtcgta tccgttacac catcaccatc atcacatggt tatcccggac      60
tacttcaaac agtctttccc ggaaggttac tcttgggaac gttctatgac ctacgaagac     120
ggtggtatct gcatcgctac caacgacatc accatggaag gtgactcttt catcaacaaa     180
atccacttca aagtaccaa cttcccgccg aacggtccgg ttatgcagaa acgtaccgtt      240
ggttgggaag ctagtaccga aaaatgtac gaacgtgacg gtgttctgaa aggtgacgtt      300
aaaatgaaac tgctgctgaa aggtggtggt cactaccgtt gcgactaccg taccacctac     360
aaagttaaac agaaaccggt taaactgccg gactaccact tcgttgacca ccgtatcgaa     420
atcctgtctc acgacaaaga ctacaacaaa gttaaactgt acgaacacgc tgttgctcgt     480
aactctaccg actctatgga cgaactgtac aaaggtggtt ctggtggtat ggtttctaaa     540
ggtgaagaaa ccatcaccct cgttatcaaa ccggacatga aaacaaact gcgtatggaa      600
ggtaacgtta acggtcacgc tttcgttatc gaaggtgaag gttctggtaa accgttcgaa     660
ggtatccaga ccatcgacct ggaagttaaa gaaggtgctc cgctgccgtt cgcttacgac     720
atcctgacca ccgcttttcca ctacggtaac cgtgttttca ccaaataccc gcgtggtggt     780
ggtaagctta tggtgagcaa gggcgaggag ctgttcaccg ggtggtgcc catcctggtc      840
```

| | |
|---|---:|
| gagctggacg gcgacgtaaa cggccacaag ttcagcgtgt ccggcgaggg cgagggcgat | 900 |
| gccacctacg gcaagctgac cctgaagttc atctgcacca ccggcaagct gcccgtgccc | 960 |
| tggcccaccc tcgtgaccac cctgacctgg ggcgtgcagt gcttcgcccg ctaccccgac | 1020 |
| cacatgaagc agcacgactt cttcaagtcc gccatgcccg aaggctacgt ccaggagcgc | 1080 |
| accatcttct tcaaggacga cggcaactac aagacccgcg ccgaggtgaa gttcgagggc | 1140 |
| gacaccctgg tgaaccgcat cgagctgaag ggcatcgact tcaaggagga cggcaacatc | 1200 |
| ctggggcaca gctggagta caacgccatc agcgacaacg tctatatcac cgccgacaag | 1260 |
| cagaagaacg gcatcaaggc caacttcaag atccgccaca acatcgagga cggcagcgtg | 1320 |
| cagctcgccg accactacca gcagaacacc cccatcggcg acggccccgt gctgctgccc | 1380 |
| gacaaccact acctgagcac ccagtccaag ctgagcaaag accccaacga gaagcgcgat | 1440 |
| cacatggtcc tgctggagtt cgtgaccgcc gccgggatca ctctcggcat ggacgagctg | 1500 |
| tacaagtaa | 1509 |

<210> SEQ ID NO 19
<211> LENGTH: 1500
<212> TYPE: DNA
<213> ORGANISM: Artificial sequence
<220> FEATURE:
<223> OTHER INFORMATION: Synthetic

<400> SEQUENCE: 19

| | |
|---|---:|
| atgggaaatg aggcgtcgta tccgttacac catcaccatc atcacatggt tatcccggac | 60 |
| tacttcaaac agtctttccc ggaaggttac tcttgggaac gttctatgac ctacgaagac | 120 |
| ggtggtatct gcatcgctac caacgacatc accatggaag gtgactcttt catcaacaaa | 180 |
| atccacttca aggtaccaa cttcccgccg aacggtccgg ttatgcagaa cgtaccgtt | 240 |
| ggttgggaag ctagtaccga aaaatgtac gaacgtgacg gtgttctgaa ggtgacgtt | 300 |
| aaaatgaaac tgctgctgaa aggtggtggt cactaccgtt gcgactaccg taccacctac | 360 |
| aaagttaaac agaaaccggt taaactgccg gactaccact tcgttgacca ccgtatcgaa | 420 |
| atcctgtctc acgacaaaga ctacaacaaa gttaaactgt acgaacacgc tgttgctcgt | 480 |
| aactctaccg actctatgga cgaactgtac aaaggtggtt ctggtggtat ggtttctaaa | 540 |
| ggtgaagaaa ccatcaccctc tgttatcaaa ccggacatga aaacaaact gcgtatggaa | 600 |
| ggtaacgtta acggtcacgc tttcgttatc gaaggtgaag gttctggtaa accgttcgaa | 660 |
| ggtatccaga ccatcgacct ggaagttaaa gaaggtgctc cgctgccgtt cgcttacgac | 720 |
| atcctgacca ccgcttttcca ctacggtaac cgtgttttca ccaaatacccc gcgtggtggt | 780 |
| ggtaagctta tggttttccaa gggcgaagaa gacaacatgg cgatcatcaa agaatttatg | 840 |
| cgttttaaag ttcacatgga aggttctgtt aacggtcatg agttcgaaat tgaaggtgag | 900 |
| ggtgaaggtc gcccgtacga aggtacccag accgcgaaac tgaaagttac caaaggtggt | 960 |
| ccgctgccgt tcgcgtggga catcctcagc ccgcagttca tgtacggttc taaagcgtac | 1020 |
| gttaaacatc cggcggacat tccagactac ctcaaactct cttttccctga aggtttcaaa | 1080 |
| tgggaacgtg ttatgaactt cgaggacggt ggtgttgtca ccgttaccca ggactcttct | 1140 |
| ctgcaggacg gcgagttcat ctacaaggtc aaactgcgtg gcaccaactt cccgtctgac | 1200 |
| ggtccggtta tgcagaaaaa aaccatgggt tgggaagcgt cttctgaacg tatgtacccg | 1260 |
| gaagatggtg cgctgaaagg cgaaatcaaa cagcgtctga agctcaaaga cggcggtcac | 1320 |
| tacgacgcgg aggttaaaac cacctacaaa gcgaaaaagc cggttcaact gccgggtgcg | 1380 |

```
tacaacgtta atatcaagct ggacatcacc tctcacaacg aagactacac catcgttgaa    1440
cagtacgaac gtgcggaagg ccgtcactct accggtggta tggacgaact gtacaagtaa    1500

<210> SEQ ID NO 20
<211> LENGTH: 474
<212> TYPE: DNA
<213> ORGANISM: Artificial sequence
<220> FEATURE:
<223> OTHER INFORMATION: Synthetic

<400> SEQUENCE: 20
atgggaaatg aggcgtcgta tccgttacac catcaccatc atcacctggc taccaccctg      60
gaacgtatcg aaaaaaactt cgttatcacc gacccgcgtc tgccggacaa cccgatcatc     120
ttcgcttctg actctttcct gcagctgacc gaatactctc gtgaagaaat cctgggtcgt     180
aactgccgtt tcctgcaggg tccggaaacc gaccgtgcta ccgttcgtaa atccgtgac     240 gctatcgaca accagaccga agttaccgtt cagctgatca actacaccaa atctggtaaa     300
aaattctgga acctgttcca cctgcagccg atgcgtgacc agaaaggtga cgttcagtac     360
ttcatcggtt tcagctgga cggtaccgaa acgttcgtg acgctgctga cgtgaaggt     420 gttatgctga tcaaaaaac cgctgaaaac atcgacgaag ctgctaaaga actg           474

<210> SEQ ID NO 21
<211> LENGTH: 933
<212> TYPE: DNA
<213> ORGANISM: Artificial sequence
<220> FEATURE:
<223> OTHER INFORMATION: Synthetic

<400> SEQUENCE: 21
atgcaccatc accatcatca catggtttcc aagggcgaag aagacaacat ggcgatcatc      60
aaagaattta tgcgttttaa agttcacatg gaaggttctg ttaacggtca tgagttcgaa     120
attgaaggtg agggtgaagg tcgcccgtac gaaggtaccc agaccgcgaa actgaaagtt     180
accaaaggtg gtccgctgcc gttcgcgtgg gacatcctca gcccgcagtt catgtacggt     240
tctaaagcgt acgttaaaca tccggcggac attccagact acctcaaact ctcttttcct     300
gaaggtttca atgggaacg tgttatgaac ttcgaggacg gtggtgttgt caccgttacc     360
caggactctt ctctgcagga cggcgagttc atctacaagg tcaaactgcg tggcaccaac     420
ttcccgtctg acggtccggt tatgcagaaa aaaccatgg ttgggaagc gtcttctgaa     480 cgtatgtacc cggaagatgg tgcgctgaaa ggcgaaatca acagcgtct gaagctcaaa     540 gacggcggtc actacgacgc ggaggttaaa accacctaca agcgaaaaa gccggttcaa     600 ctgccgggtg cgtacaacgt taatatcaag ctggacatca cctctcacaa cgaagactac     660
accatcgttg aacagtacga acgtgcggaa ggccgtcact ctaccggtgg tatggacgaa     720
ctgtacaaga gcttggtgg ttctggtggt agcatggtgg ataacaaatt caataaagaa     780
aagacgcgtg ccggtgcgga aatccattct ctgccaaacc tgaatgttga gcagaagttt     840
gccttcatcg tgagcctgtt tgatgatcca tctcagagcg ccaatctgct ggccgaagcc     900
aaaaaactga acgatgccca ggccccaaaa taa                                  933

<210> SEQ ID NO 22
<211> LENGTH: 939
<212> TYPE: DNA
<213> ORGANISM: Artificial sequence
<220> FEATURE:
```

<223> OTHER INFORMATION: Synthetic

<400> SEQUENCE: 22

```
atgcaccatc accatcatca catgcgtaaa ggcgaagagc tgttcactgg tgtcgtccct      60
attctggtgg aactggatgg tgatgtcaac ggtcataagt tttccgtgcg tggcgagggt     120
gaaggtgacg caactaatgg taaactgacg ctgaagttca tctgtactac tggtaaactg     180
ccggtacctt ggccgactct ggtaacgacg ctgacttatg gtgttcagtg ctttgctcgt     240
tatccggacc acatgaagca gcatgacttc ttcaagtccg ccatgccgga aggctatgtg     300
caggaacgca cgatttcctt taaggatgac ggcacgtaca aaacgcgtgc ggaagtgaaa     360
tttgaaggcg ataccctggt aaaccgcatt gagctgaaag gcattgactt taaagaagac     420
ggcaatatcc tgggccataa gctggaatac aattttaaca gccacaatgt ttacatcacc     480
gccgataaac aaaaaaatgg cattaaagcg aattttaaaa ttcgccacaa cgtggaggat     540
ggcagcgtgc agctggctga tcactaccag caaaacactc caatcggtga tggtcctgtt     600
ctgctgccag acaatcacta tctgagcacg caaagcgttc tgtctaaaga tccgaacgag     660
aaacgcgatc acatggttct gctggagttc gtaaccgcag cgggcatcac gcatggtatg     720
gatgaactgt acaaaaagct tggtggttct ggtggtagca tggtggataa caaattcaat     780
aaagaaaaga cgcgtgccgg tgcggaaatc cattctctgc caaacctgaa tgttgagcag     840
aagtttgcct tcatcgtgag cctgtttgat gatccatctc agagcgccaa tctgctggcc     900
gaagccaaaa aactgaacga tgcccaggcc ccaaaataa                            939
```

<210> SEQ ID NO 23
<211> LENGTH: 942
<212> TYPE: DNA
<213> ORGANISM: Artificial sequence
<220> FEATURE:
<223> OTHER INFORMATION: Synthetic

<400> SEQUENCE: 23

```
atgcaccatc accatcatca catggtgagc aagggcgagg agctgttcac cggggtggtg      60
cccatcctgg tcgagctgga cggcgacgta aacggccaca agttcagcgt gtccggcgag     120
ggcgagggcg atgccaccta cggcaagctg accctgaagt tcatctgcac caccggcaag     180
ctgcccgtgc cctggcccac cctcgtgacc accctgacct ggggcgtgca gtgcttcgcc     240
cgctaccccg accacatgaa gcagcacgac ttcttcaagt ccgccatgcc cgaaggctac     300
gtccaggagc gcaccatctt cttcaaggac gacggcaact acaagacccg cgccgaggtg     360
aagttcgagg gcgacaccct ggtgaaccgc atcgagctga agggcatcga cttcaaggag     420
gacggcaaca tcctggggca caagctggag tacaacgcca tcagcgacaa cgtctatatc     480
accgccgaca agcagaagaa cggcatcaag gccaacttca gatccgccaa catcgag       540
gacggcagcg tgcagctcgc cgaccactac cagcagaaca cccccatcgg cgacggcccc     600
gtgctgctgc ccgacaacca ctacctgagc acccagtcca gctgagcaa agaccccaac     660
gagaagcgcg atcacatggt cctgctggag ttcgtgaccg ccgccgggat cactctcggc     720
atggacgagc tgtacaagaa gcttggtggt tctggtggta gcatggtgga taacaaattc     780
aataaagaaa agacgcgtgc cggtgcggaa atccattctc tgccaaacct gaatgttgag     840
cagaagtttg ccttcatcgt gagcctgttt gatgatccat ctcagagcgc caatctgctg     900
gccgaagcca aaaaactgaa cgatgcccag gccccaaaat aa                        942
```

<210> SEQ ID NO 24
<211> LENGTH: 1017
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (52)..(52)
<223> OTHER INFORMATION: n is a, c, g, or t

<400> SEQUENCE: 24

```
atgcaccatc accatcatca catgcaccct gaaacgctgg tgaaagtaaa anatgctgaa        60
gatcagttgg gtgcacgagt gggttacatc gaactggatc tcaacagcgg taagatcctt      120
gagagttttc gccccgaaga acgttttcca atgatgagca cttttaaagt tctgctatgt      180
ggcgcggtat tatcccgtgt tgacgccggg caagagcaac tcggtcgccg catacactat      240
tctcagaatg acttggttga gtactcacca gtcacagaaa agcatcttac ggatggcatg      300
acagtaagag aattatgcag tgctgccata accatgagtg ataacactgc ggccaactta      360
cttctgacaa cgatcggagg accgaaggag ctaaccgctt ttttgcacaa catggggggat     420 catgtaactc gccttgatcg ttgggaaccg gagctgaatg aagccatacc aaacgacgag      480
cgtgacacca cgatgcctgc agcaatggca acaacgttgc gcaaactatt aactggcgaa      540
ctacttactc tagcttcccg gcaacaatta atagactgga tggaggcgga taaagttgca      600
ggaccacttc tgcgctcggc ccttccggct ggctggttta ttgctgataa atctggagcc      660
ggtgagcgtg gtctcgcgg tatcattgca gcactggggc cagatggtaa gccctcccgt       720
atcgtagtta tctacacgac ggggagtcag gcaactatgg atgaacgaaa tagacagatc      780
gctgagatag gtgcctcact gattaagcat tggaagcttg gtggttctgg tggtagcatg      840
gtggataaca aattcaataa agaaaagacg cgtgccggtg cggaaatcca ttctctgcca      900
aacctgaatg ttgagcagaa gtttgccttc atcgtgagcc tgtttgatga tccatctcag      960
agcgccaatc tgctggccga agccaaaaaa ctgaacgatg cccaggcccc aaaataa       1017
```

<210> SEQ ID NO 25
<211> LENGTH: 389
<212> TYPE: DNA
<213> ORGANISM: Artificial sequence
<220> FEATURE:
<223> OTHER INFORMATION: Synthetic

<400> SEQUENCE: 25

```
atgcaccatc accatcatca catgaacagc gacagcgagt gcccactgag ccacgacggc        60
tactgcctgc acgacggcgt gtgcatgtac atcgaggccc tggacaagta cgcctgcaac      120
tgcgtcgtgg gctacatcgg cgagcggtgc cagtaccggg acctgaagtg gtgggagctg      180
agactaagct tggtggttct ggtggtagca tggtggataa caaattcaat aaagaaaaga      240
cgcgtgccgg tgcggaaatc cattctctgc caaacctgaa tgttgagcag aagtttgcct      300
tcatcgtgag cctgtttgat gatccatctc agagcgccaa tctgctggcc gaagccaaaa      360
aactgaacga tgcccaggcc ccaaaataa                                         389
```

<210> SEQ ID NO 26
<211> LENGTH: 16
<212> TYPE: PRT
<213> ORGANISM: Artificial sequence
<220> FEATURE:
<223> OTHER INFORMATION: Synthetic
<220> FEATURE:

```
<221> NAME/KEY: MISC_FEATURE
<222> LOCATION: (16)..(16)
<223> OTHER INFORMATION: K at position 16 is modified (N3)-NH2

<400> SEQUENCE: 26

Gly Gly Gly Gly Arg Gly Pro Gln Gly Ile Trp Gly Gln Gly Arg Lys
1               5                   10                  15

<210> SEQ ID NO 27
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: C at position 6 is modified NH2

<400> SEQUENCE: 27

Gly Gly Gly Gly Arg Cys
1               5

<210> SEQ ID NO 28
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: C at position 6 is modified (H-C-OH)-NH2

<400> SEQUENCE: 28

Gly Gly Gly Gly Arg Cys
1               5

<210> SEQ ID NO 29
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: C at position 6 is modified (N3-C-OH)-NH2

<400> SEQUENCE: 29

Gly Gly Gly Gly Arg Cys
1               5

<210> SEQ ID NO 30
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: K at position 6 is modified (4-methyltrityl)-
      NH2

<400> SEQUENCE: 30

Gly Gly Gly Gly Arg Lys
1               5
```

```
<210> SEQ ID NO 31
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: K at position 6 is modified (ortho-nitrobenzyl-
      N3)-NH2

<400> SEQUENCE: 31

Gly Gly Gly Gly Arg Lys
1               5

<210> SEQ ID NO 32
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: C at position 16 is modified -NH2

<400> SEQUENCE: 32

Gly Gly Gly Gly Arg Gly Pro Gln Gly Ile Trp Gly Gln Gly Arg Cys
1               5                   10                  15

<210> SEQ ID NO 33
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: C at position 16 is modified (NH2-C-OH)-NH2

<400> SEQUENCE: 33

Gly Gly Gly Gly Arg Gly Pro Gln Gly Ile Trp Gly Gln Gly Arg Cys
1               5                   10                  15

<210> SEQ ID NO 34
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: C at position 16 is modified (N3-C-OH)-NH2

<400> SEQUENCE: 34

Gly Gly Gly Gly Arg Gly Pro Gln Gly Ile Trp Gly Gln Gly Arg Cys
1               5                   10                  15

<210> SEQ ID NO 35
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: C at position 16 is modified (N3-C-OH)-NH2
```

<400> SEQUENCE: 35

Gly Gly Gly Gly Arg Gly Pro Gln Gly Ile Trp Gly Gln Gly Arg Cys
1               5                   10                  15

<210> SEQ ID NO 36
<211> LENGTH: 6
<212> TYPE: PRT
<213> ORGANISM: Artificial sequence
<220> FEATURE:
<223> OTHER INFORMATION: Synthetic

<400> SEQUENCE: 36

Gly Gly Gly Gly Arg Gly
1               5

<210> SEQ ID NO 37
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: G at postiion 6 is modified ortho-nitrobenzyl
<220> FEATURE:
<221> NAME/KEY: MISC_FEATURE
<222> LOCATION: (9)..(9)
<223> OTHER INFORMATION: C at postiion 9 is modified NH2

<400> SEQUENCE: 37

Gly Gly Gly Gly Arg Gly Gly Arg Cys
1               5

<210> SEQ ID NO 38
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: G at position 6 is modified -ortho-nitrobenzyl-
<220> FEATURE:
<221> NAME/KEY: MISC_FEATURE
<222> LOCATION: (9)..(9)
<223> OTHER INFORMATION: C at position 9 is modified (H-C-OH)-NH2

<400> SEQUENCE: 38

Gly Gly Gly Gly Arg Gly Gly Arg Cys
1               5

<210> SEQ ID NO 39
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: G at position 6 is modified -ortho-nitrobenzyl-
<220> FEATURE:
<221> NAME/KEY: MISC_FEATURE
<222> LOCATION: (9)..(9)
<223> OTHER INFORMATION: C at position 9 is modified (N3-C-OH)-NH2

<400> SEQUENCE: 39

Gly Gly Gly Gly Arg Gly Gly Arg Cys
1               5

<210> SEQ ID NO 40
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: K at position 16 is modified (4-methyltrityl)
      -NH2

<400> SEQUENCE: 40

Gly Gly Gly Gly Arg Gly Pro Gln Gly Ile Trp Gly Gln Gly Arg Lys
1               5                   10                  15

<210> SEQ ID NO 41
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: K at position 16 is modified (ortho-
      nitrobenzyl-N3)-NH2

<400> SEQUENCE: 41

Gly Gly Gly Gly Arg Gly Pro Gln Gly Ile Trp Gly Gln Gly Arg Lys
1               5                   10                  15

<210> SEQ ID NO 42
<211> LENGTH: 22
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: K at position 22 is modified -NH2

<400> SEQUENCE: 42

Gly Gly Gly Gly Arg Gly Cys Gly Pro Gln Gly Ile Trp Gly Gln Gly
1               5                   10                  15

Gln Gly Cys Gly Arg Lys
            20

<210> SEQ ID NO 43
<211> LENGTH: 22
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: K at position 22 is modified (N3)-NH2

<400> SEQUENCE: 43

Gly Gly Gly Gly Arg Gly Cys Gly Pro Gln Gly Ile Trp Gly Gln Gly
1               5                   10                  15

Gln Gly Cys Gly Arg Lys
            20

```
<210> SEQ ID NO 44
<211> LENGTH: 22
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: K at position 22 is modified (N3)-NH2

<400> SEQUENCE: 44

Gly Gly Gly Gly Arg Gly Cys Gly Pro Gln Gly Ile Trp Gly Gln Gly
1               5                   10                  15

Gln Gly Cys Gly Arg Lys
            20

<210> SEQ ID NO 45
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: K at position 5 is modified -NH2

<400> SEQUENCE: 45

Gly Cys Gly Arg Lys
1               5

<210> SEQ ID NO 46
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: G at position 8 is modified -OH

<400> SEQUENCE: 46

Gly Gly Gly Gly Arg Gly Cys Gly
1               5

<210> SEQ ID NO 47
<211> LENGTH: 13
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: G at position 8 is modified ortho-nitrobenzyl
<220> FEATURE:
<221> NAME/KEY: MISC_FEATURE
<222> LOCATION: (13)..(13)
<223> OTHER INFORMATION: K at position 13 is modified NH2

<400> SEQUENCE: 47

Gly Gly Gly Gly Arg Gly Cys Gly Gly Cys Gly Arg Lys
1               5                   10

<210> SEQ ID NO 48
<211> LENGTH: 13
<212> TYPE: PRT
```

```
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: G at position 8 is modified ortho-nitrobenzyl
<220> FEATURE:
<221> NAME/KEY: MISC_FEATURE
<222> LOCATION: (13)..(13)
<223> OTHER INFORMATION: K at position 13 is modified N3-NH2

<400> SEQUENCE: 48

Gly Gly Gly Gly Arg Gly Cys Gly Gly Cys Gly Arg Lys
1               5                   10

<210> SEQ ID NO 49
<211> LENGTH: 13
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: G at position 8 is modified ortho-nitrobenzyl
<220> FEATURE:
<221> NAME/KEY: MISC_FEATURE
<222> LOCATION: (13)..(13)
<223> OTHER INFORMATION: K at position 13 is modified N3-NH2

<400> SEQUENCE: 49

Gly Gly Gly Gly Arg Gly Cys Gly Gly Cys Gly Arg Lys
1               5                   10

<210> SEQ ID NO 50
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: K at position 1 is modified 4-methyltrityl
<220> FEATURE:
<221> NAME/KEY: MISC_FEATURE
<222> LOCATION: (4)..(4)
<223> OTHER INFORMATION: K at position 4 is modified NH2

<400> SEQUENCE: 50

Lys Gly Arg Lys
1

<210> SEQ ID NO 51
<211> LENGTH: 17
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: K at position 7 is modified 4-methyltrityl

<400> SEQUENCE: 51

Gly Gly Gly Gly Arg Gly Lys Gly Gly Pro Gln Gly Ile Trp Gly Gln
1               5                   10                  15

Gly
```

```
<210> SEQ ID NO 52
<211> LENGTH: 21
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: K at position 7 is modified ortho-nitrobenzyl-
      N3
<220> FEATURE:
<221> NAME/KEY: MISC_FEATURE
<222> LOCATION: (18)..(18)
<223> OTHER INFORMATION: K at position 18 is modified alkyne
<220> FEATURE:
<221> NAME/KEY: MISC_FEATURE
<222> LOCATION: (21)..(21)
<223> OTHER INFORMATION: K at position 21 is modified NH2

<400> SEQUENCE: 52

Gly Gly Gly Gly Arg Gly Lys Gly Gly Pro Gln Gly Ile Trp Gly Gln
1               5                   10                  15

Gly Lys Gly Arg Lys
            20

<210> SEQ ID NO 53
<211> LENGTH: 21
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: K at position 7 is modified ortho-nitrobenzyl-
      N3
<220> FEATURE:
<221> NAME/KEY: MISC_FEATURE
<222> LOCATION: (18)..(18)
<223> OTHER INFORMATION: K at position 18 is modified alkyne
<220> FEATURE:
<221> NAME/KEY: MISC_FEATURE
<222> LOCATION: (21)..(21)
<223> OTHER INFORMATION: K at position 18 is modified NH3-NH2

<400> SEQUENCE: 53

Gly Gly Gly Gly Arg Gly Lys Gly Gly Pro Gln Gly Ile Trp Gly Gln
1               5                   10                  15

Gly Lys Gly Arg Lys
            20

<210> SEQ ID NO 54
<211> LENGTH: 21
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: K at position 7 is modified ortho-nitrobenzyl-
      N3
<220> FEATURE:
<221> NAME/KEY: MISC_FEATURE
<222> LOCATION: (18)..(18)
<223> OTHER INFORMATION: K at position 18 is modified alkyne
<220> FEATURE:
<221> NAME/KEY: MISC_FEATURE
<222> LOCATION: (21)..(21)
<223> OTHER INFORMATION: K at position 21 is modified N3-NH2

<400> SEQUENCE: 54
```

-continued

```
Gly Gly Gly Gly Arg Gly Lys Gly Gly Pro Gln Gly Ile Trp Gly Gln
1               5               10                  15
Gly Lys Gly Arg Lys
            20
```